(12) United States Patent
Greenhagen et al.

(10) Patent No.: US 11,674,162 B2
(45) Date of Patent: *Jun. 13, 2023

(54) SELECTIVE ADVANTAGE IN FERMENTATION

(71) Applicant: Ginkgo Bioworks, Inc., Boston, MA (US)

(72) Inventors: Emily H. Greenhagen, Melrose, MA (US); Maureen Hamilton, Littleton, MA (US); William G. LaTouf, Belmont, MA (US); Andrew L. Consiglio, Holden, MA (US); Kyle M. MacEwen, Braintree, MA (US); Arthur J. Shaw, IV, Belmont, MA (US)

(73) Assignee: Ginkgo Bioworks, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/303,330

(22) PCT Filed: Apr. 8, 2015

(86) PCT No.: PCT/US2015/024943
§ 371 (c)(1),
(2) Date: Oct. 11, 2016

(87) PCT Pub. No.: WO2015/157431
PCT Pub. Date: Oct. 15, 2015

(65) Prior Publication Data
US 2017/0096691 A1    Apr. 6, 2017

Related U.S. Application Data

(60) Provisional application No. 62/083,540, filed on Nov. 24, 2014, provisional application No. 61/976,672, filed on Apr. 8, 2014.

(51) Int. Cl.
| | |
|---|---|
| *C12N 9/80* | (2006.01) |
| *C12N 9/88* | (2006.01) |
| *C12N 9/78* | (2006.01) |
| *C12P 13/00* | (2006.01) |
| *C12P 7/6463* | (2022.01) |
| *C12N 9/86* | (2006.01) |
| *C12N 15/52* | (2006.01) |
| *C12N 15/70* | (2006.01) |
| *C12N 15/81* | (2006.01) |

(52) U.S. Cl.
CPC ............. *C12P 13/001* (2013.01); *C12N 9/78* (2013.01); *C12N 9/80* (2013.01); *C12N 9/86* (2013.01); *C12N 15/52* (2013.01); *C12N 15/70* (2013.01); *C12N 15/81* (2013.01); *C12P 7/6463* (2013.01); *C12Y 305/01054* (2013.01); *C12Y 305/01084* (2013.01); *C12Y 305/02015* (2013.01); *C12Y 305/04* (2013.01); *C12Y 305/04003* (2013.01); *C12Y 305/99004* (2013.01)

(58) Field of Classification Search
CPC . C12N 9/14; C12N 9/20; C12N 15/70; C12Y 302/01004; C12P 13/001
USPC ....... 435/252.3, 232, 195, 254.21, 161, 262, 435/18, 197
See application file for complete search history.

(56) References Cited

FOREIGN PATENT DOCUMENTS

| CN | 1578839 | | 2/2005 |
|---|---|---|---|
| EP | 183469 | * | 6/1986 |
| GB | 2439310 A | | 12/2007 |
| WO | WO 2003/040379 | | 5/2003 |
| WO | WO 2010/104938 | | 9/2010 |
| WO | WO-2010/127182 A1 | | 11/2010 |
| WO | WO-2011/103300 A2 | | 8/2011 |
| WO | WO 2014/107660 | | 7/2014 |
| WO | WO 2015/031441 | | 3/2015 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Cheng et al. ( APLd env. Micro, 2005, pp. 4437-4445.*
Sumrada et al. ( JBC 1981, 257, pp. 9119-9127.*
International Search Report for International Application No. PCT/US2015/24943, dated Jul. 28, 2015.

* cited by examiner

*Primary Examiner* — Robert B Mondesi
*Assistant Examiner* — Mohammad Y Meah
(74) *Attorney, Agent, or Firm* — Foley Hoag LLP; Janine S. Ladislaw; Mohanad Mossalam

(57) ABSTRACT

Disclosed are transformed cells and related nucleotide and protein sequences, and fermentation compositions and methods, all of which are related to providing selective advantage in fermentation. For example, a selective advantage results from transformation of a cell with a nucleic acid that allows a transformed cell to metabolize one or more nitrogen-, phosphorous-, and/or sulfur-containing compounds that a native cell of the same species as the transformed cell cannot metabolize, and from fermentation of the transformed cell using one or more feedstocks, such as fractioned grain, which are depleted in or free of conventional nitrogen-, phosphorous-, and/or sulfur-containing compounds that a native cell of the same species as the transformed cell can metabolize. Also disclosed are methods for improved oxygen transfer in an aerobic or microaerobic fermentation.

20 Claims, 29 Drawing Sheets
Specification includes a Sequence Listing.

SEQUENCE LISTING

```
<160> NUMBER OF SEQ ID NOS: 103

<210> SEQ ID NO 1
<211> LENGTH: 1818
<212> TYPE: DNA
<213> ORGANISM: Pseudomonas sp.

<400> SEQUENCE: 1
atgaatgacc gcgcgcccca ccctgaaaga tctggtcgag tcacgccgga tcacctgacc      60
gatctggctt cctatcaggc tgcctatgcc gccggtacag acgccgccga cgtcatttcg     120
gacctgtatg cccgtatcaa agaagacggc gaaaatccga tctggattag cctgttgccc     180
ttggaaagcg cattggcgat gctggccgac gcgcagcaac gcaaggacaa gggagaagcg     240
ttgccgctct ttggcatccc cttcggcgtc aaggacaaca tcgacgtcgc aggccttccg     300
acgactgccg ggtgtacggg gttcgcgcgt acgccccgac agcacgcctt cgtcgtacag     360
cgcctggtgg acgctggcgc gatcccgatc ggaaaaacga acctcgatca attcgcgacc     420
gggttgaacg gcactcgcac gccgtttggc attccgcgct gcgtgttcaa cgagaactac     480
gtatccggcg gctccagcag tggctccgca gtggccgtcg ccaacggcac ggtaccgttc     540
tcgctcggga cggacactgc cggttccggc cgcattcctg ctgcgttcaa caatctggtg     600
ggcttgaaac cgaccaaagg cctgttctcg ggcagtggac tggttcccgc ggcgcgaagc     660
cttgactgca tcagcgtcct cgcccatacc gtagatgacg cccttgcggt cgcacgcgtc     720
gccgccggct acgatgctga tgacgctttt tcgcgcaagg cgggcgccgc cgcactgaca     780
gaaaagagtt ggcctcgtcg cttcaatttc ggggtcccag cggcggaaca tcgccagttt     840
ttcggtgacg cggaagccga ggcgcttttc aataaagcgg ttcgcaagct tgaagagatg     900
ggtggcacct gcatctcgtt tgactatacc cccttcaggc aggctgctga actgctctac     960 gccggcccttt gggttgcgga gcgcctggcg gccatcgaga gccttgcgga cgagcatccc    1020
gaggtgctcc acccggtcgt tcgtgacatc atcttgtccg cgaagcgaat gagcgcagtc    1080
gacacgttca acggtatcta tcgcctggcc gaccttgtca gggctgcaga gagcacttgg    1140
gaaaagatcg atgtgatgct gctgccgacg gcgccgacca tctacactgt agaagacatg    1200
ctcgccgatc cggtacgcct caacagcaat ctgggcttct acacgaactt cgtgaacttg    1260
```

| | |
|---|---|
| atggatttgt ccgcgattgc tgttcccgca ggcttccgaa ccaatggcct gccatttggc | 1320 |
| gtcactttca tcggtcgggc gttcgaagat ggggcgatcg caagcttggg aaaagctttc | 1380 |
| gtggagcacg acctcgccaa gggcaacgcg ccacggcgg cgccacccaa ggataccgtc | 1440 |
| gcaatcgccg tggtaggtgc acatctctcc gaccagccct gaatcatca gctcacggag | 1500 |
| agcggcggaa agctacgggc aacaacgcgt actgcgccgg gatatgcctt gtacgcactc | 1560 |
| cgtgatgcga cgccggctaa gcctggaatg ttgcgcgacc agaatgcggt cgggagcatc | 1620 |
| gaagtggaaa tctgggatct gccggtcgcc gggttcggtg cgtttgtaag tgaaattccg | 1680 |
| gcgccgttgg gtatcgggac aataacactc gaagacggca gccatgtgaa aggctttctg | 1740 |
| tgcgagccac atgccatcga acggcgctc gacatcactc actacggcgg ctggcgagca | 1800 |
| tacctcgcgg ctcaatag | 1818 |

<210> SEQ ID NO 2
<211> LENGTH: 5508
<212> TYPE: DNA
<213> ORGANISM: Saccharomyces cerevisiae

<400> SEQUENCE: 2

| | |
|---|---|
| atgacagtta gttccgatac aactgctgaa atatcgttag gttggtcaat ccaagactgg | 60 |
| attgatttcc acaagtcatc aagctcccag gcttcactaa ggcttcttga atcactacta | 120 |
| gactctcaaa atgttgcgcc agtcgataat gcgtggatat cgctaatttc aaaggaaaat | 180 |
| ttactgcacc aattccaaat tttaaagagc agagaaaata agaaactct acctctctac | 240 |
| ggtgtcccta ttgctgttaa ggacaacatc gacgttagag gtctacgcac caccgctgca | 300 |
| tgtccatcct ttgcatatga gccttccaaa gactctaaag tagtagaact actaagaaat | 360 |
| gcaggtgcaa taatcgtggg taagacaaac ttggaccaat ttgccacagg attagtcggc | 420 |
| acacggtctc catatgggaa aacaccttgc gcttttagca aagagcatgt atctggtggt | 480 |
| tcctccgctg ggtcagcatc ggtggtcgcc agaggtatcg taccaattgc attgggtact | 540 |
| gatacagcag gttctggtag agtcccagcc gccttgaaca acctgattgg cctaaagcca | 600 |
| acaaagggcg tcttttcctg tcaaggtgta gttcccgctt gtaaatcttt agactgcgtc | 660 |
| tccatctttg cattaaacct aagtgatgct gaacgctgct ccgcatcat gtgccagcca | 720 |
| gatcctgata tgatgaata ttctagaccc tatgttccca acccaaagaa aaattttca | 780 |
| agcaatgtaa cgattgctat tcctaaaaat atcccatggt atggtgaaac caagaatcct | 840 |
| gtactgtttt ccaatgctgt cgaaaatcta tcaagaacgg cgctaacgt catagaaatt | 900 |
| gattttgagc ctcttttaga gttagctcgc tgtttatacg aaggtacttg ggtggccgag | 960 |
| cgttatcaag ctattcaatc gtttttggac agtaaaccac caaggaatc tttggaccct | 1020 |
| actgttattt caattataga aggggccaag aaatacagtg cagtagactg cttcagtttt | 1080 |
| gaatacaaaa gacaaggcat cttgcaaaaa gtgagacgac ttctcgaatc agtcgatgtc | 1140 |
| tgtgtgtgtgc ccacatgtcc cttaaatcct actatgcaac aagttgcgga tgaaccagtc | 1200 |
| ctagtcaatt caagacaagg cacatggact aattttgtca acttggcaga tttggcagcc | 1260 |
| cttgctgttc ccgcagggtt ccgagacgat ggttttgccaa atggtattac tttaatcggt | 1320 |
| aaaaaattca cagattacgc actattagag ttggctaacc gctatttcca aaatatgttc | 1380 |
| cccaacggtt ccagaacata cggtactttt acctcttctt cagtaaagcc agcaaacgat | 1440 |
| caattagtgg gaccagacta tgacccatct acgtccataa aattggctgt tgtcggtgca | 1500 |
| catcttaagg gtctgcctct acattggcaa ttggaaaagg tcaatgcaac atatttatgt | 1560 |

```
acaacaaaaa catcaaaagc ttaccagctt tttgctttgc ccaaaaatgg accagtttta    1620
aaacctggtt tgagaagagt tcaagatagc aatggctctc aaatcgaatt agaagtgtac    1680
agtgttccaa agaactgtt cggtgctttt atttccatgg ttcctgaacc attgggaata    1740
ggttcagtgg agttagaatc tggtgaatgg atcaaatcct ttatttgtga agaatctggt    1800
tacaaagcca aggtacagt tgatatcaca agtatggtg gatttagagc atattttgaa    1860
atgttgaaga aaaagagtc ccaaaagaag aagttatttg ataccgtgtt aattgccaat    1920
agaggtgaaa ttgccgttcg tattatcaag acattaaaaa aattgggtat tagatcagtt    1980
gcagtttatt ccgaccctga taaatattct caacacgtta ctgatgcaga tgtttctgta    2040
ccccttcatg gcacaaccgc agcccaaact tatttagaca tgaataagat catagatgcc    2100
gctaagcaaa ctaatgcaca ggccattatt cctggttatg gtttcttgtc ggaaaatgcg    2160
gatttttctg atgcgtgcac cagtgctggc attacctttg ttggtccttc gggagatatt    2220
atcagaggtt tagggttaaa acattctgct agacagattg cacagaaggc tggcgttcct    2280
ctagtgccag gctctttgct tatcacatca gttgaagagg ctaagaaagt cgcagcggaa    2340
ttggaatacc cagttatggt gaagtcaact gctggtggcg tggtattgg tttgcagaaa    2400 gtcgattctg aagaggacat cgagcatatt tttgagactg tgaaacatca aggtgaaaca    2460
tttttcggtg acgctggtgt atttctgaaa cggtttatcg aaaatgccag gcatgttgaa    2520
gtccaactta tgggagatgg ttttggtaag gccattgctt tgggcgaacg tgattgttct    2580
ttacagcgtc gtaaccaaaa agttatcgaa gaaactcctg caccaaattt gccagaaaag    2640
acgaggttgg cgttaagaaa ggcagctgaa agtttgggat ctttattgaa ttacaagtgt    2700
gctggtacgg ttgaatttat ttacgatgag aaaaaggacg agttttactt tttagaagtt    2760
aatacaagat tacaagttga acatccaata acagaaatgg ttacagggtt agacttggtc    2820
gagtggatga tcaggattgc cgctaatgat gcacctgatt ttgattctac aaaggtagaa    2880
gtcaatgggg tttcaatgga ggcacgtta tatgctgaaa tccattgaa aaatttcaga    2940 ccttctccag gtttacttgt cgatgtgaaa tttcctgatt gggcaagagt ggatacttgg    3000
gttaagaaag gtactaatat ttctcccgaa tatgatccaa cattggccaa aattatcgtt    3060
catgggaaag accgtgatga tgcaatttcc aagttaaatc aagcgttaga agaaacaaaa    3120
gtttacggat gtattactaa cattgactac ctgaagtcta tcattaccag tgatttcttt    3180
gctaaagcaa aagtttctac aaacattttg aactcttatc aatatgagcc taccgccatc    3240
gaaattactt tgcccggtgc acacactagt attcaggatt accccggtag agttgggtac    3300
tggagaattg gtgttccgcc ctctggtcca atggacgcat attcgtttag attggcgaac    3360
agaattgttg gtaatgacta caggactcct gccattgaag taacgttgac tggtccatcc    3420
atcgttttcc attgtgaaac tgtcattgcc attactggtg gtaccgctct atgtacatta    3480
gacggccaag aaattcccca acacaaaccg gtcgaagtta gaggggatc tactttatcc    3540 attggcaagt tgacaagcgg ctgtagagca tacttaggta tcagggtgg cattgatgtg    3600 cctaaatact tgggctctta ttctactttc actctaggaa atgtcggtgg atacaatgga    3660
agggtgctaa aacttggaga cgtactattc ttaccaagca atgaagaaaa taatcagtt    3720 gagtgccttc cacagaatat tcctcaatca ttaattcctc aaatttccga aactaaggaa    3780
tggagaattg gtgtaacatg tggtccccat gggtctccag atttttttaa acctgagtcc    3840
atcgaagaat ttttcagtga gaagtggaag gttcattaca actccaatag atttggtgtc    3900
```

-continued

```
cgtttgattg gacctaaacc taagtgggca agaagtaatg gtggtgaagg tggtatgcat      3960
ccttcaaaca ctcacgatta cgtttattct ctgggtgcaa ttaatttcac gggtgatgag      4020
ccagttatta ttacttgcga tggtccttcc ttaggtggtt ttgtgtgtca agctgttgtc      4080
ccagaagcag aactgtggaa ggttggacag gttaaacccg tgattccat tcagtttgtg       4140 ccactttctt acgaaagctc gagatcctta aaggaatctc aggaagttgc aattaaatca      4200
ttggatggta ctaagttaag gcgcttagac tctgtttcaa ttttaccatc attcgaaacg      4260
cctattcttg cacaaatgga aaagtgaat gagctttcac caaaggttgt atacagacaa       4320
gcaggtgatc gttatgtttt ggtggaatac ggtgataatg aaatgaattt taatatttcc      4380
tatagaattg aatgcctgat ctcccttgtg aaaaagaata agactattgg tattgttgaa     4440
atgtcccaag gtgttagatc tgtgttgata gaatttgatg gttacaaagt cactcaaaaa     4500
gaattgctta agtattggt ggcatatgaa acagaaatcc agtttgatga aaattggaag      4560
ataacttcta atataatcaag attaccgatg gctttcgaag actcgaagac tttggcatgt    4620
gttcaaaggt atcaagaaac aattcgttcg tctgctccat ggttgccaaa taacgttgat     4680
ttcattgcca atgtaaatgg aatttcaagg aatgaagttt atgatatgtt gtattctgcc     4740
agatttatgg ttttaggttt aggtgatgtc ttcctagggt cgccttgtgc tgttccatta     4800
gatcctcgtc acagattttt gggaagcaag tacaacccaa gtagaacata tacagaaaga     4860
ggtgcagtcg gtattggcgg tatgtatatg tgcatatatg ctgctaacag tcctggtggg    4920
taccaattag tgggtagaac aataccaatt tgggacaaac tatgtctggc cgcatcttct    4980
gaggttccgt ggttgatgaa cccatttgac caagtcgaat tttacccagt ttctgaagaa    5040
gatttggata aaatgactga agattgtgat aatggtgttt ataaagtcaa tatcgaaaag    5100 agtgttttg atcatcaaga atacttgaga tggatcaacg caaacaaaga ttccatcaca    5160
gcattccagg agggccagct tggtgaaaga gcagaggaat tgccaaatt gattcaaaat     5220 gcaaactctg aactaaaaga aagtgtcaca gtcaaacctg acgaggaaga agacttccca    5280
gaaggtgcag aaattgtata ttctgagtat tctgggcgtt tttggaaatc catagcatct    5340
gttggagatg ttattgaagc aggtcaaggg ctactaatta ttgaagccat gaaagcggaa    5400
atgattatat ccgctcctaa atcgggtaag attatcaaga tttgccatgg caatggtgat    5460
atggttgatt ctggtgacat agtggccgtc atagagacat tggcatga                 5508
```

<210> SEQ ID NO 3
<211> LENGTH: 5463
<212> TYPE: DNA
<213> ORGANISM: Yarrowia lipolytica

<400> SEQUENCE: 3

```
atgtgcaaat caatcggctg gactattgcc gaatggaagg aggcacagac caactcgtct       60
tacgaggagg cccgacatcg actgttggac ctcgtggcca ccttcaagga ctacaagcat      120
ggtgatccgg cttggatcac tgtcgcctca acagagcata tcaacaagca atggaaggag      180
cttcagttga tgaagaagaa cccagagtcc cttcccctttt acggagttcc tttcgctgta    240
aaggacaaca ttgatgtcat cgactttccc acaaccgctg catgccccgc ctatctctac     300
atccccaagg aagacgccac catggtccgt ctgatcaaag aggctggagg tatcgttgtc     360
ggcaaaacca acctcgatca gttcgctact ggtctggtcg gaacccgatc tccttacgga    420
aagactccca cacccttctc cgacaagcac gtatctggag gttcgtctgc tggctctgct    480
tccgtagtcg cccgaggcct ggttcccttt tctcttggaa cagatactgc aggctcaggt    540
```

```
cggggttcccg cctctctcaa caacctggta ggcctaaagc caaccgttgg cgcattttca    600
gccaagggtg tggtacccgc ctgcaagtcg cttgattgcg tctccatttt ctcgctggtc    660
ctgtctgacg ctcagctggt gttcaacatt gccgcccact ttgacaagga cgattgctac    720
tcgcgacgtt tcccccagcg acctctcaag tcgtttggcc ccactccagt atttgccgtc    780
cccgaaaccc ctctgtggtt tggagatgag ctcaaccctg ctctcttcga cgacgccgtt    840
gagcgtttgc gacaacaggg cgtaaaggtc gtcaagattg acttcactcc tctgttcgac    900
ctcgccaagt gcctctacga aggtccctgg gtggctgagc gatacgctgc catcaaggac    960
tttgtgcaga accgaaagga agacatggac gaaactgtgt atggcattgt caagcaggct   1020
gagaacttca ctgctgcaga cgcctttgcc tacgagtaca acgacgagc cattgtgcga   1080
aagattgagg agatcttctc ttccattgac ggtctgatcg tgcccacatg tcctctattc   1140
cccaccatgg agtctgtggc taaggagcct gtcactgtca atgcccacca gggtacctac   1200
accaactttg tcaacctcgc tgatctctct gctctagcta tccctgtcgg attccgaaag   1260
gacggtttcc cctttggaat cactctcatc tctcaaaagt caacgactac cgctctgctg   1320
gacatggctc agaagttcct gcctgcttct cgacctctgg gtgctctgcc aaaggacaag   1380
ttcaccgcca agaagggaga tcttcttgcc tcttctatcg tcgacaacat gcctcgaacc   1440
atccctctgg ctgttgtagg agcccatctc accggcatgc ctctcaactg gcagcttcaa   1500
aaggtcgagg ctactcttgc ccgacgaacc aaaactgccg actactaccg actctacgct   1560
ctggcgaaca ccgtgcctac aaagcctggt ctccgacggg ttcttccctc tgacactact   1620
ctccgaggcg aggctattga ggttgaaatc tgggacgtgc cttacagaaa ctttggagag   1680
ttcgtatcaa tggtccctca tcctcttggt atcggaacca ttgagcttgc cgacggaaaa   1740
tgggtcaagg gtttcatttg cgagcagctg ggatacgacg acgctgagga catcaccaag   1800
tttggcggct ggagagcgta caaggctgag actacccaga acctggagtc caagcctttc   1860
gagactgttc tggtcgccaa ccgaggtgag attgccgttc gactcatcaa aactcttcga   1920
aagatggata ttcgagctgt ggctgtcttc tccgagcctg atcggttcgc tcaacatgtt   1980
cttgatgctg atgactctgt gtctctgaa ggtaccactg ccgccgagac ttacttgtcc   2040
atccccaaga ttatcgctgc ttgcaagaag actggagccc aagccattct tcctggctac   2100
ggtttcctgt ctgagaatgc tgacttctcc gacgcctgtg ccgaggctgg tatcgtattc   2160
attggcccca ctggtgactc cattcgaaag ctcggtctca gcactctgc acgagagatt   2220
gctcttgctt ctgacgtgcc tcttgtgccc ggtacaggcc tgatcgagac tgtttccgag   2280
gcctccgagg ctgccgagaa gctcgagtac ccctgatga tcaagagtac cgctggtgga   2340
ggtggtattg tcttcagaa ggtcgacaaa cccgaggatc tcaagcgggc ttttgagacc   2400
gtcaagcacc aaggtaagtc tttctttgga gacgatggtg tcttcatgga gcgatttgtc   2460
gagaatgctc gacacgtgga ggttcagatt cttggtgacg gcaagggcaa cgctctcgct   2520
attggcgagc gagactgttc tcttcagcga cgaaaccaga aggtcgtcga agagactcct   2580
gccccccaact tccctgctga gactcgaact cgaatgatga aggcgtccga aatgctggca   2640
aagaacctca actatcgagg tgccggcact gtggagttca ttttcgatga aagcgaaac   2700
gagttctact tccttgaggt taacgctcgt ctgcaggtcg agcatcccat cactgagtcc   2760
gtcactggac tggatcttgt cgagtggatg attctcattg gagctggcaa ggccccagac   2820
ttcgaggccc agcgtgccaa gaccccccag ggtgcttcta tcgaggcccg tctgtacgcc   2880
```

```
gagaacccg tcaaggactt tgtgccttct cccggtcagc tcaccgacgt gcagttccct    2940
agtgatgctc gagtcgacac ctgggtcagc cgtggaacca agatctcagc agagtacgat    3000
cccactcttg ccaagattat tgttcacggc tctgaccgag ctgacgccct gcgaaagctc    3060
cagagagctc tggacgagac agtggttgcc ggcgtgacca ccaacctgga ctaccttaag    3120
tccattgtcg gatctcagat gttttgccgag gccaaggtgt ccacccgagt actggactct    3180
tacaactaca ctcccaatgc cattgagatc acttcccccg ctcctacac cactattcag    3240 gattaccccg gtcgaaccaa gctgtggcat attggtgttc ctccttctgg acccatggat    3300
gcctacgcct tccgggtggc caaccagatt gtgggcaacc accccaaggc tcctgctatc    3360
gaagctacac ttgtgggccc ctcaattatg ttccacagcg acactgtgat gccatcacc    3420 ggtggatctg ctgaggccac tcttaatggt gagcccatcg agttctggaa gcctgtgact    3480
gtcaaggctg ccagactct cgcaactggc cgtctcactt ctggctgcag attgtacatt    3540
gcgattcgaa acggtctgtc tattccagag taccttggtt ctcgatccac cttcgctctc    3600
ggtaaccttg gaggcttcaa cggtcgaact ctcaagtttg gcgatgtcat tttcatgggc    3660
gagcccgagc ttccctcctg ctccattcct gctcccatct ccgagcatgc tcctgcctct    3720
gatgacatga tcccccaagta tggcaacgcc tggactgttg gagtcacttg cggccctcac    3780
ggctcgccag acttttttgc tcacggctgg atggatacct tcttcgatgc caagtggaag    3840
atccattaca actccaaccg atttggtgtt cgtctgattg gccccaagcc cgagtgggct    3900
cgaaaggatg gaggagaggc tggtctgcat ccttccaacc agcacgacta tgtctactct    3960
ctgggtgcca tcaatttcac cggtgatgag cctgtcattc tgacctgcga tggtccttct    4020
ctcggtggct ttgtctgtgc tgctgttgtt gtagaggccg agctgtggaa gattggccag    4080
gtcaagcccg gagacactgt gcagtttgtg cccatgacta ttgactctgc tcgacagctc    4140
aagaaggccc aggacagaac cattaccaac ctgtgcggtt ccccgtacga gtctgttgat    4200
gctcttctcg ctctggagga ttacgagaac cccatcatct acaccgtccc tgcctctacc    4260
tccactcctc gagtcgtcta ccgacaggct ggagaccgat acattctggt cgagtacggt    4320
gacaacaaca tggacattaa cctgtcctat cgaatccatc ggctcattga ggaagctcag    4380
cagtctatca agggcattgt cgaaatgtct cgaggtgttc gttctgtgct gatcgagttc    4440
catccttctg cctctcgatc cactctcatg caggctttgg tcgactttga aagcgactt    4500 cagtttgtcg agacctggca ggttccctct cgaattattc gactgccgat gtgctttgag    4560
gactccaaga ccctggacgc tgtcaaacgg taccaggaga ccattcggtc aaaggctccc    4620
tggcttccca acaacgtcga cttcattcga gacgtcaaca agttctccga ccgatctcag    4680
gtccgagaca ttgtctacac tgcccgattc ctggttctgg gtcttggaga cgtgttcctt    4740
ggtgctcctt gcgcggtacc tcttgatccc cgacacagac tgcttggaac aaagtacaat    4800
ccctctcgaa cctacactcc caacggcact gtcggaattg gaggaatgta catgtgtatc    4860
tacaccatgg aatctcctgg aggctaccag ttggttggtc gaactatccc catctgggac    4920
aagctgtctc tcggccagga ccgaccttgg ctgctgtcac ccttcgacca gattgagtac    4980
taccccgtcg acgaggagga gctcaaccac attaccaccg aggtgagaa cggtcgatat    5040 gctgtggaga tggagcagtc cgtctttgat tatggcaagt attctgcctg gctcaaggac    5100
aactctaagt ccattgaggc tcacattgct tctcaggcag agggtctgga cgacttcgcc    5160
aacctgatca aggtcgccaa cgaggatctg gcctctggaa agactggagc caccaaggag    5220
gagactcctc tgtcggcctc tgccgtccag gtcttctccg aggtcactgg ccgtttctgg    5280
```

```
aagggcctgg ttgccgtcgg agatactgtt gacaagggcc agggtatcgt tgtggtggag    5340
gccatgaaga ccgagatggt cgtcaacgcc cctgttgctg aaaggttgt caagttgtac     5400 aacaccaatg gagatatggt ggatactgga gattgtgtgg ctgtcatcga gcccattgtt    5460
taa                                                                   5463
```

<210> SEQ ID NO 4
<211> LENGTH: 1374
<212> TYPE: DNA
<213> ORGANISM: Pseudomonas sp.

<400> SEQUENCE: 4

```
atgaagacag tagaaattat tgaaggtatc gcctctggca gaaccagtgc gcgcgacgtg    60
tgcgaagagg cgctcgcaac catcggcgcg accgatggac tcatcaatgc ctttacatgc    120
cgtacggttg aacgagcccg cgcagaggcg gatgccatcg atgttcgacg ggcgcgcggc    180
gaggtacttc cgcctcttgc cggcctcccc tacgcggtaa agaatctgtt cgacatcgaa    240
ggcgtgacga cgcttgccgg ctcgaagatc aaccgtactc tcccgcctgc gcgcgcagac    300
gccgtgctgc tgcaacggct gaaagctgcc ggcgccgtgc tcctgggcgg cctcaatatg    360
gacgagtttg cctatggatt tacgaccgaa aatacgcact atgggccgac ccggaacccg    420
catgacaccg gcgtatcgc tggtggttcg tcaggggggt ctggagcggc aatcgctgcg    480
gggcaggtac cactatcgct cggatcggac accaacggtt ccatacgcgt gccagcatca    540
ttgtgtggcg tgtgggggct gaagcctacc ttcggccgcc tgtcccggcg agggacatac    600
ccgtttgttc acagcattga tcacctcggg ccattggccg atagcgtgga aggcttggcg    660
ttggcctacg atgcaatgca gggcccggat ccgctcgacc ccggatgcag cgcatcgcgc    720
atccaaccct cggtaccggt cctcagtcag ggtatcgctg gctccggat cggcgtgctg    780 ggtggctggt tcgggacaa tgccggcccg ccgcgcgcag ccgcggtcga tgttgccgcg    840
cttacgctcg gcgccagcga agtcgtcatg tggcccgacg cggagatcgg gcgcgcagcc    900
gccttcgtta tcactgccag cgagggaggc tgtctgcatc tcgatgatct tcgcatccgt    960
ccgcaagact tcgagcctct gtccgtagat cgctttatct cggggttttt acaaccggtc    1020
gcgtggtact gcgtgcaca gcggtttcga cgtgtctatc gagataaggt gaatgctctt    1080
ttccgtgact gggacatatt aatcgctccc gcaacgccaa taagtgctcc cgcaatcggc    1140
accgaatgga tcgaggtaaa cggtacacgc catccgtgcc gcccggctat gggacttctc    1200
actcagccgg tctccttcgc aggctgtccg gtggtcgccg ctccaacgtg gcctggagaa    1260
aacgatggca tgccgatcgg ggtacagctc atcgcggcgc cctggaacga atctctatgc    1320
ctgcgcgcag gcaaggtatt acaagacacc ggtatcgccc gactgaaatg ttaa          1374
```

<210> SEQ ID NO 5
<211> LENGTH: 1092
<212> TYPE: DNA
<213> ORGANISM: Pseudomonas sp.

<400> SEQUENCE: 5

```
atgtatcaca tcgacgtttt ccgaatccct tgccacagcc tggtgataca tcgggtctc     60 gaggatttga ttgaaacagg ccgcgttgcc cccgccgaca tcgtcgcggt aatgggcaag    120
accgagggca atggctgcgt caacgattac acgcgtgaat acgccaccgc catgcttgct    180
gcgtgccttg ggcgtcattt gcaactccca ccccatgagg tggaaaagcg gtcgcgtttt    240
```

```
gtgatgtcag gtgggacgga aggcgtgctg tcccccccacc acacggtatt cgcaagacgt      300
ccggcaatcg acgcgcatcg tcccgctggc aaacgtctca cgcttggaat cgccttcacg      360
cgtgattttc tgccggagga aattggccgc cacgctcaga taacggagac agccggcgcc      420
gtcaaacgcg caatgcgaga tgccgggatc gcttcgattg acgatctgca ttttgtgcag      480
gtgaagtgtc cgctgctgac accagcaaag atcgcctcgg cgcgatcacg cggatgcgct      540
ccagtcacga cggatacgta tgaatcgatg ggctattcgc gcggcgcttc ggccctgggc      600
atcgctctcg ctacagaaga ggtgcccctcc tcgatgctcg tagacgaatc agtgctgaat      660
gactggagtc tctcatcgtc actgcgctcg gcgtctgcag gcatcgaact ggagcacaac      720
gtggtgatcg ctattggcat gagcgagcag gccaccagtg aactggtcat tgcccacggc      780
gtgatgagcg acgcgatcga cgcggcctcg gtgcggcgaa cgattgaatc gctgggcata      840
cgtagcgatg acgagatgga tcgcatcgtc aacgtattcg ccaaagcgga ggcgagcccg      900
gacggggttg tacgaggtat gcggcacacg atgctaagtg actccgacat taattcgacc      960
cgccatgcgc gggcggtcac cggcgcggcc attgcctcgg tagttgggca tggcatggtg     1020
tatgtgtccg gtggcgccga gcatcaggga cctgccggcg gcggcccttt tgcagtcatt     1080
gcccgcgctt aa                                                          1092

<210> SEQ ID NO 6
<211> LENGTH: 1113
<212> TYPE: DNA
<213> ORGANISM: Pseudomonas sp.

<400> SEQUENCE: 6
atgcaagcgc aagttttttcg agttccaatg agtaatccag ccgatgttag tggcgtagcc       60
aagctcatcg atgagggagt gatccgtgcc gaagaggtcg tctgcgttct cggcaagacc      120
gaaggcaacg gctgtgtcaa tgacttcacg cgtggctaca ccaccctcgc gttcaaggtc      180
tacttctccg agaaactggg cgtgtcccgg caagaggtcg gcgagcgcat cgctttcatc      240
atgtccggcg gtaccgaagg cgtcatggcg cctcactgca ccatcttcac cgtgcagaag      300
acggacaaca agcagaagac cgccgctgaa ggcaagcgac ttgccgttca gcagatcttt      360
acccgcgagt tcctgccgga ggagatcggc cgcatgccgc aggtcacgga aacagccgac      420
gctgttcgcc gcgccatgcg cgaagccggc atcgcggatg catccgatgt ccacttcgtt      480
caggtcaagt gcccactgct cactgccggc cgcatgcatg acgctgtcga gcgcgggcat      540
acggttgcca ccgaagatac ctatgagtcc atgggctact cccgcggcgc atccgcgctt      600
ggtatcgccc tggccctcgg ggaagtcgag aaggccaacc tcagtgatga agttattacc      660
gcagactaca gtctctactc ctcggttgcc tcaacttcgg cgggtatcga gttgatgaac      720
aacgagatca tcgtcatggg caacagccgc gcatggggtg gtgacctcgt catcggccac      780
gccgagatga aggacgccat cgacggtgca gcggtccggc aggccctgcg cgacgtcggg      840
tgctgcgaga acgacctgcc gaccgtcgac gagctcggcc gcgtggtcaa tgtatttgcc      900
aaggctgaag cctcccccgga cggtgaggtt cgtaaccgcc gccacacgat gctggacgat      960
tcggacatta acagcacgcg ccatgcgcga gcggtcgtca atgcagttat cgcttcgatc     1020
gtgggagatc ccatggttta tgtctccggc ggctccgagc atcagggccc cgccggtggc     1080
ggtcccgttg cagttatcgc gcgcacagct taa                                  1113

<210> SEQ ID NO 7
<211> LENGTH: 1113
```

```
<212> TYPE: DNA
<213> ORGANISM: Rhodococcus sp.

<400> SEQUENCE: 7
atgcaagcgc aagttttcg  agttccaatg agtaatccag ccgatgttag tggcgtagcc      60
aagctcatcg atgagggagt gatccgtgcc gaagaggtcg tctgcgttct cggcaagacc     120
gaaggcaacg gctgtgtcaa tgacttcacg cgtggctaca ccaccctcgc gttcaaggtc     180
tacttctccg agaaactggg cgtgtccgg caagaggtcg gcgagcgcat cgctttcatc      240
atgtccggcg gtaccgaagg cgtcatggcg cctcactgca ccatcttcac cgtgcagaag     300
acggacaaca gcagaagac  cgccgctgaa ggcaagcgac ttgccgttca gcagatcttt     360
acccgcgagt tcctgccgga ggagatcggc cgcatgccgc aggtcacgga aacagccgac     420
gctgttcgcc gcgccatgcg cgaagccggc atcgcggatg catccgatgt ccacttcgtt     480
caggtcaagt gcccactgct cactgccggc cgcatgcatg acgctgtcga gcgcgggcat     540
acggttgcca ccgaagatac ctatgagtcc atgggctact cccgcggcgc atccgcgctt     600
ggtatcgccc tggccctcgg ggaagtcgag aaggccaacc tcagtgatga agttattacc     660
gcagactaca gtctctactc ctcggttgcc tcaacttcgg cgggtatcga gttgatgaac     720
aacgagatca tcgtcatggg caacagccgc gcatggggtg gtgacctcgt catcggccac     780
gccgagatga aggacgccat cgacggtgca gcggtccggc aggccctgcg cgacgtcggg     840
tgctgcgaga cgacctgcc  gaccgtcgac gagctcggcc gcgtggtcaa tgtatttgcc     900
aaggctgaag cctccccgga cggtgaggtt cgtaaccgcc gccacacgat gctggacgat     960
tcggacatta acagcacgcg ccatgcgcga gcggtcgtca atgcagttat cgcttcgatc    1020
gtgggagatc ccatggttta tgtctccggc ggctccgagc atcagggccc cgccggtggc    1080
ggtcccgttg cagttatcgc gcgcacagct taa                                 1113

<210> SEQ ID NO 8
<211> LENGTH: 1320
<212> TYPE: DNA
<213> ORGANISM: Escherichia coli

<400> SEQUENCE: 8
atgatgtcag agaacacac  gttaaaagcg gtacgaggca gttttattga tgtcacccgt      60
acgatcgata acccggaaga gattgcctct gcgctgcgt  ttattgagga tggtttatta     120
ctcattaaac agggaaaagt ggaatggttt ggcgaatggg aaaacggaaa gcatcaaatt     180
cctgacacca ttcgcgtgcg cgactatcgc ggcaaactga tagtaccggg ctttgtcgat     240
acacatatcc attatccgca aagtgaaatg gtggggcct  atggtgagca attgctggag     300
tggttgaata aacacacctt ccctactgaa cgtcgttatg aggatttaga gtacgcccgc     360
gaaatgtcgg cgttcttcat caagcagctt ttacgtaacg gaaccaccac ggcgctggtg     420
tttggcactg ttcatccgca atctgttgat gcgctgtttg aagccgccag tcatatcaat     480
atgcgtatga ttgccggtaa ggtgatgatg accgcaacg  caccggatta tctgctcgac     540
actgccgaaa gcagctatca ccaaagcaaa gaactgatcg aacgctggca caaaatggt      600 cgtctgctat atgcgattac gccacgcttc gccccgacct catctcctga acagatggcg     660
atggcgcaac gcctgaaaga agaatatccg gatacgtggg tacataccca tctctgtgaa     720
aacaaagatg aaattgcctg ggtgaaatcg ctttatcctg accatgatgg ttatctggat     780
gtttaccatc agtacggcct gaccggtaaa aactgtgtct ttgctcactg cgtccatctc     840
```

```
gaagaaaaag agtgggatcg tctcagcgaa accaaatcca gcattgcttt ctgtccgacc    900 tccaacctt  acctcggcag cggcttattc aacttgaaaa aagcatggca gaagaaagtt    960
aaagtgggca tgggaacgga tatcggtgcc ggaaccactt tcaacatgct gcaaacgctg   1020
aacgaagcct acaaagtatt gcaattacaa ggctatcgcc tctcggcata tgaagcgttt   1080
tacctggcca cgctcggcgg agcgaaatct ctgggccttg acgatttgat tggcaacttt   1140
ttacctggca agaggctga  tttcgtggtg atggaaccca ccgccactcc gctacagcag   1200
ctgcgctatg acaactctgt ttctttagtc gacaaattgt tcgtgatgat gacgttgggc   1260
gatgaccgtt cgatctaccg cacctacgtt gatggtcgtc tggtgtacga acgcaactaa   1320
```

<210> SEQ ID NO 9
<211> LENGTH: 1398
<212> TYPE: DNA
<213> ORGANISM: Bradyrhizobium japonicum

<400> SEQUENCE: 9

```
atgaccaccg tcggtattcg cggcacgttc ttcgatttcg tcgacgatcc ctggaagcac     60
atcggcaacg agcaggcggc tgcgcgcttt catcaggacg gcctcatggt cgtcaccgac    120
ggcgtcatca aggcgttcgg tccgtacgag aagatcgccg ccgcgcatcc gggcgttgag    180 atcaccata tcaaggaccg catcatcgtc ccgggcttca tcgacggcca tccatctg     240 cctcagaccc gcgtgctcgg tgcctatggc gagcagctct gccgtggct gcagaagtcg    300 atctatcccg aggagatcaa gtacaaggat cgcaactacg cgcgcgaagg cgtgaagcgt    360
tttctcgatg cactgctcgc cgccggcacc accacctgcc aggccttcac cagctcctca    420
ccggtcgcga ccgaagagct gttcgaggag caagcaggc gcaacatgcg cgtgatcgcg    480
ggtctcaccg ggatcgaccg caacgcgccg gccgaattca tcgatacgcc cgagaatttc    540
tatcgcgaca gcaagcggct gatcgcgcag tatcacgaca agggccgtaa cctctacgct    600
atcacgccgc gcttcgcctt cggcgcctcg cccgagctgc tgaaggcgtg tcagcgcctc    660
aagcacgagc atccggactg ctgggtcaat acccacatct ccgagaaccc ggccgaatgc    720
agcggcgtgc tggtcgagca cccggactgc caggattatc tcggcgtcta cgagaagttc    780
gacctggtcg gcccaaagtt ctccggcggc cacggcgtct atctctcgaa caacgaattc    840
cgccgcatgt ccaagaaagg cgcggcggta gtgttctgcc cgtgctcgaa cctgttcctc    900
ggcagcggcc tgttccgtct cggccgcgcc accgatccgg agcatcgcgt gaagatgtcg    960
ttcggcaccg atgtcggcgg cggcaaccgc ttctcgatga tctccgtgct cgacgacgct   1020
tacaaggtcg gcatgtgcaa caacacgctg ctcgacggca gcatcgatcc gtcgcgcaag   1080
gacctcgcgg aagccgagcg caacaagctc tcgccctatc gtggcttctg gtcggtcacg   1140
ctcggcggcg ccgaaggcct ctacatcgac gacaagctcg gcaatttcga gcccggcaag   1200
gaggccgatt tcgtcgcgct cgatccgaac ggcggacaac tggcgcaacc ctggcaccag   1260
tcgctgattg ccgacggtgc aggtccgcgc acgttgatg aggccgcgag catgctgttc   1320
gccgtcatga tggtcggcga cgatcgctgc gtcgacgaga cctgggtgat gggcaagcgc   1380
ctctacaaga agagctga                                                 1398
```

<210> SEQ ID NO 10
<211> LENGTH: 1470
<212> TYPE: DNA
<213> ORGANISM: Saccharomyces cerevisiae

<400> SEQUENCE: 10

```
atgacaaaaa gtgatttatt atttgataaa ttcaacgaca acatggaaa gtttctagtt      60
ttttttggta cctttgtaga taccctaaa ttaggagagc tgagaatcag agagaaaaca     120
tctgttggag ttctcaacgg aatcatcagg tttgtgaaca gaaattcact cgatcctgtc    180
aaagattgtt tagatcacga tagtagctta tcaccagagg atgtcacggt ggttgacata    240
attggaaaag acaagactcg aaataacagc ttttattttc caggttttgt tgacacgcat    300
aaccatgtct cgcaatatcc aaatgtcggc gtatttggga attctaccct gctggattgg    360
ctagagaagt ataccttccc catagaagcc gcactagcaa acgaaaatat tgcgagagaa    420
gtttacaata aggtaataag taagacgctt tctcacggta caacgactgt ggcttactat    480
aataccattg atctcaagtc cactaagctc ttggctcaac taagctcctt attggggcag    540
cgtgttcttg ttggaaaagt gtgcatggat accaatggtc ccgagtatta tattgaagat    600
actaaaactt cctttgaaag cactgtgaaa gttgttaagt acatacggga accatttgt     660
gatcccctcg taaatcctat agtgacacca aggttcgcgc cctcttgttc tagagaacta    720
atgcaacagt tgtccaagct agtcaaggat gaaacatac acgttcaaac ccacttgtcg     780
gaaaataagg aggagataca gtgggttcaa gatttatttc ccgaatgtga gagctatact    840
gatgtatacg acaaatatgg gctgctcaca gaaaaaacag tattggcaca ttgtattcat    900
ctaacagatg ccgaagcgcg tgtgattaaa cagcgtcgct gtggtatatc tcattgtccc    960
atttccaact cctctctgac ttctggagag tgtagggttc gatggttgct ggaccagggc   1020
ataaaggttg gtctaggcac cgacgtttca gccggtcatt cttgtagcat actcaccacc   1080
ggaaggcagg cctttgcagt ttcaaggcat ttggcaatga gagaaactga tcatgcaaaa   1140
ctttcagtct ccgagtgcct atttcttgct acaatgggcg gagcacaagt cttgcgtatg   1200
gatgagacct tggggacttt tgacgtcggt aagcagtttg acgctcaaat gatcgatacc   1260
aatgctcccg gctcaaacgt ggatatgttt cattggcagc taaggagaa ggatcaaatg    1320
caagagcaag agcaagagca agggcaagac ccttataaga acccaccgct gcttactaat   1380
gaagacataa tcgcaaaatg gttctttaac ggtgatgatc gcaacaccac taaagtttgg   1440
gtagccggcc agcaagtcta ccagatttag                                    1470

<210> SEQ ID NO 11
<211> LENGTH: 1356
<212> TYPE: DNA
<213> ORGANISM: Yarrowia lipolytica

<400> SEQUENCE: 11
atgactgctt caaacaccac agtttttttc ggagccatcg tcaatcccgc cagaagagca      60
cttgaatacc tgccccaagc tgctatcggt gtcaggaag gggaaatcgt cttttcgac     120
agacatgctg aatcggcttc ggcgtctgct gccacccaca acattaagaa cttcgacacg    180
gtggacttgt cgaaaaccac ctcgttcctt ttccccggtt tcatcgacac tcacattcat    240
gcgccccagt accccaacag cggtattttc ggcaagacca cactgctaga ctggctgact    300
acctacacct ttcccctgga gtcgtctctc aaggacccca aaatcgccca ggacgtgtac    360
tccagggtag tcaagaagac tctcgccaac ggaactacaa cggctgctta ctacgccact    420
gtccacgtgg agtccacaaa gaaactggct gacatttgtc tgtctcaagg tcagagagca    480
cttgtgggaa gagtgtgcat ggaccaaaac actcctgatt actacagaga tgcaagcgtg    540
gaggaggcca agaagagcga ccgggaagtt gttgagtata ttcagtctct taacaaaccc    600
```

| | |
|---|---:|
| gatcgcatcc tccccatcat cacacccgt tttgcgccct cttgcactgg tgaaatcatg | 660 |
| tcctggcagg gagactatgc ccagaagaac aacctgcaca tccagactca catttctgaa | 720 |
| aacaagggcg agattgcctg ggtcaaggag ctgtaccctg cttgcaaatc gtatgcagac | 780 |
| acataccacc agcatggact gctgacagaa aagacgcttc tggcccatgc catctatctg | 840 |
| accgacgaag aactcaacct ggtggagcag caaaagtgtg gactttccca ttgccccatt | 900 |
| tccaactcgt cgctgacatc aggcgagttc catgctcgaa aaattctcga caggaacatt | 960 |
| cccttggtc tgggaaccga tgtttctgga ggttacgctc cttccattct cagcacagcc | 1020 |
| agacacggtc ttctggtgtc tcgtcacgtg gccatgaagt ccgaaaacga cgccgacaag | 1080 |
| ctgtctgtgg atgaggtact gtacttggcc actctgggtg gcgccgaggc tctcaaactg | 1140 |
| gactcaaaga ttggttcttt cgaggtgggc aagaagttcg acgcccagca gattgatctc | 1200 |
| gagactaacg gttctcctgt tgacattttt gactgggaat gcctatttc cgagggaaac | 1260 |
| aagctcgaga acctggtgca caagtggttg tttaatggag acgaccgaaa cacttctact | 1320 |
| gtctgggtca acggagacaa ggtggtgacc aagtag | 1356 |

<210> SEQ ID NO 12
<211> LENGTH: 1437
<212> TYPE: DNA
<213> ORGANISM: Williamsia sp.

<400> SEQUENCE: 12

| | |
|---|---:|
| atgaccagaa tcgcaatcac cggcggacga gtcctgacca tggaccccga gcgccgcgtg | 60 |
| ctcgaaccag gaacggttgt ggtcgaggac cagttcatcg cacaagtggg atccccggac | 120 |
| gacgtcgaca tccgcggcgc cgaaatcatc gacgccaccg ggatggcagt gctccccggc | 180 |
| ttcgtcaaca cccacaccca cgtcccacaa atcctcctca ggggtggtgc atcccatgac | 240 |
| cgcaacctcc tcgaatggct gcacaacgtg ctctatcccg gcctcgctgc ctacacagac | 300 |
| gacgacatcc gagtcggaac actgctgtac tgcgccgaag cccttcgttc tggcatcacc | 360 |
| actgtcgtcg acaacgagga cgtccgaccc aacgacttcg cccgcgccgg ggccgccggg | 420 |
| atcggcgcct tcaccgacgc aggaatccga gccatttacg cgcgcatgta cttcgacgcg | 480 |
| ccacgcgccg aactcgaaga actcgtcgcc accatccacg ccaaggcccc cggcgccgtg | 540 |
| cgcatggacg aatcagccag caccgaccac gtactggcag acctagacca actcatcacc | 600 |
| cgccacgacc gcacagcaga tggccgcatc agggtgtggc ccgcacccgc catccccttc | 660 |
| atggtcagtg aaaaaggaat gaaggcagcg caagagatcg cagcgagccg caccgacggc | 720 |
| tggaccatgc acgtcagcga ggatcccatc gaggcccgag tgcactccat gaacgccccg | 780 |
| gaatatttac accacctcgg ctgcctcgac gaccgactcc ttgccgcgca ctgcgtgcat | 840 |
| atcgacagcc gagacatccg cctgttccgc cagcacgacg taaaaatttc tacccaacca | 900 |
| gtatcgaaca gctacctggc ggccggaatt gcaccggtcc ccgaaatgct cgcccacggc | 960 |
| gtgaccgtgg gcatcggtac cgacgacgcc aactgcaacg acagcgtgaa cctcatctcg | 1020 |
| gacatgaaag tgctagcgct cattcaccga gctgcacatc gagatgcctc aatcatcaca | 1080 |
| cctgaaaaaa tcatcgaaat ggccaccatc gacggagccc gctgcatcgg tatggccgat | 1140 |
| cagattggtt ccctcgaggc gggtaaacgc gccgacatca tcaccctcga ccttcgtcac | 1200 |
| gcccaaacaa cccagcgca cgacttggcg gccaccatcg tctttcaggc ctacggcaac | 1260 |
| gaggtcaacg acgtcctcgt caatggctcg gtagtgatgc gcgatcgagt actttctttt | 1320 |
| ctgccgactc cccaagaaga aaaagcgctc tacgacgatg cgtcggagcg atcggctgca | 1380 |

| atgctcgcac gggccggcct caccggcaca cgcacatggc aaacactggg atcgtag | 1437 |

<210> SEQ ID NO 13
<211> LENGTH: 1425
<212> TYPE: DNA
<213> ORGANISM: Pseudomonas sp.

<400> SEQUENCE: 13

| atgcaaacgc tcagcatcca gcacggtacc ctcgtcacga tggatcagta ccgcagagtc | 60 |
| cttggggata gctgggttca cgtgcaggat ggacggatcg tcgcgctcgg agtgcacgcc | 120 |
| gagtcggtgc ctccgccagc ggatcgggtg atcgatgcac gcggcaaggt cgtgttaccc | 180 |
| ggtttcatca atgcccacac ccatgtgaac cagatcctcc tgcgcggagg gccctcgcac | 240 |
| gggcgtcaac tctatgactg gctgttcaac gttttgtatc cggacaaaaa ggcgatgaga | 300 |
| ccggaggacg tagcggtggc ggtgaggttg tattgtgcgg aagctgtgcg cagcgggatt | 360 |
| acgacgatca cgacaacgc cgattcggcc atctacccag caacatcga ggccgcgatg | 420 |
| gcggtctatg gtgaggtggg tgtgagggtc gtctacgccc gcatgttctt tgatcggatg | 480 |
| gacgggcgca ttcaagggta tgtggacgcc ttgaaggctc gctctcccca agtcgaactg | 540 |
| tgctcgatca tggaggaaac ggctgtggcc aaagatcgga tcacagccct gtcagatcag | 600 |
| tatcatggca cggcaggagg tcgtatatca gtttggcccg ctcctgccat taccccggcg | 660 |
| gtgacagttg aaggaatgcg atgggcacaa gccttcgccc gtgatcgggc ggtaatgtgg | 720 |
| acgcttcaca tggcggagag cgatcatgat gagcggcttc attggatgag tcccgccgag | 780 |
| tacatggagt gttacggact cttggatgag cgtctgcagg tcgcgcattg cgtgtacttt | 840 |
| gaccggaagg atgttcggct gctgcaccgc acaatgtga aggtcgcgtc gcaggttgtg | 900 |
| agcaatgcct acctcggctc aggggtggcc cccgtgccag atggtgga gcgcggcatg | 960 |
| gccgtgggca ttggaacaga tgacgggaat tgtaatgact ccgtaaacat gatcggagac | 1020 |
| atgaagttta tggcccatat tcaccgcgcg gtgcatcggg atgcggacgt gctgaccccca | 1080 |
| gagaagattc ttgaaatggc gacgatcgat ggggcgcgtt cgttgggaat ggaccacgag | 1140 |
| attggttcca tcgaaaccgg caagcgcgcg gaccttatcc tgcttgacct gcgtcaccct | 1200 |
| cagacgactc ctcaccatca tttggcggcc acgatcgtgt ttcaggctta cggcaatgag | 1260 |
| gtggacactg tcctgattga cggaaacgtt gtgatggaga accgccgctt gagctttctt | 1320 |
| cccctgaac gtgagttggc gttccttgag gaagcgcaga gccgcgccac agctattttg | 1380 |
| cagcgggcga acatggtggc taacccagct tggcgcagcc tctag | 1425 |

<210> SEQ ID NO 14
<211> LENGTH: 1212
<212> TYPE: DNA
<213> ORGANISM: Pseudomonas p.

<400> SEQUENCE: 14

| atgagtaaag attttgattt aatcattaga aacgcctatc taagtgaaaa agacagtgta | 60 |
| tatgatattg ggattgttgg tgacagaata atcaaaatag aagctaaaat tgaaggaacc | 120 |
| gtaaaagacg aaattgatgc aaagggtaac cttgtgtctc ccggatttgt cgatgcacat | 180 |
| acccatatgg ataagtcatt tacgagcaca ggtgaaagat taccgaagtt ttggagcaga | 240 |
| ccttatacaa gggatgctgc catcgaggat ggcttgaaat attataaaaa tgctacccca | 300 |
| gaagaaataa aaagacatgt gatagaacat gctcacatgc aggtactcca tgggactta | 360 |

```
tacacccgga cccatgtaga tgtagattca gttgctaaaa caaaagcagt ggaagcagtt      420
ttagaagcca aggaagagtt aaaggatctt atcgatatac aagtcgtagc ctttgcacag      480
agtggatttt tcgttgattt ggaatctgaa tcattgatta gaaaatcctt ggatatgggc      540
tgtgatttag ttgggggagt tgatcctgct acgcgggaaa ataatgttga gggttcttta      600
gacctatgct ttaaattagc aaaggaatac gatgttgata tcgactatca catacatgat      660
attggaactg ttggagtata ttcgataaat cgtcttgccc aaaagacaat tgaaaatggg      720
tataagggta gagtaactac gagtcatgcc tggtgttttg cagatgctcc gtccgaatgg      780
ctcgatgagg caatcccatt gtacaaggat tcgggtatga aatttgttac ctgtttttagt     840 agtacaccgc ctactatgcc ggtgataaag ctgcttgaag ctggcatcaa tcttggctgt      900
gcttcggaca atatcagaga ttttttgggtt ccctttggca acggtgatat ggtacaaggg     960
gctctgatcg aaactcagag attagagtta aagacaaaca gagatttggg actaatttgg     1020
aaaatgataa cgtcagaggg tgctagagtt ttaggaattg aaaagaacta tgggatagaa     1080
gttggtaaaa aggccgatct tgttgtatta aattcgttgt caccacaatg ggcaataatc      1140
gaccaagcaa aaagactatg cgtaattaaa aatggacgta tcattgtgaa ggatgaggtt     1200
atagttgcct aa                                                         1212

<210> SEQ ID NO 15
<211> LENGTH: 735
<212> TYPE: DNA
<213> ORGANISM: Myrothecium verrucaria

<400> SEQUENCE: 15
atgtcttctt cagaagtcaa agccaacgga tggactgccg ttccagtcag cgcaaaggcc       60
attgttgact ccctgggaaa gcttggtgat gtctcctcat attctgtgga agatatcgcg      120
ttccctgcgg cagacaaact tgttgccgag gcacaggcct tgtgaaggc ccgattgagt        180 cccgaaacct acaatcactc catgcgcgtt ttctactggg gaaccgtcat cgcgagacgt      240
ttacttcccg agcaagctaa agacttgtct ccaagtacat gggcactgac atgtcttctg      300
catgacgttg gtactgcgga ggcatacttt acatctacac gaatgtcctt cgatatttac      360
ggtggcatta aggctatgga ggtgctcaag gtccttggga gtagcaccga ccaggctgag      420
gctgttgccg aggccatcat tcgtcatgag gatgtgggg tagatggcaa catcacattc        480
ctcggtcagt tgatccagct ggctacgctt tatgacaatg tcggggccta cgatgggatt      540
gatgattttg gtagctgggt tgatgacacc acacgcaaca gtatcaacac ggcattccca      600
cgacatggtt ggtgttcttg gtttgcctgc acggttcgta aggaagaaag taacaagcct      660
tggtgccaca caacgcatat ccctcagttc gataaacaga tggaagcgaa cactttgatg      720
aagccttggg agtaa                                                       735

<210> SEQ ID NO 16
<211> LENGTH: 4268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ttatcgatga taagctgtca aagatgagaa ttaattccac ggactataga ctatactaga       60
tactccgtct actgtacgat acacttccgc tcaggtcctt gtcctttaac gaggccttac      120
```

-continued

| | |
|---|---|
| cactcttttg ttactctatt gatccagctc agcaaaggca gtgtgatcta agattctatc | 180 |
| ttcgcgatgt agtaaaacta gctagaccga gaaagagact agaaatgcaa aaggcacttc | 240 |
| tacaatggct gccatcatta ttatccgatg tgacgctgca gcttctcaat gatattcgaa | 300 |
| tacgctttga ggagatacag cctaatatcc gacaaactgt tttacagatt tacgatcgta | 360 |
| cttgttaccc atcattgaat tttgaacatc cgaacctggg agttttccct gaaacagata | 420 |
| gtatatttga acctgtataa taatatatag tctagcgctt tacggaagac aatgtatgta | 480 |
| tttcggttcc tggagaaact attgcatcta ttgcataggt aatcttgcac gtcgcatccc | 540 |
| cggttcattt tctgcgtttc catcttgcac ttcaatagca tatctttgtt aacgaagcat | 600 |
| ctgtgcttca ttttgtagaa caaaaatgca acgcgagagc gctaattttt caaacaaaga | 660 |
| atctgagctg catttttaca gaacagaaat gcaacgcgaa agcgctattt taccaacgaa | 720 |
| gaatctgtgc ttcattttg taaaacaaaa atgcaacgcg acgagagcgc taattttca | 780 |
| aacaaagaat ctgagctgca ttttacaga acagaaatgc aacgcgagag cgctatttta | 840 |
| ccaacaaaga atctatactt cttttttgtt ctacaaaaat gcatcccgag agcgctattt | 900 |
| ttctaacaaa gcatcttaga ttactttttt tctcctttgt gcgctctata atgcagtctc | 960 |
| ttgataactt tttgcactgt aggtccgtta aggttagaag aaggctactt tggtgtctat | 1020 |
| tttctcttcc ataaaaaaag cctgactcca cttcccgcgt ttactgatta ctagcgaagc | 1080 |
| tgcgggtgca ttttttcaag ataaaggcat ccccgattat attctatacc gatgtggatt | 1140 |
| gcgcatactt tgtgaacaga aagtgatagc gttgatgatt cttcattggt cagaaaatta | 1200 |
| tgaacggttt cttctatttt gtctctatat actacgtata gaaatgttt acattttcgt | 1260 |
| attgttttcg attcactcta tgaatagttc ttactacaat tttttgtct aaagagtaat | 1320 |
| actagagata aacataaaaa atgtagaggt cgagtttaga tgcaagttca aggagcgaaa | 1380 |
| ggtggatggg taggttatat agggatatag cacagagata tatagcaaag agatactttt | 1440 |
| gagcaatgtt tgtggaagcg gtattcgcaa tttaattaag tttaaacggc gcgcttttcc | 1500 |
| ataggctccg ccccctgac gagcatcaca aaaatcgacg ctcaagtcag aggtggcgaa | 1560 |
| acccgacagg actataaaga taccaggcgt ttccccctgg aagctccctc gtgcgctctc | 1620 |
| ctgttccgac cctgccgctt accggatacc tgtccgcctt tctcccttcg ggaagcgtgg | 1680 |
| cgctttctca tagctcacgc tgtaggtatc tcagttcggt gtaggtcgtt cgctccaagc | 1740 |
| tgggctgtgt gcacgaaccc cccgttcagc ccgaccgctg cgccttatcc ggtaactatc | 1800 |
| gtcttgagtc caacccggta agacacgact tatcgccact ggcagcagcc actggtaaca | 1860 |
| ggattagcag agcgaggtat gtaggcggtg ctacagagtt cttgaagtgg tggcctaact | 1920 |
| acggctacac tagaagaaca gtatttggta tctgcgctct gctgaagcca gttaccttcg | 1980 |
| gaaaaagagt tggtagctct tgatccggca aacaaaccac cgctggtagc ggtggttttt | 2040 |
| ttgtttgcaa gcagcagatt acgcgcagaa aaaaaggatc tcaagaagat cctttgatct | 2100 |
| tttctacggg gtctgacgct cagtggaacg aaaactcacg ttaagggatt ttggtcatga | 2160 |
| gattatcaaa aaggatcttc acctagatcc ttttaaatta aaaatgaagt tttaaatcaa | 2220 |
| tctaaagtat atatgagtaa acttggtctg acagttacca atgcttaatc agtgaggcac | 2280 |
| ctatctcagc gatctgtcta tttcgttcat ccatagttgc ctgactcccc gtcgtgtaga | 2340 |
| taactacgat acgggagggc ttaccatctg gccccagtgc tgcaatgata ccgcgagacc | 2400 |
| cacgctcacc ggctccagat ttatcagcaa taaaccagcc agccggaagg gccgagcgca | 2460 |
| gaagtggtcc tgcaacttta tccgcctcca tccagtctat taattgttgc cgggaagcta | 2520 |

```
gagtaagtag ttcgccagtt aatagtttgc gcaacgttgt tgccattgct acaggcatcg    2580
tggtgtcacg ctcgtcgttt ggtatggctt cattcagctc cggttcccaa cgatcaaggc    2640
gagttacatg atcccccatg ttgtgcaaaa aagcggttag ctccttcggt cctccgatcg    2700
ttgtcagaag taagttggcc gcagtgttat cactcatggt tatggcagca ctgcataatt    2760
ctcttactgt catgccatcc gtaagatgct tttctgtgac tggtgagtac tcaaccaagt    2820
cattctgaga atagtgtatg cggcgaccga gttgctcttg cccggcgtca atacgggata    2880
ataccgcgcc acatagcaga actttaaaag tgctcatcat tggaaaacgt tcttcggggc    2940
gaaaactctc aaggatctta ccgctgttga gatccagttc gatgtaaccc actcgtgcac    3000
ccaactgatc ttcagcatct tttactttca ccagcgtttc tgggtgagca aaaacaggaa    3060
ggcaaaatgc cgcaaaaaag ggaataaggg cgacacggaa atgttgaata ctcatactct    3120
tcctttttca atattattga agcatttatc agggttattg tctcatgagc ggatacatat    3180
ttgaatgtat ttagaaaaat aaacagcgat cgcgcggccg cgggtaataa ctgatataat    3240
taaattgaag ctctaatttg tgagtttagt atacatgcat ttacttataa tacagttttt    3300
tagttttgct ggccgcatct tctcaaatat gcttcccagc ctgcttttct gtaacgttca    3360
ccctctacct tagcatccct tccctttgca aatagtcctc ttccaacaat aataatgtca    3420
gatcctgtag agaccacatc atccacggtt ctatactgtt gacccaatgc gtctcccttg    3480
tcatctaaac ccacaccggg tgtcataatc aaccaatcgt aaccttcatc tcttccaccc    3540
atgtctcttt gagcaataaa gccgataaca aaatctttgt cgctcttcgc aatgtcaaca    3600
gtacccttag tatattctcc agtagctagg gagcccttgc atgacaattc tgctaacatc    3660
aaaaggcctc taggttcctt tgttacttct tccgccgcct gcttcaaacc gctaacaata    3720
cctgggccca ccacaccgtg tgcattcgta atgtctgccc attctgctat tctgtataca    3780
cccgcagagt actgcaattt gactgtatta ccaatgtcag caaattttct gtcttcgaag    3840
agtaaaaaat tgtacttggc ggataatgcc tttagcggct taactgtgcc ctccatggaa    3900
aaatcagtca agatatccac atgtgttttt agtaaacaaa ttttgggacc taatgcttca    3960
actaactcca gtaattcctt ggtggtacga acatccaatg aagcacacaa gtttgtttgc    4020
ttttcgtgca tgatattaaa tagcttggca gcaacaggac taggatgagt agcagcacgt    4080
tccttatatg tagctttcga catgatttat cttcgtttcc tgcaggtttt tgttctgtgc    4140
agttgggtta agaatactgg gcaatttcat gtttcttcaa caccacatat gcgtatatat    4200
accaatctaa gtctgtgctc cttccttcgt tcttccttct gctcggagat taccgaatca    4260
aagctagc                                                              4268
```

<210> SEQ ID NO 17  
<211> LENGTH: 6706  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 17

```
gatactttg agcaatgttt gtggaagcgg tattcgcaat tataaacggt attttcacaa     60
ttgcacccca gccagaccga tagccggtcg caatccgcca cccacaaccg tctacctccc    120
acagaacccc gtcacttcca ccctttttcca ccagatcata tgtcccaact tgccaaatta    180
aaaccgtgcg aattttcaaa ataaactttg gcaaagaggc tgcaaaggag gggctggtga    240
```

```
gggcgtctgg aagtcgacca gagaccgggt tggcggcgca tttgtgtccc aaaaaacagc    300
cccaattgcc ccaattgacc ccaaattgac ccagtagcgg gcccaacccc ggcgagagcc    360
cccttctccc cacatatcaa acctccccg gttcccacac ttgccgttaa gggcgtaggg     420
tactgcagtc tggaatctac gcttgttcag actttgtact agtttctttg tctggccatc    480
cgggtaaccc atgccggacg caaaatagac tactgaaaat ttttttgctt tgtggttggg    540
actttagcca agggtataaa agaccaccgt ccccgaatta cctttcctct tcttttctct    600
ctctccttgt caactcacac ccgaaatcgt taagcatttc cttctgagta taagaatcat    660
tcaaaatgac tagaatcgct atcacaggtg gtagagtttt gactatggac ccagaaagaa    720
gagtattaga accaggtaca gttgttgttg aagatcaatt cattgcacaa gtcggttcac    780
cagatgacgt agacatcaga ggtgctgaaa ttatagatgc cactggtatg gctgtattac    840
caggtttcgt taatacacat acccacgttc ctcaaatttt gttaagaggt ggtgcttcac    900
atgatagaaa tttgttggaa tggttgcaca acgtcttata tccaggtttg gctgcataca    960
ctgatgacga tatcagagtt ggtacattgt tatattgtgc tgaagcattg agatccggta   1020
ttactacagt tgtcgacaat gaagatgtta gacctaacga ttttgccaga gctggtgccg   1080
ctggtattgg tgcattcact gatgccggta tcagagcaat ctatgccaga atgtactttg   1140
atgctccaag agcagaattg gaagaattag tcgcaacaat acatgcaaaa gcccctggtg   1200
ccgtaagaat ggacgaatct gcttcaaccg atcatgtttt ggcagactta gatcaattga   1260
ttaccagaca tgcagaact gctgatggta gaattagagt atggccagct cctgcaatac   1320
cattcatggt ttctgaaaag ggtatgaagg cagcccaaga aatagctgca tccagaactg   1380
acggttggac aatgcatgtt agtgaagatc caatcgaagc cagagtccac tctatgaatg   1440
ctcctgaata tttgcatcac ttgggttgtt tagacgatag attgttagcc gctcattgcg   1500
ttcacataga ctcaagagat atcagattgt ttagacaaca tgatgttaag atatccacac   1560
aacctgtctc caatagttac ttagcagccg gtatagcacc agttcctgaa atgttggctc   1620
atggtgtcac agtaggtatt ggtaccgacg atgctaattg taacgactcc gtaaacttaa   1680
tcagtgatat gaaggttttg gcattgatac atagagctgc acacagagat gctagtatca   1740
ttaccccaga aaagataatc gaaatggcca ctattgacgg tgctagatgc attggtatgg   1800
ctgatcaaat cggttctttg gaagctggta aaagagcaga cataatcact ttggatttga   1860
gacatgcaca aaccactcct gcccacgatt tggccgctac aattgtcttt caagcttatg   1920
gtaatgaagt aaacgatgtt ttggtcaacg gttctgtagt tatgagagat agagttttgt   1980
cattcttacc aaccctcaa gaagaaaagg ctttatacga cgatgcatct gaaagatcag   2040
cagccatgtt agccagagct ggtttgactg gtacaagaac ctggcaaact ttgggttctt   2100
aagctgcttg tacctagtgc aaccccagtt tgttaaaaat tagtagtcaa aaacttctga   2160
gttagaaatt tgtgagtgta gtgagattgt agagtatcat gtgtgtccgt aagtgaagtg   2220
ttattgactc ttagttagtt tatctagtac tcgtttagtt gacactgatc tagtattta   2280 cgaggcgtat gactttagcc aagtgttgta cttagtcttc tctccaaaca tgagagggct   2340
ctgtcactca gtcggcctat gggtgagatg gcttggtgag atctttcgat agtctcgtca   2400
agatggtagg atgatggggg aatacattac tgctctcgtc aaggaaacca caatcagatc   2460
acaccatcct ccatggtatc cgatgactct cttctccaca gttttccata ggctccgccc   2520
ccctgacgag catcacaaaa atcgacgctc aagtcagagg tggcgaaacc cgacaggact   2580
```

```
ataaagatac caggcgtttc ccoctggaag ctccctcgtg cgctctcctg ttccgaccct    2640
gccgcttacc ggatacctgt ccgccttct cccttcggga agcgtggcgc tttctcatag     2700
ctcacgctgt aggtatctca gttcggtgta ggtcgttcgc tccaagctgg gctgtgtgca    2760
cgaacccccc gttcagcccg accgctgcgc cttatccggt aactatcgtc ttgagtccaa    2820
cccggtaaga cacgacttat cgccactggc agcagccact ggtaacagga ttagcagagc    2880
gaggtatgta ggcggtgcta cagagttctt gaagtggtgg cctaactacg gctacactag    2940
aagaacagta tttggtatct gcgctctgct gaagccagtt accttcggaa aaagagttgg    3000
tagctcttga tccggcaaac aaaccaccgc tggtagcggt ggtttttttg tttgcaagca    3060
gcagattacg cgcagaaaaa aaggatctca agaagatcct ttgatctttt ctacggggtc    3120
tgacgctcag tggaacgaaa actcacgtta agggattttg gtcatgagat tatcaaaaag    3180
gatcttcacc tagatccttt taaattaaaa atgaagtttt aaatcaatct aaagtatata    3240
tgagtaaact tggtctgaca gttaccaatg cttaatcagt gaggcaccta tctcagcgat    3300
ctgtctattt cgttcatcca tagttgcctg actccccgtc gtgtagataa ctacgatacg    3360
ggagggctta ccatctggcc ccagtgctgc aatgataccg cgagacccac gctcaccggc    3420
tccagattta tcagcaataa accagccagc cggaagggcc gagcgcagaa gtggtcctgc    3480
aactttatcc gcctccatcc agtctattaa ttgttgccgg gaagctagag taagtagttc    3540
gccagttaat agtttgcgca acgttgttgc cattgctaca ggcatcgtgg tgtcacgctc    3600
gtcgtttggt atggcttcat tcagctccgg ttcccaacga tcaaggcgag ttacatgatc    3660
ccccatgttg tgcaaaaaag cggttagctc cttcggtcct ccgatcgttg tcagaagtaa    3720
gttggccgca gtgttatcac tcatggttat ggcagcactg cataattctc ttactgtcat    3780
gccatccgta agatgctttt ctgtgactgg tgagtactca accaagtcat tctgagaata    3840
gtgtatgcgg cgaccgagtt gctcttgccc ggcgtcaata cgggataata ccgcgccaca    3900
tagcagaact ttaaaagtgc tcatcattgg aaaacgttct cggggcgaaa actctcaag    3960 gatcttaccg ctgttgagat ccagttcgat gtaacccact cgtgcaccca actgatcttc    4020
agcatctttt actttcacca gcgtttctgg gtgagcaaaa acaggaaggc aaaatgccgc    4080
aaaaaaggga ataagggcga cacggaaatg ttgaatactc atactcttcc ttttcaata    4140 ttattgaagc atttatcagg gttattgtct catgagcgga tacatatttg aatgtattta    4200
gaaaaataaa cagcgatcgc gcggccgcgg gtaataactg atataattaa attgaagctc    4260
taatttgtga gttagtata catgcattta cttataatac agttttttag ttttgctggc    4320
cgcatcttct caaatatgct tcccagcctg ctttttctgta acgttcaccc tctaccttag    4380
catcccttcc ctttgcaaat agtcctcttc aacaataat aatgtcagat cctgtagaga    4440
ccacatcatc cacggttcta tactgttgac ccaatgcgtc tccccttgtca tctaaaccca    4500 caccgggtgt cataatcaac caatcgtaac cttcatctct tccacccatg tctctttgag    4560
caataaagcc gataacaaaa tctttgtcgc tcttcgcaat gtcaacagta cccttagtat    4620
attctccagt agctagggag cccttgcatg acaattctgc taacatcaaa aggcctctag    4680
gttcctttgt tacttcttcc gccgcctgct tcaaaccgct aacaatacct gggcccacca    4740
caccgtgtgc attcgtaatg tctgcccatt ctgctattct gtatacaccc gcagagtact    4800
gcaatttgac tgtattacca atgtcagcaa attttctgtc ttcgaagagt aaaaaattgt    4860
acttggcgga taatgccttt agcggcttaa ctgtgccctc catggaaaaa tcagtcaaga    4920
tatccacatg tgtttttagt aaacaaattt tgggacctaa tgcttcaact aactccagta    4980
```

```
attccttggt ggtacgaaca tccaatgaag cacacaagtt tgtttgcttt tcgtgcatga    5040
tattaaatag cttggcagca acaggactag gatgagtagc agcacgttcc ttatatgtag    5100
ctttcgacat gatttatctt cgtttcctgc aggttttttgt tctgtgcagt tgggttaaga    5160
atactgggca atttcatgtt tcttcaacac cacatatgcg tatatatacc aatctaagtc    5220
tgtgctcctt ccttcgttct tccttctgct cggagattac cgaatcaaag ctagcttatc    5280
gatgataagc tgtcaaagat gagaattaat tccacggact atagactata ctagatactc    5340
cgtctactgt acgatacact tccgctcagg tccttgtcct ttaacgaggc cttaccactc    5400
ttttgttact ctattgatcc agctcagcaa aggcagtgtg atctaagatt ctatcttcgc    5460
gatgtagtaa aactagctag accgagaaag agactagaaa tgcaaaaggc acttctacaa    5520
tggctgccat cattattatc cgatgtgacg ctgcagcttc tcaatgatat tcgaatacgc    5580
tttgaggaga tacagcctaa tatccgacaa actgttttac agatttacga tcgtacttgt    5640
tacccatcat tgaattttga acatccgaac ctgggagttt tccctgaaac agatagtata    5700
tttgaacctg tataataata tatagtctag cgctttacgg aagacaatgt atgtatttcg    5760
gttcctggag aaactattgc atctattgca taggtaatct tgcacgtcgc atccccggtt    5820
cattttctgc gtttccatct tgcacttcaa tagcatatct ttgttaacga agcatctgtg    5880
cttcattttg tagaacaaaa atgcaacgcg agagcgctaa ttttttcaaac aaagaatctg    5940 agctgcattt ttacagaaca gaaatgcaac gcgaaagcgc tattttacca acgaagaatc    6000
tgtgcttcat ttttgtaaaa caaaaatgca acgcgacgag agcgctaatt tttcaaacaa    6060
agaatctgag ctgcattttt acagaacaga atgcaacgc gagagcgcta ttttaccaac    6120
aaagaatcta tacttctttt ttgttctaca aaaatgcatc ccgagagcgc tattttcta    6180 acaaagcatc ttagattact tttttctcc tttgtgcgct ctataatgca gtctcttgat    6240 aacttttgc actgtaggtc cgttaaggtt agaagaaggc tactttggtg tctatttttct    6300 cttccataaa aaagcctga ctccacttcc cgcgtttact gattactagc gaagctgcgg    6360
gtgcattttt tcaagataaa ggcatccccg attatattct ataccgatgt ggattgcgca    6420
tactttgtga acagaaagtg atagcgttga tgattcttca ttggtcagaa aattatgaac    6480
ggtttcttct attttgtctc tatatactac gtataggaaa tgtttacatt ttcgtattgt    6540
tttcgattca ctctatgaat agttcttact acaattttttt tgtctaaaga gtaatactag    6600
agataaacat aaaaaatgta gaggtcgagt ttagatgcaa gttcaaggag cgaaaggtgg    6660
atgggtaggt tatataggga tatagcacag agatatatag caaaga         6706
```

<210> SEQ ID NO 18
<211> LENGTH: 8336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gtttgtggaa gcggtattcg caatttaatt aaagctggtg acaattaatc atcggctcgt      60
ataatgtgtg gaattgaatc gatataagga ggttaatcat atgactagaa tcgctatcac     120
aggtggtaga gttttgacta tggacccaga aagaagagta ttagaaccag gtacagttgt     180
tgttgaagat caattcattg cacaagtcgg ttcaccagat gacgtagaca tcagaggtgc     240
tgaaattata gatgccactg gtatggctgt attaccaggt ttcgttaata cacataccca     300
```

```
cgttcctcaa attttgttaa gaggtggtgc ttcacatgat agaaatttgt tggaatggtt      360
gcacaacgtc ttatatccag gtttggctgc atacactgat gacgtatca gagttggtac      420 attgttatat tgtgctgaag cattgagatc cggtattact acagttgtcg acaatgaaga     480
tgttagacct aacgattttg ccagagctgg tgccgctggt attggtgcat tcactgatgc     540
cggtatcaga gcaatctatg ccagaatgta ctttgatgct ccaagagcag aattggaaga     600
attagtcgca acaatacatg caaaagcccc tggtgccgta agaatggacg aatctgcttc     660
aaccgatcat gttttggcag acttagatca attgattacc agacatgaca gaactgctga     720
tggtagaatt agagtatggc cagctcctgc aataccattc atggtttctg aaagggtat      780 gaaggcagcc caagaaatag ctgcatccag aactgacggt tggacaatgc atgttagtga     840
agatccaatc gaagccagag tccactctat gaatgctcct gaatatttgc atcacttggg     900
ttgtttagac gatagattgt tagccgctca ttgcgttcac atagactcaa gagatatcag     960
attgtttaga acatgatg ttaagatatc cacacaacct gtctccaata gttacttagc      1020
agccggtata gcaccagttc ctgaaatgtt ggctcatggt gtcacagtag gtattggtac     1080
cgacgatgct aattgtaacg actccgtaaa cttaatcagt gatatgaagg ttttggcatt     1140
gatacataga gctgcacaca gagatgctag tatcattacc ccagaaaaga taatcgaaat     1200
ggccactatt gacggtgcta gatgcattgg tatggctgat caaatcggtt ctttggaagc     1260
tggtaaaaga gcagacataa tcactttgga tttgagacat gcacaaacca ctcctgccca     1320
cgatttggcc gctacaattg tctttcaagc ttatggtaat gaagtaaacg atgttttggt     1380
caacggttct gtagttatga gagatagagt tttgtcattc ttaccaaccc ctcaagaaga     1440
aaaggcttta tacgacgatg catctgaaag atcagcagcc atgttagcca gagctggttt     1500
gactggtaca agaacctggc aaactttggg ttcttaagga aatccattat gatgtcagga     1560
gaacacacgt taaaagcggt acgaggcagt tttattgatg tcacccgtac gatcgataac     1620
ccggaagaga ttgcctctgc gctgcggttt attgaggatg gttattact cattaaacag     1680 ggaaaagtgg aatggtttgg cgaatgggaa aacggaaagc atcaaattcc tgacaccatt     1740
cgcgtgcgcg actatcgcgg caaactgata gtaccgggct tgtcgatac acatatccat     1800 tatccgcaaa gtgaaatggt gggggcctat ggtgagcaat tgctggagtg gttgaataaa     1860
cacaccttcc ctactgaacg tcgttatgag gatttagagt acgcccgcga atgtcggcg      1920 ttcttcatca agcagctttt acgtaacgga accaccacgg cgctggtgtt tggcactgtt     1980
catccgcaat ctgttgatgc gctgtttgaa gccgccagtc atatcaatat gcgtatgatt     2040
gccggtaagg tgatgatgga ccgcaacgca ccggattatc tgctcgacac tgccgaaagc     2100
agctatcacc aaagcaaaga actgatcgaa cgctggcaca aaaatggtcg tctgctatat     2160
gcgattacgc cacgcttcgc cccgacctca tctcctgaac agatggcgat ggcgcaacgc     2220
ctgaaagaag aatatccgga tacgtgggta catacccatc tctgtgaaaa caaagatgaa     2280
attgcctggg tgaaatcgct ttatcctgac catgatggtt atctggatgt ttaccatcag     2340
tacggcctga ccggtaaaaa ctgtgtcttt gctcactgcg tccatctcga agaaaaagag     2400
tgggatcgtc tcagcgaaac caaatccagc attgctttct gtccgacctc caacctttac     2460
ctcggcagcg gcttattcaa cttgaaaaaa gcatggcaga gaaagttaa agtgggcatg      2520 ggaacggata tcggtgccgg aaccactttc aacatgctgc aaacgctgaa cgaagcctac     2580
aaagtattgc aattacaagg ctatcgcctc tcggcatatg aagcgtttta cctggccacg     2640
```

```
ctcggcggag cgaaatctct gggccttgac gatttgattg gcaactttt  acctggcaaa  2700
gaggctgatt tcgtggtgat ggaacccacc gccactccgc tacagcagct gcgctatgac  2760
aactctgttt ctttagtcga caaattgttc gtgatgatga cgttgggcga tgaccgttcg  2820
atctaccgca cctacgttga tggtcgtctg gtgtacgaac gcaactaagg aacgaccatg  2880
agagaagtcc aattgttaga tggtagaaga gttgatgtcg cctgtgctgg tcctttgatt  2940
agtgaaatag gtgcccactt agatttgact gctccagttg aaattgattg tggtggtggt  3000
ttagcaacta gaccttttac tgaacctcat ttgcacttag acaaagcagg tactgccgat  3060
agattgcctg ccggtgcttc cacaatcggt gacgctattg ctgcaatgca aagtgtcaag  3120
gtaaccgaaa gagataatgt cgccgctgta gcagccagaa tgcatagagt tttaaacaga  3180
atcgtcgatg acggttccca cgctattaga gcattggttg atgtcgacga agtttgggt   3240
ttaacagctt ttcatgctgc acaacaagtc caagccgctt tggccccaag agctgttgtc  3300
caaattgtcg ctttcccaca acacggttta acccctcaag tattggcaat gttagaacaa  3360
gcagccgctg aaggtgcagg tgccttgggt gctcatactg atgttgaccc agatcctgca  3420
gcccacgttg gtgccgtcgc tgcaatagcc gctggtgctt ccttgccatt agaagttcat  3480
actgacgaag gtgctagtcc agataaattt tatttgcctg cagtattgga agttttagat  3540
agattcccag gtttgtctac tacattagct cattgtttgt cattaggtac aattgcacct  3600
aagcaacaac aacattggat cgaagaatta gctcacagag atatcaaagt atgcgttgca  3660
ccatctattt tgggtttcgg tttgccatta gcacctgtta gagccttaat agaagctggt  3720
gtcggtatct tagtaggttc agacaatttg caagatgttt tctttccttt gggtacaggt  3780
agagcaattg aaaacgttag attgttagcc accgcagccc aattaactgc accagaattg  3840
gccggtcctt taattgctgg tgtaaccgac atagcttacg caaccgttac tggtgctgca  3900
gatgccttgg ctgttgaatc tccagctaca ttagtagttc atgatgctac ctcacctgca  3960
gaattgttaa gaggtataga cggtacaaga attaccgtta tagatggttt gttgacatct  4020
ccattgcaat tggataaagg tatcaagtaa gtttaaacta atcccacagc cgccagttcc  4080
gctggcggca tttaactttt ctttaatggg cgcgcctttc cataggctcc gccccctga   4140
cgagcatcac aaaaatcgac gctcaagtca gaggtggcga acccgacag gactataag   4200
ataccaggcg tttccccctg gaagctccct cgtgcgctct cctgttccga ccctgccgct  4260
taccggatac ctgtccgcct ttctcccttc gggaagcgtg gcgctttctc atagctcacg  4320
ctgtaggtat ctcagttcgg tgtaggtcgt tcgctccaag ctgggctgtg tgcacgaacc  4380
ccccgttcag cccgaccgct gcgccttatc cggtaactat cgtcttgagt ccaacccggt  4440
aagacacgac ttatcgccac tggcagcagc cactggtaac aggattagca gagcgaggta  4500
tgtaggcggt gctacagagt tcttgaagtg gtggcctaac tacggctaca ctagaagaac  4560
agtatttggt atctgcgctc tgctgaagcc agttaccttc ggaaaaagag ttggtagctc  4620
ttgatccggc aaacaaacca ccgctggtag cggtggtttt tttgtttgca agcagcagat  4680
tacgcgcaga aaaaaaggat ctcaagaaga tcctttgatc ttttctacgg ggtctgacgc  4740
tcagtggaac gaaaactcac gttaagggat tttggtcatg agattatcaa aaaggatctt  4800
cacctagatc cttttaaatt aaaaatgaag ttttaaatca atctaaagta tatatgagta  4860
aacttggtct gacagttacc aatgcttaat cagtgaggca cctatctcag cgatctgtct  4920
atttcgttca tccatagttg cctgactccc cgtcgtgtag ataactacga tacgggaggg  4980
cttaccatct ggccccagtg ctgcaatgat accgcgagac ccacgctcac cggctccaga  5040
```

```
tttatcagca ataaaccagc cagccggaag ggccgagcgc agaagtggtc ctgcaacttt    5100
atccgcctcc atccagtcta ttaattgttg ccgggaagct agagtaagta gttcgccagt    5160
taatagtttg cgcaacgttg ttgccattgc tacaggcatc gtggtgtcac gctcgtcgtt    5220
tggtatggct tcattcagct ccggttccca acgatcaagg cgagttacat gatccccat    5280 gttgtgcaaa aaagcggtta gctccttcgg tcctccgatc gttgtcagaa gtaagttggc    5340
cgcagtgtta tcactcatgg ttatggcagc actgcataat tctcttactg tcatgccatc    5400
cgtaagatgc ttttctgtga ctggtgagta ctcaaccaag tcattctgag aatagtgtat    5460
gcggcgaccg agttgctctt gcccggcgtc aatacgggga ataccgcgc cacatagcag    5520 aactttaaaa gtgctcatca ttggaaaacg ttcttcgggg cgaaaactct caaggatctt    5580
accgctgttg agatccagtt cgatgtaacc cactcgtgca cccaactgat cttcagcatc    5640
ttttactttc accagcgttt ctgggtgagc aaaaacagga aggcaaaatg ccgcaaaaaa    5700
gggaataagg gcgacacgga aatgttgaat actcatactc ttcctttttc aatattattg    5760
aagcatttat cagggttatt gtctcatgag cggatacata tttgaatgta tttagaaaaa    5820
taaacagcga tcgcgcggcc gcgggtaata actgatataa ttaaattgaa gctctaattt    5880
gtgagtttag tatacatgca tttacttata atacagtttt ttagttttgc tggccgcatc    5940
ttctcaaata tgcttcccag cctgcttttc tgtaacgttc accctctacc ttagcatccc    6000
ttccctttgc aaatagtcct cttccaacaa taataatgtc agatcctgta gagaccacat    6060
catccacggt tctatactgt tgacccaatg cgtctccctt gtcatctaaa cccacaccgg    6120
gtgtcataat caaccaatcg taaccttcat ctcttccacc catgtctctt tgagcaataa    6180
agccgataac aaaatctttg tcgctcttcg caatgtcaac agtacccctta gtatattctc    6240 cagtagctag ggagcccttg catgacaatt ctgctaacat caaaaggcct ctaggttcct    6300
ttgttacttc ttccgccgcc tgcttcaaac cgctaacaat acctgggccc accacaccgt    6360
gtgcattcgt aatgtctgcc cattctgcta ttctgtatac acccgcagag tactgcaatt    6420
tgactgtatt accaatgtca gcaaattttc tgtcttcgaa gagtaaaaaa ttgtacttgg    6480
cggataatgc ctttagcggc ttaactgtgc cctccatgga aaaatcagtc aagatatcca    6540
catgtgtttt tagtaaacaa attttgggac ctaatgcttc aactaactcc agtaattcct    6600
tggtggtacg aacatccaat gaagcacaca agtttgtttg cttttcgtgc atgatattaa    6660
atagcttggc agcaacagga ctaggatgag tagcagcacg ttccttatat gtagctttcg    6720
acatgattta tcttcgtttc ctgcaggttt ttgttctgtg cagttgggtt aagaatactg    6780
ggcaatttca tgtttcttca acaccacata tgcgtatata taccaatcta agtctgtgct    6840
ccttccttcg ttcttccttc tgctcggaga ttaccgaatc aaagctagct tatcgatgat    6900
aagctgtcaa agatgagaat taattccacg gactatagac tatactagat actccgtcta    6960
ctgtacgata cacttccgct caggtccttg tcctttaacg aggccttacc actcttttgt    7020
tactctattg atccagctca gcaaaggcag tgtgatctaa gattctatct tcgcgatgta    7080
gtaaaactag ctagaccgag aaagagacta gaaatgcaaa aggcacttct acaatggctg    7140
ccatcattat tatccgatgt gacgctgcag cttctcaatg atattcgaat acgctttgag    7200
gagatacagc ctaatatccg acaaactgtt ttacagattt acgatcgtac ttgttaccca    7260
tcattgaatt tgaacatcc gaacctggga gttttccctg aaacagatag tatatttgaa    7320
cctgtataat aatatatagt ctagcgcttt acggaagaca atgtatgtat ttcggttcct    7380
```

| | |
|---|---|
| ggagaaacta ttgcatctat tgcataggta atcttgcacg tcgcatcccc ggttcatttt | 7440 |
| ctgcgtttcc atcttgcact tcaatagcat atctttgtta acgaagcatc tgtgcttcat | 7500 |
| tttgtagaac aaaaatgcaa cgcgagagcg ctaattttc aaacaaagaa tctgagctgc | 7560 |
| attttacag aacagaaatg caacgcgaaa gcgctatttt accaacgaag aatctgtgct | 7620 |
| tcattttgt aaaacaaaaa tgcaacgcga cgagagcgct aattttcaa acaaagaatc | 7680 |
| tgagctgcat ttttacagaa cagaaatgca acgcgagagc gctattttac caacaaagaa | 7740 |
| tctatacttc ttttttgttc tacaaaaatg catcccgaga gcgctatttt tctaacaaag | 7800 |
| catcttagat tactttttt ctcctttgtg cgctctataa tgcagtctct tgataacttt | 7860 |
| ttgcactgta ggtccgttaa ggttagaaga aggctacttt ggtgtctatt ttctcttcca | 7920 |
| taaaaaagc ctgactccac ttcccgcgtt tactgattac tagcgaagct gcgggtgcat | 7980 |
| ttttcaaga taaaggcatc cccgattata ttctataccg atgtggattg cgcatacttt | 8040 |
| gtaacagaa agtgatagcg ttgatgattc ttcattggtc agaaaattat gaacggtttc | 8100 |
| ttctattttg tctctatata ctacgtatag gaaatgttta catttttcgta ttgttttcga | 8160 |
| ttcactctat gaatagttct tactacaatt tttttgtcta agagtaata ctagagataa | 8220 |
| acataaaaaa tgtagaggtc gagtttagat gcaagttcaa ggagcgaaag gtggatgggt | 8280 |
| aggttatata gggatatagc acagagatat atagcaaaga gatacttttg agcaat | 8336 |

<210> SEQ ID NO 19
<211> LENGTH: 8063
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

| | |
|---|---|
| gtttgtggaa gcggtattcg caatttaatt aaagctggtg acaattaatc atcggctcgt | 60 |
| ataatgtgtg gaattgaatc gatataagga ggttaatcat atgtcctcca cagcattata | 120 |
| caccgttcct accgcaggtc cagacgatgt tgccgccttg aaagcattag atggtcattc | 180 |
| cgcctccgat atttggctg taataggtaa acagagggg aatggttgtg ttaacgactt | 240 |
| tagtagaacc ttatctgctg cagttttggca tccattgtta gaagattcag ccattacagt | 300 |
| cttttccggt ggtgcagaag gtgtaataag tccacatgta aacatcttcg ttagagatga | 360 |
| aagacaatat tctggtcacc ctagaggttt ggtaactgct gttggtagaa caagagttat | 420 |
| cggtccagaa gaaattggta gacctgctca agtcgatgca gtacatgaaa ccgttgtcgc | 480 |
| attgttaact gaattgggtg ttggtccaga tgacgttcac ttggtcttga ttaaatgccc | 540 |
| tttgttatct tcagacgcta tagcaggtgt tcatagaaga ggtttaagac tgtcactac | 600 |
| agatacttac gaatctatgt caagatccag agccgcttct gctttgggta tagccatggc | 660 |
| tttaaaggaa tgtgatagag acagagcatt gttagccttg gaaggtagag atgacgtttg | 720 |
| gtcagcaaga gcctccgctt ccagtggtgc tgaattggat gactgccaca ttttagtagt | 780 |
| tgcagaatca gatgcagccg ctaatccatt aagagcagcc catactgcca tgagagatgc | 840 |
| tttggacatc caagctttaa cagaagtttt tgacagaatt gctgcagaag gtggtaccgt | 900 |
| cagacaaata ttcgcaaagg ccgaagctga tccttcaggt gctatcagag gttatagaca | 960 |
| taccatgtta actgattccg acgtcaatgc aacaagacac gccagagccg ctgtaggtgg | 1020 |
| tttgattgca gccttacatg gtaacggtgc tgtctatgta tcaggtggtg cagaacacca | 1080 |

```
aggtccaagt ggtggtggtt ctgttactgt tatatatgat gttcctgcaa cagccaacgc   1140
taccggtgaa gcttctagat aaggaaatcc attatgatat actcaacagt caacgctaat   1200
ccttacgctt ggccttacga tggttcaata gaccctgctc acaccgcttt aatcttaatc   1260
gattggcaaa tagacttttg tggtccaggt ggttatgtcg attccatggg ttacgactta   1320
tccttgacta gaagtggttt agaacctaca gcaagagtat tggctgcagc cagagatact   1380
ggtatgacag ttatccatac tagagaaggt cacagaccag atttggctga cttgccacct   1440
aataagagat ggagatctgc atcagccggt gctgaaatcg gttcagttgg tccatgtggt   1500
agaattttag tcagaggtga acctggttgg gaaatagtac cagaagttgc acctagagaa   1560
ggtgaaccaa ttatagataa acctggtaaa ggtgctttct acgcaacaga tttggacttg   1620
ttgttgagaa caagaggtat cacccatttg attttgaccg gtataactac agatgtttgc   1680
gtccacacca ctatgagaga agccaacgat agaggttacg aatgtttaat tttgtctgat   1740
tgcaccggtg ctactgacag aaagcatcac gaagctgcat tatctatggt caccatgcaa   1800
ggtggtgtat tcggtgcaac tgcccattca gatgacttat tggccgcttt gggtacaacc   1860
gttccagcag ccgctggtcc tagagctaga acagaataag gaacgaccat gacagttagt   1920
tccgatacaa ctgctgaaat atcgttaggt tggtcaatcc aagactggat tgatttccac   1980
aagtcatcaa gctcccaggc ttcactaagg cttcttgaat cactactaga ctctcaaaat   2040
gttgcgccac tcgataatgc gtggatatcg ctaatttcaa aggaaatttt actgcaccaa   2100
ttccaaattt taaagagcag agaaaataaa gaaactctac ctctctacgg tgtccctatt   2160
gctgttaagg acaacatcga cgttagaggt ctacccacca ccgctgcatg tccatccttt   2220
gcatatgagc cttccaaaga ctctaaagta gtagaactac taagaaatgc aggtgcgata   2280
atcgtgggta agacaaactt ggaccaattt gccacaggat tagtcggcac acggtctcca   2340
tatgggaaaa caccttgcgc ttttagcaaa gagcatgtat ctggtggttc ctccgctggg   2400
tcagcatcgg tggtcgccag aggtatcgta ccaattgcat tgggtactga tacagcaggt   2460
tctggtagag tcccagccgc cttgaacaac ctgattggcc taaagccaac aaagggcgtc   2520
ttttcctgtc aaggtgtagt tcccgcttgt aaatctttag actgcgtctc catctttgca   2580
ttaaacctaa gtgatgctga acgctgcttc cgcatcatgt gccagccaga tcctgataat   2640
gatgaatatt ctagacccta tgtttccaac ccttttgaaaa aattttcaag caatgtaacg   2700
attgctattc ctaaaaatat cccatggtat ggtgaaacca agaatcctgt actgttttcc   2760
aatgctgtcg aaaatctatc aagaacgggc gctaacgtca tagaaattga ttttgagcct   2820
cttttagagt tagctcgctg tttatacgaa ggtacttggg tggccgagcg ttatcaagct   2880
attcaatcgt ttttggacag taaaccacca aaggaatctt tggacccctac tgttatttca   2940 attatagaag gggccaagaa atacagtgca gtagactgct tcagttttga atacaaaaga   3000
caaggcatct tgcaaaaagt gagacgactt ctcgaatcag tcgatgtatt gtgtgtgccc   3060
acatgtcctt taaatcctac tatgcaacaa gttgcggatg aaccagtcct agtcaattca   3120
agacaaggca catggactaa ttttgtcaac ttggcagatt tggcagccct tgctgttccc   3180
gcagggttcc gagacgatgg tttgccaaat ggtattactt taatcggtaa aaaattcaca   3240
gattacgcac tattagagtt ggctaaccgc tatttccaaa atatattccc caacggttcc   3300
agaacatacg gtactttttac ctcttcttca gtaaagccag caaacgatca attagtggga   3360
ccagactatg acccatctac gtccataaaa ttggctgttg tcggtgcaca tcttaagggt   3420
ctgcctctac attggcaatt ggaaaaggtc aatgcaacat atttatgtac aacaaaaaca   3480
```

```
tcaaaagctt accagctttt tgctttgccc aaaaatggac cagttttaaa acctggtttg    3540
agaagagttc aagatagcaa tggctctcaa atcgaattag aagtgtacag tgttccaaaa    3600
gaactgttcg gtgcttttat ttccatggtt cctgaaccat taggaatagg ttcagtggag    3660
ttagaatctg tgaatggat caaatccttt atttgtgaag aatctggtta caaagccaaa     3720
ggtacagttg atatcacaaa gtatggtgga tttagagcat attttgaaat gttgtaagtt    3780
taaactaatc ccacagccgc cagttccgct ggcggcattt taactttctt taatgggcgc    3840
gcctttccat aggctccgcc ccctgacga gcatcacaaa atcgacgct caagtcagag      3900 gtggcgaaac ccgacaggac tataaagata ccaggcgttt ccccctggaa gctccctcgt    3960
gcgctctcct gttccgaccc tgccgcttac cggatacctg tccgcctttc tcccttcggg    4020
aagcgtggcg ctttctcata gctcacgctg taggtatctc agttcggtgt aggtcgttcg    4080
ctccaagctg ggctgtgtgc acgaaccccc cgttcagccc gaccgctgcg ccttatccgg    4140
taactatcgt cttgagtcca acccggtaag cacgactta tcgccactgg cagcagccac     4200
tggtaacagg attagcagag cgaggtatgt aggcggtgct acagagttct tgaagtggtg    4260
gcctaactac ggctacacta gaagaacagt atttggtatc tgcgctctgc tgaagccagt    4320
taccttcgga aaagagttg gtagctcttg atccggcaaa caaaccaccg ctggtagcgg     4380
tggttttttt gtttgcaagc agcagattac gcgcagaaaa aaaggatctc aagaagatcc    4440
tttgatcttt tctacggggt ctgacgctca gtggaacgaa aactcacgtt aagggatttt    4500
ggtcatgaga ttatcaaaaa ggatcttcac ctagatcctt ttaaattaaa aatgaagttt    4560
taaatcaatc taaagtatat atgagtaaac ttggtctgac agttaccaat gcttaatcag    4620
tgaggcacct atctcagcga tctgtctatt tcgttcatcc atagttgcct gactccccgt    4680
cgtgtagata actacgatac gggagggctt accatctggc cccagtgctg caatgatacc    4740
gcgagaccca cgctcaccgg ctccagattt atcagcaata aaccagccag ccggaagggc    4800
cgagcgcaga agtggtcctg caactttatc cgcctccatc cagtctatta attgttgccg    4860
ggaagctaga gtaagtagtt cgccagttaa tagtttgcgc aacgttgttg ccattgctac    4920
aggcatcgtg gtgtcacgct cgtcgtttgg tatggcttca ttcagctccg gttcccaacg    4980
atcaaggcga gttacatgat cccccatgtt gtgcaaaaaa gcggttagct ccttcggtcc    5040
tccgatcgtt gtcagaagta agttggccgc agtgttatca ctcatggtta tggcagcact    5100
gcataattct cttactgtca tgccatccgt aagatgcttt tctgtgactg gtgagtactc    5160
aaccaagtca ttctgagaat agtgtatgcg gcgaccgagt tgctcttgcc cggcgtcaat    5220
acgggataat accgcgccac atagcagaac tttaaaagtg ctcatcattg gaaaacgttc    5280
ttcggggcga aaactctcaa ggatcttacc gctgttgaga tccagttcga tgtaacccac    5340
tcgtgcaccc aactgatctt cagcatcttt tactttcacc agcgtttctg ggtgagcaaa    5400
aacaggaagg caaaatgccg caaaaaaggg aataagggcg acacggaaat gttgaatact    5460
catactcttc cttttcaat attattgaag catttatcag ggttattgtc tcatgagcgg     5520
atacatattt gaatgtattt agaaaaataa acagcgatcg cgcggccgcg gtaataact     5580 gatataatta aattgaagct ctaatttgtg agtttagtat acatgcattt acttataata    5640
cagtttttta gttttgctgg ccgcatcttc tcaaatatgc ttcccagcct gcttttctgt    5700
aacgttcacc ctctacctta gcatcccttc cctttgcaaa tagtcctctt ccaacaataa    5760
taatgtcaga tcctgtagag accacatcat ccacggttct atactgttga cccaatgcgt    5820
```

```
ctcccttgtc atctaaaccc acaccgggtg tcataatcaa ccaatcgtaa ccttcatctc    5880
ttccacccat gtctctttga gcaataaagc cgataacaaa atctttgtcg ctcttcgcaa    5940
tgtcaacagt acccttagta tattctccag tagctaggga gcccttgcat gacaattctg    6000
ctaacatcaa aaggcctcta ggttcctttg ttacttcttc cgccgcctgc ttcaaaccgc    6060
taacaatacc tgggcccacc acaccgtgtg cattcgtaat gtctgcccat tctgctattc    6120
tgtatacacc cgcagagtac tgcaatttga ctgtattacc aatgtcagca aattttctgt    6180
cttcgaagag taaaaaattg tacttggcgg ataatgcctt tagcggctta actgtgccct    6240
ccatggaaaa atcagtcaag atatccacat gtgtttttag taaacaaatt ttgggaccta    6300
atgcttcaac taactccagt aattccttgg tggtacgaac atccaatgaa gcacacaagt    6360
ttgtttgctt ttcgtgcatg atattaaata gcttggcagc aacaggacta ggatgagtag    6420
cagcacgttc cttatatgta gctttcgaca tgatttatct tcgtttcctg caggttttg    6480
ttctgtgcag ttgggttaag aatactgggc aatttcatgt ttcttcaaca ccacatatgc    6540
gtatatatac caatctaagt ctgtgctcct tccttcgttc ttccttctgc tcggagatta    6600
ccgaatcaaa gctagcttat cgatgataag ctgtcaaaga tgagaattaa ttccacggac    6660
tatagactat actagatact ccgtctactg tacgatacac ttccgctcag gtccttgtcc    6720
tttaacgagg ccttaccact cttttgttac tctattgatc cagctcagca aaggcagtgt    6780
gatctaagat tctatcttcg cgatgtagta aaactagcta gaccgagaaa gagactagaa    6840
atgcaaaagg cacttctaca atggctgcca tcattattat ccgatgtgac gctgcagctt    6900
ctcaatgata ttcgaatacg ctttgaggag atacagccta atatccgaca aactgtttta    6960
cagatttacg atcgtacttg ttacccatca ttgaattttg aacatccgaa cctgggagtt    7020
ttccctgaaa cagatagtat atttgaacct gtataataat atatagtcta gcgctttacg    7080
gaagacaatg tatgtatttc ggttcctgga gaaactattg catctattgc ataggtaatc    7140
ttgcacgtcg catccccggt tcattttctg cgtttccatc ttgcacttca atagcatatc    7200
tttgttaacg aagcatctgt gcttcatttt gtagaacaaa aatgcaacgc gagagcgcta    7260
atttttcaaa caaagaatct gagctgcatt tttacagaac agaaatgcaa cgcgaaagcg    7320
ctattttacc aacgaagaat ctgtgcttca tttttgtaaa acaaaaatgc aacgcgacga    7380
gagcgctaat ttttcaaaca agaatctga gctgcatttt tacagaacag aaatgcaacg    7440
cgagagcgct attttaccaa caaagaatct atacttcttt tttgttctac aaaaatgcat    7500
cccgagagcg ctattttct aacaaagcat cttagattac ttttttttctc ctttgtgcgc    7560
tctataatgc agtctcttga taacttttg cactgtaggt ccgttaaggt tagaagaagg    7620
ctactttggt gtctattttc tcttccataa aaaaagcctg actccacttc ccgcgtttac    7680
tgattactag cgaagctgcg ggtgcatttt ttcaagataa aggcatcccc gattatattc    7740
tataccgatg tggattgcgc atactttgtg aacagaaagt gatagcgttg atgattcttc    7800
attggtcaga aaattatgaa cggtttcttc tattttgtct ctatatacta cgtataggaa    7860
atgtttacat tttcgtattg ttttcgattc actctatgaa tagttcttac tacaattttt    7920
ttgtctaaag agtaatacta gagataaaca taaaaaatgt agaggtcgag tttagatgca    7980
agttcaagga gcgaaaggtg gatgggtagg ttatataggg atatagcaca gagatatata    8040
gcaaagagat acttttgagc aat                                              8063
```

<210> SEQ ID NO 20
<211> LENGTH: 6004

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20 gatactttttg agcaatgttt gtggaagcgg tattcgcaat tataaacggt attttcacaa      60
ttgcacccca gccagaccga tagccggtcg caatccgcca cccacaaccg tctacctccc     120
acagaacccc gtcacttcca ccctttttcca ccagatcata tgtcccaact tgccaaatta    180
aaaccgtgcg aattttcaaa ataaactttg gcaaagaggc tgcaaaggag gggctggtga    240
gggcgtctgg aagtcgacca gagaccgggt tggcggcgca tttgtgtccc aaaaaacagc    300
cccaattgcc ccaattgacc ccaaattgac ccagtagcgg gcccaacccc ggcgagagcc    360
cccttctccc cacatatcaa acctcccccg gttcccacac ttgccgttaa gggcgtaggg    420
tactgcagtc tggaatctac gcttgttcag actttgtact agtttctttg tctggccatc    480
cgggtaaccc atgccggacg caaaatagac tactgaaaat ttttttgctt tgtggttggg    540
actttagcca agggtataaa agaccaccgt ccccgaatta cctttcctct tctttttctct    600
ctctccttgt caactcacac ccgaaatcgt taagcatttc cttctgagta taagaatcat    660
tcaaaatgtc atcctcagaa gtaaaagcaa atggttggac cgcagttcct gtttccgcaa    720
aagcaatagt agactccttg ggtaaattag gagatgtctc ttcatattcc gtagaagata    780
ttgccttttcc agctgcagac aaattggtag ccgaagctca agcattcgtt aaggctagat    840
tatctcctga aacctacaac cattcaatga gagttttcta ttggggtact gtcattgcca    900
gaagattgtt accagaacaa gctaaagatt tgtctccttc aacatgggca ttaacctgtt    960
tgttacacga cgttggtact gccgaagctt atttttacctc cactagaatg agtttcgata   1020
tctacggtgg tattaaagct atggaagtat tgaaggtttt aggttccagt acagatcaag   1080
cagaagccgt tgctgaagca attataagac atgaagatgt tggtgtcgac ggtaacatca   1140
cattttttggg tcaattgatc caattggcaa cattgtacga taacgtcggt gcctacgacg   1200
gtattgatga cttcggttcc tgggttgatg acactacaag aaacagtata aacactgctt   1260
tcccaagaca tggttggtgt tcttggttcg catgcacagt tagaaaagaa gaatcaaaca   1320
agccttggtg ccacaccaca cacataccac aattcgacaa acaaatggaa gcaaacacct   1380
tgatgaaacc ttgggaataa gctgcttgta cctagtgcaa ccccagtttg ttaaaaatta   1440
gtagtcaaaa acttctgagt tagaaatttg tgagtgtagt gagattgtag agtatcatgt   1500
gtgtccgtaa gtgaagtgtt attgactctt agttagttta tctagtactc gtttagttga   1560
cactgatcta gtatttttacg aggcgtatga ctttagccaa gtgttgtact tagtcttctc   1620
tccaaacatg agagggctct gtcactcagt cggcctatgg gtgagatggc ttggtgagat   1680
cttttcgatag tctcgtcaag atggtaggat gatgggggaa tacattactg ctctcgtcaa   1740
ggaaaccaca atcagatcac accatcctcc atggtatccg atgactctct tctccacagt   1800
tttccatagg ctccgccccc ctgacgagca tcacaaaaat cgacgctcaa gtcagaggtg   1860
gcgaaacccg acaggactat aaagatacca ggcgtttccc cctggaagct ccctcgtgcg   1920
ctctcctgtt ccgaccctgc cgcttaccgg atacctgtcc gcctttctcc cttcgggaag   1980
cgtggcgctt tctcatagct cacgctgtag gtatctcagt tcggtgtagg tcgttcgctc   2040
caagctgggc tgtgtgcacg aaccccccgt tcagcccgac cgctgcgcct tatccggtaa   2100
ctatcgtctt gagtccaacc cggtaagaca cgacttatcg ccactggcag cagccactgg   2160
```

```
taacaggatt agcagagcga ggtatgtagg cggtgctaca gagttcttga agtggtggcc    2220
taactacggc tacactagaa gaacagtatt tggtatctgc gctctgctga agccagttac    2280
cttcggaaaa agagttggta gctcttgatc cggcaaacaa accaccgctg gtagcggtgg    2340 ttttttgtt tgcaagcagc agattacgcg cagaaaaaaa ggatctcaag aagatccttt    2400
gatcttttct acggggtctg acgctcagtg gaacgaaaac tcacgttaag ggattttggt    2460
catgagatta tcaaaaagga tcttcaccta gatcctttta aattaaaaat gaagttttaa    2520
atcaatctaa agtatatatg agtaaacttg gtctgacagt taccaatgct taatcagtga    2580
ggcacctatc tcagcgatct gtctatttcg ttcatccata gttgcctgac tccccgtcgt    2640
gtagataact acgatacggg agggcttacc atctggcccc agtgctgcaa tgataccgcg    2700
agacccacgc tcaccggctc cagatttatc agcaataaac cagccagccg gaagggccga    2760
gcgcagaagt ggtcctgcaa ctttatccgc ctccatccag tctattaatt gttgccggga    2820
agctagagta agtagttcgc cagttaatag tttgcgcaac gttgttgcca ttgctacagg    2880
catcgtggtg tcacgctcgt cgtttggtat ggcttcattc agctccggtt cccaacgatc    2940
aaggcgagtt acatgatccc ccatgttgtg caaaaaagcg gttagctcct tcggtcctcc    3000
gatcgttgtc agaagtaagt tggccgcagt gttatcactc atggttatgg cagcactgca    3060
taattctctt actgtcatgc catccgtaag atgcttttct gtgactggtg agtactcaac    3120
caagtcattc tgagaatagt gtatgcggcg accgagttgc tcttgcccgg cgtcaatacg    3180
ggataatacc gcgccacata gcagaacttt aaaagtgctc atcattggaa aacgttcttc    3240
ggggcgaaaa ctctcaagga tcttaccgct gttgagatcc agttcgatgt aacccactcg    3300
tgcacccaac tgatcttcag catcttttac tttcaccagc gtttctgggt gagcaaaaac    3360
aggaaggcaa aatgccgcaa aaaagggaat aagggcgaca cggaaatgtt gaatactcat    3420
actcttcctt tttcaatatt attgaagcat ttatcagggt tattgtctca tgagcggata    3480
catatttgaa tgtatttaga aaaataaaca gcgatcgcgc ggccgcgggt aataactgat    3540
ataattaaat tgaagctcta atttgtgagt ttagtataca tgcatttact tataatacag    3600 tttttttagtt ttgctggccg catcttctca aatatgcttc ccagcctgct tttctgtaac    3660
gttcaccctc tacctagca tcccttccct ttgcaaatag tcctcttcca acaataataa    3720
tgtcagatcc tgtagagacc acatcatcca cggttctata ctgttgaccc aatgcgtctc    3780
ccttgtcatc taaacccaca ccgggtgtca taatcaacca atcgtaacct tcatctcttc    3840
cacccatgtc tctttgagca ataaagccga taacaaaatc tttgtcgctc ttcgcaatgt    3900
caacagtacc cttagtatat tctccagtag ctagggagcc cttgcatgac aattctgcta    3960
acatcaaaag gcctctaggt tcctttgtta cttcttccgc cgcctgcttc aaaccgctaa    4020
caatacctgg gcccaccaca ccgtgtgcat tcgtaatgtc tgcccattct gctattctgt    4080
atacacccgc agagtactgc aatttgactg tattaccaat gtcagcaaat tttctgtctt    4140
cgaagagtaa aaaattgtac ttggcggata atgcctttag cggcttaact gtgccctcca    4200
tggaaaaatc agtcaagata tccacatgtg tttttagtaa acaaattttg ggacctaatg    4260
cttcaactaa ctccagtaat tccttggtgg tacgaacatc caatgaagca cacaagtttg    4320
tttgcttttc gtgcatgata ttaaatagct tggcagcaac aggactagga tgagtagcag    4380
cacgttcctt atatgtagct ttcgacatga tttatcttcg tttcctgcag gttttgttc    4440 tgtgcagttg ggttaagaat actgggcaat ttcatgtttc ttcaacacca catatgcgta    4500
```

```
tatataccaa tctaagtctg tgctccttcc ttcgttcttc cttctgctcg gagattaccg    4560
aatcaaagct agcttatcga tgataagctg tcaaagatga gaattaattc cacggactat    4620
agactatact agatactccg tctactgtac gatacacttc cgctcaggtc cttgtccttt    4680
aacgaggcct taccactctt ttgttactct attgatccag ctcagcaaag gcagtgtgat    4740
ctaagattct atcttcgcga tgtagtaaaa ctagctagac cgagaaagag actagaaatg    4800
caaaaggcac ttctacaatg gctgccatca ttattatccg atgtgacgct gcagcttctc    4860
aatgatattc gaatacgctt tgaggagata cagcctaata tccgacaaac tgttttacag    4920
atttacgatc gtacttgtta cccatcattg aattttgaac atccgaacct gggagttttc    4980
cctgaaacag atagtatatt tgaacctgta taataatata tagtctagcg ctttacggaa    5040
gacaatgtat gtatttcggt tcctggagaa actattgcat ctattgcata ggtaatcttg    5100
cacgtcgcat ccccggttca ttttctgcgt ttccatcttg cacttcaata gcatatcttt    5160
gttaacgaag catctgtgct tcattttgta gaacaaaaat gcaacgcgag agcgctaatt    5220
tttcaaacaa agaatctgag ctgcatttt acagaacaga aatgcaacgc gaaagcgcta    5280
ttttaccaac gaagaatctg tgcttcattt ttgtaaaaca aaaatgcaac gcgacgagag    5340
cgctaatttt tcaaacaaag aatctgagct gcatttttac agaacagaaa tgcaacgcga    5400
gagcgctatt ttaccaacaa agaatctata cttctttttt gttctacaaa atgcatccc    5460 gagagcgcta tttttctaac aaagcatctt agattacttt ttttctcctt tgtgcgctct    5520
ataatgcagt ctcttgataa cttttgcac tgtaggtccg ttaaggttag aagaaggcta    5580
ctttggtgtc tatttctct tccataaaaa agcctgact ccacttcccg cgtttactga    5640
ttactagcga agctgcgggt gcatttttc aagataaagg catccccgat tatattctat    5700
accgatgtgg attgcgcata ctttgtgaac agaaagtgat agcgttgatg attcttcatt    5760
ggtcagaaaa ttatgaacgg tttcttctat tttgtctcta tatactacgt ataggaaatg    5820
tttacatttt cgtattgttt tcgattcact ctatgaatag ttcttactac aatttttttg    5880
tctaaagagt aatactagag ataaacataa aaaatgtaga ggtcgagttt agatgcaagt    5940
tcaaggagcg aaaggtggat gggtaggtta tatagggata tagcacagag atatatagca    6000
aaga                                                                 6004
```

<210> SEQ ID NO 21
<211> LENGTH: 10640
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
gtttgtggaa gcggtattcg caatttaatt aaagctggtg acaattaatc atcggctcgt     60
ataatgtgtg gaattgaatc gatataagga ggttaatcat atgacagtta gttccgatac    120
aactgctgaa atatcgttag gttggtcaat ccaagactgg attgatttcc acaagtcatc    180
aagctcccag gcttcactaa ggcttcttga atcactacta gactctcaaa atgttgcgcc    240
agtcgataat gcgtggatat cgctaatttc aaaggaaaat ttactgcacc aattccaaat    300
tttaaagagc agagaaaata agaaactct acctctctac ggtgtcccta ttgctgttaa    360
ggacaacatc gacgttagag gtctacccac caccgctgca tgtccatcct ttgcatatga    420
gccttccaaa gactctaaag tagtagaact actaagaaat gcaggtgcga taatcgtggg    480
```

```
taagacaaac ttggaccaat ttgccacagg attagtcggc acacggtctc catatgggaa    540
aacaccttgc gcttttagca aagagcatgt atctggtggt tcctccgctg ggtcagcatc    600
ggtggtcgcc agaggtatcg taccaattgc attgggtact gatacagcag gttctggtag    660
agtcccagcc gccttgaaca acctgattgg cctaaagcca acaaagggcg tcttttcctg    720
tcaaggtgta gttcccgctt gtaaatcttt agactgcgtc tccatctttg cattaaacct    780
aagtgatgct gaacgctgct tccgcatcat gtgccagcca gatcctgata atgatgaata    840
ttctagaccc tatgtttcca acccttttgaa aaaattttca agcaatgtaa cgattgctat    900
tcctaaaaat atcccatggt atggtgaaac caagaatcct gtactgtttt ccaatgctgt    960
cgaaaatcta tcaagaacgg cgctaacgt catagaaatt gattttgagc ctcttttaga    1020
gttagctcgc tgtttatacg aaggtacttg ggtggccgag cgttatcaag ctattcaatc    1080 gttttttggac agtaaaccac caaaggaatc tttggaccct actgttattt caattataga    1140
aggggccaag aaatacagtg cagtagactg cttcagtttt gaatacaaaa gacaaggcat    1200
cttgcaaaaa gtgagacgac ttctcgaatc agtcgatgta ttgtgtgtgc ccacatgtcc    1260
tttaaatcct actatgcaac aagttgcgga tgaaccagtc ctagtcaatt caagacaagg    1320
cacatggact aattttgtca acttggcaga tttggcagcc cttgctgttc ccgcagggtt    1380
ccgagacgat ggtttgccaa atggtattac tttaatcggt aaaaaattca cagattacgc    1440
actattagag ttggctaacc gctatttcca aaatatattc cccaacggtt ccagaacata    1500
cggtactttt acctcttctt cagtaaagcc agcaaacgat caattagtgg gaccagacta    1560
tgacccatct acgtccataa aattggctgt gtcggtgca catcttaagg gtctgcctct    1620
acattggcaa ttggaaaagg tcaatgcaac atatttatgt acaacaaaaa catcaaaagc    1680
ttaccagctt tttgctttgc ccaaaaatgg accagtttta aaacctggtt tgagaagagt    1740
tcaagatagc aatggctctc aaatcgaatt agaagtgtac agtgttccaa aagaactgtt    1800
cggtgctttt atttccatgg ttcctgaacc attaggaata ggttcagtgg agttagaatc    1860
tggtgaatgg atcaaatcct ttatttgtga agaatctggt tacaaagcca aggtacagt    1920 tgatatcaca aagtatggtg gatttagagc atattttgaa atgttgaaga aaaaagagtc    1980
ccaaaagaag aagttatttg ataccgtgtt aattgccaat agaggtgaaa ttgccgttcg    2040
tattatcaag acattaaaaa aattgggtat tagatcagtt gcagtttatt ccgaccctga    2100
taaatattct caacacgtta ctgatgcaga tgtttctgta ccccttcatg gcacaaccgc    2160
agcccaaact tatttagaca tgaataagat catagatgcc gctaagcaaa ctaatgcaca    2220
ggccattatt cctggttatg gtttcttgtc ggaaaatgcg gattttctg atgcgtgcac    2280 cagtgctggc attaccttg ttggtccttc gggagatatt atcagaggtt tagggttaaa    2340
acattctgct agacagattg cacagaaggc tggcgttcct ctagtgccag gctctttgct    2400
tatcacatca gttgaagagg ctaagaaagt cgcagcggaa ttggaatacc cagttatggt    2460
gaagtcaact gctggtggcg gtggtattgg tttcagaaaa gtcgattctg aagaggacat    2520
cgagcatatt tttgagactg tgaaacatca aggtgaaaca ttttcggtg acgctggtgt    2580 atttctggaa cggttatcg aaaatgccag gcatgttgaa gtccaactta tgggagatgg    2640
ttttggtaag gccattgctt gggcgaacg tgattgttct ttacagcgtc gtaaccaaaa    2700
agttatcgaa gaactcctg caccaaattt gccagaaaag acgaggttgg cgttaagaaa    2760
ggcagctgaa agttgggat ctttattgaa ttacaagtgt gctggtacgg ttgaatttat    2820
ttacgatgag aaaaaggacg agttttactt tttagaagtt aatacaagat tacaagttga    2880
```

```
acatccaata acagaaatgg ttacagggtt agacttggtc gagtggatga tcaggattgc    2940
cgctaatgat gcacctgatt ttgattctac aaaggtagaa gtcaatgggg tttcaatgga    3000
ggcacgttta tatgctgaaa atccattgaa aaatttcaga ccttctccag gtttacttgt    3060
cgatgtgaaa tttcctgatt gggcaagagt ggatacttgg gttaagaaag gtactaatat    3120
ttctcccgaa tatgatccaa cattggccaa aattatcgtt catgggaaag accgtgatga    3180
tgcaatttcc aagttaaatc aagcgttaga agaaacaaaa gttacggat gtattactaa     3240
cattgactac ctgaagtcta tcattaccag tgatttcttt gctaaagcaa aagtttctac    3300
aaacattttg aactcttatc aatatgagcc taccgccatc gaaattactt tgcccggtgc    3360
acacactagt attcaggatt accccggtag agttgggtac tggagaattg gtgttccgcc    3420
ctctggtcca atggacgcat attcgtttag attggcgaac agaattgttg gtaatgacta    3480
caggactcct gccattgaag taacgttgac tggtccatcc atcgttttcc attgtgaaac    3540
tgtcattgcc attactggtg gtaccgctct atgtacatta gacggccaag aaattcccca    3600
acacaaaccg gtcgaagtta agaggggatc tactttatcc attggcaagt tgacaagcgg    3660
ctgtagagca tacttaggta tcaggggtgg cattgatgtg cctaaatact tgggctctta    3720
ttctactttc actctaggaa atgtcggtgg atacaatgga agggtgctaa aacttggaga    3780
cgtactattc ttaccaagca atgaagaaaa taaatcagtt gagtgccttc cacagaatat    3840
tcctcaatca ttaattcctc aaatttccga aactaaggaa tggagaattg gtgtaacatg    3900
tggtccccat gggtctccag attttttaa acctgagtcc atcgaagaat ttttcagtga    3960
gaagtggaag gttcattaca actccaatag atttggtgtc cgtttgattg gacctaaacc    4020
taagtgggca agaagtaatg gtggtgaagg tggtatgcat ccttcaaaca ctcacgatta    4080
cgtttattct ctgggtgcaa ttaatttcac gggtgatgag ccagttatta ttacttgcga    4140
tggtccttcc ttaggtggtt ttgtgtgtca agctgttgtc ccagaagcag aactgtggaa    4200
ggttggacag gttaaacccg gtgattccat tcagtttgtg ccactttctt acgaaagctc    4260
gagatcctta aaggaatctc aggatgttgc aattaaatca ttggatggta ctaagttaag    4320
gcgcttagac tctgtttcaa ttttaccatc attcgaaacg cctattcttg cacaaatgga    4380
aaaagtgaat gagctttcac caaaggttgt atacagacaa gcaggtgatc gttatgtttt    4440
ggtggaatac ggtgataatg aaatgaattt taatatttcc tatagaattg aatgcctgat    4500
ctcccttgtg aaaagaata agactattgg tattgttgaa atgtcccaag gtgttagatc    4560
tgtattgata gaatttgatg gttacaaagt cactcaaaaa gaattgctta agtattggt    4620
ggcatatgaa acagaaatcc agtttgatga aaattggaag ataacttcta atataataag    4680
attaccgatg gctttcgaag actcgaagac tttggcatgt gttcaaaggt atcaagaaac    4740
aattcgttcg tctgctccat ggttgccaaa taacgttgat ttcattgcca atgtaaatgg    4800
aatttcaagg aatgaagttt atgatatgtt gtattctgcc agatttatgg ttttaggttt    4860
aggtgatgtc ttcctagggt cgccttgtgc tgttccatta gatcctcgtc acagatttt    4920
gggaagcaag tacaacccaa gtagaacata tacagaaaga ggtgcagtcg gtattggcgg    4980
tatgtatatg tgcatatatg ctgctaacag tcctggtggg taccaattag tgggtagaac    5040
aataccaatt tgggacaaac tatgtctggc cgcatcttct gaggttccgt ggttgatgaa    5100
cccatttgac caagtcgaat tttacccagt ttctgaagaa gatttggata aaatgactga    5160
agattgtgat aatggtgttt ataaagtcaa tatcgaaaag agtgttttg atcatcaaga    5220
```

```
atacttgaga tggatcaacg caaacaaaga ttccatcaca gcattccagg agggccagct    5280
tggtgaaaga gcagaggaat ttgccaaatt gattcaaaat gcaaactctg aactaaaaga    5340
aagtgtcaca gtcaaacctg acgaggaaga agacttccca gaaggtgcag aaattgtata    5400
ttctgagtat tctgggcgtt tttgaaaatc catagcatct gttggagatg ttattgaagc    5460
aggtcaaggg ctactaatta ttgaagccat gaaagcggaa atgattatat ccgctcctaa    5520
atcgggtaag attatcaaga tttgccatgg caatggtgat atggttgatt ctggtgacat    5580
agtggccgtc atagagacat ggcatgagg aaatccatta tgtcatcctc agaagtaaaa     5640
gcaaatggtt ggaccgcagt tcctgtttcc gcaaaagcaa tagtagactc cttgggtaaa    5700
ttaggagatg tctcttcata ttccgtagaa gatattgcct ttccagctgc agacaaattg    5760
gtagccgaag ctcaagcatt cgttaaggct agattatctc ctgaaaccta caaccattca    5820
atgagagttt tctattgggg tactgtcatt gccagaagat tgttaccaga acaagctaaa    5880
gatttgtctc cttcaacatg gcattaacc tgtttgttac acgacgttgg tactgccgaa      5940
gcttatttta cctccactag aatgagtttc gatatctacg tggtattaa agctatggaa     6000 gtattgaagg ttttaggttc cagtacagat caagcagaag ccgttgctga agcaattata    6060
agacatgaag atgttggtgt cgacggtaac atcacatttt tgggtcaatt gatccaattg    6120
gcaacattgt acgataacgt cggtgcctac gacggtattg atgacttcgg ttcctgggtt    6180
gatgacacta caagaaacag tataaacact gctttcccaa gacatggttg gtgttcttgg    6240
ttcgcatgca cagttagaaa agaagaatca acaagcctt ggtgccacac cacacacata     6300
ccacaattcg acaaacaaat ggaagcaaac accttgatga aaccttggga ataagtttaa    6360
actaatccca cagccgccag ttccgctggc ggcattttaa ctttctttaa tgggcgcgcc    6420
tttccatagg ctccgccccc ctgacgagca tcacaaaaat cgacgctcaa gtcagaggtg    6480
gcgaaacccg acaggactat aaagatacca ggcgtttccc cctggaagct ccctcgtgcg    6540
ctctcctgtt ccgaccctgc cgcttaccgg atacctgtcc gcctttctcc cttcgggaag    6600
cgtggcgctt tctcatagct cacgctgtag gtatctcagt tcggtgtagg tcgttcgctc    6660
caagctgggc tgtgtgcacg aaccccccgt tcagcccgac cgctgcgcct tatccggtaa    6720
ctatcgtctt gagtccaacc cggtaagaca cgacttatcg ccactggcag cagccactgg    6780
taacaggatt agcagagcga ggtatgtagg cggtgctaca gagttcttga agtggtggcc    6840
taactacggc tacactagaa gaacagtatt tggtatctgc gctctgctga agccagttac    6900
cttcggaaaa agagttggta gctcttgatc cggcaaacaa accaccgctg gtagcggtgg    6960 ttttttttgtt tgcaagcagc agattacgcg cagaaaaaaa ggatctcaag aagatccttt    7020
gatcttttct acggggtctg acgctcagtg gaacgaaaac tcacgttaag ggattttggt    7080
catgagatta tcaaaaagga tcttcaccta gatccttta aattaaaaat gaagttttaa     7140
atcaatctaa agtatatatg agtaaacttg gtctgacagt taccaatgct taatcagtga    7200
ggcacctatc tcagcgatct gtctatttcg ttcatccata gttgcctgac tccccgtcgt    7260
gtagataact acgatacggg agggcttacc atctggcccc agtgctgcaa tgataccgcg    7320
agacccacgc tcaccggctc cagatttatc agcaataaac cagccagccg gaagggccga    7380
gcgcagaagt ggtcctgcaa ctttatccgc ctccatccag tctattaatt gttgccggga    7440
agctagagta agtagttcgc cagttaatag tttgcgcaac gttgttgcca ttgctacagg    7500
catcgtggtg tcacgctcgt cgtttggtat ggcttcattc agctccggtt cccaacgatc    7560
aaggcgagtt acatgatccc ccatgttgtg caaaaaagcg gttagctcct tcggtcctcc    7620
```

```
gatcgttgtc agaagtaagt tggccgcagt gttatcactc atggttatgg cagcactgca      7680
taattctctt actgtcatgc catccgtaag atgcttttct gtgactggtg agtactcaac      7740
caagtcattc tgagaatagt gtatgcggcg accgagttgc tcttgcccgg cgtcaatacg      7800
ggataatacc gcgccacata gcagaacttt aaaagtgctc atcattggaa aacgttcttc      7860
ggggcgaaaa ctctcaagga tcttaccgct gttgagatcc agttcgatgt aacccactcg      7920
tgcacccaac tgatcttcag catcttttac tttcaccagc gtttctgggt gagcaaaaac      7980
aggaaggcaa aatgccgcaa aaagggaat aagggcgaca cggaaatgtt gaatactcat      8040
actcttcctt tttcaatatt attgaagcat ttatcagggt tattgtctca tgagcggata      8100
catatttgaa tgtatttaga aaaataaaca gcgatcgcgc ggccgcgggt aataactgat      8160
ataattaaat tgaagctcta atttgtgagt ttagtataca tgcatttact tataatacag      8220 tttttttagtt ttgctggccg catcttctca aatatgcttc ccagcctgct tttctgtaac      8280
gttcaccctc tacctttagca tcccttccct ttgcaaatag tcctcttcca acaataataa      8340
tgtcagatcc tgtagagacc acatcatcca cggttctata ctgttgaccc aatgcgtctc      8400
ccttgtcatc taaacccaca ccgggtgtca taatcaacca atcgtaacct tcatctcttc      8460
cacccatgtc tctttgagca ataaagccga taacaaaatc tttgtcgctc ttcgcaatgt      8520
caacagtacc cttagtatat tctccagtag ctagggagcc cttgcatgac aattctgcta      8580
acatcaaaag gcctctaggt tcctttgtta cttcttccgc cgcctgcttc aaaccgctaa      8640
caatacctgg gcccaccaca ccgtgtgcat tcgtaatgtc tgcccattct gctattctgt      8700
atacacccgc agagtactgc aatttgactg tattaccaat gtcagcaaat tttctgtctt      8760
cgaagagtaa aaaattgtac ttggcggata atgcctttag cggcttaact gtgccctcca      8820
tggaaaaatc agtcaagata tccacatgtg ttttagtaa acaaattttg ggacctaatg      8880
cttcaactaa ctccagtaat tccttggtgg tacgaacatc caatgaagca cacaagtttg      8940
tttgcttttc gtgcatgata ttaaatagct tggcagcaac aggactagga tgagtagcag      9000
cacgttcctt atatgtagct ttcgacatga tttatcttcg tttcctgcag gttttttgttc      9060 tgtgcagttg ggttaagaat actgggcaat ttcatgtttc ttcaacacca catatgcgta      9120
tatataccaa tctaagtctg tgctccttcc ttcgttcttc cttctgctcg gagattaccg      9180
aatcaaagct agcttatcga tgataagctg tcaaagatga gaattaattc cacggactat      9240
agactatact agatactccg tctactgtac gatacacttc cgctcaggtc cttgtccttt      9300
aacgaggcct taccactctt tgttactct attgatccag ctcagcaaag gcagtgtgat      9360
ctaagattct atcttcgcga tgtagtaaaa ctagctagac cgagaaagag actagaaatg      9420
caaaaggcac ttctacaatg gctgccatca ttattatccg atgtgacgct gcagcttctc      9480
aatgatattc gaatacgctt tgaggagata cagcctaata tccgacaaac tgttttacag      9540
atttacgatc gtacttgtta cccatcattg aattttgaac atccgaacct gggagttttc      9600
cctgaaacag atagtatatt tgaacctgta taataatata tagtctagcg ctttacggaa      9660
gacaatgtat gtatttcggt tcctggagaa actattgcat ctattgcata ggtaatcttg      9720
cacgtcgcat ccccggttca ttttctgcgt ttccatcttg cacttcaata gcatatcttt      9780
gttaacgaag catctgtgct tcattttgta gaacaaaaat gcaacgcgag agcgctaatt      9840
tttcaaacaa agaatctgag ctgcattttt acagaacaga aatgcaacgc gaaagcgcta      9900
ttttaccaac gaagaatctg tgcttcattt ttgtaaaaca aaaatgcaac gcgacgagag      9960
```

```
cgctaatttt tcaaacaaag aatctgagct gcattttttac agaacagaaa tgcaacgcga    10020
gagcgctatt ttaccaacaa agaatctata cttctttttt gttctacaaa aatgcatccc    10080
gagagcgcta ttttttctaac aaagcatctt agattacttt ttttctcctt tgtgcgctct    10140
ataatgcagt ctcttgataa cttttttgcac tgtaggtccg ttaaggttag aagaaggcta    10200
ctttggtgtc tattttctct tccataaaaa aagcctgact ccacttcccg cgtttactga    10260
ttactagcga agctgcgggt gcattttttc aagataaagg catccccgat tatattctat    10320
accgatgtgg attgcgcata ctttgtgaac agaaagtgat agcgttgatg attcttcatt    10380
ggtcagaaaa ttatgaacgg tttcttctat tttgtctcta tatactacgt ataggaaatg    10440
tttacatttt cgtattgttt tcgattcact ctatgaatag ttcttactac aattttttg    10500 tctaaagagt aatactagag ataaacataa aaaatgtaga ggtcgagttt agatgcaagt    10560
tcaaggagcg aaaggtggat gggtaggtta tatagggata tagcacagag atatatagca    10620
aagagatact tttgagcaat                                                10640
```

<210> SEQ ID NO 22
<211> LENGTH: 4127
<212> TYPE: DNA
<213> ORGANISM: Pseudomonas stutzeri

<400> SEQUENCE: 22

```
atgacgcccc atccgataca ggacgccgtg ctgcgggtcg accggttgag cgtcgtctat      60
ccaggcggcg tgacagccct acgcgatacc tcgattgcat tcggcgtgg tgagttcacc     120 gtgctgcttg gtctctcggg cgcaggcaag tcgaccttgc tccgtagtct caatcgactc     180
gtcacgccca ctggcggcag tgtcaccagc gaactcggtg aactcggcag cggctcggcc     240
ttgcgtcagc atcgtcggcg taccgccatg atctttcagc accaccagct aatcgaacgt     300
caaagcgcac tggctaatgt gctgaccggt cggctggcct tcacaacac gctccgctcg     360 ctgtttcctc tgccgcgtgc cgatcaggag attgcgctca gttgcctcgc tcgggtcggt     420
ctggcagaca aggcgctaag ccgggtggac aaactgtccg gtggccagca gcagcgggta     480
ggcatcgcgc gtgcgctagc gcaacagccg gcgatcattc tggccgatga gccggtagcc     540
agtctcgacc cggccacttc ggtccgtgtt ctcggattgc tgcgcgacat ctgcaaggaa     600
gacggcatca ccgccatcgt ttcgctgcat caactcgaat atgcccgccg cttcgccgat     660
cgcgtcgtcg ggctggccga ttctcagatc gttttcgatg ccgcgccctc ggaactcacc     720
gatgcgcagc ttgagcgcat ctatgcaggc cgctctacga ctcagccagc gaatgctccg     780
gctgaaccac ctgtcatgct cgaaccttca ctggagatgt cccgatgaaa cgcttatccg     840
cgctcttatt gacttgcttg ctgtccgctg tttcaagttt gtccgcccta gcggccgatg     900
ccgatccgga tgtgctaaag gttgccctgc tgccggacga aaacgcctcc gagctgatca     960
agcgtaacca gccgctgaag gattatctgg aagagcatct ggacaagaag gtgcagctga    1020
tcgtaaccac cgactattcc tcgatgattg aggcgatgcg ctttggccgt atcgacctgg    1080
cgtatttcgg tccgctgtcc tacgtcatgg ccaaaagcaa aagcgacatc gagcccttcg    1140
ctgccatggt catcgacggc aagccgacct atcgctcggt gattatcgcc aatgtggcgt    1200
caggcgtgaa tgagtatgcc gaccttaagg gcaagagaat ggcctatggt gaccgggcat    1260
cgacgtccag ccatttgatt cccaaaaccg tgcttcttga cggccgat ttgacgggtg    1320 ggcaggacta cgaacaacat tttgtgggca cgcatgacgc cgttgccgtc aacgtggcga    1380
acggcaacgc cgatgcgggt gggctgtcgg aggtaatttt caatcacgca gccgaacgtg    1440
```

```
gcctgatcga tccgagcaag gtgaaagtac ttggttacag cggcgaatac ccccagtacc    1500
cctgggcgat gcgctcgaac ctgagccccg agctgaaaac caaggtgcgg gatgtattcg    1560
tcggtatcga cgatcccgaa gtgctgcgca acttcaaggc cgaggccttc gcgccaatca    1620
ccgacgccga ctacgatgtg atccgcaaca tgggatcgct gctcggcctc gacttcgcca    1680
cgatgtgagc accgatatgt cttctcatta cgacgtgcag gcgctgcctg cagagcaacg    1740
cgagcacatc cttcgaggct tcggcctcgg ttggtggcgc cagctggggc aggtggcgat    1800
tgtattcgga gtggtgctgt tggcctgctg gtacgtgggg ctgctcgatg ccaccacgct    1860
gctgaacggg ctgcccctcca tcgcgaccct ggcaggcgag gccatgccgc cagacttttc    1920
gggctatcga agctggattc gccccttgat cgacaccttg gcgatgagca tcgccggtac    1980
ggccatcgca gtggtgttct cgctggtggt ggccttcgtt gcagcgcgca atacggcgcc    2040 gcacccccctt gtgttcggtg ttgcccgggt gctgctcaat gccctgcggt cggtgccgga    2100
gctgatcatg ggcatcatct tcgttgcagc cgtagggttc ggcgccttgc cgggcgtgct    2160
tgccctgggt ctgcattcgg tcggcatggt cggcaagttc ttcgccgagg ccatcgagca    2220
cgtcgacgaa gcgccggtgg aagccgctcg ggcggcgggg gctacgccga tgcaagtgct    2280
gctgcacgcg gttttgccac aggtgacgcc gcagttcgcc gacgtggcga tctaccgctg    2340
ggaatacaac tttcgcgcct ccaccgtgat gggcatggtt ggcgccggcg gtatcggctt    2400
cgaactcatg ggctcgctgc gcatcatgca gtaccaggag gttgcagcaa tcctgctggt    2460
catcctggcc atggtcacgc tagtagacgc cttcagtggc gtgctgcgca aacatttcaa    2520
ataggacaaa ccatgctgcc gaaactcgtt ataactcacc gagtacacga tgagatcctg    2580
caactgctgg cgccacattg cgagctgatg accaaccaga ccgacagcac gctgacgcgc    2640
gaggaaattc tgcgccgctg tcgcgatgct caggcgatga tggcgttcat gcccgatcgg    2700
gtcgatgcag actttcttca gcctgcccct gagctgcgtg tagtcggctg cgcgctcaag    2760
ggcttcgaca atttcgatgt ggacgccgtg actgcccgcg gggtctggct gaccttcgtg    2820
cctgatctgt tgacggtccc gactgccgag ctggcgatcg gactggcggt ggggctgggg    2880
cggcatctgc gggcagcaga tgcgttcgtc cgctctggcg agttccaggg ctggcaacca    2940
cagttctacg gcacggggct ggataacgct acggtcggca tccttggcat gggcgccatc    3000
ggactggcca tggctgatcg cttgcaggga tggggcgcga ccctgcagta ccacgaggcg    3060
aaggctctgg atacacaaac cgagcaacgg ctcggcctgc gccaggtggc gtgcagcgaa    3120
ctcttcgcca gctcggactt catcctgctg gcgcttccct tgaatgccga tacccagcat    3180
ctggtcaacg ccgagctgct tgccctcgta cggccgggcg ctctgcttgt aaacccctgt    3240
cgtggttcgg tagtggatga agccgccgtg ctcgcgcgcg ttgagcgagg ccagctcggc    3300
gggtatgcgg cggatgtatt cgaaatggaa gactgggctc gcgcggaccg gccgcggctg    3360
atcgatcctg cgctgctcgc gcatccgaat acgctgttca ctccgcacat agggtcggca    3420
gtgcgcgcgg tgcgcctgga gattgaacgt gtgtgcagcgc agaacatcat ccaggtattg    3480
gcaggtgcgc gcccaatcaa cgctgcgaac cgtctgccca aggccgagcc tgccgcatgt    3540
tgaatccggt ctggctgaag agcctggtag cgatcgttca acaggcagt tttcagagcg    3600 cggcgagggc gttggggctg gcccagccga cggtgtcgca gcacttgcag aagcttgaag    3660
agcaggtcgg cgtaacgctg gtgcagcgca gtcgtagcgg ctgccagcct accacacggg    3720
cgctggcctt catgccgcat gcgaccgcct tgctcgacat gcacgcccgg gcgctagaag    3780
```

| | |
|---|---:|
| ccctgcatgg caatcgtgag cgcgtcgggg ccagctccaa catcggcacc taccttctcc | 3840 |
| agccattcgt gcgcaactat ctgacgaccg caaatgagag gggcgaggtg gatctgcgca | 3900 |
| tcgccgccaa cccggatgtg gccgaccagc tactggcggg ccagctcgac gccgcgatca | 3960 |
| tggaatggtg gctacctcac cccgacttcg aataccgcct ctggcgggtc gagccgctgg | 4020 |
| tgcttatcgt cagccccgac catgcgctgg ctgaagcagg gtgcatagaa cgtgatcgtc | 4080 |
| tggtggacct gccgatgctg ggaggtgaac cgggtagcgg tacctag | 4127 |

```
<210> SEQ ID NO 23
<211> LENGTH: 13771
<212> TYPE: DNA
<213> ORGANISM: Pseudomonas stutzeri

<400> SEQUENCE: 23
```

| | |
|---|---:|
| atgtttgcag agcagcaacg cgaatatctc gacaagggat atacgaagat tgaaagcttt | 60 |
| ttctccgcgg aggaagtagc gaagattctt gaagacgtca agcaaattga attgggagct | 120 |
| attggcgtag cttcggacaa tgagacttac cagttcgaaa agaagaatgg cgagacgacg | 180 |
| aagctactgc gtcgcgtcga gaatcctcac ctttatttcg atgcaataga ttctttggtc | 240 |
| aggtcggaaa aaatcgtcga tttgcttcgg catttcctgg gcgaaaacat ccgtttgcac | 300 |
| aatagcaaaa tcaacttcaa gccgccatca ggcgcgccag tccagtggca tcaggactgg | 360 |
| gcattctatc cccacacaaa cgatgatttt cttactctcg aattttcct cgacgagaca | 420 |
| agtgagaaaa atggcgcgat ggcatgcttg ccaggctccc acaaggaaa agtgtacgac | 480 |
| caccggaacg tcgagacggg cgagttttgc cacgcgatct ctcgctccaa ctgggacgaa | 540 |
| gcgctcgacc cgacagaagg ggagttactg acgggacccg taggaactgt cacgttgcat | 600 |
| cacgtccgga cccttcatgg ttcaggccca aaccactcaa cgatcaggcg cgttttctg | 660 |
| ctcatcggct atgccgcggc tgatgcctgg ccacttctgg gctgtggcaa ctatgggat | 720 |
| tatgaaagcc tcatggtctc tggccgatcc accgtattcc cgcgcatggt ggaactccct | 780 |
| ttgactgtcc cgtatccgtt gtcgatgtac ggtgatcgca tctttgaaag tcaacgagct | 840 |
| ttgactcaaa agtactactg aagtctttaa ctcactgagg tcataatgca gttttttact | 900 |
| ctgttttcga aattcaagaa ggcgttaacg cgcgccattc ttgcctttat cgccacaatc | 960 |
| atagtgtgca cacccgcgca ggcagctgag gttgtcaatg gtaaacttca cctgcgtttt | 1020 |
| gcaattgcgc cgatgcgtcc aacgcctagc cagaccatca aagagtttga gccgatattc | 1080 |
| aagtatctcg ccgaccagct cggcgcgacc tatgaaatcg tctccccgga agctggggcg | 1140 |
| gcaatatctg tggcaatgac aaatggccat gtcgatgtgg gctggctcgg accctggggc | 1200 |
| tatgtcttgt cgaataaaaa ggccggcacc gaagtgcttg caacggtcaa gtaccgcggg | 1260 |
| gagccgttct acaaagccct cattgtcggt cgcgccgatc tgccgatcaa aaaatggccc | 1320 |
| gaggacgcga agggtttgaa gctgtcactc agtgatcagg gcaacacttc tggctggctc | 1380 |
| atcccgatgg cgtacttcaa gagcatcggc atcgaccctg cgagctattt tgaatatcgt | 1440 |
| gaaggtgcca cgtttggcca gaacgaatca cagattcagc acggactgat cgacctcgga | 1500 |
| tccgatatgg atcggggccg gaacgggatg atcgaagcgg gtcaaatcga tccttcgaag | 1560 |
| tccaagatcg tgtgggaatc cagcaagctg ccgaacgacg cgatatccgt gccgaaggat | 1620 |
| tttgatcctc tctgaaagc gcgcatcacg gaaatactga cgtccttgtc cgaagagaaa | 1680 |
| gcacagtcgc tgatgggctc gggctataac ggcttcgtga aggcaaagca cagcgattac | 1740 |
| aaggtaatcg aagacgccgg ccgcatcctg gaaaaactgt aaagcacgag gggtccgttc | 1800 |

```
ttggatgagg gcagcggacg acaaggtgga ctgacgcacg ccagctcctt gtctccgctg    1860
cacgaacata cgggcgcgca tcgcaatacc acagaggatg aaccaatgaa tcagcgaatc    1920
gaagaagtca tgctggctaa tgtcaagagg gacgtagcca ggagaaagcg gcattttgca    1980
acgtcggtcg tagtactcag tttgctggca gtggcctggt acgtgtgtca gatagaattc    2040
cagaagctag gcgccggttt accgagacta tggtcattcg tcgtgcagat gtttccaccc    2100
gacctgagcg acctggacgt cattctaaaa ggggctggcg agacgctcgc catggcgacg    2160
attggcacga tattcgccac aatcattgca tttccgctgg cactcatggc tgcgcgtaat    2220
acctgtccga acaagtggac ctatcgggta tcccgcgcca tcctgaacgc cagccgcggc    2280
acggagacat tgtctatgc acttgtattt gtagcagcag tgggcttcgg tccgttctcc    2340
ggcgtactgg ccattacttt ccacatggta ggggcaatcg gcaaaatgtt tgctgaagcc    2400
atcgagcccg ttgaccaagg gccgttggat gcgctcgcct tgaccggtgc cagcagggca    2460
aagattatcc gctacggtct gatcccggat gttatgccgc acctgatcgc gagcgttcta    2520
tacatttggg aattcagtgt cagaacgtcc acagtactgg gcatcgtagg cgcaggtgga    2580
attgggcaga ccctgaaaga tactgtggac ttgttggaat tcaacaagat gattacggta    2640
ctggcggttg tattgctgat ggtgtcggca atcgatttca tcagtgaccg gctcaggtac    2700
ttgatattgg acacaaaacg cgagggattc gaaactctcc ctgcgaataa ctgattgctt    2760
cacgtattac tggaagggag gttcgcaatg aaagatgtag cgttgcagtt aaagaatgtc    2820
ggtaagtcat acggcaataa agttgtcctg gaatcgattg acttcgaagt acgtcacggc    2880
tcaatggttg ccttgctcgg cacaagcggg gcagggaagt cgacgctttt ccgatgtctc    2940
actggccttg agccgattga ctccggttct atcgtggcgc tcggagaatc catacatgaa    3000
ctgtctccgg cgcgtctgcg ggcagtacgt ggccagatcg ggttcgtgtt ccaacaactg    3060
cacctggtga aaaggttctc agcactcgag aatgtattgg gtgcgcgtct ggcagagatg    3120
cccatttggc gcgtcacatt gaaaagcttc agccgggctg acaaagtgct cgcgttcgaa    3180
tgtctggacc gggtcggcat gctcgattat gcaaacacgc ctacgcaact gctgtcaggc    3240
ggtcagcaac agcgtattgc gatagcgcga gccttggcgc agaagcccaa gattattatt    3300
gcggacgaac ccgtctccag cctcgatccg ctgacggcgc gctcggttct gcaaacgctg    3360
aaagccgcgg ctacagatct taatgtcgcg gtcctgtgca gcctgcacca ggtagacctg    3420
gcccgtgagt ttggcgaccg catcgtgggc atgcgcgacg gacgtgtcgt tttcgacggc    3480
acgccagcgg aattcaccga cgagcgcgtg catgcgcttt accaggtgcc cgctgggaag    3540
atgcaccagc ggccgagagc gacgcgcagc actcggtggc cggtctggct gtggcatgag    3600
gggcgaagcg atgaccacat ccacacgccc catacccgtg ccgccccagg gcaccgcact    3660
gcactggcac ctgagcgcgc cctacaacgc caaacatctg ctggtgctga tcgccgtcat    3720
ggtgctgttg ttcgtgaccg gacaacgcac cgaaatggac cgcatggtgg ccatgacggc    3780
acaggccgtg gccaagaccg tgggcctggc tgacgattca caagtcgcgc gcggcttgtc    3840
gcgcgtcggt caagccatgt ggccaccgc catcgcagaa accgaagagg tgggccggat    3900
tcaggacctg gatcgccaga agctgcccct gttctcgcac atcgagaccc aggagcgcgt    3960
cgagcagaag atgaatctgg acacgctgaa gatggaagcc acgacggaaa ccgtcgaagt    4020
gctggtcaag ccggtcggct atgtctggac ggttttcatc aagatgatcg agacctggag    4080
attgcgctgt ggggcacgat cctgtcggtg ctggtgtcga ttcccctggc gtatttcgcg    4140
```

```
gcccgcaact actagcccca accgttttac ctacaccgct gcccgcggca ccatcagtct      4200
gctgcgttca gcgccggaac tcatcgtcgc tttgttcctg gtgctggcct acggctttgg      4260
ccccatcgct ggcgtgctgg cgctgggcct gcatgcggcc ggcttcctgg gcaagttcta      4320
cgccgaggac atcgagaacg ccgacaagaa gccgcaagag gcgctggagg ccatcggcgc      4380
gggcaagctc aagacgctgt ggtacggcgt catcccccag gtcttgccgc aatacatcgc      4440
ctacaccgcc tacatcctgg accgcaacct gcgcatggcc accgtcatcg gtctggtggg      4500
cgcgggcggc atcggccagg aactcaaggg ccgttttgac atgttccagt acggccatgt      4560
catgaccatc ctgatcgcga tcttcgtctt tgtgttcgtg ctggaccagt tgcaggcgcg      4620
catccgcgcc aagctgatct gaggcgaccg ctgacaacaa ggaacaacat gacaaacact      4680
tctgaagcac cggatcgtgc gcagtggctg cggctgtggt cggccttgcc ggccgcagcg      4740
gtcaaggccc tggcggccga tctggcgggc cagcaccggg tcgaagacct ggcgttgccg      4800
caatccggtc tgggcctgct gccgctgacc gacagcgccc tgggcgatac ctatttcatc      4860
ggtgagattc ccttggcaca agcgcatgtg cgggtcacga ccacccaagg gcagtcgatc      4920
gaaggcgcgg ccattctggt ggacgaccgt gccggtgtgg cccgttccat ggccatcctg      4980
gacgcggtgc tggcggcccg catgccaggt tgtgaagcgg ccctgcggtt gctcacccag      5040
ggtgcgaccg ccgtggcgga acaaggccgc cagcgccgcg ccttactcgc ggccacgcgg      5100
gtggactttg ccctgctggg aacgaacgag gaggacgatg atgaatgaga ctgggatggc      5160
ggcggcaccg gcagaagccg cgtggcgcat ctggcaagcg ccgcgccagc aaacggcgtt      5220
tcgccagttg atgaccgcgt tttcctatcc gggccgcgtg gtgccactgg ccgatgcgc       5280 tgaatcggcg ctcctgctgg tgttgaccac cctggtggac agcgcctgtg cgctggccga      5340
tccgctgcac gcgctatcaa gcgacgatct gcgccgactg ggcgtgcgct cggccagtgt      5400
ggaggcggcc gagttcgtgc tggccgatgg caaccgtttg ctggaggcca cgccgcgcct      5460
gggatcgctg gaaaaccccg aacaaggcgc gaccgtggtg atgcgcgtct cccgtttcgg      5520
tgagggtccc catctgcggc tcaccgggcc gggtattcaa cacgagcagg tgctgcaggt      5580
cagcggcatc gatccgggct ggtggaagca acggtccgaa tggaatgccc acttcccgct      5640
gggcgtggac ctgattctgg tgagcgggca cgaggtcgcg gtattgcccc gaaccaccca      5700
catcaacctc aaaggagccc actgatggga tacgttgcca tcaagggcgg tggccgggcc      5760
atcgccggtg ccgaagccgc cgtcgaagcc ctgcgctgcg ccgaagggcc agcgggtacg      5820
ccgctcacgc tgtcggccat cgaacagcag ttgcggttgc tgacatcgcg cgtcgtgtcg      5880 gaaggggcc tctaccaccc acgcctggcc gctctggcca tcaaacagat gcagggcgac       5940
acactggaag cggcgttcgc tctgcgcgcc taccgctcca ccaagccacg cctgatggat      6000
gtgccggtgc aggacacgag ccgcatgcgc ctaatccgcc ggatttcgag cgcttttcaag    6060 gacatccccg cgcgacagat gctgggcccg accaccgact acgcgctgcg cctgatgcgt      6120
ctggatttgg ccaacgagtc gcccgaggac tttcgcgcgg tctcgcggcg gtttctggac      6180
agcgtggccg acaccgacct gcccgacagc ttccccaagg tggtcgatgc cttcgtgac       6240 gaaggcttgc tgccgccgct gacccggcgc gcccatgcgg cgttcgacat cacccgcgac      6300
ccgctggttt tcccagtgcc gcgttcggcg gccctggcca ccatggcacg cgccgaaacc      6360
ggctcgctct tggcgattgc gtattccaac atgcgtggct atggcgacgt gcacccacc       6420 atcgccgagc tgcgcgtggg ctatgtgccg gtgatgctgc cgcacccggt gacaggcgag      6480
cccatcgaag ccggtgaggt actgatgacc gaatgcgaag tggtggccat gtttgagggt      6540
```

-continued

```
gatgctaccg acggcccacc cactttcacc ctaggctatg cgcctgtttt cggtcacaac    6600
gaagtcaagg ccatcgccat ggccatcctc gaccgcgccc tgcaaaaggg tatgcgcgac    6660
ggtcccagca acccgtcgga agacccggaa ttcgtgctgc tgcacgtcga tggcgtggat    6720
tcgatgggct ttgccagtca ctacaagatg ccgcactacg tgaccttcca gtccgacatg    6780
gaccggctgc gcaccacgca ggacaaggca accgcacaac cgacccaaga aggagcgcca    6840
tcatgaaccc gggctacgaa ctgccccctgg acgaggcggg ctacagcttc ggcttcctgg    6900
acgaatacgc caagcgcgag gtgcgccgca ccatcctcaa ggcgatcagc atccccggtt    6960
accagacgcc ctatgcctca cgcgaaatgc ctatggggcg cggctttggc accggcggtc    7020
tgcaggttac gctgtcgctg attggcgagg gcgacaccct gaaggtgatc gaccagggcg    7080
cggacgactc cgtcaacgcg gtgaacctgc gtcactttgt ggaactgacc tgcccggggcg    7140
tggacaccac agaacacacg cttgatgcca ctctgatcca gtcgcgccac cgcattccgg    7200
aaacgccgct gaccgaagcg caggtgttga tcctgcaagt gccgtatccg acccactgg    7260
tggtggtgga accctccgag gctcgacgca aggtcatgca cggcgaaggc gactattcgc    7320
ggctgctgac caagctgtac gaggacatcg tgcagtttga cgagatcacc atctcgcacc    7380
gctaccccac gcgcatcaac ggccactatg tgatcgaccc cagcccgatc ccgcgctacg    7440
acgtgccgca gttgcaccag agccggcgc tgatcctgct gggtgcgggg cgcgagaaaa    7500
aaatctatgc ggtgccgccg tacacccgcg ccgacccgct ggcgttcgac gacgtgccat    7560
tccgcaccga agacttcacc aacgaacacg gccagcgccg cgcctgcgaa cggtgcggcg    7620
ccaccgacag cttcctcgac gagctcattg ccgacgatgg cggcaagcac tggcattgct    7680
cggactcgga ttttttgcaat agccgtatgg cccgccaggc tgaacaagct caggagacca    7740
cggtatgaaa aaaattctgg aagtacgcgg actgaccaag atccacggcc ggggttgcga    7800
actctgcctg gagagcactg gccccgacat ggacaccaac atctgcccac actgtggctc    7860
ggtggtggcc tgccacaaca tcagcctgga cctgcacgag ggcgagatcc tcggcatcat    7920
gggcgagtcc ggcagcggca agtccaccgt ggtcaagacg ctgttcttcg acgatgagcc    7980
caccgctggt gaagccctgt ttttgacggg cgagcgccag tgggacatgt tcgcgctcaa    8040
cgccgcgcag cagcgctggc ttgcgcaacc accgcttttgg catggtgtac cagaacccgc    8100
atctgggact caatttcaac gtctcggccg gcggaaacat ttgccgagcg ccttgctgat    8160
gagcgacctg gcccactacg gcgaaatccg cgaacgggcg cgcagcttgt tggcgcgcac    8220
tgaggtgttg gcagaacgca tggacgagtc gcccaagaag ttctcgggcg gcatgcagca    8280
gcgcgtgcag atcgccaagg cactggccac ccagccgccg ctgctctacc tcgacgaggt    8340
caccaccggc ctggaccttt cggtgcaggc gcgcatcctg gacctgattc tggaaatcca    8400
gcaggagctg ggcaccgcca tgatcgtggt cacccacgat ctgggtgtca tccgcctgct    8460
gaccggacgc acgatcgtca tgaaatacgg ccgcggtcat cgaagtccgg gctgaccgac    8520
cagatcctcg aagacccca gcacgcctac acccagcgcc tggtcgcgtc ggcttctctg    8580
aggaaacctg aatcatgcaa gaagccatcc tcaaaatcga aggtctctcc aaacagttcc    8640
agctgcacga ccagaacaaa ctgatcccgt cgtgtgcaca ggttcaactg gaggtgtttg    8700
ccggcgagct gaccgcgctg atcggcccga ccggcgccgg caaatcgtcg gtgctcaagg    8760
ccatttaccg cacctacctg cccagcagtg ggcgcatcct ttaccgggac gccaacggtg    8820
ccatcaccga tctggcccag gccagcgaac accgcatgct ggagctgcgc aagcaggacc    8880
```

```
tgggtttcgt cacccaattt ctgcactgtc taccgcgcaa gtcggcggtc gaggtagtgg    8940
ccgagccgct ggtgcagcgg ggcagcccgc gcgaagctgc tgccgagcgc gcgcgcgaac    9000
tgctggccct gctcaacgtg ccggaacgct tgtgggcggt accacccgcc accttctcgg    9060
gcggcgagaa acagcgcgtc aacctggcac gcgggctgat cgcccggcct cggctgctgt    9120
tgcttgacga acccacggcc agcctagacc cgtccaccac cgaccgcgtg gtggagctgt    9180
tgaagtccat caaggccgaa ggcgtggcca tgctggccta cttccacgac ccgaacttg     9240
tccgacgcct ggccgatcgc gtcgtaaccc tcacgccccc ggtgtctgcg gcggcattgc    9300
tggagacctg tgcctcatga atcccatttt gctgacccat gcccgcgtgg tgttccccac    9360
cgaagtccgt gacaacgtgg ccatcctgat cgaaggcgac accatcacag catcgacccg    9420
gccagcagcg caggtgccac cgagatcgac ctgcgcggct cgcaccctga tgccaggtct    9480
gatcgacctg cactgcgacg caatggagaa agaggtggag ccgcggcccg gcgtgcactt    9540
cccgctggag ttcgcctgtg cccaggccga caagcgcaat gcggcggccg gcatcacgac    9600
ggtgtttcat gccctgtcct tgccaaccac cgagctgggc gtgcgcaaca acgccttcgc    9660
cgccgagatc gcccgttcga ttggcgactg gcaggcccat gccctgatcg acaaccgggt    9720
gcatgtgcgt tacgaggtga cggacgaaac ggcgccgccg gtgctgtcgg cgctgctgca    9780
ggacggtcat gcgcacctca tgtctttcat ggatcacagc cccggtcagg gtcagttccg    9840
cgatgtcgag gcgtaccgcg cctacctggc caagacctac aagaccgatg aggcgcagat    9900
cgacgacatc ctggcgcgca aagccggggc cgcacagggc gccatgcggc gcatggagca    9960
gcttgcggaa ctggccgtg cgtgcggcgt gtccattgcc agccacgacg acgacagccc   10020
gcagaaagtg gcgaccgtca aggccctggg cgctgtggtg tcggagtttc cggtgaacct   10080
ggagacggca caggccgccc gtgcacaagg cctggccacc ttgtttggcg ctcccaacat   10140
cctgcgcggc aagtcccagt cgggcaacat gcgtgccctc gatgccgtgc tggccggtgt   10200
cgccgactgc ctgtgcggtg actactcgcc agcggcgctg ttgccgtcgg tcatgcgctt   10260
gcccgatctg gccggcatcc ccctggccga ggctgtggcc ctcgtcacgt gcaacccagc   10320
tcgtgctgca ggtttgcacg accggggcga atcgccgtg ggcaagcgcg cagacctgat    10380
tgcggtcaaa accatgggcg gactgccaca ggccgagcgg gtctggtcgg gcggtaaagc    10440
ttcgctggtc gcgcattttg accacgcctg agagggactg gcacatgcga actcgcctca    10500
tctacgtggt cggcgcctcg gcagcggca aggacacgct catgggccat gcccgccaga    10560
agctggcggg tgatcccagg gtgtgttttg cccatcgcta catcacccga cccgcaacgg    10620
caggcggcga aaaccatgtg gccttgacca cggaggaatt caccgctcgc cagaacggca    10680
agctcttgc catgcactgg tccagccacg gcctgcatta cggaatcggc atcgagatca     10740
accagtggct gggcaaaggc atcacggtgg tgatcaacgg ctcgcgggaa tacctggacg    10800
aggcccgcca acgttacccg gagctgctgc cggtgacgat tgacgtggcc accaccgtgc    10860
tgcgtgatcg gctgctggcc cgtggccgcg aggatgccga atccattgag cagcgcctgc    10920
accgccatga acgttgcgc ctgcagcccg tgcccggtgt gctcatccag aacaacggac    10980
ccgtcgaggt ggccggcgaa gcgctgatcc ggttgatcgc agaacacacc caaggagcgc    11040
cagtatgcgt gtgagttttc tgggcacggg cgctgcgggc ggggttccgc tctacggttg    11100
cacctgccgg gcctgtgaac gcgcaaggac cgagccacac ttcgtccgcc gcccttgcag    11160
cgccctgatt gaatcggag gtaccgggt gctactggat gccgggctga tggaccttca     11220
cgaacggttt gcgccgggta gcctggacgc gattgttctc acgcactacc accccgacca    11280
```

```
cgtgcaggga ctctttcatc tgcgctgggg taagggggacg cccatcacag tctatggccc   11340
accagacagc gaaggctgcg ccgatttgtt caagcaccct ggtgtactgg ccttcgagac   11400
ggtgcacaag ttcgaggcct tcaccgtcgg ggcgctgcgc ctgacgcccc tgccgctgct   11460
tcactccaaa cccacgctgg gctatgccat cgagggcacc cagggccaac gcttcgccta   11520
cctcacagac accctgggtt tgccgccgaa gtcggccaag ttcctgcgcg cctggggcga   11580 cttttgacatg gccatcgact gttcctatcc gccgcacccg accccgaaaa accacaacga   11640
ttgggacgaa gcacatcggt gtgccatcga atctggtgcc cgcatcacct ggctcaccca   11700
tgccggtcat gcgctggacg actggatgat ggaagagacg ccgagcgtcg caagtcatat   11760
ccggctggcc cgggacggca gcacggccga cataccgtcc caaacgcaat gaacgcgccg   11820
ctggcactgg ccctgtcgt  ggccatgcac gtcacctgga acctgatggc acggcatttg   11880
cccagggaat cgaacccgct gtggtgggtg ttgctcgccc atctggtgct gtttgcgccc   11940
tgggggttct gggagctggc gacaaccgtc gtttggtcac tggagatgac gctgctactg   12000
atcgtatcgg ccactgcgaa tgtggtttat ttctccggtc tggccagggc ctacgagcac   12060
gcaccggtcg cactggtcta tcctctggtg cgcagttcac ctcttttcat tgcgatctgg   12120
ggcacgctgt tcttcggtca aaatctcccg cccattgcct ggctgggcat tggcatcagc   12180
gtgctgggct tgctcgtcat ggcatcgagt gctcaacagg ggtcggatcg acgagcattc   12240
cgatgggcca tgctggccat gttggcgaca agcgtttatt ccctgagtga caaggcggcc   12300
accgaacaca tcccaagctt catggggctc gtgggttttc tgtccgtcgg ctacctggca   12360
tcctggatca gcatgacctt gcgcatgcat cggcacaccc gcagttgggt gccggcacag   12420
cgcattgatc tcgcgtcgct ggctcttggc ggaacctgta tcggtctcgc ctacgccttg   12480
gttatccacg ccatgcgcca gttgcctgcg gcggaggtcg tgtcgtacac caacgccggt   12540
atcgtgctcg ctgcagttct ctccattttt ttgttcaatg acaaagtcgg atggcaaaag   12600
agaatcatgg gggtcgtgat catcacgagt ggtttggggg tgcttgccat gaggtgagcg   12660
acacaatacc aaccatcgca caccagcatt ccaacccggc tcgcgacctg ccggtgaagt   12720
aaaagcgact tccgatatgt cccaaatttc ccgatacgtc gaggccgccg agcgtgacaa   12780
cacgcgtcga agctatgccg cagccattcg ccatttcgag gtggagtgga aaggcttgct   12840
gccaacgacc gctgatgcaa cctcccgtta cctggctgac cacgcggcca cgctggcgat   12900 cagcacccctc cgtcagcggc tcgccgcgct ctcgcgctgg cacatcgacc atggttttgc   12960
agacccgacc aaggcaccct tggtgcgcca ggttctcaaa ggcattcgct ccattcactc   13020
ggttgcagaa aagcgggcac gccccctttga aatcgatgtc gtccagcaga tcgatcaatg   13080 gctggggggtg gccatcggca acgcagaacg cagcgatgac cgattggcgc tgcttcgcca   13140
cacccgcaac cgcagtttgc tgctgctggg tttctggcgg ggatttcgat cggacgagtt   13200
ggtcaacctg cgggtggaga acgtggaagt ctcgcctggc gaagggctgt cgtgctacct   13260
gagccgcagc aagggcgatc ggcagatgct gggccgcgta tacaaatgtc cggcgctgtc   13320
ccgcctgtgt cctgtgacgg ctttcacggc atgggtcagt ctggtcggcc tgacccaagg   13380
cccggtgttt cgcaagatcg accgctgggg gcgaatcggt caagaagggc tgcatgccaa   13440
cagcctgatc ccattgttgc gcagcctttt ggctgaggcc ggggtccccg cttccgaggc   13500
atacagcagc cactccctgc gtcgcggatt tgccggttgg gctcgcgcca gcggttggga   13560
catcaaggaa ctcatggagt acgtgggctg gaaggatgtc aaatcggcca tgcgttatct   13620
```

| | |
|---|---|
| ggatgcctcc ggcagcgcac ttcaggcccg gtttgaggcg ggtctcgcaa cactggcccc | 13680 |
| agcagatcga gcggatcggt caccaccgcc ttcgatgcac gcgccggccg agcaaaccaa | 13740 |
| gggaacaggc ccagaggccc cgtctgcctg a | 13771 |

<210> SEQ ID NO 24
<211> LENGTH: 792
<212> TYPE: DNA
<213> ORGANISM: Delftia acidovorans

<400> SEQUENCE: 24

| | |
|---|---|
| atgcacaagt tcatccacat cacggacatt catcttgtcg agcagggtcg cgccctctac | 60 |
| ggccatgacc ccggcaaacg gttcgagcgc tgcatcgaca gcgtgatcgc cgagcacgcg | 120 |
| gacgcagcgt cttgcgtgat cacgggcgac ctcgcacatg tcgggcaccc ggacgcctac | 180 |
| cgccagctgt cggagcaatg cgcgcggttg ccaatgccgg ttcatctgat tctcggcaac | 240 |
| cacgacagcc ggaccaactt ccgcgagcgc ttcccacagg tgccggtgga cagcaatggg | 300 |
| ttcgtccagt acgagcaggc catcggggag ttcaggggtc tgtttctgga taccaacgaa | 360 |
| ccgggaacgc attgcggcgt cttctgcgag caacgggcaa actggctttc ccagcgcttg | 420 |
| gcggaggatg attcaccggt gctcctgttc atgcatcatc cggcattcca ccttggcatc | 480 |
| ccgtcatgg atcgaatcgg attggtcgac aacgaatggt tgctgacggc gttgaagggc | 540 |
| cacgagcacc gcgtcaagca cttgttcttc ggccacatta tcgcccat ctcgggcagc | 600 |
| tggcgcggca tcccgttctc gacattgcgc ggaaccaacc accaggtggc gctgcacctt | 660 |
| cgggaatcgg aagacatccc gggaagcttc gagccaccac agtacgccgt cgtcctgctc | 720 |
| gacgacgatt cggtgatcgt gcacctgcat gactttctcg atcgcagcga gagattctgg | 780 |
| ctaggcgcgt ag | 792 |

<210> SEQ ID NO 25
<211> LENGTH: 4967
<212> TYPE: DNA
<213> ORGANISM: Enterobacter aerogenes

<400> SEQUENCE: 25

| | |
|---|---|
| atgaataagc gctggctccc ctggctgata ctgtcgcctt ccctgttgtt tttactgctg | 60 |
| tttacctggt ttccgcttgg ccgttcggtc tatgacagcc tgtttgatac ccgcatggcc | 120 |
| agcgacggcg cacagtacgt cgggctggat aacttcgccc gctgtttgc cgacggcgtt | 180 |
| ttctggcaat cgctggtcaa taatctgctc tatatcctgc tgacggtggt gcccggcgtg | 240 |
| acgctcgctc tgctgctggc ggtggcgctg agcgagaatc accgcgtcaa ccgctggctg | 300 |
| cgcaccgcct ttttcttccc gatgattatc ccgatggtta gcgccgccgc gctgtggctg | 360 |
| tttattttta tgcccggcct cggcctgctc gatcactatc tggcgaagct atttggccct | 420 |
| cagaacaaca actggctggg cgcagcaac agcgcgctgc tggcgctggc gctgattggc | 480 |
| gtgtggaaat cgctggcta ctacatgctg ttttcctcg ccgggctgca gagcattccg | 540 |
| gcctcaacgc gggaagcggc gctgatggaa ggggccagcc gcacccaggt gttttttaag | 600 |
| gtcacgctgc gctgctgcg cccgacgctg agctttgtta tcaccaccgc gctgatttac | 660 |
| tccattaccc agattgatca cgtcgcggtg atgacgcgcg gcgggccgga taacgccacg | 720 |
| accgtgctgc tctattacat ccagaatctc gcctgggata cccacgacct cggcaaagcc | 780 |
| tccgccgcca ccttcctgac gctggccggg ctgtttgcct tctcgctgat taacctgaaa | 840 |
| ttgctggaaa aaggagccca ctatgagcgc tgaaatctcg ccgctgatgg tccgctcgcc | 900 |

```
cgccgctgcg cgtccgctgt ggttgcgcct gcgtcgctca cagcccttta ccctgacggt    960
aatcatgtgc tgcctggcgc tgctatgggt gagcccgttt atctggatgc tggcgacctc   1020
gttcagcgcc accaccttcg gcgaagatat ggcctcattg ctgccgcgcc tgccgctgac   1080
cctcgataac ttccgcgacg cctgggacag cgccgactgg ctgagcctgt acgccaacac   1140
ccttatcttt accttcggca ctttcttcgt gcagctactc accatcacca ccgccggcta   1200
cgtcttcgcc tgccacgaat tcgcggcaa gaaaatgcta tttctgctgt ttctcgtcca   1260
gctgatgatc atgccggtgg tgatgatggt gccgaacatg ctgaccctga aaaccttcgg   1320
cctgctcaac actctgaccg gcgtgatgat gccttacttt accctcggcgt tcggcgtgtt   1380
tctgatgcgc caggcgttcc tcgccatccc gaaagagctg gaagaggcgg cgctgatgga   1440
gggatgccgc tggtggcagg tgctattccg cgtactgctg ccgatgtcct ggccgtcggt   1500
gctggccttc gccaccgtca gcattaccta ccactggaac gagtacctgt ggccgctgat   1560
gatgctcaac gatcccgata agcaggtgct gacggtcggg ctggtctctt cgccatggg   1620
cgctgaatcc ggcggccagt ggggcaccat cggcgccggg acgctgatgg tctgcctgcc   1680
gctgatgctg gcgttcatcc ttttccagaa acagttcctg cgaagcttcg gcttctccgg   1740
gatcaaataa ggagttattc atgctgttag cgcacatttc cgatacccat ttccgcagcc   1800
gcggcgagaa gctgtacggc tttatcgacg tcaacgccgc caatgctgat gtggtttctc   1860
aacttaacgc gctgcgcgaa cgcccggatg cggtggtggt gagcggcgat atcgtcaact   1920
gcggccgtcc ggaggagtat caggtcgccc gccagatcct cggcagcctg aactatccgc   1980
tgtatctcat ccccggcaac cacgatgata aagcgctgtt tctggagtac ctgcagccgc   2040
tgtgtccaca gctcggtagc gatgccaata atatgcgctg tgcggttgac gacttcgcta   2100
cccgcctgct gtttatcgac tccagccgcg ccggcacttc aaaaggctgg ctgaccgacg   2160
agaccattag ctggctggaa gcgcagctgt tcgagggcgg cgacaaaccg gcaacgatct   2220
ttatgcacca cccgccgctg ccgctgggca atgcgcagat ggacccgatt gcctgcgaaa   2280
acggccaccg tctgctggcg ttggtagagc gtttcccgtc gctgacgcgc atcttttgcg   2340
gtcataacca tagcctgacc atgacccagt atcgccaggc gctgatctcc accctccccg   2400
gcaccgtcca tcaggtgcct tactgccacg aagacactcg cccgtattac gatctctcgc   2460
cggcttcgtg cctgatgcac cgccaggtcg gcgagcaatg ggtgagctac cagcactcgc   2520
tggcccacta cgccgggccg tggctgtacg acgaaaacat cagttgtcca acggaagagc   2580
gctaaccgcc atgctcagtc tgcaaaacat cagtaaacat ttcgacggta accggcgct   2640
cagcgcgctg tcgcttgata tccacgaagg tgaatttgtg gtgctggtcg gcccgtcggg   2700
ctgcggtaaa agcaccctac tgcgcctgct gccgggttg gatcaggtca gcgaaggcga   2760
aatctggctg catgatgaga acatcaccga caccacgccg cgcgaacgca ttttgcgat   2820
gatcttccag aactatgcgc tgtttccaca tctctctgtg cgcgacaaca tcaccttcgg   2880
catgaaggta cgcaaggaag agaaaagcgg ctggcagccg cgggtagata agtggcgca   2940
gatgctgcag ctggaggcgc tgctcgatcg caaaccggcg aagctctccg gcggccaacg   3000
gcagcgggta gcgatggcgc gggcgatcgt gcgtaatccg cggctgttct taatggatga   3060
accgctgtcc aacctcgacg ctcgtctgcg cagcgaagtc cgcgacagca ttatggacct   3120
ccaccagcag ttaaaaacca gtaccgtcta cgtcacccac gatcaaaccg aagccatgtc   3180
gatggccgac cgcatcgtgg tgatgaacgg cggccacgtg cagcaagtgg ggcggccaga   3240
```

```
gtatctgtat gccaacccgg ccaatctgtt cgtggccaga tttatcggtt caccggcaat    3300
gaatctgcta tcgctcccct gcgttgacgg caacgttcag cttggcgaac aacgccatcc    3360
gctaccgccg cgccatcgca gccagacccg tgtctggctg ggcattcgcc cggaacatat    3420
taccgaccgc gtggagcacg gccatctgcg cctgccgggc accgtcctgc aacgagaact    3480
gatgggagcc gattatctgc tccacgtcag caccccgatc ggcaccctgc gctttagccg    3540
ccgccaccgt ggcacggtgc cggaaaaagg cgaatcgctg atcctcggct tctcgcctgc    3600
cgatgtgcat cttttcatg ctgagaccca gcataattta ctgatggagt gtaatcatgt    3660
ttaaccccct caccgccctg acggttgggc tcagcctcgc cctgagcggc acggcgctgg    3720
cgaaagagaa aatagacttc atgttcccgg ccccggtaga cggcaagctg acgatggaga    3780
tgacacgcgt cattaaagcc tttaacgagt cgcagcagga tgtcgaagtg cgcggcatct    3840
tcaccggcaa ctatgacacc accaagatca agccgaatc cgcgcagaag gccgggcaac    3900
ccccggcgct ggtgatcatg tccgccaact tcaccaccga tctggcgctg aaggatgaga    3960
tcctgccgat ggatgagctg tttaaatatg gcgatcaaaa ggccggcgat ttctgcaaa    4020 aggaattctg gcccgcgatg cataagaacg cccaggtgat gggcaccacc tatgcgatcc    4080
cgttccataa ctcgacaccg atcctctact acaacaagc gctgttagat cgagctggga    4140
tcgcgcaacc accgcagacc tgggccgagc tgctggccga tgccaaaaag ctgaccgacg    4200
agagcaaagg ccagtggggg atcatgctgc cgtcgaccaa cgacgactac ggcggctgga    4260
tcttctcggc gctggtgcgc ccaacggcg gtaaatattt caatgaagac tatccgggtg    4320
aggtttatta caactcgccg accgctatcg gcgctctgcg cttctggcag atctgatct     4380 acaaagacaa agtgatgcct tccggggtac tgaattcgaa gcagatcagc gcttcattct    4440
tctccggcaa acttggcatg gcgatgctca gcaccggcgc actgggcttt atgcgcgaga    4500
acagtaaaga ttttgaactc ggtgtcgcca tgctaccagc caaagagcag cgcgcggtgc    4560
caattggcgg cgccagcctg gtgagcttta aaggcatcaa cgacgcgcag aagaaagcgg    4620
cctaccagtt cctgacttat ctggtgagcc cgcaggtaaa cggcgcgtgg agccgcttta    4680
ccggctactt ctcgccgcgt aaggcttctt acgatactcc ggagatgaaa gcttatctgc    4740
agcaggatcc acgagcagcg atcgcccttg aacagctgaa gtacgcgcat ccgtggtact    4800
ccacctggga gaccgtcgcc gtgcgtaagg cgatggagaa ccagctggcg gcagtggtca    4860
acgatgccaa agtaacgccg gaagccgcgg tacaggcagc gcagaaggaa gctgacgcgc    4920
taatgaaacc ttatgttgat aagactgcgc tgggagaagt gcagtag               4967
```

<210> SEQ ID NO 26
<211> LENGTH: 1014
<212> TYPE: DNA
<213> ORGANISM: Flavobacterium sp.

<400> SEQUENCE: 26

```
atgtcgatcg gcacaggcga tcggatcaat accgtgcgcg gtcctatcac aatctctgaa     60
gcgggtttca cactgactca cgagcacatc tgcggcagct cggcaggatt cttgcgtgct    120
tggccagagt tcttcggtag ccgcaaagct ctagcgaaa aggctgtgag aggattgcgc    180
cgcgccagag cggctggcgt gcgaacgatt gtcgatgtgt cgactttcga tatcggtcgc    240
gacgtcagtt tattggccga ggtttcgcgg gctgccgacg ttcatatcgt ggcggcgacc    300
ggcttgtggt tcgacccgcc actttcgatg cgattgagga gtgtagagga actcacacag    360
ttcttcctgc gtgagattca atatggcatc gaagacaccg gaattagggc gggcattatc    420
```

| | | |
|---|---|---|
| aaggtcgcga ccacaggcaa ggcgaccccc tttcaggagt tagtgttaaa ggcggccgcc | 480 | |
| cgggccagct tggccaccgg tgttccggta accactcaca cggcagcaag tcagcgcgat | 540 | |
| ggtgagcagc aggccgccat ttttgagtcc gaaggcttga gcccctcacg ggtttgtatt | 600 | |
| ggtcacagcg atgatactga cgatttgagc tatctcaccg ccctcgctgc gcgcggatac | 660 | |
| ctcatcggtc tagaccacat cccgcacagt gcgattggtc tagaagataa tgcgagtgca | 720 | |
| tcagccctcc tgggcatccg ttcgtggcaa acacgggctc tcttgatcaa ggcgctcatc | 780 | |
| gaccaaggct acatgaaaca atcctcgtt tcgaatgact ggctgttcgg gttttcgagc | 840 | |
| tatgtcacca acatcatgga cgtgatggat cgcgtgaacc ccgacgggat ggccttcatt | 900 | |
| ccactgagag tgatcccatt cctacgagag aagggcgtcc cacaggaaac gctggcaggc | 960 | |
| atcactgtga ctaacccggc gcggttcttg tcaccgacct tgcgggcgtc atga | 1014 | |

<210> SEQ ID NO 27
<211> LENGTH: 1431
<212> TYPE: DNA
<213> ORGANISM: Pseudomonas aeruginosa

<400> SEQUENCE: 27

| | | |
|---|---|---|
| atgaccccag gttatcccct cgccctctct cttgccgtct ccatggccgt gctcggcagc | 60 | |
| gccttgccgg cccaggcgcg ccaggacgat ccgtcactgt tcaaccgcca ggcccgtggc | 120 | |
| gaactcagcg agtacggcgg cgcacggcgc gtcgagcagg acctgaccca ggccctgaag | 180 | |
| cagtcgctgt cgaagaagaa ggcgaagaac gtgatcctgc tgatcggcga cggcatgggc | 240 | |
| gactccgaga tcaccgtggc gcgcaactac gcgcgcggcg cgggcggcta cttcaagggt | 300 | |
| atcgatgcgc tgccgctgac cggtcagtac acccactact ccctgcacaa ggacagcggc | 360 | |
| ctgccggact acgtgaccga ttccgccgcc tccgccaccg cctggtccac cggggtcaag | 420 | |
| tcgtacaacg gcgcgatcgg cgtggatatc acgaacagc cgcaccgcaa cctgctggag | 480 | |
| ctggccaagc tcaacggcaa ggccaccggc aacgtctcca ccgccgagct gcaggacgcc | 540 | |
| accccccgccg ccctgctcgc ccacgtcacc gctcgcaagt gctacggtcc cgaggccacc | 600 | |
| agcaagcagt gcccgagcaa tgccctggag aacggcggcg ccggctcgat caccgagcag | 660 | |
| tggctgaaga cccgccctga cgtggttctc ggcggcggcg ccgcgacctt cgcggaaacc | 720 | |
| gccaaggctg gccgctatgc cggcaagacc ctccgcgccc aggccgaagc ccgcggctac | 780 | |
| cggatcgtcg agaacctcga cgagctgaaa gccgtgcgcc gcgccaacca gaagcagccg | 840 | |
| ctgatcggcc tgttcgcgcc gggcaacatg ccagtgcgct ggctcggtcc gaccgccacc | 900 | |
| taccacggca acctgaacca gccggcggtg agctgcgagg cgaacccgaa gcgcaccgcc | 960 | |
| gacatcccga ccctggcgca aatgaccagc aaggccatcg agctgctgaa ggacaatccg | 1020 | |
| aacggcttct tcctgcaggt cgagggcgcg tccatcgaca gcaggaccat gccgcgaat | 1080 | |
| ccgtgcggcc agatcggcga gaccgtcgac ctcgacgaag ccgtgcagaa ggccctggcc | 1140 | |
| tttgccaagg ccgatggcga gaccctggtg atcgtcaccg ccgaccacgc ccactccagc | 1200 | |
| cagatcatcc cgccggaaac cgccgcgccg gggctgaccc aactgctcac gaccaaggac | 1260 | |
| ggcgcgccgc tggcgatcag ctacggcaac tccgaggaaa gctcccagga gcacaccggc | 1320 | |
| acccagttgc gcatcgccgc ctacggcccg caggccgcca atgtcaccgg cctgaccgac | 1380 | |
| cagaccgacc tgttcttcac catccgtcgc gcactgaacc tgcgcgactg a | 1431 | |

<210> SEQ ID NO 28

<211> LENGTH: 504
<212> TYPE: DNA
<213> ORGANISM: Pseudomonas monteilii

<400> SEQUENCE: 28

```
atgaagaac taaaaacctg gaagtgggaa gataaagaga gaacaatgct gagaaaaatc      60
tctgttggag atatattttg cctcaccaaa gacaacagca actatcattt cggtaaaatc    120
ttgtcaaaaa tgattgtagg ccacgcagtc gaaatattaa atatcactaa agacagccca    180
tcaatcaccc agcaagaact tgaacaatca gccttagcag gccgaccgct actgctagat    240
agttacgctt tattcgacaa gaaaattgac aaaggtggcg actggagaat aattggccat    300
caagagatat catcaccaga atcctatcga aactactact tcctgttcct gtacggaaca    360
cacaacaact ggaaaaaagt caacatcctc aatgaggaag ttgaaatatc aaatacagag    420
gccctaacgc tccccttgct aaagctcctt agcaatcaca gattctggga aacaataaac    480
gaagaactaa agctaaactg gtaa                                           504
```

<210> SEQ ID NO 29
<211> LENGTH: 579
<212> TYPE: DNA
<213> ORGANISM: Rhodococcus sp.

<400> SEQUENCE: 29

```
ttgtctgaca agccgaatgc cgtttccagc cacaccaccc ccgacgtccc cgaagtagcg     60
gcgacgcccg agttgtccac cggcatctgc gccggtgact accgcgctgc gcttcgccgc    120
cacccggccg gtgtcaccgt cgtgaccctc gattcgggta ccggcccggt gggtttcacc    180
gccacctcgt tctcgtccgt ctccctcgag ccgccgctcg tctcgttcaa catcgcggag    240
acgtcgtcga gcatcaatgc actcaaggca gccgagtcct tggtgatcca ccttctcggc    300
gaacatcagc agcatctggc ccagcgcttt gcgcgtagtg ccgatcagcg ttttgcagac    360
gagtcactgt gggcagtgct cgacaccggg gaaccggtgc tgcacggcac cccagctgg    420
atgcgcgtca aggtcgacca gctgatccct gtcggcgacc acacgctggt catcggactc    480
gtcacgcggg ttcacgccga agaagacgac gaatccgctg ccgcgccgct gctctaccac    540
gagggcaagt actaccgccc gactccgtta ggtcaatag                           579
```

<210> SEQ ID NO 30
<211> LENGTH: 3720
<212> TYPE: DNA
<213> ORGANISM: Rhodococcus sp.

<400> SEQUENCE: 30

```
atgactcaac aacgacaaat gcatctggcc ggtttcttct cggccggcaa tgtgactcat     60
gcacatgggg cgtggcggca cacggacgcg tcgaatgact ttctgtcggg gaagtactac    120
caacacatcg cccgtactct ggagcgcggc aagttcgatc tgttgtttct gcctgacggg    180
ttggccgtcg aggacagcta cggggacaac ctggacaccg tgtcggcct gggcgggcag    240
ggtgcagtcg ccttggagcc ggccagtgtg gtcgcaacca tggccgcggt gaccgagcac    300
ctgggtcttg ggcaaccat tcggcgacc tactatcccc cgtatcacgt tgctcgggtg    360
ttcgcgacgc tcgatcagtt gtcaggggt cgggtgtcct ggaacgtcgt cacctcgctc    420
aacgacgctg aagcgcgcaa cttcggcatt aatcagcatc tggaacacga cgcccgctat    480
gaccgcgccg atgagttctt ggaagcgtc aagaaactct ggaacagctg ggacgaggac    540
gccctcgtgc tggacaaggc ggccggcgtg ttcgccgatc ccgcgaaggt gcactacgtc    600
```

```
gatcaccacg gggagtggct gaatgtgcgc ggacctctgc aggtaccgcg ttcacctcag    660
ggtgagccgg tgatcctgca ggccggcctg tcgccccggg gtcggcgctt cgccgggaag    720
tgggccgagg ccgtcttcag tcttgcaccc aacctcgagg tgatgcaggc cacctaccag    780
ggcatcaaag ccgaggtcga cgctgcgggg cgcgatcccg atcagacgaa aatcttcacc    840
gccgtgatgc cggtactcgg cgaaagccag gcggtggcac aggaacgact ggaatatctc    900
aacagtctgg tccatccgga agtgggactg tcgacgctat ccagtcacac cggcatcaac    960
ctggcggcgt accctctcga cactccgatc aaggacatcc tgcgggatct gcaggatcgg   1020
aatgtcccga cgcaactgca catgttcgcc gccgcaacgc acagcgaaga gctcacgctg   1080
gcggaaatgg gtcggcgcta tggaaccaac gtggggttcg ttcctcagtg ggccggtacc   1140
ggggagcaga tcgctgacga gctgatccgc acttcgagg gcggcgccgc ggatggtttc    1200
atcatctctc cggccttcct gccgggctcc tacgacgagt tcgtcgacca ggtggttccg   1260
gttctgcagg atcgcggcta cttccgcacc gagtaccagg gcaacactct gcgcgaccac   1320
ttgggtctgc gcgtaccaca actgcaagga caaccttcat gacaagccgc gtcgaccccg   1380
caaacccggg ttcagaactc gattccgcca tccgcgacac actgacctac agcaactgcc   1440
cggtacccaa cgctctgctc acggcatcgg aatcgggctt cctcgacgcc gccggcatcg   1500
aactcgacgt cctcagcggc cagcagggca cggttcattt cacctacgac cagcctgcct   1560
acaccgtttt gggggtgag atcccgccac tgctcagcga ggggttgcgg gcacctgggc    1620
gcacgcgtct actcggcatc accccgctct gggggcgcca gggcttcttt gtccgcgacg   1680
acagcccgat cacagcggcc gccgaccttg ccggacgtcg aatcggcgtc tcggcctcgg   1740
caattcgcat cctgcgcggc cagctgggcg actacctcga gttggatccc tggcggcaaa   1800
cgctggtagc gctgggctcg tgggaggcgc gcgccttgtt gcacaccctt gagcacggtg   1860
aactgggtgt ggacgacgtc gagctggtgc cgatcagcag tcctggtgtc gatgttcccg   1920
ctgagcagct cgaagaatcg gcgaccgtca agggtgcgga cctctttccc gatgtcgccc   1980
gcggtcaggc cgcggtgttg gccagcggag acgttgacgc cctgtacagt tggctgccct   2040
gggccgggga gttgcaagcc accggggccc gcccagtggt ggatctcggc ctcgatgagc   2100
gcaatgccta cgccagtgtg tggacggtca gcagcgggct ggttcgccag cgacctggcc   2160
ttgttcaacg actggtcgac gcggccgtcg acgccgggct gtgggcacgc gatcattccg   2220
acgcggtgac cagcctgcac gccgcgaacc tgggcgtatc gaccggagca gtaggccagg   2280
gcttcggcgc cgacttccag cagcgtctgg ttccacgcct ggatcacgac gccctcgccc   2340
tcctggagcg cacacagcaa ttcctgctca ccaacaactt gctgcaggaa cccgtcgccc   2400
tcgatcagtg ggcggctccg gaatttctga caacagcct caatcgccac cgataggaac    2460
atccgcatga cactgtcacc tgaaaagcag cacgttcgac cacgcgacgc cgccgacaac   2520
gatcccgtcg cggttgcccg tgggctagcc gaaaagtggc gagccaccgc cgtcgagcgt   2580
gatcgcgccg ggggttcggc aacagccgag cgcgaagacc tgcgcgcgag cgcgctgctg   2640
tcgctcctcg tcccgcgcga atacggcggc tggggcgcag actggcccac cgccatcgag   2700
gtcgtccgcg aaatcgcggc agccgatgga tctttggac acctgttcgg ataccacctc    2760
accaacgccc cgatgatcga actgatcggc tcgcaggaac aagaagaaca cctgtacacc   2820
cagatcgcgc agaacaactg gtggaccgga aatgcctcca gcgagaacaa cagccacgtg   2880
ctggactgga aggtcagcgc caccccgacc gaagacggcg gctacgtgct caatggcacg   2940
```

-continued

```
aagcacttct gcagcggcgc caaggggtcg gacctgctgt tcgtgttcgg cgtcgtccag   3000
gatgattctc cgcagcaggg tgcgatcatt gctgccgcta tcccgacatc gcgggctggc   3060
gttacgccca acgacgactg gccgccatc ggcatgcggc agaccgacag cggttccacg    3120
gacttccaca acgtcaaggt cgagcctgac gaagtgctgg gcgcgcccaa cgccttcgtt   3180
ctcgccttca tacaatccga gcgcggcagc ctcttccggc ccatagcgca attgatcttc   3240
gccaacgtct atctggggat cgcgcacggc gcactcgatg ccgccaggga gtacacccgt   3300
acccaggcga ggccctggac accggccggt attcaacagg caaccgagga tccctacacc   3360
atccgctcct acggtgagtt caccatcgca ttgcagggag ctgacgccgc cgcccgtgaa   3420
gcggcccacc tgctgcagac ggtgtgggac aagggcgacg cgctcacccc cgaggaccgc   3480
ggcgaactga tggtgaaggt ctcgggagtc aaagcgttgg ccaccaacgc cgccctcaac   3540
atcagcagcg gcgtcttcga ggtgatcggc gcgcgcggaa cacatcccag gtacggtttc   3600
gaccgcttct ggcgcaacgt gcgcacccac tccctgcacg accggtgtc ctacaagatc    3660 gccgacgtcg gcaagcacac cttgaacggt caataccga ttcccggctt cacctcctga    3720
```

<210> SEQ ID NO 31
<211> LENGTH: 244
<212> TYPE: PRT
<213> ORGANISM: Fusarium oxysporum

<400> SEQUENCE: 31

```
Met Leu Pro Thr Glu Val Glu Ala Asn Gly Trp Thr Ala Val Pro Val
1               5                   10                  15

Ser Ala Lys Ala Ile Lys Asp Ser Val Gly Gln Leu Val Pro Thr Gln
            20                  25                  30

Thr Tyr Thr Leu Gln Asp Ile Val Phe Pro Ser Glu Asp Lys Leu Val
        35                  40                  45

Ser Glu Ala Gln Ala Phe Val Lys Ala Arg Leu Ser Gln Glu Ala Tyr
    50                  55                  60

Asn His Ser Met Arg Val Phe Tyr Trp Gly Ser Ile Ile Ala Lys Arg
65                  70                  75                  80

Leu Leu Pro Lys His Ala Glu Ala Leu Ser Pro Ser Thr Trp Ala Leu
                85                  90                  95

Thr Cys Leu Leu His Asp Ile Gly Thr Ala Glu Ala Tyr Phe Thr Ser
            100                 105                 110

Thr Arg Met Ser Phe Asp Ile Tyr Gly Gly Ile Lys Ala Met Glu Val
        115                 120                 125

Leu Lys Val Leu Gly Ser Ser Asp Asp Gln Ala Glu Ala Val Ala Glu
    130                 135                 140

Ala Ile Ile Arg His Glu Asp Met Gly Val Asp Gly Ser Ile Thr Phe
145                 150                 155                 160

Leu Gly Gln Leu Ile Gln Leu Ala Thr Leu Tyr Asp Asn Val Gly Thr
                165                 170                 175

Tyr Glu Gly Ile Asp Asp Phe Gly Gly Trp Ile Asp Glu Ala Thr Arg
            180                 185                 190

Asp Asn Val Asn Lys Ala Ile Pro Arg His Gly Trp Cys Ser Trp Phe
        195                 200                 205

Ala Cys Thr Val Arg Lys Glu Glu Ser Asn Lys Pro Trp Cys His Thr
    210                 215                 220

Thr His Ile Pro Gln Phe Asp Lys Gln Met Glu Ala Asn Thr Leu Met
225                 230                 235                 240
```

Lys Gln Trp Glu

<210> SEQ ID NO 32
<211> LENGTH: 735
<212> TYPE: DNA
<213> ORGANISM: Fusarium oxysporum

<400> SEQUENCE: 32

```
atgttgccca ccgaagtcga ggccaacggc tggactgccg tgcctgtcag cgccaaggca      60
atcaaggact cggtcggaca gcttgtaccc acgcaaacct acactctcca agacatcgtt     120
ttcccctctg aggacaaact tgtgtctgaa gctcaaggcc ttgtcaaggc acggctaagt     180
caagaagctt ataaccactc tatgcgagtt ttctactggg gatccattat tgccaagcgt     240
ttgctaccca gcacgcaga ggccctgtcc ccgtccacct gggcgctgac atgtctttg      300
catgatatcg gtactgctga gcttacttc acttcaactc gcatgtcttt tgatatctat     360
ggtggaatca aggcaatgga ggtgctcaaa gtcctcggta gcagcgacga tcaggccgag     420
gcagtcgcag aggctatcat ccgtcatgaa gacatgggcg tggacggttc gattactttc     480
ctaggccagt taattcagct tgctacgctg tatgacaacg ttgggacgta cgagggcatt     540
gacgattttg gcggctggat tgacgaagct actcgggata atgtcaacaa agctattcct     600
cgtcacggtt ggtgctcctg gtttgcctgt actgtccgca aggaggaatc caacaagcct     660
tggtgccata ctacccatat tcctcaattt gataagcaga tggaggcaaa cactttgatg     720
aaacagtggg agtag                                                      735
```

<210> SEQ ID NO 33
<211> LENGTH: 245
<212> TYPE: PRT
<213> ORGANISM: Fusarium pseudograminearum

<400> SEQUENCE: 33

```
Met Ser Ser Pro Glu Val Lys Ile Asn Gly Trp Thr Ala Val Pro Leu
  1               5                  10                  15
Asn Ala Lys Asn Ile Leu Asp Ser Val Gly Lys Leu Ala Glu Val Pro
             20                  25                  30
Thr Tyr Lys Ala Glu Asp Ile Lys Phe Pro Ser Asn Asp Lys Leu Val
         35                  40                  45
Ala Glu Ala Gln Ala Phe Val Lys Ala Arg Leu Ser Pro Glu Ala Tyr
     50                  55                  60
Asn His Ser Met Arg Val Phe Tyr Trp Gly Asn Ile Leu Ala Lys Arg
 65                  70                  75                  80
Leu Leu Pro Glu His Phe Glu Ala Leu Ser Thr Ser Thr Trp Ala Leu
                 85                  90                  95
Thr Cys Leu Leu His Asp Ile Gly Thr Ala Asp Ala Phe Phe Thr Ser
            100                 105                 110
Thr His Met Ser Phe Asp Leu Tyr Gly Gly Ile Lys Ala Met Glu Val
        115                 120                 125
Leu Lys Val Leu Gly Gly Thr Thr Asp Gln Ala Glu Ala Val Ala Glu
    130                 135                 140
Ala Ile Ile Arg His Gln Asp Val Gly Val Asp Gly Thr Ile Thr Phe
145                 150                 155                 160
Leu Gly Gln Leu Ile Gln Leu Ala Thr Leu Tyr Asp Asn Val Gly Val
                165                 170                 175
Tyr Glu Gly Ile Glu Asp Tyr Gly Ser Trp Val Asp Glu Val Thr Arg
            180                 185                 190
```

Asp Asn Ile Asn Arg Glu Phe Pro Arg His Lys Trp Ala Ser Cys Phe
        195                 200                 205

Ala Ser Val Ile Arg Gln Glu Glu Ser Asn Lys Pro Trp Cys His Ser
    210                 215                 220

Thr His Ile Val Gly Phe Pro Glu Lys Leu Glu Ala Asn Thr Leu Met
225                 230                 235                 240

Lys Pro Trp Glu Glu
                245

<210> SEQ ID NO 34
<211> LENGTH: 738
<212> TYPE: DNA
<213> ORGANISM: Fusarium pseudograminearum

<400> SEQUENCE: 34

| | |
|---|---|
| atgtcttcac ctgaagtcaa gattaacggt tggactgctg tcccctcaa cgccaagaac | 60 |
| attctcgatt ctgtaggaaa actcgcagaa gttcccacct acaaggcaga ggatattaaa | 120 |
| ttcccatcaa atgacaagct cgtcgccgaa gcccaggcct tgtcaaggc gcgactgagc | 180 |
| ccagaagcgt ataatcactc catgagagta ttttactggg aaacattct tgcaaagcgt | 240 |
| tgctgcccg agcattttga agctttgtcc acgtctacct gggcactcac ctgtctctta | 300 |
| cacgacatag gaacggccga tgccttcttc acctccacgc acatgtcgtt cgatctctat | 360 |
| ggcggcataa aggctatgga agtgctcaag gtgctcggcg gtactaccga ccaagctgaa | 420 |
| gctgtcgccg aggccatcat acgtcatcag gatgtgggcg tggacggcac catcactttt | 480 |
| cttgggcagc tgattcaact tgccacactt tacgacaacg tcggcgttta tgagggcatt | 540 |
| gaggactatg gcagttgggt tgatgaggtc actcgcgata atatcaatag ggaatttcct | 600 |
| cggcacaagt gggcatcttg ctttgcttct gtcattcgtc aggaggagtc caacaaaccc | 660 |
| tggtgccatt ctacacatat tgtaggcttt cctgaaaagc ttgaggccaa cactcttatg | 720 |
| aagccttggg aggagtag | 738 |

<210> SEQ ID NO 35
<211> LENGTH: 245
<212> TYPE: PRT
<213> ORGANISM: Gibberella zeae

<400> SEQUENCE: 35

Met Ser Ser Pro Glu Ala Lys Thr Asn Gly Trp Thr Ala Val Pro Leu
1               5                   10                  15

Asn Ala Lys Asn Ile Leu Asp Thr Val Gly Lys Leu Ala Glu Val Pro
            20                  25                  30

Thr Tyr Lys Ala Glu Asp Ile Gln Phe Pro Ser Asp Asp Lys Leu Val
        35                  40                  45

Ala Glu Ala Gln Ala Phe Ala Lys Ala Arg Leu Ser Pro Glu Ala Tyr
    50                  55                  60

Asn His Ser Met Arg Val Phe Tyr Trp Gly Asn Ile Leu Ala Lys Arg
65                  70                  75                  80

Leu Leu Pro Glu His Phe Gly Ala Leu Ser Thr Ser Thr Trp Ala Leu
                85                  90                  95

Thr Cys Leu Leu His Asp Ile Gly Thr Ala Asp Val Phe Phe Thr Ser
            100                 105                 110

Thr His Met Ser Phe Asp Leu Tyr Gly Gly Ile Lys Ala Met Glu Val
        115                 120                 125

Leu Lys Val Leu Gly Gly Thr Thr Asp Gln Ala Glu Ala Val Ala Glu
130                 135                 140

Ala Ile Ile Arg His Gln Asp Val Gly Val Asp Gly Thr Ile Thr Phe
145                 150                 155                 160

Leu Gly Gln Leu Ile Gln Leu Ala Thr Leu Tyr Asp Asn Val Gly Val
                165                 170                 175

Tyr Glu Gly Ile Gln Asp Tyr Gly Ser Trp Val Asp Glu Ala Thr Arg
                180                 185                 190

Asp Asn Ile Asn Arg Ala Phe Pro Arg His Lys Trp Thr Ser Cys Phe
                195                 200                 205

Ala Ser Val Ile Arg Gln Glu Glu Ser Asn Lys Pro Trp Cys His Ser
210                 215                 220

Thr His Ile Val Asp Phe Pro Glu Lys Leu Glu Ala Asn Thr Leu Met
225                 230                 235                 240

Lys Pro Trp Glu Glu
              245

<210> SEQ ID NO 36
<211> LENGTH: 738
<212> TYPE: DNA
<213> ORGANISM: Gibberella zeae

<400> SEQUENCE: 36
atgtcttcac ctgaagccaa aactaacggt tggactgctg tcccctcaa cgctaagaat    60 attctcgaca ctgtaggaaa gctcgcagaa gttcccacct acaaggcaga ggatattcaa   120
tttccatcag acgacaagct agtcgccgaa gcccaagctc ttgccaaggc acgactaagc   180
cctgaagcct ataatcactc catgcgagta ttttactggg aaacattct gcaaagcgt    240 ttgctgccag agcattttgg agctttgtcc acgtctacct gggcactcac ctgtctctta   300
cacgacatag gaacggccga tgtcttcttc acatccacac acatgtcgtt cgatctctat   360
ggcggcataa aggctatgga agtgctcaag gtgctcggtg gtaccaccga ccaagctgaa   420
gctgtcgccg aggccatcat acgtcatcag gatgtgggcg tggacggcac catcactttt   480
cttgggcagc tgattcaact tgccacactt tatgataacg tcggcgttta tgagggcatt   540
caagactatg gcagttgggt tgatgaggcc actcgcgata tatcaatag gcatttcct    600 cgacacaagt ggacgtcttg ctttgcttcc gtcattcgtc aggaggagtc caacaaaccc   660
tggtgccatt ctacacatat tgtggacttt cctgaaaagc ttgaggccaa cactcttatg   720
aagccttggg aggagtag                                                 738

<210> SEQ ID NO 37
<211> LENGTH: 244
<212> TYPE: PRT
<213> ORGANISM: Aspergillus kawachii

<400> SEQUENCE: 37

Met Cys Asn Asp Glu Ile Lys Ala Asn Gly Trp Ser Ser Met Pro Ala
1               5                   10                  15

Asn Ala Gly Ala Ile Phe Thr Asp Gln Ser Phe Ile Glu Arg Ala Glu
                20                  25                  30

Ala Met Gln Leu Asp Thr Ile Ile Phe Pro Phe Asp Pro Val Val
            35                  40                  45

Ser Lys Thr Trp Glu Tyr Ala Arg Ala Val Leu His Pro Gln Thr Leu
        50                  55                  60

Asn His Ser Met Arg Val Tyr Phe Tyr Gly Met Val Ile Thr Thr Gln

Gln Phe Pro Glu Ile Ala Ala Ser Leu Asn Pro Val Thr Trp Ala Leu
         65                  70                  75                  80

Thr Cys Leu Leu His Asp Ile Gly Thr Ala Glu Glu Asn Leu Thr Ala
         85                  90                  95

Thr Arg Met Ser Phe Asp Ile Tyr Gly Gly Ile Lys Ala Leu His Val
        100                 105                 110

Leu Lys Glu Phe Gly Ala Thr Ala Asp Gln Ala Glu Ala Val Ala Glu
        115                 120                 125

Ala Ile Ile Arg His Glu Asp Met Gly Val Asp Gly Thr Ile Thr Tyr
130                 135                 140

Phe Gly Gln Leu Ile Gln Leu Ala Thr Thr Tyr Asp Asn Thr Gly Val
    145                 150                 155                 160

His Pro His Val Lys Ser Phe Glu Gly Leu Val His Gln Thr Thr Arg
            165                 170                 175

Lys Gln Ile Asn Glu Ala Tyr Pro Arg Leu Lys Trp Cys Glu Phe Phe
                180                 185                 190

Ser Gly Met Ile Arg Lys Glu Thr Ile Lys Pro Trp Cys His Ser
        195                 200                 205

Thr His Leu Val Asp Phe Asp Arg Glu Ile Glu Asn Thr Leu Met
    210                 215                 220

Arg Glu Trp Glu
225                 230                 235                 240

<210> SEQ ID NO 38
<211> LENGTH: 735
<212> TYPE: DNA
<213> ORGANISM: Aspergillus kawachii

<400> SEQUENCE: 38
atgtgcaacg acgaaataaa agccaacggc tggtccagca tgcccgccaa tgccggtgcc      60
atatttacgg accaatcctt catcgaaagg gcagaagcca tgcagctcga acaatcata     120
ttccccttcg acgatcctgt cgtttcaaag acctgggaat acgccagggc tgttcttcac    180
ccccagacat tgaaccattc catgagggtc tacttctacg gaatggtaat caccacccag    240
caattccctg aaatagcagc atccctcaac ccagtcacct gggctctgac ctgcctcctc    300
cacgacatcg gtactgcgga ggagaaccta actgcaacgc gcatgtcatt cgatatctat    360
ggcggtatca aggccctcca tgtgctgaag gagtttggtg ccactgcgga ccaggccgag    420
gccgttgctg aggcgatcat tcgacatgag gatatgggcg tcgatggaac tattacatat    480
ttcggtcagc ttattcagtt ggctactaca tatgataata ccggagttca tccgcatgtg    540
aagagttttg agggcttggt gcatcagaca actcgcaaac agatcaatga ggcgtatccg    600
cggttgaagt ggtgtgaatt tttctcgggg atgattagga aggaagagac gatcaagcct    660
tggtgtcatt cgacccattt ggtggacttt gacagggaga tagaagagaa tacgcttatg    720
agggagtggg agtaa                                                     735

<210> SEQ ID NO 39
<211> LENGTH: 244
<212> TYPE: PRT
<213> ORGANISM: Aspergillus niger

<400> SEQUENCE: 39

Met Cys His Asp Glu Ile Lys Ala Asn Gly Trp Ser Ser Thr Pro Ala
1               5                   10                  15

```
Asn Ala Gly Ala Ile Phe Thr Asp Gln Ser Phe Ile Glu Arg Ala Glu
                20                  25                  30

Ala Val Glu Leu Asp Thr Ile Gln Phe Pro Asp Asp Pro Val Val
        35                  40                  45

Ser Lys Thr Leu Glu Tyr Val Lys Ala Val Leu His Pro Glu Thr Leu
 50                  55                  60

Asn His Ser Met Arg Val Tyr Tyr Gly Met Val Ile Thr Thr Gln
 65              70                  75                  80

Gln Phe Pro Glu Gln Ala Ala Ser Ile Asn Pro Val Thr Trp Ala Leu
                85                  90                  95

Thr Cys Leu Leu His Asp Leu Gly Thr Ala Glu Glu Asn Leu Thr Ala
            100                 105                 110

Thr Arg Met Ser Phe Asp Ile Tyr Gly Gly Ile Lys Ala Leu His Val
            115                 120                 125

Leu Lys Glu Phe Gly Ala Thr Ala Asp Gln Ala Glu Ala Ala Ala Glu
130                 135                 140

Ala Ile Ile Arg His Glu Asp Met Gly Val Asp Gly Thr Ile Thr Tyr
145                 150                 155                 160

Phe Gly Gln Leu Ile Gln Leu Ala Thr Thr Tyr Asp Asn Thr Gly Ile
                165                 170                 175

His Pro His Val Lys Gly Phe Glu Gly Leu Val His Arg Thr Thr Arg
            180                 185                 190

Lys Gln Ile Asn Glu Ala Tyr Pro Arg Leu Lys Trp Cys Ala Phe Phe
            195                 200                 205

Ser Gly Leu Ile Arg Lys Glu Glu Thr Ile Lys Pro Trp Cys His Ser
210                 215                 220

Thr His Leu Val Asp Phe Asp Lys Glu Ile Glu Glu Asn Thr Leu Met
225                 230                 235                 240

Arg Glu Trp Glu

<210> SEQ ID NO 40
<211> LENGTH: 735
<212> TYPE: DNA
<213> ORGANISM: Aspergillus niger

<400> SEQUENCE: 40
atgtgccacg acgaaatcaa agccaacggc tggtccagca ctcccgccaa tgccggtgcc       60
atatttacgg accaatcctt cattgaaagg gcagaagccg tggagctcga tacgatccag      120 ttccccttttg acgaccctgt agtctcgaag acattggaat atgtcaaggc tgttcttcac     180
cccgagactt tgaatcattc catgagggtt tactattacg gaatggtaat caccacccaa      240
caattccccg aacaagcagc atccataaac ccagtgacct gggctctgac ttgtctcctc      300
cacgacctcg gaaccgcgga ggagaacctc accgcaacgc gcatgtcatt cgatatctac      360
ggcggcatca aagccctcca tgtgctgaag gagtttggtg ccactgcgga ccaggccgaa      420
gcagcagctg aggcaatcat tcgacatgaa gatatgggag tcgatggaac gattacctac      480
ttcggtcagc ttattcagct ggctacgacg tatgataata ccgggattca tccgcatgtg      540
aagggctttg agggggttggt ccatcgcacg actcgcaagc agattaatga ggcgtatccg      600
cggttgaagt ggtgtgcgtt tttctccggg ttgattagaa aggaggagac gattaagcct      660
tggtgtcatt cgactcattt ggtggatttt gataaggaga tcgaggagaa tacgcttatg      720
agggagtggg agtaa                                                      735
```

<210> SEQ ID NO 41
<211> LENGTH: 241
<212> TYPE: PRT
<213> ORGANISM: Aspergillus niger

<400> SEQUENCE: 41

```
Met Cys His Asp Lys Ile Pro Leu Asn Gly Trp Thr Ser Thr Pro Ala
1               5                   10                  15

Asn Ala Gly Ala Ile Phe Pro Asp Lys Pro Phe Ile His Pro Pro Thr
            20                  25                  30

Pro Ile Ser Ile Thr Asp Ile Pro Phe Pro Ser Thr Asp Pro Leu Val
        35                  40                  45

Ala Lys Thr Leu Glu Tyr Val Gln Ser Leu Leu Pro Arg Glu Thr Val
50                  55                  60

Asn His Ser Met Arg Val Tyr Ser Tyr Gly Met Ile Leu Leu Thr Gln
65                  70                  75                  80

Gln Phe Pro Ser His His Leu Ser Pro Thr Thr Trp Ala Leu Thr Cys
                85                  90                  95

Leu Leu His Asp Ile Gly Thr Ala Pro Ser Leu Leu Thr Ser Thr Asn
            100                 105                 110

Met Ser Phe Asp Leu Tyr Gly Gly Ile Lys Ala His Ser Val Leu Thr
        115                 120                 125

Ser Phe Asp Cys Pro Ala Asp Val Ala Asp Ala Val Ala Glu Ala Ile
130                 135                 140

Ile Arg His Gln Asp Leu Gly Val Asp Gly Asn Ile Thr Phe Leu Gly
145                 150                 155                 160

Gln Leu Ile Gln Leu Ala Thr Ile Tyr Asp Asn Val Gly Glu His Pro
                165                 170                 175

His Val Lys Asp Phe Gly Gly Leu Ile His Glu Asp Ala Arg Arg Glu
            180                 185                 190

Val Asn Glu Arg Trp Arg Arg Glu Gly Trp Cys Gly Val Phe Ala Asp
        195                 200                 205

Val Val Lys Leu Glu Val Gly Arg Lys Pro Trp Cys His Ser Thr His
210                 215                 220

Ile Val Gly Phe Glu Gly Lys Val Arg Gly Asn Ala Leu Phe Gly Glu
225                 230                 235                 240

Lys
```

<210> SEQ ID NO 42
<211> LENGTH: 726
<212> TYPE: DNA
<213> ORGANISM: Aspergillus niger

<400> SEQUENCE: 42

```
atgtgccacg acaagatccc cctcaacggc tggaccagca cccccgccaa cgctggtgcc      60
atcttccccg acaagccctt catccaccca cccacgccca tctccatcac cgacatcccc     120
ttcccctcca ccgatcccct cgtcgccaag accctcgaat acgtccaatc cctcctcccc     180
cgcgagaccg tcaaccactc catgcgcgta tactcctacg gaatgatcct cctcacccag     240
caattccctt ccaccatct atctccaaca acctgggccc taacctgcct tctgcatgac     300
atcggcaccg cccctcct cctcacctca acaaacatgt cctttgacct ctacggcggc     360
atcaaagccc actccgtact tacttccttc gactgtcccg ctgatgttgc tgacgccgta     420
gcggaagcta ttatccggca tcaggatcta ggcgtggatg gaaatatcac gttcctggga     480
cagttgatcc agctggctac catttatgat aatgtggggg aacatccgca cgtcaaggac     540
```

```
tttggagggt tgattcatga ggatgcgagg agggaggtta atgagcgctg gagaagggag    600
ggatggtgtg gggtgtttgc tgatgtggtg aagttggagg tggggaggaa gccgtggtgt    660
cattcgacgc atattgtggg gtttgagggg aaggttaggg ggaatgcgct ttttggggag    720
aaatag                                                                726
```

```
<210> SEQ ID NO 43
<211> LENGTH: 242
<212> TYPE: PRT
<213> ORGANISM: Aspergillus oryzae

<400> SEQUENCE: 43
```

| Met | Ser | Pro | Thr | Arg | Ala | Ala | Gln | Val | Glu | Glu | Tyr | Gly | Trp | Thr | Ala |
|---|---|---|---|---|---|---|---|---|---|---|---|---|---|---|---|
| 1 | | | | 5 | | | | | 10 | | | | | 15 | |

| Val | Ser | Cys | Asp | Pro | Gln | Gln | Arg | Ala | Ala | Thr | Asn | Pro | Pro | Thr | Lys |
| | | | 20 | | | | | 25 | | | | | 30 | | |

| Pro | Ser | Val | Pro | Gln | Leu | Val | Lys | Asp | Thr | Thr | Leu | Pro | Asp | Thr | Pro |
| | | 35 | | | | | 40 | | | | | 45 | | | |

| Leu | Val | Lys | Asp | Ala | Met | Glu | Tyr | Val | Lys | Ala | Glu | Leu | Pro | Ala | His |
| 50 | | | | | 55 | | | | | 60 | | | | | |

| Thr | Phe | Asn | His | Ser | Met | Arg | Val | Tyr | Tyr | Gly | Leu | Ala | Ile | Ala |
| 65 | | | | | 70 | | | | 75 | | | | | 80 |

| Arg | Gln | His | Phe | Pro | Glu | Trp | Lys | Phe | Ser | Asp | Glu | Thr | Trp | Leu | Leu |
| | | | | 85 | | | | | 90 | | | | | 95 | |

| Thr | Cys | Leu | Phe | His | Asp | Ile | Gly | Thr | Ile | Asp | Lys | Tyr | Thr | Gln | Asp |
| | | | | 100 | | | | | 105 | | | | | 110 | |

| Val | Phe | Met | Ser | Phe | Asp | Ile | Tyr | Gly | Gly | Ile | Val | Ala | Leu | Asn | Val |
| | | | 115 | | | | | 120 | | | | | 125 | | |

| Leu | Thr | Glu | Lys | Gly | Ala | Pro | Ala | Pro | Gln | Ala | Glu | Ser | Val | Ala | Glu |
| | 130 | | | | | 135 | | | | | 140 | | | | |

| Ala | Ile | Ile | Arg | His | Gln | Asp | Pro | Val | Lys | Val | Gly | Thr | Ile | His | Ser |
| 145 | | | | | 150 | | | | | 155 | | | | | 160 |

| Val | Gly | Leu | Leu | Ile | Gln | Leu | Ala | Thr | Gln | Phe | Asp | Asn | Leu | Gly | Ala |
| | | | | 165 | | | | | 170 | | | | | 175 | |

| His | Lys | Glu | Tyr | Val | His | Pro | Asp | Thr | Val | Glu | Asp | Val | Asn | Gln | His |
| | | | 180 | | | | | 185 | | | | | 190 | | |

| Tyr | Pro | Arg | Arg | Gln | Trp | Ser | Lys | Cys | Phe | Ser | Ser | Lys | Leu | Arg | Glu |
| | | | 195 | | | | | 200 | | | | | 205 | | |

| Glu | Ile | Gly | Leu | Lys | Pro | Trp | Cys | His | Thr | Thr | Ala | Glu | Gly | Glu | Gly |
| | 210 | | | | | 215 | | | | | 220 | | | | |

| Phe | Pro | Val | Gly | Ile | Glu | Asn | Asn | Thr | Leu | Met | Glu | Pro | Tyr | Asp | Gly |
| 225 | | | | | 230 | | | | | 235 | | | | | 240 |

| Arg | Phe |
|---|---|

```
<210> SEQ ID NO 44
<211> LENGTH: 729
<212> TYPE: DNA
<213> ORGANISM: Aspergillus oryzae

<400> SEQUENCE: 44
atgtcaccca ccagagcagc tcaagtcgaa gaatacggtt ggacagcggt gtcctgcgat    60
cctcagcagc gagctgctac aaacccacct accaagcctt ctgttcccca gttggtcaaa   120
gatacaactc ttcccgatac tcctctagtc aaagatgcca tggaatatgt taaggcagag   180
ctacccgctc acactttaa ccacagcatg cgtgtctact attatggcct tgcaatcgcc   240
```

```
agacaacact tcccagaatg gaagttcagc gatgaaacct ggcttctcac ctgcctcttc    300
cacgacatcg gcactatcga caagtacacc caagacgtct ttatgtcctt cgatatctac    360
ggtggaattg tcgctctgaa cgtcctcacg gagaaaggtg cgccagcacc ccaggctgaa    420
agtgtcgcag aagccatcat ccgtcatcag gatccggtga agttgggac tattcattct     480 gtcggtttac ttattcagct tgctacgcag tttgacaacc ttggtgccca caaggagtat    540
gtccaccctg atactgtgga agatgtgaac cagcattatc cgcgtcgtca gtggtcgaag    600
tgcttctcga gtaagctgag ggaggaaatt gggctcaagc cttggtgcca tactactgcg    660
gagggcgagg ggttccctgt tgggatcgag aacaacactt tgatggagcc ttatgatgga    720
cgcttctag                                                             729
```

```
<210> SEQ ID NO 45
<211> LENGTH: 243
<212> TYPE: PRT
<213> ORGANISM: Saccharomyces cerevisiae

<400> SEQUENCE: 45
```

Met Lys Leu Leu Arg Thr Val Phe Leu Pro Cys Ser Ser Lys Glu
1               5                   10                  15

Ser Ile Met Ser Gln Tyr Gly Phe Val Arg Val Pro Arg Glu Val Glu
            20                  25                  30

Lys Ala Ile Pro Val Val Asn Ala Ser Arg Pro Arg Ala Val Val Pro
        35                  40                  45

Pro Pro Asn Ser Glu Thr Ala Arg Leu Val Arg Glu Tyr Ala Ala Lys
    50                  55                  60

Glu Leu Thr Ala Pro Val Leu Asn His Ser Leu Arg Val Phe Gln Tyr
65                  70                  75                  80

Ser Leu Ala Ile Ile Arg Asp Gln Phe Pro Ala Trp Asp Leu Asp Gln
                85                  90                  95

Glu Val Leu Tyr Val Thr Cys Leu Leu His Asp Ile Ala Thr Thr Asp
            100                 105                 110

Lys Asn Met Arg Ala Thr Lys Met Ser Phe Glu Tyr Tyr Gly Gly Ile
        115                 120                 125

Leu Ser Arg Glu Leu Val Phe Asn Ala Thr Gly Gly Asn Gln Asp Tyr
    130                 135                 140

Ala Asp Ala Val Thr Glu Ala Ile Ile Arg His Gln Asp Leu Thr Gly
145                 150                 155                 160

Thr Gly Tyr Ile Thr Thr Leu Gly Leu Ile Leu Gln Ile Ala Thr Thr
                165                 170                 175

Leu Asp Asn Val Gly Ser Asn Thr Asp Leu Ile His Ile Asp Thr Val
            180                 185                 190

Arg Ala Ile Asn Glu Gln Phe Pro Arg Leu His Trp Leu Ser Cys Phe
        195                 200                 205

Ala Thr Val Val Asn Thr Glu Asn Ser Arg Lys Pro Trp Gly His Thr
    210                 215                 220

Ser Ser Leu Gly Asp Asp Phe Ser Lys Lys Val Ile Cys Asn Thr Phe
225                 230                 235                 240

Gly Tyr Asn

```
<210> SEQ ID NO 46
<211> LENGTH: 732
<212> TYPE: DNA
<213> ORGANISM: Saccharomyces cerevisiae
```

<400> SEQUENCE: 46

```
ttagttatac ccaaatgtat tgcatatgac tttctttgaa aaatcatcac ccaaagaact      60
ggtgtggccc cacggttttc tcgagttttc agtgttcacc accgtagcaa aacatgataa     120
ccagtgcagt cttggaaatt gctcattaat ggctctaact gtatcgatat gaatcagatc     180
ggtattggat ccgacattgt caagcgtagt agcaatctgc agaatgagcc ccaaggtggt     240
aatgtagcca gtcccagtca atcctggtg acgaatgatg gcctcagtta ctgcatctgc      300
atagtcctga tttccacctg tcgcattaaa tacaagctcc cttgaaagta tgccaccata     360
atactcaaat gacatcttcg tggctctcat attcttatct gttgttgcaa tatcatgaag     420
taagcaggtg acgtacaaaa cttcctgatc caagtcccat gctggaaatt ggtctcttat     480
gatagctaaa ctatattgaa aaacacgcaa agagtggttt agaacggggg cagtcaattc     540
tttagcggca tattcccgaa caagcctagc agtttcactg tttggaggcg aacaacggc      600
ccgtggtcta gatgcattca ccactggaat ggccttttct acctctctag gaactcttac     660
aaatccgtac tgtgacatga ttgattcttt tgaagaggag caaggcaaaa aaacagtacg     720
aagcaacttc at                                                        732
```

<210> SEQ ID NO 47
<211> LENGTH: 390
<212> TYPE: PRT
<213> ORGANISM: Rhodococcus sp.

<400> SEQUENCE: 47

```
Met Arg Glu Val Gln Leu Leu Asp Gly Arg Arg Val Asp Val Ala Cys
  1               5                  10                  15

Ala Gly Pro Leu Ile Ser Glu Ile Gly Ala His Leu Asp Leu Thr Ala
             20                  25                  30

Pro Val Glu Ile Asp Cys Gly Gly Leu Ala Thr Arg Pro Phe Thr
         35                  40                  45

Glu Pro His Leu His Leu Asp Lys Ala Gly Thr Ala Asp Arg Leu Pro
     50                  55                  60

Ala Gly Ala Ser Thr Ile Gly Asp Ala Ile Ala Ala Met Gln Ser Val
 65                  70                  75                  80

Lys Val Thr Glu Arg Asp Asn Val Ala Ala Val Ala Ala Arg Met His
                 85                  90                  95

Arg Val Leu Asn Arg Ile Val Asp Asp Gly Ser His Ala Ile Arg Ala
            100                 105                 110

Leu Val Asp Val Asp Glu Val Trp Gly Leu Thr Ala Phe His Ala Ala
        115                 120                 125

Gln Gln Val Gln Ala Ala Leu Ala Pro Arg Ala Val Val Gln Ile Val
    130                 135                 140

Ala Phe Pro Gln His Gly Leu Thr Pro Gln Val Leu Ala Met Leu Glu
145                 150                 155                 160

Gln Ala Ala Ala Glu Gly Ala Gly Ala Leu Gly Ala His Thr Asp Val
                165                 170                 175

Asp Pro Asp Pro Ala Ala His Val Gly Ala Val Ala Ala Ile Ala Ala
            180                 185                 190

Gly Ala Ser Leu Pro Leu Glu Val His Thr Asp Glu Gly Ala Ser Pro
        195                 200                 205

Asp Lys Phe Tyr Leu Pro Ala Val Leu Glu Val Leu Asp Arg Phe Pro
    210                 215                 220
```

```
Gly Leu Ser Thr Thr Leu Ala His Cys Leu Ser Leu Gly Thr Ile Ala
225                 230                 235                 240

Pro Lys Gln Gln Gln His Trp Ile Glu Glu Leu Ala His Arg Asp Ile
            245                 250                 255

Lys Val Cys Val Ala Pro Ser Ile Leu Gly Phe Gly Leu Pro Leu Ala
        260                 265                 270

Pro Val Arg Ala Leu Ile Glu Ala Gly Val Gly Ile Leu Val Gly Ser
    275                 280                 285

Asp Asn Leu Gln Asp Val Phe Phe Pro Leu Gly Thr Gly Arg Ala Ile
290                 295                 300

Glu Asn Val Arg Leu Leu Ala Thr Ala Ala Gln Leu Thr Ala Pro Glu
305                 310                 315                 320

Leu Ala Gly Pro Leu Ile Ala Gly Val Thr Asp Ile Ala Tyr Ala Thr
                325                 330                 335

Val Thr Gly Ala Ala Asp Ala Leu Ala Val Glu Ser Pro Ala Thr Leu
            340                 345                 350

Val Val His Asp Ala Thr Ser Pro Ala Glu Leu Leu Arg Gly Ile Asp
        355                 360                 365

Gly Thr Arg Ile Thr Val Ile Asp Gly Leu Leu Thr Ser Pro Leu Gln
370                 375                 380

Leu Asp Lys Gly Ile Lys
385                 390

<210> SEQ ID NO 48
<211> LENGTH: 1173
<212> TYPE: DNA
<213> ORGANISM: Rhodococcus sp.

<400> SEQUENCE: 48
ttgcgggaag tccaactgct cgacggccgc cgagttgatg ttgcatgcgc cggaccgttg      60
atctccgaaa tcggcgccca tctcgacctc accgctccag tggagatcga ctgtggcggc     120
ggcctggcga cgcgaccgtt caccgaaccc catttgcacc tcgacaaggc ggggaccgcc     180
gatcgtctac cggcaggcgc cagcaccatc ggtgatgcga tcgccgccat gcaatcggtg     240
aaagtcactg agcgcgacaa tgtggcggcg tcgccgcaca gaatgcaccg cgtcctgaac     300
cgcattgtcg acgatggttc ccacgccatt cgcgctctcg tcgacgtcga tgaggtctgg     360
ggattgaccg cttttcatgc agcccaacaa gtccaagctg ctctcgcgcc gcgcgcggta     420
gtacaaatcg tggccttccc acaacatggc ctcaccccgc aggtacttgc catgctcgag     480
caagcggccg cagaaggtgc aggagcactc ggcgcccaca ccgacgtcga ccctgaccca     540
gcggcgcacg tcggtgctgt ggccgccatt gccgccgggg catcgctacc gctcgaagtc     600
cacactgatg aaggcgccag tcccgacaag ttctacttgc ctgcagtact ggaggtcctc     660
gaccggtttc ctggactctc gacgaccctc gcacactgtc tgtcactcgg aacgatcgcg     720
ccgaaacaac agcagcactg gattgaggaa ctggcccatc gggacatcaa agtctgtgtc     780
gcgcctagca ttttaggttt cggcctgccc ttggcgccag tccgggcact catcgaggcc     840
ggcgtcggaa tacttgtcgg atcagacaac ctgcaggacg ttttctttcc gctcggtacg     900
ggccgcgcca tcgaaaacgt gcgtctgctg gcgaccgcag cacagctcac cgcacctgag     960
ctcgctggcc cgctcatcgc aggtgtcacc gacatcgcgt acgccaccgt gaccggcgca    1020
gcagatgcac tggcggtgga atccccgca accctcgtcg tccacgacgc gacctcgccg    1080
gcggagctgc ttcgcggcat cgacggtact cgaatcaccg ttatcgacgg cctgttgaca    1140
```

```
tccccgctcc aactcgacaa aggaatcaag tga                             1173
```

<210> SEQ ID NO 49
<211> LENGTH: 412
<212> TYPE: PRT
<213> ORGANISM: Unknown
<220> FEATURE:
<223> OTHER INFORMATION: Description of Unknown: trzC 12227
      sequence

<400> SEQUENCE: 49

```
Met Ser Met Glu Thr His Ser Tyr Val Asp Val Ala Ile Arg Asn Ala
1               5                   10                  15

Arg Leu Ala Asp Thr Glu Gly Ile Val Asp Ile Leu Ile His Asp Gly
            20                  25                  30

Arg Ile Ala Ser Ile Val Lys Ser Thr Lys Thr Lys Gly Ser Val Glu
        35                  40                  45

Ile Asp Ala His Glu Gly Leu Val Thr Ser Gly Leu Val Glu Pro His
    50                  55                  60

Ile His Leu Asp Lys Ala Leu Thr Ala Asp Arg Val Pro Ala Gly Ser
65                  70                  75                  80

Ile Gly Asp Leu Arg Thr Arg Arg Gly Leu Glu Met Ala Ile Arg Ala
                85                  90                  95

Thr Arg Asp Ile Lys Arg Thr Phe Thr Val Glu Asp Val Arg Glu Arg
            100                 105                 110

Ala Ile Arg Ala Ala Leu Met Ala Ser Arg Ala Gly Thr Thr Ala Leu
        115                 120                 125

Arg Thr His Val Asp Val Asp Pro Ile Val Gly Leu Ala Gly Ile Arg
    130                 135                 140

Gly Val Leu Glu Ala Arg Glu Val Cys Ala Gly Leu Ile Asp Ile Gln
145                 150                 155                 160

Ile Val Ala Phe Pro Gln Glu Gly Leu Phe Cys Ser Ala Gly Ala Val
                165                 170                 175

Asp Leu Met Arg Glu Ala Ile Lys Leu Gly Ala Asp Ala Val Gly Gly
            180                 185                 190

Ala Pro Ala Leu Asp Asp Arg Pro Gln Asp His Val Arg Ala Val Phe
        195                 200                 205

Asp Leu Ala Ala Glu Phe Gly Leu Pro Val Asp Met His Val Asp Glu
    210                 215                 220

Ser Asp Arg Arg Glu Asp Phe Thr Leu Pro Phe Val Ile Glu Ala Ala
225                 230                 235                 240

Arg Glu Arg Arg Val Pro Asn Val Thr Val Ala His Ile Ser Ser Leu
                245                 250                 255

Ser Val Gln Thr Asp Asp Val Ala Arg Ser Thr Ile Ala Ala Leu Ala
            260                 265                 270

Asp Ala Asp Val Asn Val Val Asn Pro Ile Ile Val Lys Ile Thr
        275                 280                 285

Arg Leu Ser Glu Leu Leu Asp Ala Gly Val Ser Val Met Phe Gly Ser
    290                 295                 300

Asp Asn Leu Arg Asp Pro Phe Tyr Pro Leu Gly Ala Ala Asn Pro Leu
305                 310                 315                 320

Gly Ser Ala Ile Phe Ala Cys Gln Ile Ala Ala Leu Gly Thr Pro Gln
                325                 330                 335

Asp Leu Arg Arg Val Phe Asp Ala Val Thr Ile Asn Ala Ala Arg Met
            340                 345                 350
```

Leu Gly Phe Pro Ser Leu Leu Gly Val Val Glu Gly Val Ala Asp
            355                 360                 365

Leu Ala Val Phe Pro Ser Ala Thr Pro Glu Glu Val Val Leu Asp Gln
        370                 375                 380

Gln Ser Pro Leu Phe Val Leu Lys Gly Gly Arg Val Val Ala Met Arg
385                 390                 395                 400

Leu Ala Ala Gly Ser Thr Ser Phe Arg Asp Tyr Ser
                405                 410

<210> SEQ ID NO 50
<211> LENGTH: 1239
<212> TYPE: DNA
<213> ORGANISM: Unknown
<220> FEATURE:
<223> OTHER INFORMATION: Description of Unknown: trzC 12227
      sequence

<400> SEQUENCE: 50

```
atgtcaatgg aaacccatag ttatgtagac gtcgcaattc gtaacgcgcg tcttgccgat      60
acggagggaa ttgtcgatat tcttattcac gatgggcgca ttgcgtccat cgtgaagtcg     120
acaaaaacaa aaggatcggt ggagatcgat gctcatgagg gtctggtcac ttccggcctg     180
gtagagcctc acatccatct cgataaggcc ctgacggcag atcgggttcc cgcaggaagc     240
attggcgacc ttcgaacgcg acgaggcctt gagatggcaa ttcgggccac cgtgatatc      300
aagcgtacgt tcacggttga agatgttcga gaacgggcca tacgtgcggc cctgatggca     360
tcccgtgcgg gaaccaccgc attgcggaca cacgtcgatg tcgacccgat tgtcggcctc     420
gcaggtatcc gtggtgtcct tgaggcgcgt gaagtctgcg cgggattgat cgatatccag     480
atcgtcgcct tccctcagga gggactcttc tgctctgcgg gggccgtgga cctcatgcgg     540
gaggcgatca aactgggcgc ggatgccgtc ggcggcgcac ccgcgctgga tgatcgcccg     600
caggaccatg tccgagccgt ttttgaccttgctgctgagt tcggcctgcc cgtagacatg     660
cacgtcgatg agtccgaccg gcgggaagac tttacgcttc cctttgtgat tgaagctgcc     720
cgtgaacggc gtgtgcccaa tgtgaccgtc gcgcacatca gctcgctgtc cgtacagacg     780
gatgacgtag cacggtcgac cattgccgcc cttgcggacg ccgatgttaa tgtcgtggtt     840
aatccgatca ttgtcaaaat tacgcggctg agtgaattac tcgatgccgg agtctccgta     900
atgtttggct cggacaacct gcgggatccg ttctatccgc tcggagcggc gaatcccctt     960
ggatcagcca tttttgcctg tcaaattgcc gcgctgggaa caccgcaaga tctcagacgg    1020
gtattcgatg cggtcaccat caacgctgcc cgcatgctgg gattccctc acttttaggc    1080
gtcgtggaag gggcagtcgc ggatctcgca gtattcccat cggcgacgcc cgaggaggtt    1140
gttctggatc aacagtctcc gctcttcgta ctcaagggcg gacgtgtcgt tgccatgcga    1200
ttggccgctg gatcaacgtc gttccgcgac tactcatga                           1239
```

<210> SEQ ID NO 51
<211> LENGTH: 241
<212> TYPE: PRT
<213> ORGANISM: Rhodococcus sp.

<400> SEQUENCE: 51

Met Ile Tyr Ser Thr Val Asn Ala Asn Pro Tyr Ala Trp Pro Tyr Asp
1               5                   10                  15

Gly Ser Ile Asp Pro Ala His Thr Ala Leu Ile Leu Ile Asp Trp Gln
            20                  25                  30

```
Ile Asp Phe Cys Gly Pro Gly Tyr Val Asp Ser Met Gly Tyr Asp
         35                  40                  45

Leu Ser Leu Thr Arg Ser Gly Leu Glu Pro Thr Ala Arg Val Leu Ala
 50                  55                  60

Ala Ala Arg Asp Thr Gly Met Thr Val Ile His Thr Arg Glu Gly His
 65                  70                  75                  80

Arg Pro Asp Leu Ala Asp Leu Pro Pro Asn Lys Arg Trp Arg Ser Ala
                 85                  90                  95

Ser Ala Gly Ala Glu Ile Gly Ser Val Gly Pro Cys Gly Arg Ile Leu
                100                 105                 110

Val Arg Gly Glu Pro Gly Trp Glu Ile Val Pro Glu Val Ala Pro Arg
                115                 120                 125

Glu Gly Glu Pro Ile Ile Asp Lys Pro Gly Lys Gly Ala Phe Tyr Ala
130                 135                 140

Thr Asp Leu Asp Leu Leu Arg Thr Arg Gly Ile Thr His Leu Ile
145                 150                 155                 160

Leu Thr Gly Ile Thr Thr Asp Val Cys Val His Thr Thr Met Arg Glu
                165                 170                 175

Ala Asn Asp Arg Gly Tyr Glu Cys Leu Ile Leu Ser Asp Cys Thr Gly
                180                 185                 190

Ala Thr Asp Arg Lys His His Glu Ala Ala Leu Ser Met Val Thr Met
                195                 200                 205

Gln Gly Gly Val Phe Gly Ala Thr His Ser Asp Asp Leu Leu Ala
                210                 215                 220

Ala Leu Gly Thr Thr Val Pro Ala Ala Ala Gly Pro Arg Ala Arg Thr
225                 230                 235                 240

Glu
```

<210> SEQ ID NO 52
<211> LENGTH: 726
<212> TYPE: DNA
<213> ORGANISM: Rhodococcus sp.

<400> SEQUENCE: 52

```
atgatatact caacagtcaa cgctaatcct tacgcttggc cttacgatgg ttcaatagac    60
cctgctcaca ccgctttaat cttaatcgat tggcaaatag acttttgtgg tccaggtggt   120
tatgtcgatt ccatgggtta cgactatcc ttgactagaa gtggtttaga acctacagca   180
agagtattgg ctgcagccag agatactggt atgacagtta tccatactag agaaggtcac   240
agaccagatt tggctgactt gccacctaat aagagatgga gatctgcatc agccggtgct   300
gaaatcggtt cagttggtcc atgtggtaga attttagtca gaggtgaacc tggttgggaa   360
atagtaccag aagttgcacc tagagaaggt gaaccaatta tagataaacc tggtaaaggt   420
gcttttctacg caacagattt ggacttgttg ttgagaacaa gaggtatcac ccatttgatt   480
ttgaccggta taactacaga tgtttgcgtc cacaccacta tgagagaagc caacgataga   540
ggttacgaat gtttaatttt gtctgattgc accggtgcta ctgacagaaa gcatcacgaa   600
gctgcattat ctatggtcac catgcaaggt ggtgtattcg gtgcaactgc ccattcagat   660
gacttattgg ccgctttggg tacaaccgtt ccagcagccg ctggtcctag agctagaaca   720
gaataa                                                              726
```

<210> SEQ ID NO 53
<211> LENGTH: 233
<212> TYPE: PRT

<213> ORGANISM: Rhizobium leguminosarum

<400> SEQUENCE: 53

| | | | | | | | | | | | | | | |
|---|---|---|---|---|---|---|---|---|---|---|---|---|---|---|
| Met | Asp | Ala | Met | Val | Glu | Thr | Asn | Arg | His | Phe | Ile | Asp | Ala | Asp | Pro |
| 1 | | | | 5 | | | | | 10 | | | | | 15 | |

Tyr Pro Trp Pro Tyr Asn Gly Ala Leu Arg Pro Asp Asn Thr Ala Leu
            20                 25                30

Ile Ile Ile Asp Met Gln Thr Asp Phe Cys Gly Lys Gly Gly Tyr Val
      35                 40                 45

Asp His Met Gly Tyr Asp Leu Ser Leu Val Gln Ala Pro Ile Glu Pro
 50                 55                 60

Ile Lys Arg Val Leu Ala Ala Met Arg Ala Lys Gly Tyr His Ile Ile
65                 70                 75                80

His Thr Arg Glu Gly His Arg Pro Asp Leu Ala Asp Leu Pro Ala Asn
             85                 90                95

Lys Arg Trp Arg Ser Gln Arg Ile Gly Ala Gly Ile Gly Asp Pro Gly
          100               105              110

Pro Cys Gly Arg Ile Leu Thr Arg Gly Glu Pro Gly Trp Asp Ile Ile
        115               120              125

Pro Glu Leu Tyr Pro Ile Glu Gly Glu Thr Ile Ile Asp Lys Pro Gly
 130                135               140

Lys Gly Ser Phe Cys Ala Thr Asp Leu Glu Leu Val Leu Asn Gln Lys
145               150               155             160

Arg Ile Glu Asn Ile Ile Leu Thr Gly Ile Thr Thr Asp Val Cys Val
          165               170              175

Ser Thr Thr Met Arg Glu Ala Asn Asp Arg Gly Tyr Glu Cys Leu Leu
        180               185              190

Leu Glu Asp Cys Cys Gly Ala Thr Asp Tyr Gly Asn His Leu Ala Ala
       195              200              205

Ile Lys Met Val Lys Met Gln Gly Gly Val Phe Gly Ser Val Ser Asn
 210                215               220

Ser Ala Ala Leu Val Glu Ala Leu Pro
225               230

<210> SEQ ID NO 54
<211> LENGTH: 702
<212> TYPE: DNA
<213> ORGANISM: Rhizobium leguminosarum

<400> SEQUENCE: 54

| | |
|---|---|
| atggacgcga tggtcgaaac caaccggcat tttatcgacg ccgatccgta tccgtggccc | 60 |
| tataacggag ctctgaggcc tgacaatacc gccctcatca tcatcgacat gcagacggat | 120 |
| ttctgcggca agggcggtta tgtcgaccac atgggctacg acctgtcgct ggtgcaggcg | 180 |
| ccgatcgaac ccatcaaacg cgtgcttgcc gccatgcggg ccaagggtta tcacatcatc | 240 |
| cacacccgcg agggccaccg ccccgacctc gccgatctgc cagcaaacaa acgctggcgc | 300 |
| tcgcaacgga tcggggccgg catcggtgat cccggcccct gcggccgaat cctgacgcgt | 360 |
| ggcgaacccg gctgggacat catccccgaa ctctacccga tcgaaggcga gacgatcatc | 420 |
| gacaagcccg gcaagggttc gttctgcgcc accgacctcg aactcgtcct caaccagaaa | 480 |
| cgcatcgaga acattatcct caccgggatc accaccgatg tctgcgtctc gacgacgatg | 540 |
| cgcgaggcga cgaccgcgg ctacgaatgc ctgctgctgg aggactgctg tggtgcgacc | 600 |
| gactacggaa accacctcgc cgccatcaag atggtgaaga tgcagggcgg cgtcttcggc | 660 | tcggtctcca attccgcggc tctagtcgag gcgctgccct ga         702

<210> SEQ ID NO 55
<211> LENGTH: 4268
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gtttgtggaa gcggtattcg caatttaatt aagtttaaac ggcgcgcctt tccataggct    60
ccgcccccct gacgagcatc acaaaaatcg acgctcaagt cagaggtggc gaaacccgac   120
aggactataa agataccagg cgtttccccc tggaagctcc ctcgtgcgct ctcctgttcc   180
gaccctgccg cttaccggat acctgtccgc ctttctccct tcgggaagcg tggcgctttc   240
tcatagctca cgctgtaggt atctcagttc ggtgtaggtc gttcgctcca agctgggctg   300
tgtgcacgaa ccccccgttc agcccgaccg ctgcgcctta tccggtaact atcgtcttga   360
gtccaacccg gtaagacacg acttatcgcc actggcagca gccactggta acaggattag   420
cagagcgagg tatgtaggcg gtgctacaga gttcttgaag tggtggccta actacggcta   480
cactagaaga acagtatttg gtatctgcgc tctgctgaag ccagttacct tcggaaaaag   540
agttggtagc tcttgatccg gcaaacaaac caccgctggt agcggtggtt ttttgtttg    600
caagcagcag attacgcgca gaaaaaaagg atctcaagaa gatcctttga tctttttctac   660
ggggtctgac gctcagtgga acgaaaactc acgttaaggg attttggtca tgagattatc   720
aaaaaggatc ttcacctaga tccttttaaa ttaaaaatga agttttaaat caatctaaag   780
tatatatgag taaacttggt ctgacagtta ccaatgctta atcagtgagg cacctatctc   840
agcgatctgt ctatttcgtt catccatagt tgcctgactc cccgtcgtgt agataactac   900
gatacgggag ggcttaccat ctggccccag tgctgcaatg ataccgcgag acccacgctc   960
accggctcca gatttatcag caataaacca gccagccgga agggccgagc gcagaagtgg  1020
tcctgcaact ttatccgcct ccatccagtc tattaattgt tgccgggaag ctagagtaag  1080
tagttcgcca gttaatagtt tgcgcaacgt tgttgccatt gctacaggca tcgtggtgtc  1140
acgctcgtcg tttggtatgg cttcattcag ctccggttcc caacgatcaa ggcgagttac  1200
atgatccccc atgttgtgca aaaaagcggt tagctccttc ggtcctccga tcgttgtcag  1260
aagtaagttg gccgcagtgt tatcactcat ggttatggca gcactgcata attctcttac  1320
tgtcatgcca tccgtaagat gcttttctgt gactggtgag tactcaacca agtcattctg  1380
agaatagtgt atgcggcgac cgagttgctc ttgcccggcg tcaatacggg ataataccgc  1440
gccacatagc agaactttaa aagtgctcat cattggaaaa cgttcttcgg ggcgaaaact  1500
ctcaaggatc ttaccgctgt tgagatccag ttcgatgtaa cccactcgtg cacccaactg  1560
atcttcagca tcttttactt tcaccagcgt ttctgggtga gcaaaaacag gaaggcaaaa  1620
tgccgcaaaa aagggaataa gggcgacacg gaaatgttga atactcatac tcttcctttt  1680
tcaatattat tgaagcattt atcagggtta ttgtctcatg agcggataca tatttgaatg  1740
tatttagaaa aataaacagc gatcgcgcgg ccgcgggtaa taactgatat aattaaattg  1800
aagctctaat ttgtgagttt agtatacatg catttactta taatacagtt ttttagtttt  1860
gctggccgca tcttctcaaa tatgcttccc agcctgcttt tctgtaacgt tcaccctcta  1920
ccttagcatc ccttcccttt gcaaatagtc ctcttccaac aataataatg tcagatcctg  1980

```
tagagaccac atcatccacg gttctatact gttgacccaa tgcgtctccc ttgtcatcta    2040
aacccacacc gggtgtcata atcaaccaat cgtaaccttc atctcttcca cccatgtctc    2100
tttgagcaat aaagccgata acaaaatctt tgtcgctctt cgcaatgtca acagtaccct    2160
tagtatattc tccagtagct agggagccct tgcatgacaa ttctgctaac atcaaaaggc    2220
ctctaggttc ctttgttact tcttccgccg cctgcttcaa accgctaaca atacctgggc    2280
ccaccacacc gtgtgcattc gtaatgtctg cccattctgc tattctgtat acacccgcag    2340
agtactgcaa tttgactgta ttaccaatgt cagcaaattt tctgtcttcg aagagtaaaa    2400
aattgtactt ggcggataat gcctttagcg gcttaactgt gccctccatg aaaaatcag    2460 tcaagatatc cacatgtgtt tttagtaaac aaattttggg acctaatgct tcaactaact    2520
ccagtaattc cttggtggta cgaacatcca atgaagcaca caagtttgtt tgcttttcgt    2580
gcatgatatt aaatagcttg gcagcaacag gactaggatg agtagcagca cgttccttat    2640
atgtagcttt cgacatgatt tatcttcgtt tcctgcaggt ttttgttctg tgcagttggg    2700
ttaagaatac tgggcaattt catgtttctt caacaccaca tatgcgtata tataccaatc    2760
taagtctgtg ctccttcctt cgttcttcct tctgctcgga gattaccgaa tcaaagctag    2820
cttatcgatg ataagctgtc aaagatgaga attaattcca cggactatag actatactag    2880
atactccgtc tactgtacga tacacttccg ctcaggtcct tgtcctttaa cgaggcctta    2940
ccactctttt gttactctat tgatccagct cagcaaaggc agtgtgatct aagattctat    3000
cttcgcgatg tagtaaaact agctagaccg agaaagagac tagaaatgca aaaggcactt    3060
ctacaatggc tgccatcatt attatccgat gtgacgctgc agcttctcaa tgatattcga    3120
atacgctttg aggagataca gcctaatatc cgacaaactg ttttacagat ttacgatcgt    3180
acttgttacc catcattgaa ttttgaacat ccgaacctgg gagttttccc tgaaacagat    3240
agtatatttg aacctgtata ataatatata gtctagcgct ttacggaaga caatgtatgt    3300
atttcggttc ctggagaaac tattgcatct attgcatagg taatcttgca cgtcgcatcc    3360
ccggttcatt ttctgcgttt ccatcttgca cttcaatagc atatctttgt taacgaagca    3420
tctgtgcttc attttgtaga acaaaaatgc aacgcgagag cgctaatttt tcaaacaaag    3480
aatctgagct gcattttttac agaacagaaa tgcaacgcga aagcgctatt ttaccaacga    3540
agaatctgtg cttcattttt gtaaaacaaa atgcaacgc gacgagagcg ctaatttttc    3600
aaacaaagaa tctgagctgc atttttacag aacagaaatg caacgcgaga gcgctatttt    3660
accaacaaag aatctatact cttttttgt tctacaaaaa tgcatcccga gagcgctatt    3720
tttctaacaa agcatcttag attactttt ttctcctttg tgcgctctat aatgcagtct    3780
cttgataact ttttgcactg taggtccgtt aaggttagaa gaaggctact ttggtgtcta    3840
ttttctcttc cataaaaaaa gcctgactcc acttcccgcg tttactgatt actagcgaag    3900
ctgcgggtgc atttttttcaa gataaaggca tccccgatta tattctatac cgatgtggat    3960
tgcgcatact ttgtgaacag aaagtgatag cgttgatgat tcttcattgg tcagaaaatt    4020
atgaacggtt tcttctatt tgtctctata tactacgtat aggaaatgtt tacatttcg    4080 tattgttttc gattcactct atgaatagtt cttactacaa tttttttgtc taaagagtaa    4140
tactagagat aaacataaaa aatgtagagg tcgagtttag atgcaagttc aaggagcgaa    4200
aggtggatgg gtaggttata tagggatata gcacagagat atatagcaaa gagatacttt    4260
tgagcaat                                                              4268
```

<210> SEQ ID NO 56
<211> LENGTH: 4399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

| | |
|---|---|
| gtttgtggaa gcggtattcg caatttaatt aaagctggtg acaattaatc atcggctcgt | 60 |
| ataatgtgtg gaattgaatc gatataagga ggttaatcat gtttaaaccc tcaaaatata | 120 |
| ttttccctct atcttctcgt tgcgcttaat ttgactaatt ctcattagcg aggcgcgcct | 180 |
| ttccataggc tccgccccccc tgacgagcat cacaaaaatc gacgctcaag tcagaggtgg | 240 |
| cgaaacccga caggactata agataccag gcgtttcccc ctggaagctc cctcgtgcgc | 300 |
| tctcctgttc cgaccctgcc gcttaccgga tacctgtccg cctttctccc ttcgggaagc | 360 |
| gtggcgcttt ctcatagctc acgctgtagg tatctcagtt cggtgtaggt cgttcgctcc | 420 |
| aagctgggct gtgtgcacga accccccgtt cagcccgacc gctgcgcctt atccggtaac | 480 |
| tatcgtcttg agtccaaccc ggtaagacac gacttatcgc cactggcagc agccactggt | 540 |
| aacaggatta gcagagcgag gtatgtaggc ggtgctacag agttcttgaa gtggtggcct | 600 |
| aactacggct acactagaag aacagtattt ggtatctgcg ctctgctgaa gccagttacc | 660 |
| ttcggaaaaa gagttggtag ctcttgatcc ggcaaacaaa ccaccgctgg tagcggtggt | 720 |
| ttttttgttt gcaagcagca gattacgcgc agaaaaaaag gatctcaaga agatcctttg | 780 |
| atcttttcta cggggtctga cgctcagtgg aacgaaaact cacgttaagg gattttggtc | 840 |
| atgagattat caaaaaggat cttcacctag atcctttaa attaaaaatg aagttttaaa | 900 |
| tcaatctaaa gtatatatga gtaaacttgg tctgacagtt accaatgctt aatcagtgag | 960 |
| gcacctatct cagcgatctg tctatttcgt tcatccatag ttgcctgact ccccgtcgtg | 1020 |
| tagataacta cgatacggga gggcttacca tctggcccca gtgctgcaat gataccgcga | 1080 |
| gacccacgct caccggctcc agatttatca gcaataaacc agccagccgg aagggccgag | 1140 |
| cgcagaagtg gtcctgcaac tttatccgcc tccatccagt ctattaattg ttgccgggaa | 1200 |
| gctagagtaa gtagttcgcc agttaatagt ttgcgcaacg ttgttgccat gctacaggc | 1260 |
| atcgtggtgt cacgctcgtc gtttggtatg gcttcattca gctccggttc caacgatca | 1320 |
| aggcgagtta catgatcccc catgttgtgc aaaaaagcgg ttagctcctt cggtcctccg | 1380 |
| atcgttgtca gaagtaagtt ggccgcagtg ttatcactca tggttatggc agcactgcat | 1440 |
| aattctctta ctgtcatgcc atccgtaaga tgcttttctg tgactggtga gtactcaacc | 1500 |
| aagtcattct gagaatagtg tatgcggcga ccgagttgct cttgcccggc gtcaatacgg | 1560 |
| gataataccg cgccacatag cagaaccttta aaagtgctca tcattggaaa acgttcttcg | 1620 |
| gggcgaaaac tctcaaggat cttaccgctg ttgagatcca gttcgatgta acccactcgt | 1680 |
| gcacccaact gatcttcagc atcttttact ttcaccagcg tttctgggtg agcaaaaaca | 1740 |
| ggaaggcaaa atgccgcaaa aaagggaata agggcgacac ggaaatgttg aatactcata | 1800 |
| ctcttccttt ttcaatatta ttgaagcatt tatcagggtt attgtctcat gagcggatac | 1860 |
| atatttgaat gtatttagaa aaataaacag cgatcgcgcg gccgcgggta ataactgata | 1920 |
| taattaaatt gaagctctaa tttgtgagtt tagtatacat gcattacttt ataatacagt | 1980 |
| tttttagttt tgctggccgc atcttctcaa atatgcttcc cagcctgctt ttctgtaacg | 2040 |
| ttcaccctct accttagcat cccttccctt tgcaaatagt cctcttccaa caataataat | 2100 |

```
gtcagatcct gtagagacca catcatccac ggttctatac tgttgaccca atgcgtctcc    2160
cttgtcatct aaacccacac cgggtgtcat aatcaaccaa tcgtaaccct catctcttcc    2220
acccatgtct ctttgagcaa taaagccgat aacaaaatct ttgtcgctct tcgcaatgtc    2280
aacagtaccc ttagtatatt ctccagtagc tagggagccc ttgcatgaca attctgctaa    2340
catcaaaagg cctctaggtt cctttgttac ttcttccgcc gcctgcttca aaccgctaac    2400
aatacctggg cccaccacac cgtgtgcatt cgtaatgtct gcccattctg ctattctgta    2460
tacacccgca gagtactgca atttgactgt attaccaatg tcagcaaatt ttctgtcttc    2520
gaagagtaaa aaattgtact tggcggataa tgcctttagc ggcttaactg tgccctccat    2580
ggaaaaatca gtcaagatat ccacatgtgt ttttagtaaa caaattttgg gacctaatgc    2640
ttcaactaac tccagtaatt ccttggtggt acgaacatcc aatgaagcac acaagtttgt    2700
ttgcttttcg tgcatgatat taaatagctt ggcagcaaca ggactaggat gagtagcagc    2760
acgttcctta tatgtagctt tcgacatgat ttatcttcgt ttcctgcagg ttttgttct     2820 gtgcagttgg gttaagaata ctgggcaatt tcatgtttct tcaacaccac atatgcgtat    2880
atataccaat ctaagtctgt gctccttcct tcgttcttcc ttctgctcgg agattaccga    2940
atcaaagcta gcttatcgat gataagctgt caaagatgag aattaattcc acggactata    3000
gactatacta gatactccgt ctactgtacg atacacttcc gctcaggtcc ttgtccttta    3060
acgaggcctt accactcttt tgttactcta ttgatccagc tcagcaaagg cagtgtgatc    3120
taagattcta tcttcgcgat gtagtaaaac tagctagacc gagaaagaga ctagaaatgc    3180
aaaaggcact tctacaatgg ctgccatcat tattatccga tgtgacgctg cagcttctca    3240
atgatattcg aatacgcttt gaggagatac agcctaatat ccgacaaact gttttacaga    3300
tttacgatcg tacttgttac ccatcattga attttgaaca tccgaacctg ggagttttcc    3360
ctgaaacaga tagtatattt gaacctgtat aataatatat agtctagcgc tttacggaag    3420
acaatgtatg tatttcggtt cctggagaaa ctattgcatc tattgcatag gtaatcttgc    3480
acgtcgcatc cccggttcat tttctgcgtt tccatcttgc acttcaatag catatctttg    3540
ttaacgaagc atctgtgctt cattttgtag aacaaaaatg caacgcgaga gcgctaattt    3600
ttcaaacaaa gaatctgagc tgcattttta cagaacagaa atgcaacgcg aaagcgctat    3660
tttaccaacg aagaatctgt gcttcatttt tgtaaaacaa aaatgcaacg cgacgagagc    3720
gctaattttt caaacaaaga atctgagctg cattttttaca gaacagaaat gcaacgcgag    3780
agcgctattt taccaacaaa gaatctatac ttctttttg ttctacaaaa atgcatcccg    3840
agagcgctat ttttctaaca aagcatctta gattactttt tttctccttt gtgcgctcta    3900
taatgcagtc tcttgataac ttttttgcact gtaggtccgt taaggttaga agaaggctac    3960
tttggtgtct atttttctctt ccataaaaaa agcctgactc cacttcccgc gtttactgat    4020
tactagcgaa gctgcgggtg cattttttca agataaaggc atccccgatt atattctata    4080
ccgatgtgga ttgcgcatac tttgtgaaca gaaagtgata gcgttgatga ttcttcattg    4140
gtcagaaaat tatgaacggt ttcttctatt ttgtctctat atactacgta taggaaatgt    4200
ttacattttc gtattgtttt cgattcactc tatgaatagt tcttactaca attttttgt    4260 ctaaagagta atactagaga taaacataaa aaatgtagag gtcgagttta gatgcaagtt    4320
caaggagcga aggtggatg ggtaggttat atagggatat agcacagaga tatatagcaa    4380
agagatactt ttgagcaat                                               4399
```

<210> SEQ ID NO 57
<211> LENGTH: 8762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

| | | | | | |
|---|---|---|---|---|---|
| gtttgtggaa | gcggtattcg | caatcattta | gtcgtgcaat | gtatgacttt | aagatttgtg | 60 |
| agcaggaaga | aaagggagaa | tcttctaacg | ataaacccct | gaaaaactgg | gtagactacg | 120 |
| ctatgttgag | ttgctacgca | ggctgcacaa | ttacacgaga | atgctcccgc | ctaggattta | 180 |
| aggctaaggg | acgtgcaatg | cagacgacag | atctaaatga | ccgtgtcggt | gaagtgttcg | 240 |
| ccaaactttt | cggttaacac | atgcagtgat | gcacgcgcga | tggtgctaag | ttacatatat | 300 |
| atatatatat | atatatatat | atatatatag | ccatagtgat | gtctaagtaa | cctttatggt | 360 |
| atatttctta | atgtggaaag | atactagcgc | gcgcacccac | acacaagctt | cgtcttttct | 420 |
| tgaagaaaag | aggaagctcg | ctaaatggga | ttccactttc | cgttccctgc | cagctgatgg | 480 |
| aaaaaggtta | gtgaacgat | gaagaataaa | aagagagatc | cactgaggtg | aaatttcagc | 540 |
| tgacagcgag | tttcatgatc | gtgatgaaca | atggtaacga | gttgtggctg | ttgccaggga | 600 |
| gggtggttct | caacttttaa | tgtatggcca | aatcgctact | tgggtttgtt | atataacaaa | 660 |
| gaagaaataa | tgaactgatt | ctcttcctcc | ttcttgtcct | ttcttaattc | tgttgtaatt | 720 |
| accttccttt | gtaattttt | ttgtaattat | tcttcttaat | aatccaaaca | aacacacata | 780 |
| ttacaataat | gaagaagccc | gagctgaccg | ctacctctgt | tgagaagttc | ctgattgaga | 840 |
| agtttgattc | cgtttccgac | ctgatgcagc | tgtccgaggg | cgaggagtct | cgagccttct | 900 |
| cctttgacgt | gggcggacga | ggttacgttc | tgcgagtgaa | ctcgtgtgcc | gacggcttct | 960 |
| acaaggatcg | atacgtctac | cgacactttg | cttctgccgc | tctgcccatc | cctgaggttc | 1020 |
| tcgacattgg | cgagttctct | gagtcccctca | cctactgcat | ctctcgacga | gctcagggag | 1080 |
| tcaccctgca | ggacctccct | gagactgagc | tgcctgctgt | cctccagcct | gttgctgagg | 1140 |
| ccatggacgc | tatcgctgct | gctgatctgt | cccagacctc | gggtttcggc | ccctttggac | 1200 |
| ctcagggaat | tggacagtac | accacttggc | gagacttcat | ctgtgctatt | gccgatcctc | 1260 |
| acgtctacca | ttggcagacc | gttatggacg | atactgtgtc | ggcttctgtc | gctcaggctc | 1320 |
| tggacgagct | gatgctctgg | gccgaggatt | gccccgaggt | tcgacacctg | gtgcatgctg | 1380 |
| acttcggttc | caacaacgtt | ctcaccgaca | acggccgaat | cactgccgtg | attgactggg | 1440 |
| ccgaggctat | gtttggcgac | tcgcagtacg | aggtggccaa | catcttcttt | tggcgaccct | 1500 |
| ggctggcttg | tatggagcag | cagacccgat | acttcgagcg | acgacatcct | gagctcgctg | 1560 |
| gatcccctcg | actgcgagct | tacatgctcc | gaattggtct | ggaccagctc | taccagtcgc | 1620 |
| tggtggatgg | caactttgac | gatgctgcct | gggctcaggg | acgatgtgac | gccatcgtgc | 1680 |
| gatctggcgc | tggaaccgtc | ggacgaactc | agattgcccg | acgatccgct | gctgtctgga | 1740 |
| ccgacggatg | cgtggaggtc | ctggctgatt | cgggtaaccg | acgaccctct | actcgacctc | 1800 |
| gagctaagga | gtaataaacg | gcgcgccgtc | tgaagaatga | atgatttgat | gatttctttt | 1860 |
| tccctccatt | tttcttactg | aatatatcaa | tgatatagac | ttgtatagtt | tattatttca | 1920 |
| aattaagtag | ctatatatag | tcaagataac | gtttgtttga | cacgattaca | ttattcgtcg | 1980 |
| acatcttttt | tcagcctgtc | gtggtagcaa | tttgaggagt | attattaatt | gaataggttc | 2040 |

```
attttgcgct cgcataaaca gttttcgtca gggacagtat gttggaatga gtggtaatta    2100
atggtgacat gacatgttat agcaataacc ttgatgttta catcgtagtt taatgtacac    2160
cccgcgaatt cgttcaagta ggagtgcacc aattgcaaag ggaaaagctg aatgggcagt    2220
tcgaatagta cttttccat aggctccgcc cccctgacga gcatcacaaa atcgacgct     2280
caagtcagag gtggcgaaac ccgacaggac tataaagata ccaggcgttt cccctggaa    2340
gctccctcgt gcgctctcct gttccgaccc tgccgcttac cggatacctg tccgcctttc    2400
tcccttcggg aagcgtggcg ctttctcata gctcacgctg taggtatctc agttcggtgt    2460
aggtcgttcg ctccaagctg gctgtgtgc acgaaccccc cgttcagccc gaccgctgcg    2520
ccttatccgg taactatcgt cttgagtcca acccggtaag acacgactta cgccactgg    2580
cagcagccac tggtaacagg attagcagag cgaggtatgt aggcggtgct acagagttct    2640
tgaagtggtg gcctaactac ggctacacta gaagaacagt atttggtatc tgcgctctgc    2700
tgaagccagt taccttcgga aaagagttg gtagctcttg atccggcaaa caaaccaccg    2760
ctggtagcgg tggtttttt gtttgcaagc agcagattac gcgcagaaaa aaaggatctc    2820
aagaagatcc tttgatcttt tctacggggt ctgacgctca gtggaacgaa aactcacgtt    2880
aagggatttt ggtcatgaga ttatcaaaaa ggatcttcac ctagatcctt ttaaattaaa    2940
aatgaagttt taaatcaatc taaagtatat atgagtaaac ttggtctgac agttaccaat    3000
gcttaatcag tgaggcacct atctcagcga tctgtctatt tcgttcatcc atagttgcct    3060
gactccccgt cgtgtagata actacgatac gggagggctt accatctggc cccagtgctg    3120
caatgatacc gcgagaccca cgctcaccgg ctccagattt atcagcaata aaccagccag    3180
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat ccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa acaggaagg caaatgccg caaaaaggg aataagggcg acacggaaat    3840
gttgaatact catactcttc ctttttcaat attattgaag catttatcag ggttattgtc    3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca aagaatttat tcgtacgaat cacagggacg    4260
gccgccctca ccgaaccagc gaatacctca gcggtcccct gcagtgactc aacaaagcga    4320
tatgaacatc ttgcgatggt atcctgctga tagtttttac tgtacaaaca cctgtgtagc    4380
tccttctagc attttttaagt tattcacacc tcaaggggag ggataaatta aataaattcc    4440
```

```
aaaagcgaag atcgagaaac taaattaaaa ttccaaaaac gaagttggaa cacaacccccc    4500 cgaaaaaaaa caacaaacaa aaacccaac aaaataaaca aaaacaaaat aaatatataa      4560
ctaccagtat ctgactaaaa gttcaaatac tcgtacttac aacaaataga aatgagccgg     4620
ccaaaattct gcagaaaaaa atttcaaaca agtactggta taattaaatt aaaaaacaca    4680
tcaaagtatc ataacgttag ttattttatt ttatttaata aagaaaaaca acaagatggg    4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttacatttca cagtctgaac ttttgcagat tacctaattt ggtaagatat   4980
taattatgaa ctgaaagttg atggcggccg catagcttca aaatgtttct actccttttt   5040
tactcttcca gattttctcg gactccgcgc atcgccgtac cacttcaaaa cacccaagca   5100
cagcatacta aatttccccct ctttcttcct ctagggtgtc gttaattacc cgtactaaag  5160
gtttggaaaa gaaaaagag accgcctcgt ttcttttttct tcgtcgaaaa aggcaataaa   5220 aattttttatc acgtttcttt ttcttgaaaa ttttttttttt tgattttttt ctctttcgat  5280
gacctcccat tgatatttaa gttaataaac ggtcttcaat ttctcaagtt tcagtttcat   5340
ttttcttgtt ctattacaac ttttttttact tcttgctcat tagaaagaaa gcatagcaat  5400
ctaatctaag ttttaattac aaaatgacca ctctggatga caccgcttac cgataccgaa   5460
cttccgttcc tggcgatgcc gaggctattg aggctctgga tggatctttc accactgaca   5520
ccgttttccg agtgaccgct actggcgacg gcttcaccct gcgagaggtg cctgtcgacc    5580
ctcctctcac caaggttttc cctgacgatg agtcggacga tgagtctgac gctggagagg    5640
acggcgaccc tgactctcga actttcgtgg cttacggcga cgatggagac ctggccggct   5700
ttgtggtcgt ttcttactcc ggatggaacc gacgactgac cgtggaggac atcgaggtcg   5760
ctcctgagca ccgaggtcat ggtgtcggac gagctctgat gggtctcgct actgagttcg    5820
ctcgagagcg aggtgctggc cacctgtggc tcgaggtcac caacgttaac gcccctgcta   5880
ttcatgccta ccgacgaatg ggttttaccc tgtgtggcct cgatactgcc ctgtacgacg   5940
gaaccgcttc cgatggagag caggccctct acatgtcgat gccctgccct taaacaggcc   6000 cctttttcctt tgtcgatatc atgtaattag ttatgtcacg cttacattca cgccctcctc   6060
ccacatccgc tctaaccgaa aaggaaggag ttagacaacc tgaagtctag gtccctattt    6120 attttttttta atagttatgt tagtattaag aacgttattt atatttcaaa tttttctttt   6180
ttttctgtac aaacgcgtgt acgcatgtaa cattatactg aaaaccttgc ttgagaaggt    6240
tttgggacgc tcgaaggctt taatttgcgg gtaataactg atataattaa attgaagctc    6300
taatttgtga gtttagtata catgcattta cttataatac agtttttag ttttgctggc    6360 cgcatcttct caaatatgct tcccagcctg cttttctgta acgttcaccc tctaccttag   6420 catccccttcc ctttgcaaat agtcctcttc caacaataat aatgtcagat cctgtagaga  6480
ccacatcatc cacggttcta tactgttgac ccaatgcgtc tcccttgtca tctaaaccca   6540
caccgggtgt cataatcaac caatcgtaac cttcatctct tccacccatg tctctttgag   6600
caataaagcc gataacaaaa tctttgtcgc tcttcgcaat gtcaacagta cccttagtat   6660
attctccagt agctagggag cccttgcatg acaattctgc taacatcaaa aggcctctag   6720
gttcctttgt tacttcttcc gccgcctgct tcaaaccgct aacaatacct gggcccacca    6780
```

```
caccgtgtgc attcgtaatg tctgcccatt ctgctattct gtatacaccc gcagagtact    6840
gcaatttgac tgtattacca atgtcagcaa attttctgtc ttcgaagagt aaaaaattgt    6900
acttggcgga taatgccttt agcggcttaa ctgtgccctc catggaaaaa tcagtcaaga    6960
tatccacatg tgttttagt aaacaaattt tgggacctaa tgcttcaact aactccagta     7020
attccttggt ggtacgaaca tccaatgaag cacacaagtt tgtttgcttt tcgtgcatga    7080
tattaaatag cttggcagca acaggactag gatgagtagc agcacgttcc ttatatgtag    7140
ctttcgacat gatttatctt cgtttcctgc aggttttgt tctgtgcagt tgggttaaga     7200
atactgggca atttcatgtt tcttcaacac cacatatgcg tatatatacc aatctaagtc    7260
tgtgctcctt ccttcgttct tccttctgct cggagattac cgaatcaaag ctagcttatc    7320
gatgataagc tgtcaaagat gagaattaat tccacggact atagactata ctagatactc    7380
cgtctactgt acgatacact tccgctcagg tccttgtcct ttaacgaggc cttaccactc    7440
ttttgttact ctattgatcc agctcagcaa aggcagtgtg atctaagatt ctatcttcgc    7500
gatgtagtaa aactagctag accgagaaag agactagaaa tgcaaaaggc acttctacaa    7560
tggctgccat cattattatc cgatgtgacg ctgcagcttc tcaatgatat tcgaatacgc    7620
tttgaggaga tacagcctaa tatccgacaa actgttttac agatttacga tcgtacttgt    7680
tacccatcat tgaattttga acatccgaac ctgggagttt tccctgaaac agatagtata    7740
tttgaacctg tataataata tatagtctag cgctttacgg aagacaatgt atgtatttcg    7800
gttcctggag aaactattgc atctattgca taggtaatct tgcacgtcgc atccccggtt    7860
cattttctgc gtttccatct tgcacttcaa tagcatatct ttgttaacga agcatctgtg    7920
cttcattttg tagaacaaaa atgcaacgcg agagcgctaa tttttcaaac aaagaatctg    7980
agctgcattt ttacagaaca gaatgcaac gcgaaagcgc tatttaccaa acgaagaatc    8040
tgtgcttcat ttttgtaaaa caaaatgca acgcgacgag agcgctaatt tttcaaacaa    8100
agaatctgag ctgcattttt acagaacaga atgcaacgc gagagcgcta ttttaccaac    8160
aaagaatcta tacttctttt ttgttctaca aaaatgcatc ccgagagcgc tatttttcta    8220
acaaagcatc ttagattact ttttttctcc tttgtgcgct ctataatgca gtctcttgat    8280
aacttttgc actgtaggtc cgttaaggtt agaagaaggc tactttggtg tctatttct     8340
cttccataaa aaaagcctga ctccacttcc cgcgtttact gattactagc gaagctgcgg    8400
gtgcattttt tcaagataaa ggcatccccg attatattct ataccgatgt ggattgcgca    8460
tactttgtga acgaaaagtg atagcgttga tgattcttca ttggtcagaa aattatgaac    8520
ggtttcttct attttgtctc tatatactac gtataggaaa tgtttacatt ttcgtattgt    8580
tttcgattca ctctatgaat agttcttact acaattttt tgtctaaaga gtaatactag    8640
agataaacat aaaaatgta gaggtcgagt ttagatgcaa gttcaaggag cgaaaggtgg    8700
atgggtaggt tatatatggga tatagcacag agatatatag caaagagata cttttgagca    8760
at                                                                  8762
```

<210> SEQ ID NO 58
<211> LENGTH: 5824
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

| | |
|---|---|
| gtttgtggaa gcggtattcg caatttaatt aaagctggtg acaattaatc atcggctcgt | 60 |
| ataatgtgtg gaattgaatc gatataagga ggttaatcat atgcaaacgc tcagcatcca | 120 |
| gcacggtacc ctcgtcacga tggatcagta ccgcagagtc cttggggata gctgggttca | 180 |
| cgtgcaggat ggacggatcg tcgcgctcgg agtgcacgcc gagtcggtgc ctccgccagc | 240 |
| ggatcgggtg atcgatgcac gcggcaaggt cgtgttaccc ggtttcatca atgcccacac | 300 |
| ccatgtgaac cagatcctcc tgcgcggagg cccctcgcac gggcgtcaac tctatgactg | 360 |
| gctgttcaac gttttgtatc cgggacaaaa ggcgatgaga ccggaggacg tagcggtggc | 420 |
| ggtgaggttg tattgtgcgg aagctgtgcg cagcgggatt acgacgatca acgacaacgc | 480 |
| cgattcggcc atctacccag gcaacatcga ggccgcgatg gcggtctatg gtgaggtggg | 540 |
| tgtgagggtc gtctacgccc gcatgttctt tgatcggatg gacgggcgca ttcaagggta | 600 |
| tgtggacgcc ttgaaggctc gctctcccca gtcgaactg tgctcgatca tggaggaaac | 660 |
| ggctgtggcc aaagatcgga tcacagccct gtcagatcag tatcatggca cggcaggagg | 720 |
| tcgtatatca gtttggcccg ctcctgccat taccccggcg gtgacagttg aaggaatgcg | 780 |
| atgggcacaa gccttcgccc gtgatcgggc ggtaatgtgg acgcttcaca tggcggagag | 840 |
| cgatcatgat gagcggcttc attggatgag tcccgccgag tacatggagt gttacggact | 900 |
| cttggatgag cgtctgcagg tcgcgcattg cgtgtacttt gaccggaagg atgttcggct | 960 |
| gctgcaccgc cacaatgtga aggtcgcgtc gcaggttgtg agcaatgcct acctcggctc | 1020 |
| agggggtggcc cccgtgccag atggtggga gcgcggcatg gccgtgggca ttggaacaga | 1080 |
| tgacgggaat tgtaatgact ccgtaaacat gatcggagac atgaagttta tggcccatat | 1140 |
| tcaccgcgcg gtgcatcggg atgcggacgt gctgacccca gagaagattc ttgaaatggc | 1200 |
| gacgatcgat ggggcgcgtt cgttgggaat ggaccacgag attggttcca tcgaaaccgg | 1260 |
| caagcgcgcg gaccttatcc tgcttgacct gcgtcaccct cagacgactc ctcaccatca | 1320 |
| tttggcggcc acgatcgtgt ttcaggctta cggcaatgag gtggacactg tcctgattga | 1380 |
| cggaaacgtt gtgatggaga accgccgctt gagctttctt ccccctgaac gtgagttggc | 1440 |
| gttccttgag gaagcgcaga gccgcgccac agctattttg cagcgggcga acatggtggc | 1500 |
| taacccagct tggcgcagcc tctaggttta acccctcaaa atatattttc cctctatctt | 1560 |
| ctcgttgcgc ttaatttgac taattctcat tagcgaggcg cgccttttcca taggctccgc | 1620 |
| cccccctgacg agcatcacaa aaatcgacgc tcaagtcaga ggtggcgaaa cccgacagga | 1680 |
| ctataaagat accaggcgtt tcccctggaa gctccctcg tgcgctctcc tgttccgacc | 1740 |
| ctgccgctta ccggatacct gtccgccttt ctcccttcgg gaagcgtggc gctttctcat | 1800 |
| agctcacgct gtaggtatct cagttcggtg taggtcgttc gctccaagct gggctgtgtg | 1860 |
| cacgaacccc ccgttcagcc cgaccgctgc gccttatccg gtaactatcg tcttgagtcc | 1920 |
| aacccggtaa gacacgactt atcgccactg gcagcagcca ctggtaacag gattagcaga | 1980 |
| gcgaggtatg taggcggtgc tacagagttc ttgaagtggt ggcctaacta cggctacact | 2040 |
| agaagaacag tatttggtat ctgcgctctg ctgaagccag ttaccttcgg aaaaagagtt | 2100 |
| ggtagctctt gatccggcaa acaaaccacc gctggtagcg tggtttttt tgtttgcaag | 2160 |
| cagcagatta cgcgcagaaa aaaggatct caagaagatc ctttgatctt ttctacgggg | 2220 |
| tctgacgctc agtggaacga aaactcacgt taagggattt tggtcatgag attatcaaaa | 2280 |
| aggatcttca cctagatcct tttaaattaa aaatgaagtt ttaaatcaat ctaaagtata | 2340 |
| tatgagtaaa cttggtctga cagttaccaa tgcttaatca gtgaggcacc tatctcagcg | 2400 |

```
atctgtctat tcgttcatc catagttgcc tgactcccg tcgtgtagat aactacgata    2460
cgggagggct taccatctgg ccccagtgct gcaatgatac cgcgagaccc acgctcaccg    2520
gctccagatt tatcagcaat aaaccagcca gccggaaggg ccgagcgcag aagtggtcct    2580
gcaactttat ccgcctccat ccagtctatt aattgttgcc gggaagctag agtaagtagt    2640
tcgccagtta atagtttgcg caacgttgtt gccattgcta caggcatcgt ggtgtcacgc    2700
tcgtcgtttg gtatggcttc attcagctcc ggttcccaac gatcaaggcg agttacatga    2760
tcccccatgt tgtgcaaaaa agcggttagc tccttcggtc ctccgatcgt tgtcagaagt    2820
aagttggccg cagtgttatc actcatggtt atggcagcac tgcataattc tcttactgtc    2880
atgccatccg taagatgctt ttctgtgact ggtgagtact caaccaagtc attctgagaa    2940
tagtgtatgc ggcgaccgag ttgctcttgc ccggcgtcaa tacgggataa taccgcgcca    3000
catagcagaa ctttaaaagt gctcatcatt ggaaaacgtt cttcggggcg aaaactctca    3060
aggatcttac cgctgttgag atccagttcg atgtaaccca ctcgtgcacc caactgatct    3120
tcagcatctt ttactttcac cagcgtttct gggtgagcaa aaacaggaag gcaaaatgcc    3180
gcaaaaaagg gaataagggc gacacggaaa tgttgaatac tcatactctt cctttttcaa    3240
tattattgaa gcatttatca gggttattgt ctcatgagcg gatacatatt tgaatgtatt    3300
tagaaaaata acagcgatc gcgcggccgc gggtaataac tgatataatt aaattgaagc    3360
tctaatttgt gagtttagta tacatgcatt tacttataat acagtttttt agttttgctg    3420
gccgcatctt ctcaaatatg cttcccagcc tgcttttctg taacgttcac cctctacctt    3480
agcatccctt ccctttgcaa atagtcctct tccaacaata ataatgtcag atcctgtaga    3540
gaccacatca tccacggttc tatactgttg acccaatgcg tctcccttgt catctaaacc    3600
cacaccgggt gtcataatca accaatcgta accttcatct cttccaccca tgtctctttg    3660
agcaataaag ccgataacaa atctttgtc gctcttcgca atgtcaacag taccttagt    3720
atattctcca gtagctaggg agcccttgca tgacaattct gctaacatca aaaggcctct    3780
aggttccttt gttacttctt ccgccgcctg cttcaaaccg ctaacaatac ctgggcccac    3840
cacaccgtgt gcattcgtaa tgtctgccca ttctgctatt ctgtatacac ccgcagagta    3900
ctgcaatttg actgtattac caatgtcagc aaattttctg tcttcgaaga gtaaaaaatt    3960
gtacttggcg gataatgcct ttagcggctt aactgtgccc tccatggaaa aatcagtcaa    4020
gatatccaca tgtgttttta gtaaacaaat tttgggacct aatgcttcaa ctaactccag    4080
taattccttg gtggtacgaa catccaatga agcacacaag tttgtttgct tttcgtgcat    4140
gatattaaat agcttggcag caacaggact aggatgagta gcagcacgtt ccttatatgt    4200
agctttcgac atgatttatc ttcgtttcct gcaggttttt gttctgtgca gttgggttaa    4260
gaatactggg caatttcatg tttcttcaac accacatatg cgtatatata ccaatctaag    4320
tctgtgctcc ttccttcgtt cttccttctg ctcggagatt accgaatcaa agctagctta    4380
tcgatgataa gctgtcaaag atgagaatta attccacgga ctatagacta tactagatac    4440
tccgtctact gtacgataca cttccgctca ggtccttgtc ctttaacgag gccttaccac    4500
tcttttgtta ctctattgat ccagctcagc aaaggcagtg tgatctaaga ttctatcttc    4560
gcgatgtagt aaaactagct agaccgagaa agagactaga aatgcaaaag gcacttctac    4620
aatggctgcc atcattatta tccgatgtga cgctgcagct tctcaatgat attcgaatac    4680
gctttgagga gatacagcct aatatccgac aaactgtttt acagatttac gatcgtactt    4740
```

-continued

```
gttacccatc attgaattttt gaacatccga acctgggagt tttccctgaa acagatagta    4800
tatttgaacc tgtataataa tatatagtct agcgctttac ggaagacaat gtatgtattt    4860
cggttcctgg agaaactatt gcatctattg cataggtaat cttgcacgtc gcatccccgg    4920
ttcattttct gcgtttccat cttgcacttc aatagcatat cttTgttaac gaagcatctg    4980
tgcttcattt tgtagaacaa aaatgcaacg cgagagcgct aattttTcaa acaaagaatc    5040
tgagctgcat ttttacagaa cagaaatgca acgcgaaagc gctattttac caacgaagaa    5100
tctgtgcttc attttTgtaa aacaaaaatg caacgcgacg agagcgctaa tttttcaaac    5160
aaagaatctg agctgcattt ttacagaaca gaaatgcaac gcgagagcgc tattttacca    5220
acaaagaatc tatacttctt ttttgttcta caaaaatgca tcccgagagc gctattttc    5280 taacaaagca tcttagatta ctttttttct cctttgtgcg ctctataatg cagtctcttg    5340 ataactttt gcactgtagg tccgttaagg ttagaagaag gctactttgg tgtctatttt    5400
ctcttccata aaaaaagcct gactccactc cccgcgttta ctgattacta gcgaagctgc    5460
gggtgcattt tttcaagata aaggcatccc cgattatatt ctataccgat gtggattgcg    5520
catactttgt gaacagaaag tgatagcgtt gatgattctt cattggtcag aaaattatga    5580
acggtttctt ctattttgtc tctatatact acgtatagga aatgtttaca ttttcgtatt    5640
gttttcgatt cactctatga atagttctta ctacaattTt tttgtctaaa gagtaatact    5700
agagataaac ataaaaatg tagaggtcga gtttagatgc aagttcaagg agcgaaaggt    5760
ggatgggtag gttatatagg gatatagcac agagatatat agcaaagaga tacttttgag    5820
caat                                                                5824
```

<210> SEQ ID NO 59
<211> LENGTH: 8336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
gtttgtggaa gcggtattcg caatttaatt aaagctggtg acaattaatc atcggctcgt     60
ataatgtgtg gaattgaatc gatataagga ggttaatcat atgactagaa tcgctatcac    120
aggtggtaga gttttgacta tggacccaga agaagagta ttagaaccag gtacagttgt    180
tgttgaagat caattcattg cacaagtcgg ttcaccagat gacgtagaca tcagaggtgc    240
tgaaattata gatgccactg gtatggctgt attaccaggt ttcgttaata cacataccca    300
cgttcctcaa attttgttaa gaggtggtgc ttcacatgat agaaatttgt tggaatggtt    360
gcacaacgtc ttatatccag gtttggctgc atacactgat gacgatatca gagttggtac    420
attgttatat tgtgctgaag cattgagatc cggtattact acagttgtcg acaatgaaga    480
tgttagacct aacgattttg ccagagctgg tgccgctggt attggtgcat tcactgatgc    540
cggtatcaga gcaatctatg ccagaatgta ctttgatgct ccaagagcag aattggaaga    600
attagtcgca acaatacatg caaaagcccc tggtgccgta agaatggacg aatctgcttc    660
aaccgatcat gttttggcag acttagatca attgattacc agacatgaca gaactgctga    720
tggtagaatt agagtatggc cagctcctgc aataccattc atggtttctg aaaagggtat    780
gaaggcagcc caagaaatag ctgcatccag aactgacggt tggacaatgc atgttagtga    840
agatccaatc gaagccagag tccactctat gaatgctcct gaatatttgc atcacttggg    900
```

```
ttgtttagac gatagattgt tagccgctca ttgcgttcac atagactcaa gagatatcag      960
attgtttaga caacatgatg ttaagatatc cacacaacct gtctccaata gttacttagc     1020
agccggtata gcaccagttc ctgaaatgtt ggctcatggt gtcacagtag gtattggtac     1080
cgacgatgct aattgtaacg actccgtaaa cttaatcagt gatatgaagg ttttggcatt     1140
gatacataga gctgcacaca gagatgctag tatcattacc ccagaaaaga taatcgaaat     1200
ggccactatt gacggtgcta gatgcattgg tatggctgat caaatcggtt ctttggaagc     1260
tggtaaaaga gcagacataa tcactttgga tttgagacat gcacaaacca ctcctgccca     1320
cgatttggcc gctacaattg tctttcaagc ttatggtaat gaagtaaacg atgttttggt     1380
caacggttct gtagttatga gagatagagt tttgtcattc ttaccaaccc ctcaagaaga     1440
aaaggcttta tacgacgatg catctgaaag atcagcagcc atgttagcca gagctggttt     1500
gactggtaca agaacctggc aaactttggg ttcttaagga aatccattat gatgtcagga     1560
gaacacacgt taaaagcggt acgaggcagt tttattgatg tcacccgtac gatcgataac     1620
ccggaagaga ttgcctctgc gctgcggttt attgaggatg gtttattact cattaaacag     1680
ggaaaagtgg aatggtttgg cgaatgggaa aacggaaagc atcaaattcc tgacaccatt     1740
cgcgtgcgcg actatcgcgg caaactgata gtaccgggct tgtcgataca acatatccat     1800
tatccgcaaa gtgaaatggt gggggcctat ggtgagcaat tgctggagtg gttgaataaa     1860
cacaccttcc ctactgaacg tcgttatgag gatttagagt acgcccgcga aatgtcggcg     1920
ttcttcatca agcagctttt acgtaacgga accaccacgg cgctggtgtt tggcactgtt     1980
catccgcaat ctgttgatgc gctgtttgaa gccgccagtc atatcaatat gcgtatgatt     2040
gccggtaagg tgatgatgga ccgcaacgca ccggattatc tgctcgacac tgccgaaagc     2100
agctatcacc aaagcaaaga actgatcgaa cgctggcaca aaaatggtcg tctgctatat     2160
gcgattacgc cacgcttcgc cccgacctca tctcctgaac agatggcgat ggcgcaacgc     2220
ctgaaagaag aatatccgga tacgtgggta catacccatc tctgtgaaaa caaagatgaa     2280
attgcctggg tgaaatcgct ttatcctgac catgatggtt atctggatgt ttaccatcag     2340
tacggcctga ccggtaaaaa ctgtgtcttt gctcactgcg tccatctcga agaaaaagag     2400
tgggatcgtc tcagcgaaac caaatccagc attgctttct gtccgacctc caacctttac     2460
ctcggcagcg gcttattcaa cttgaaaaaa gcatggcaga agaaagttaa agtgggcatg     2520
ggaacggata tcggtgccgg aaccactttc aacatgctgc aaacgctgaa cgaagcctac     2580
aaagtattgc aattacaagg ctatcgcctc tcggcatatg aagcgtttta cctggccacg     2640
ctcggcggag cgaaatctct gggccttgac gatttgattg caactttttt acctggcaaa     2700
gaggctgatt tcgtggtgat ggaacccacc gccactccgc tacagcagct gcgctatgac     2760
aactctgttt ctttagtcga caaattgttc gtgatgatga cgttgggcga tgaccgttcg     2820
atctaccgca cctacgttga tggtcgtctg gtgtacgaac gcaactaagg aacgaccatg     2880
agagaagtcc aattgttaga tggtagaaga gttgatgtcg cctgtgctgg tcctttgatt     2940
agtgaaatag gtgcccactt agatttgact gctccagttg aaattgattg tggtggtggt     3000
ttagcaacta gaccttttac tgaacctcat ttgcacttag acaaagcagg tactgccgat     3060
agattgcctg ccggtgcttc cacaatcggt gacgctattg ctgcaatgca agtgtcaag      3120 gtaaccgaaa gagataatgt cgccgctgta gcagccagaa tgcatagagt tttaaacaga     3180
atcgtcgatg acggttccca cgctattaga gcattggttg atgtcgacga agtttggggt     3240
ttaacagctt ttcatgctgc acaacaagtc caagccgctt tggccccaag agctgttgtc     3300
```

```
caaattgtcg ctttcccaca acacggttta acccctcaag tattggcaat gttagaacaa   3360
gcagccgctg aaggtgcagg tgccttgggt gctcatactg atgttgaccc agatcctgca   3420
gcccacgttg gtgccgtcgc tgcaatagcc gctggtgctt ccttgccatt agaagttcat   3480
actgacgaag gtgctagtcc agataaattt tatttgcctg cagtattgga agttttagat   3540
agattcccag gtttgtctac tacattagct cattgtttgt cattaggtac aattgcacct   3600
aagcaacaac aacattggat cgaagaatta gctcacagag atatcaaagt atgcgttgca   3660
ccatctattt tgggtttcgg tttgccatta gcacctgtta gagccttaat agaagctggt   3720
gtcggtatct tagtaggttc agacaatttg caagatgttt tctttccttt gggtacaggt   3780
agagcaattg aaaacgttag attgttagcc accgcagccc aattaactgc accagaattg   3840
gccggtcctt taattgctgg tgtaaccgac atagcttacg caaccgttac tggtgctgca   3900
gatgccttgg ctgttgaatc tccagctaca ttagtagttc atgatgctac ctcacctgca   3960
gaattgttaa gaggtataga cggtacaaga attaccgtta tagatggttt gttgacatct   4020
ccattgcaat tggataaagg tatcaagtaa gtttaaacta atcccacagc cgccagttcc   4080
gctggcggca ttttaacttt ctttaatggg cgcgcctttc cataggctcc gccccctga   4140
cgagcatcac aaaaatcgac gctcaagtca gaggtggcga acccgacag gactataaag   4200
ataccaggcg tttccccctg gaagctccct cgtgcgctct cctgttccga ccctgccgct   4260
taccggatac ctgtccgcct ttctcccttc gggaagcgtg gcgctttctc atagctcacg   4320
ctgtaggtat ctcagttcgg tgtaggtcgt tcgctccaag ctgggctgtg tgcacgaacc   4380
ccccgttcag cccgaccgct gcgccttatc cggtaactat cgtcttgagt ccaacccggt   4440
aagacacgac ttatcgccac tggcagcagc cactggtaac aggattagca gagcgaggta   4500
tgtaggcggt gctacagagt tcttgaagtg gtggcctaac tacggctaca ctagaagaac   4560
agtatttggt atctgcgctc tgctgaagcc agttaccttc ggaaaaagag ttggtagctc   4620
ttgatccggc aaacaaacca ccgctggtag cggtggtttt tttgtttgca agcagcagat   4680
tacgcgcaga aaaaaaggat ctcaagaaga tcctttgatc ttttctacgg ggtctgacgc   4740
tcagtggaac gaaaactcac gttaagggat tttggtcatg agattatcaa aaaggatctt   4800
cacctagatc cttttaaatt aaaaatgaag ttttaaatca atctaaagta tatatgagta   4860
aacttggtct gacagttacc aatgcttaat cagtgaggca cctatctcag cgatctgtct   4920
atttcgttca tccatagttg cctgactccc cgtcgtgtag ataactacga tacgggaggg   4980
cttaccatct ggccccagtg ctgcaatgat accgcgagac ccacgctcac cggctccaga   5040
tttatcagca ataaccagc cagccggaag ggccgagcgc agaagtggtc ctgcaacttt   5100
atccgcctcc atccagtcta ttaattgttg ccgggaagct agagtaagta gttcgccagt   5160
taatagtttg cgcaacgttg ttgccattgc tacaggcatc gtggtgtcac gctcgtcgtt   5220
tggtatggct tcattcagct ccggttccca acgatcaagg cgagttacat gatcccccat   5280
gttgtgcaaa aaagcggtta gctccttcgg tcctccgatc gttgtcagaa gtaagttggc   5340
cgcagtgtta tcactcatgg ttatggcagc actgcataat tctcttactg tcatgccatc   5400
cgtaagatgc ttttctgtga ctggtgagta ctcaaccaag tcattctgag aatagtgtat   5460
gcggcgaccg agttgctctt gcccggcgtc aatacgggat aataccgcgc cacatagcag   5520
aactttaaaa gtgctcatca ttggaaaacg ttcttcgggg cgaaaactct caaggatctt   5580
accgctgttg agatccagtt cgatgtaacc cactcgtgca cccaactgat cttcagcatc   5640
```

```
ttttactttc accagcgttt ctgggtgagc aaaaacagga aggcaaaatg ccgcaaaaaa    5700
gggaataagg gcgacacgga aatgttgaat actcatactc ttcctttttc aatattattg    5760
aagcatttat cagggttatt gtctcatgag cggatacata tttgaatgta tttagaaaaa    5820
taaacagcga tcgcgcggcc gcgggtaata actgatataa ttaaattgaa gctctaattt    5880
gtgagtttag tatacatgca tttacttata atacagtttt ttagttttgc tggccgcatc    5940
ttctcaaata tgcttcccag cctgcttttc tgtaacgttc accctctacc ttagcatccc    6000
ttccctttgc aaatagtcct cttccaacaa taataatgtc agatcctgta gagaccacat    6060
catccacggt tctatactgt tgacccaatg cgtctccctt gtcatctaaa cccacaccgg    6120
gtgtcataat caaccaatcg taaccttcat ctcttccacc catgtctctt tgagcaataa    6180
agccgataac aaaatctttg tcgctcttcg caatgtcaac agtaccctta gtatattctc    6240
cagtagctag ggagcccttg catgacaatt ctgctaacat caaaaggcct ctaggttcct    6300
ttgttacttc ttccgccgcc tgcttcaaac cgctaacaat acctgggccc accacaccgt    6360
gtgcattcgt aatgtctgcc cattctgcta ttctgtatac acccgcagag tactgcaatt    6420
tgactgtatt accaatgtca gcaaattttc tgtcttcgaa gagtaaaaaa ttgtacttgg    6480
cggataatgc ctttagcggc ttaactgtgc cctccatgaa aaaatcagtc aagatatcca    6540 catgtgttt tagtaaacaa attttgggac ctaatgcttc aactaactcc agtaattcct    6600
tggtggtacg aacatccaat gaagcacaca agtttgtttg cttttcgtgc atgatattaa    6660
atagcttggc agcaacagga ctaggatgag tagcagcacg ttccttatat gtagctttcg    6720
acatgattta tcttcgtttc ctgcaggttt ttgttctgtg cagttgggtt aagaatactg    6780
ggcaatttca tgtttcttca acaccacata tgcgtatata taccaatcta agtctgtgct    6840
ccttccttcg ttcttccttc tgctcggaga ttaccgaatc aaagctagct tatcgatgat    6900
aagctgtcaa agatgagaat taattccacg gactatagac tatactagat actccgtcta    6960
ctgtacgata cacttccgct caggtccttg tcctttaacg aggccttacc actcttttgt    7020
tactctattg atccagctca gcaaaggcag tgtgatctaa gattctatct tcgcgatgta    7080
gtaaaactag ctagaccgag aaagagacta gaaatgcaaa aggcacttct acaatggctg    7140
ccatcattat tatccgatgt gacgctgcag cttctcaatg atattcgaat acgctttgag    7200
gagatacagc ctaatatccg acaaactgtt ttacagattt acgatcgtac ttgttaccca    7260
tcattgaatt ttgaacatcc gaacctggga gttttccctg aaacagatag tatatttgaa    7320
cctgtataat aatatatagt ctagcgcttt acgaagaca atgtatgtat ttcggttcct    7380
ggagaaacta ttgcatctat tgcataggta atcttgcacg tcgcatcccc ggttcatttt    7440
ctgcgttccc atcttgcact tcaatagcat atctttgtta acgaagcatc tgtgcttcat    7500
tttgtagaac aaaaatgcaa cgcgagagcg ctaatttttc aaacaaagaa tctgagctgc    7560
atttttacag aacagaaatg caacgcgaaa gcgctatttt accaacgaag aatctgtgct    7620 tcattttgt aaaacaaaaa tgcaacgcga cgagagcgct aatttttcaa acaagaatc    7680 tgagctgcat ttttacagaa cagaaatgca acgcgagagc gctattttac caacaaagaa    7740
tctatacttc ttttttgttc tacaaaaatg catcccgaga cgctattttt ctaacaaag    7800 catcttagat tactttttt ctcctttgtg cgctctataa tgcagtctct tgataacttt    7860
ttgcactgta ggtccgttaa ggttagaaga aggctacttt ggtgtctatt ttctcttcca    7920
taaaaaaagc ctgactccac ttcccgcgtt tactgattac tagcgaagct gcgggtgcat    7980
tttttcaaga taaaggcatc cccgattata ttctataccg atgtggattg cgcatacttt    8040
```

| | |
|---|---|
| gtgaacagaa agtgatagcg ttgatgattc ttcattggtc agaaaattat gaacggtttc | 8100 |
| ttctattttg tctctatata ctacgtatag gaaatgttta cattttcgta ttgttttcga | 8160 |
| ttcactctat gaatagttct tactacaatt tttttgtcta aagagtaata ctagagataa | 8220 |
| acataaaaaa tgtagaggtc gagtttagat gcaagttcaa ggagcgaaag gtggatgggt | 8280 |
| aggttatata gggatatagc acagagatat atagcaaaga gatacttttg agcaat | 8336 |

<210> SEQ ID NO 60
<211> LENGTH: 8063
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

| | |
|---|---|
| gtttgtggaa gcggtattcg caatttaatt aaagctggtg acaattaatc atcggctcgt | 60 |
| ataatgtgtg gaattgaatc gatataagga ggttaatcat atgtcctcca cagcattata | 120 |
| caccgttcct accgcaggtc cagacgatgt tgccgccttg aaagcattag atggtcattc | 180 |
| cgcctccgat attttggctg taataggtaa acagagggg aatggttgtg ttaacgactt | 240 |
| tagtagaacc ttatctgctg cagttttggca tccattgtta gaagattcag ccattacagt | 300 |
| cttttccggt ggtgcagaag gtgtaataag tccacatgta aacatcttcg ttagagatga | 360 |
| aagacaatat tctggtcacc ctagaggttt ggtaactgct gttggtagaa caagagttat | 420 |
| cggtccagaa gaaattggta gacctgctca agtcgatgca gtacatgaaa ccgttgtcgc | 480 |
| attgttaact gaattgggtg ttggtccaga tgacgttcac ttggtcttga ttaaatgccc | 540 |
| tttgttatct tcagacgcta tagcaggtgt tcatagaaga ggtttaagac ctgtcactac | 600 |
| agatacttac gaatctatgt caagatccag agccgcttct gctttgggta tagccatggc | 660 |
| tttaaaggaa tgtgatagag acagagcatt gttagccttg gaaggtagag atgacgtttg | 720 |
| gtcagcaaga gcctccgctt ccagtggtgc tgaattggat gactgccaca ttttagtagt | 780 |
| tgcagaatca gatgcagccg ctaatccatt aagagcagcc catactgcca tgagagatgc | 840 |
| tttggacatc caagctttaa cagaagtttt tgacagaatt gctgcagaag gtggtaccgt | 900 |
| cagacaaata ttcgcaaagg ccgaagctga tccttcaggt gctatcagag gttatagaca | 960 |
| taccatgtta actgattccg acgtcaatgc aacaagacac gccagagccg ctgtaggtgg | 1020 |
| tttgattgca gccttacatg gtaacggtgc tgtctatgta tcaggtggtg cagaacacca | 1080 |
| aggtccaagt ggtggtggtt ctgttactgt tatatatgat gttcctgcaa cagccaacgc | 1140 |
| taccggtgaa gcttctagat aaggaaatcc attatgatat actcaacagt caacgctaat | 1200 |
| ccttacgctt ggccttacga tggttcaata gaccctgctc acaccgcttt aatcttaatc | 1260 |
| gattggcaaa tagacttttg tggtccaggt ggttatgtcg attccatggg ttacgactta | 1320 |
| tccttgacta gaagtggttt agaacctaca gcaagagtat tggctgcagc cagagatact | 1380 |
| ggtatgacag ttatccatac tagagaaggt cacagaccag atttggctga cttgccacct | 1440 |
| aataagagat ggagatctgc atcagccggt gctgaaatcg gttcagttgg tccatgtggt | 1500 |
| agaatttttag tcagaggtga acctggttgg gaaatagtac cagaagttgc acctagagaa | 1560 |
| ggtgaaccaa ttatagataa acctggtaaa ggtgctttct acgcaacaga tttggacttg | 1620 |
| ttgttgagaa caagagggtat cacccatttg attttgaccg gtataactac agatgtttgc | 1680 |
| gtccacacca ctatgagaga agccaacgat agaggttacg aatgtttaat tttgtctgat | 1740 |

```
tgcaccggtg ctactgacag aaagcatcac gaagctgcat tatctatggt caccatgcaa    1800
ggtggtgtat tcggtgcaac tgcccattca gatgactttat tggccgcttt gggtacaacc    1860
gttccagcag ccgctggtcc tagagctaga acagaataag gaacgaccat gacagttagt    1920
tccgatacaa ctgctgaaat atcgttaggt tggtcaatcc aagactggat tgatttccac    1980
aagtcatcaa gctcccaggc ttcactaagg cttcttgaat cactactaga ctctcaaaat    2040
gttgcgccaa tcgataatgc gtggatatcg ctaatttcaa aggaaaattt actgcaccaa    2100
ttccaaattt taaagagcag agaaaataaa gaaactctac ctctctacgg tgtccctatt    2160
gctgttaagg acaacatcga cgttagaggt ctacccacca ccgctgcatg tccatccttt    2220
gcatatgagc cttccaaaga ctctaaagta gtagaactac taagaaatgc aggtgcgata    2280
atcgtgggta agacaaactt ggaccaattt gccacaggat tagtcggcac acggtctcca    2340
tatgggaaaa caccttgcgc ttttagcaaa gagcatgtat ctggtggttc ctccgctggg    2400
tcagcatcgg tggtcgccag aggtatcgta ccaattgcat tgggtactga tacagcaggt    2460
tctggtagag tcccagccgc cttgaacaac ctgattggcc taaagccaac aaagggcgtc    2520
ttttcctgtc aaggtgtagt tcccgcttgt aaatctttag actgcgtctc catctttgca    2580
ttaaacctaa gtgatgctga acgctgcttc cgcatcatgt gccagccaga tcctgataat    2640
gatgaatatt ctagacccta tgtttccaac cctttgaaaa aatttcaag caatgtaacg    2700 attgctattc ctaaaaatat cccatggtat ggtgaaacca agaatcctgt actgttttcc    2760
aatgctgtcg aaaatctatc aagaacgggc gctaacgtca tagaaattga ttttgagcct    2820
cttttagagt tagctcgctg tttatacgaa ggtacttggg tggccgagcg ttatcaagct    2880
attcaatcgt ttttggacag taaaccacca aaggaatctt tggaccctac tgttattca    2940 attatagaag gggccaagaa atacagtgca gtagactgct tcagttttga atacaaaaga    3000
caaggcatct tgcaaaaagt gagacgactt ctcgaatcag tcgatgtatt gtgtgtgccc    3060
acatgtcctt taaatcctac tatgcaacaa gttgcggatg aaccagtcct agtcaattca    3120
agacaaggca catggactaa ttttgtcaac ttggcagatt tggcagccct tgctgttccc    3180
gcagggttcc gagacgatgg tttgccaaat ggtattactt taatcggtaa aaaattcaca    3240
gattacgcac tattagagtt ggctaaccgc tatttccaaa atatattccc caacggttcc    3300
agaacatacg gtacttttac ctcttcttca gtaaagccag caaacgatca attagtggga    3360
ccagactatg acccatctac gtccataaaa ttggctgttg tcggtgcaca tcttaagggt    3420
ctgcctctac attggcaatt ggaaaaggtc aatgcaacat atttatgtac aacaaaaaca    3480
tcaaaagctt accagctttt tgctttgccc aaaaatggac cagtttttaaa acctggtttg    3540 agaagagttc aagatagcaa tggctctcaa atcgaattag aagtgtacag tgttccaaaa    3600
gaactgttcg gtgctttttat ttccatggtt cctgaaccat taggaatagg ttcagtggag    3660
ttagaatctg gtgaatggat caaatccttt atttgtgaag aatctggtta caaagccaaa    3720
ggtacagttg atatcacaaa gtatggtgga tttagagcat attttgaaat gttgtaagtt    3780
taaactaatc ccacagccgc cagttccgct ggcggcattt taactttctt taatgggcgc    3840
gcctttccat aggctccgcc cccctgacga gcatcacaaa aatcgacgct caagtcagag    3900
gtggcgaaac ccgacaggac tataaagata ccaggcgttt ccccctggaa gctccctcgt    3960
gcgctctcct gttccgaccc tgccgcttac cggatacctg tccgcctttc tcccttcggg    4020
aagcgtggcg ctttctcata gctcacgctg taggtatctc agttcggtgt aggtcgttcg    4080
```

```
ctccaagctg ggctgtgtgc acgaaccccc cgttcagccc gaccgctgcg ccttatccgg      4140
taactatcgt cttgagtcca acccggtaag acacgactta tcgccactgg cagcagccac      4200
tggtaacagg attagcagag cgaggtatgt aggcggtgct acagagttct tgaagtggtg      4260
gcctaactac ggctacacta aagaacagt atttggtatc tgcgctctgc tgaagccagt       4320
taccttcgga aaagagttg gtagctcttg atccggcaaa caaccaccg ctggtagcgg         4380 tggttttttt gtttgcaagc agcagattac gcgcagaaaa aaggatctc aagaagatcc        4440 tttgatcttt tctacggggt ctgacgctca gtggaacgaa aactcacgtt aagggatttt      4500
ggtcatgaga ttatcaaaaa ggatcttcac ctagatcctt ttaaattaaa aatgaagttt      4560
taaatcaatc taaagtatat atgagtaaac ttggtctgac agttaccaat gcttaatcag      4620
tgaggcacct atctcagcga tctgtctatt tcgttcatcc atagttgcct gactccccgt      4680
cgtgtagata actacgatac gggagggctt accatctggc cccagtgctg caatgatacc      4740
gcgagaccca cgctcaccgg ctccagattt atcagcaata aaccagccag ccggaagggc      4800
cgagcgcaga agtggtcctg caactttatc cgcctccatc cagtctatta attgttgccg      4860
ggaagctaga gtaagtagtt cgccagttaa tagtttgcgc aacgttgttg ccattgctac      4920
aggcatcgtg gtgtcacgct cgtcgtttgg tatggcttca ttcagctccg gttcccaacg      4980
atcaaggcga gttacatgat cccccatgtt gtgcaaaaaa gcggttagct ccttcggtcc      5040
tccgatcgtt gtcagaagta agttggccgc agtgttatca ctcatggtta tggcagcact      5100
gcataattct cttactgtca tgccatccgt aagatgcttt tctgtgactg gtgagtactc      5160
aaccaagtca ttctgagaat agtgtatgcg gcgaccgagt tgctcttgcc cggcgtcaat      5220
acgggataat accgcgccac atagcagaac tttaaaagtg ctcatcattg gaaaacgttc      5280
ttcggggcga aaactctcaa ggatcttacc gctgttgaga tccagttcga tgtaacccac      5340
tcgtgcaccc aactgatctt cagcatcttt tactttcacc agcgtttctg ggtgagcaaa      5400
aacaggaagg caaaatgccg caaaaaaggg aataagggcg acacggaaat gttgaatact      5460
catactcttc ctttttcaat attattgaag catttatcag ggttattgtc tcatgagcgg      5520
atacatattt gaatgtattt agaaaaataa acagcgatcg cgcggccgcg ggtaataact      5580
gatataatta aattgaagct ctaatttgtg agtttagtat acatgcattt acttataata      5640
cagtttttta gttttgctgg ccgcatcttc tcaaatatgc ttcccagcct gcttttctgt      5700
aacgttcacc ctctacctta gcatcccttc cctttgcaaa tagtcctctt ccaacaataa      5760
taatgtcaga tcctgtagag accacatcat ccacggttct atactgttga cccaatgcgt      5820
ctcccttgtc atctaaaccc acaccgggtg tcataatcaa ccaatcgtaa ccttcatctc      5880
ttccacccat gtctctttga gcaataaagc cgataacaaa atctttgtcg ctcttcgcaa      5940
tgtcaacagt acccttagta tattctccag tagctaggga gccttgcat gacaattctg       6000 ctaacatcaa aaggcctcta ggttcctttg ttacttcttc cgccgcctgc ttcaaaccgc      6060
taacaatacc tgggcccacc acaccgtgtg cattcgtaat gtctgcccat tctgctattc      6120
tgtatacacc cgcagagtac tgcaatttga ctgtattacc aatgtcagca aattttctgt      6180
cttcgaagag taaaaaattg tacttggcgg ataatgcctt tagcggctta actgtgccct      6240
ccatggaaaa atcagtcaag atatccacat gtgtttttag taaacaaatt ttgggaccta      6300
atgcttcaac taactccagt aattccttgg tggtacgaac atccaatgaa gcacacaagt      6360
ttgtttgctt ttcgtgcatg atattaaata gcttggcagc aacaggacta ggatgagtag      6420
cagcacgttc cttatatgta gctttcgaca tgatttatct tcgtttcctg caggttttg      6480
```

```
ttctgtgcag ttgggttaag aatactgggc aatttcatgt ttcttcaaca ccacatatgc    6540
gtatatatac caatctaagt ctgtgctcct tccttcgttc ttccttctgc tcggagatta    6600
ccgaatcaaa gctagcttat cgatgataag ctgtcaaaga tgagaattaa ttccacggac    6660
tatagactat actagatact ccgtctactg tacgatacac ttccgctcag gtccttgtcc    6720
tttaacgagg ccttaccact cttttgttac tctattgatc cagctcagca aaggcagtgt    6780
gatctaagat tctatcttcg cgatgtagta aaactagcta daccgagaaa gagactagaa    6840
atgcaaaagg cacttctaca atggctgcca tcattattat ccgatgtgac gctgcagctt    6900
ctcaatgata ttcgaatacg ctttgaggag atacagccta atatccgaca aactgtttta    6960
cagatttacg atcgtacttg ttacccatca ttgaattttg aacatccgaa cctgggagtt    7020
ttccctgaaa cagatagtat atttgaacct gtataataat atatagtcta gcgctttacg    7080
gaagacaatg tatgtatttc ggttcctgga gaaactattg catctattgc ataggtaatc    7140
ttgcacgtcg catccccggt tcattttctg cgtttccatc ttgcacttca atagcatatc    7200
tttgttaacg aagcatctgt gcttcatttt gtagaacaaa aatgcaacgc gagagcgcta    7260 attttttcaaa caaagaatct gagctgcatt tttacagaac agaaatgcaa cgcgaaagcg    7320 ctatttacc aacgaagaat ctgtgcttca tttttgtaaa acaaaaatgc aacgcgacga    7380
gagcgctaat ttttcaaaca aagaatctga gctgcatttt tacagaacag aaatgcaacg    7440
cgagagcgct attttaccaa caaagaatct atacttcttt tttgttctac aaaaatgcat    7500
cccgagagcg ctatttttct aacaaagcat cttagattac ttttttttctc ctttgtgcgc    7560 tctataatgc agtctcttga taactttttg cactgtaggt ccgttaaggt tagaagaagg    7620
ctactttggt gtctatttc tcttccataa aaaaagcctg actccacttc ccgcgtttac    7680
tgattactag cgaagctgcg ggtgcatttt ttcaagataa aggcatcccc gattatattc    7740
tataccgatg tggattgcgc atactttgtg aacagaaagt gatagcgttg atgattcttc    7800
attggtcaga aaattatgaa cggtttcttc tattttgtct ctatatacta cgtataggaa    7860
atgtttacat tttcgtattg ttttcgattc actctatgaa tagttcttac tacaattttt    7920
ttgtctaaag agtaatacta gagataaaca taaaaatgt agaggtcgag tttagatgca    7980
agttcaagga gcgaaaggtg gatgggtagg ttatataggg atatagcaca gagatatata    8040
gcaaagagat acttttgagc aat                                            8063
```

<210> SEQ ID NO 61
<211> LENGTH: 8927
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
gtttgtggaa gcggtattcg caatcattta gtcgtgcaat gtatgacttt aagatttgtg      60
agcaggaaga aaagggagaa tcttctaacg ataaacccctt gaaaaactgg gtagactacg     120
ctatgttgag ttgctacgca ggctgcacaa ttacacgaga atgctcccgc ctaggattta     180
aggctaaggg acgtgcaatg cagacgacag atctaaatga ccgtgtcggt gaagtgttcg     240
ccaaactttt cggttaacac atgcagtgat gcacgcgcga tggtgctaag ttacatatat     300
atatatatat atatatatat atatatatag ccatagtgat gtctaagtaa cctttatggt     360
atatttctta atgtggaaag atactagcgc gcgcacccac acacaagctt cgtcttttct     420
```

```
tgaagaaaag aggaagctcg ctaaatggga ttccactttc cgttccctgc cagctgatgg    480
aaaaaggtta gtggaacgat gaagaataaa aagagagatc cactgaggtg aaatttcagc    540
tgacagcgag tttcatgatc gtgatgaaca atggtaacga gttgtggctg ttgccaggga    600
gggtggttct caacttttaa tgtatggcca aatcgctact tgggtttgtt atataacaaa    660
gaagaaataa tgaactgatt ctcttcctcc ttcttgtcct ttcttaattc tgttgtaatt    720
accttccttt gtaattttt ttgtaattat tcttcttaat aatccaaaca acacacata     780 ttacaataat gaagaagccc gagctgaccg ctacctctgt tgagaagttc ctgattgaga    840
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcaggag    1080 tcaccctgca ggacctccct gagactgagc tgcctgctgt cctccagcct gttgctgagg   1140
ccatggacgc tatcgctgct gctgatctgt cccagacctc gggtttcggc ccctttggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gataggttc     2040 attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta ctttttccat aggctccgcc ccctgacga gcatcacaaa aatcgacgct    2280
caagtcagag gtggcgaaac ccgacaggac tataaagata ccaggcgttt ccccctggaa   2340 gctcctcgt gcgctctcct gttccgaccc tgccgcttac cggatacctg tccgcctttc    2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta gaagaacagt atttggtatc tgcgctctgc   2700
tgaagccagt taccttcgga aaaagagttg gtagctcttg atccggcaaa caaaccaccg   2760
```

```
ctggtagcgg tggtttttttt gtttgcaagc agcagattac gcgcagaaaa aaaggatctc    2820
aagaagatcc tttgatcttt tctacggggt ctgacgctca gtggaacgaa aactcacgtt    2880
aagggatttt ggtcatgaga ttatcaaaaa ggatcttcac ctagatcctt ttaaattaaa    2940
aatgaagttt taaatcaatc taaagtatat atgagtaaac ttggtctgac agttaccaat    3000
gcttaatcag tgaggcacct atctcagcga tctgtctatt tcgttcatcc atagttgcct    3060
gactccccgt cgtgtagata actacgatac gggagggctt accatctggc cccagtgctg    3120
caatgatacc gcgagaccca cgctcaccgg ctccagattt atcagcaata aaccagccag    3180
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa acaggaagg caaaatgccg caaaaaggg aataagggcg acacggaaat    3840
gttgaatact catactcttc ctttttcaat attattgaag catttatcag ggttattgtc    3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca aagaatttat tcgtacgaat cacagggacg    4260
gccgccctca ccgaaccagc gaatacctca gcggtcccct gcagtgactc aacaaagcga    4320
tatgaacatc ttgcgatggt atcctgctga tagttttttac tgtacaaaca cctgtgtagc    4380
tccttctagc atttttaagt tattcacacc tcaaggggag ggataaatta aataaattcc    4440
aaaagcgaag atcgagaaac taaattaaaa ttccaaaaac gaagttggaa cacaaccccc    4500
cgaaaaaaaa caacaaacaa aaacccaac aaaataaaca aaacaaaat aaatatataa    4560 ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
tcaaagtatc ataacgttag ttattttatt ttatttaata aaagaaaaca acaagatggg    4740
ctcaaaactt tcaacttata cgatacatac caaataacaa tttagtattt atctaagtgc    4800
ttttcgtaga taatggaata caaatggata tccagagtat acacatggat agtatacact    4860
gacacgacaa ttctgtatct ctttatgtta actactgtga ggcattaaat agagcttgat    4920
atataaaatg ttacatttca cagtctgaac ttttgcagat tacctaattt ggtaagatat    4980
taattatgaa ctgaaagttg atggcggccg catagcttca aaatgtttct actccttttt    5040
tactcttcca gattttctcg gactccgcgc atcgccgtac cacttcaaaa cacccaagca    5100
cagcatacta aatttcccct ctttcttcct ctagggtgtc gttaattacc cgtactaaag    5160
```

```
gtttggaaaa gaaaaaagag accgcctcgt ttcttttttct tcgtcgaaaa aggcaataaa      5220 aattttatc acgtttcttt ttcttgaaaa tttttttttt tgatttttt ctctttcgat        5280 gacctcccat tgatatttaa gttaataaac ggtcttcaat ttctcaagtt tcagtttcat      5340
ttttcttgtt ctattacaac ttttttact tcttgctcat tagaaagaaa gcatagcaat      5400
ctaatctaag ttttaattac aaaatgtcat cctcagaagt aaaagcaaat ggttggaccg      5460
cagttcctgt ttccgcaaaa gcaatagtag actccttggg taaattagga gatgtctctt      5520
catattccgt agaagatatt gccttttccag ctgcagacaa attggtagcc gaagctcaag     5580
cattcgttaa ggctagatta tctcctgaaa cctacaacca ttcaatgaga gttttctatt     5640
ggggtactgt cattgccaga agattgttac cagaacaagc taaagatttg tctccttcaa     5700
catgggcatt aacctgtttg ttacacgacg ttggtactgc cgaagcttat tttacctcca    5760
ctagaatgag tttcgatatc tacggtggta ttaaagctat ggaagtattg aaggttttag     5820
gttccagtac agatcaagca gaagccgttg ctgaagcaat tataagacat gaagatgttg     5880
gtgtcgacgg taacatcaca ttttttgggtc aattgatcca attggcaaca ttgtacgata    5940
acgtcggtgc ctacgacggt attgatgact tcggttcctg ggttgatgac actacaagaa     6000
acagtataaa cactgctttc ccaagacatg gttggtgttc ttggttcgca tgcacagtta     6060
gaaaagaaga atcaaacaag ccttggtgcc acaccacaca cataccacaa ttcgacaaac     6120
aaatggaagc aaacaccttg atgaaacctt gggaataaac aggcccctt tcctttgtcg      6180 atatcatgta attagttatg tcacgcttac attcacgccc tcctcccaca tccgctctaa     6240
ccgaaaagga aggagttaga caacctgaag tctaggtccc tattttatttt ttttaatagt    6300 tatgttagta ttaagaacgt tatttatatt tcaaatttt ctttttttc tgtacaaacg     6360 cgtgtacgca tgtaacatta tactgaaaac cttgcttgag aaggttttgg gacgctcgaa     6420
ggctttaatt tgcgggtaat aactgatata attaaattga agctctaatt tgtgagttta    6480
gtatacatgc atttacttat aatacagttt tttagttttg ctggccgcat cttctcaaat    6540
atgcttccca gcctgctttt ctgtaacgtt caccctctac cttagcatcc cttcccttgg    6600
caaatagtcc tcttccaaca ataataatgt cagatcctgt agagaccaca tcatccacgg     6660
ttctatactg ttgacccaat gcgtctccct tgtcatctaa acccacaccg ggtgtcataa     6720
tcaaccaatc gtaaccttca tctcttccac ccatgtctct ttgagcaata aagccgataa     6780
caaaatcttt gtcgctcttc gcaatgtcaa cagtacccct agtatattct ccagtagcta   6840
gggagcccct tgcatgacaat tctgctaaca tcaaaaggcc tctaggttcc tttgttactt    6900
cttccgccgc ctgcttcaaa ccgctaacaa tacctgggcc caccacaccg tgtgcattcg     6960
taatgtctgc ccattctgct attctgtata caccccgcaga gtactgcaat ttgactgtat    7020
taccaatgtc agcaaatttt ctgtcttcga agagtaaaaa attgtacttg gcggataatg     7080
cctttagcgg cttaactgtg ccctccatgg aaaaatcagt caagatatcc acatgtgttt     7140
ttagtaaaca aattttggga cctaatgctt caactaactc cagtaattcc ttggtggtac     7200
gaacatccaa tgaagcacac aagtttgttt gcttttcgtg catgatatta aatagcttgg     7260
cagcaacagg actaggatga gtagcagcac gttccttata tgtagctttc gacatgattt     7320
atcttcgttt cctgcaggtt tttgttctgt gcagttgggt taagaatact gggcaatttc     7380 atgttttcttc aacaccacat atgcgtatat ataccaatct aagtctgtgc tccttccttc    7440
gttcttcctt ctgctcggag attaccgaat caaagctagc ttatcgatga taagctgtca    7500
```

| | | | | | |
|---|---|---|---|---|---|
| aagatgagaa | ttaattccac | ggactataga | ctatactaga | tactccgtct | actgtacgat | 7560 |
| acacttccgc | tcaggtcctt | gtcctttaac | gaggccttac | cactcttttg | ttactctatt | 7620 |
| gatccagctc | agcaaaggca | gtgtgatcta | agattctatc | ttcgcgatgt | agtaaaacta | 7680 |
| gctagaccga | gaaagagact | agaaatgcaa | aaggcacttc | tacaatggct | gccatcatta | 7740 |
| ttatccgatg | tgacgctgca | gcttctcaat | gatattcgaa | tacgctttga | ggagatacag | 7800 |
| cctaatatcc | gacaaactgt | tttacagatt | tacgatcgta | cttgttaccc | atcattgaat | 7860 |
| tttgaacatc | cgaacctggg | agttttccct | gaaacagata | gtatatttga | acctgtataa | 7920 |
| taatatatag | tctagcgctt | tacggaagac | aatgtatgta | tttcggttcc | tggagaaact | 7980 |
| attgcatcta | ttgcataggt | aatcttgcac | gtcgcatccc | cggttcattt | tctgcgtttc | 8040 |
| catcttgcac | ttcaatagca | tatctttgtt | aacgaagcat | ctgtgcttca | ttttgtagaa | 8100 |
| caaaaatgca | acgcgagagc | gctaattttt | caaacaaaga | atctgagctg | catttttaca | 8160 |
| gaacagaaat | gcaacgcgaa | agcgctattt | taccaacgaa | gaatctgtgc | ttcattttg | 8220 |
| taaaacaaaa | atgcaacgcg | acgagagcgc | taatttttca | aacaaagaat | ctgagctgca | 8280 |
| ttttacaga | acagaaatgc | aacgcgagag | cgctatttta | ccaacaaaga | atctatactt | 8340 |
| cttttttgtt | ctacaaaaat | gcatcccgag | agcgctattt | tctaacaaa | gcatcttaga | 8400 |
| ttactttttt | tctcctttgt | gcgctctata | atgcagtctc | ttgataactt | tttgcactgt | 8460 |
| aggtccgtta | aggttagaag | aaggctactt | tggtgtctat | tttctcttcc | ataaaaaaag | 8520 |
| cctgactcca | cttcccgcgt | ttactgatta | ctagcgaagc | tgcgggtgca | ttttttcaag | 8580 |
| ataaaggcat | ccccgattat | attctatacc | gatgtggatt | gcgcatactt | tgtgaacaga | 8640 |
| aagtgatagc | gttgatgatt | cttcattggt | cagaaaatta | tgaacggttt | cttctatttt | 8700 |
| gtctctatat | actacgtata | ggaaatgttt | acatttcgt | attgttttcg | attcactcta | 8760 |
| tgaatagttc | ttactacaat | ttttttgtct | aaagagtaat | actagagata | aacataaaaa | 8820 |
| atgtagaggt | cgagtttaga | tgcaagttca | aggagcgaaa | ggtggatggg | taggttatat | 8880 |
| agggatatag | cacagagata | tatagcaaag | agatactttt | gagcaat | | 8927 |

<210> SEQ ID NO 62
<211> LENGTH: 8918
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

| | | | | | |
|---|---|---|---|---|---|
| gtttgtggaa | gcggtattcg | caatcattta | gtcgtgcaat | gtatgacttt | aagatttgtg | 60 |
| agcaggaaga | aaagggagaa | tcttctaacg | ataaaccctt | gaaaaactgg | gtagactacg | 120 |
| ctatgttgag | ttgctacgca | ggctgcacaa | ttacacgaga | atgctcccgc | ctaggattta | 180 |
| aggctaaggg | acgtgcaatg | cagacgcacg | atctaaatga | ccgtgtcggt | gaagtgttcg | 240 |
| ccaaactttt | cggttaacac | atgcagtgat | gcacgcgcga | tggtgctaag | ttacatatat | 300 |
| atatatatat | atatatatat | atatatatag | ccatagtgat | gtctaagtaa | cctttatggt | 360 |
| atatttctta | atgtggaaag | atactagcgc | gcgcacccac | acacaagctt | cgtcttttct | 420 |
| tgaagaaaag | aggaagctcg | ctaaatggga | ttccactttc | cgttccctgc | cagctgatgg | 480 |
| aaaaaggtta | gtggaacgat | gaagaataaa | aagagagatc | cactgaggtg | aaatttcagc | 540 |
| tgacagcgag | tttcatgatc | gtgatgaaca | atggtaacga | gttgtggctg | ttgccaggga | 600 |

-continued

```
gggtggttct caacttttaa tgtatggcca aatcgctact tgggtttgtt atataacaaa      660
gaagaaataa tgaactgatt ctcttcctcc ttcttgtcct ttcttaattc tgttgtaatt      720 accttcctt  gtaatttttt ttgtaattat tcttcttaat aatccaaaca aacacacata      780
ttacaataat gaagaagccc gagctgaccg ctacctctgt tgagaagttc ctgattgaga      840
agtttgattc cgtttccgac ctgatgcagc tgtccgaggg cgaggagtct cgagccttct      900
cctttgacgt gggcggacga ggttacgttc tgcgagtgaa ctcgtgtgcc gacggcttct      960
acaaggatcg atacgtctac cgacactttg cttctgccgc tctgcccatc cctgaggttc     1020
tcgacattgg cgagttctct gagtccctca cctactgcat ctctcgacga gctcagggag     1080
tcaccctgca ggacctccct gagactgagc tgcctgctgt cctccagcct gttgctgagg     1140
ccatggacgc tatcgctgct gctgatctgt cccagacctc gggtttcggc ccctttggac     1200
ctcagggaat tggacagtac accacttggc gagacttcat ctgtgctatt gccgatcctc     1260
acgtctacca ttggcagacc gttatggacg atactgtgtc ggcttctgtc gctcaggctc     1320
tggacgagct gatgctctgg gccgaggatt gccccgaggt tcgacacctg gtgcatgctg     1380
acttcggttc caacaacgtt ctcaccgaca acggccgaat cactgccgtg attgactggt     1440
ccgaggctat gtttggcgac tcgcagtacg aggtggccaa catcttcttt tggcgacccct     1500 ggctggcttg tatggagcag cagacccgat acttcgagcg acgacatcct gagctcgctg     1560
gatcccctcg actgcgagct acatgctccc gaattggtct ggaccagctc taccagtcgc     1620
tggtggatgg caactttgac gatgctgcct gggctcaggg acgatgtgac gccatcgtgc     1680
gatctggcgc tggaaccgtc ggacgaactc agattgcccg acgatccgct gctgtctgga     1740
ccgacggatg cgtggaggtc ctggctgatt cgggtaaccg acgaccctct actcgacctc     1800
gagctaagga gtaataaacg cgcgccgtc tgaagaatga atgatttgat gatttctttt      1860
tccctccatt tttcttactg aatatatcaa tgatatagac ttgtatagtt tattatttca     1920
aattaagtag ctatatatag tcaagataac gtttgtttga cacgattaca ttattcgtcg     1980
acatcttttt tcagcctgtc gtggtagcaa tttgaggagt attattaatt gaataggttc     2040
attttgcgct cgcataaaca gttttcgtca gggacagtat gttggaatga gtggtaatta     2100
atggtgacat gacatgttat agcaataacc ttgatgttta catcgtagtt taatgtacac     2160
cccgcgaatt cgttcaagta ggagtgcacc aattgcaaag ggaaaagctg aatgggcagt     2220
tcgaatagta cttttttccat aggctccgcc ccctgacga gcatcacaaa aatcgacgct     2280
caagtcagag gtggcgaaac ccgacaggac tataaagata ccaggcgttt ccccctggaa     2340
gctccctcgt gcgctctcct gttccgaccc tgccgcttac cggatacctg tccgcctttc     2400
tcccttcggg aagcgtggcg ctttctcata gctcacgctg taggtatctc agttcggtgt     2460
aggtcgttcg ctccaagctg gctgtgtgc acgaaccccc cgttcagccc gaccgctgcg      2520
ccttatccgg taactatcgt cttgagtcca acccggtaag acacgactta tcgccactgg     2580
cagcagccac tggtaacagg attagcagag cgaggtatgt aggcggtgct acagagttct     2640
tgaagtggtg gcctaactac ggctacacta agaacagt atttggtatc tgcgctctgc       2700
tgaagccagt taccttcgga aaagagttg gtagctcttg atccggcaaa caaccaccg        2760 ctggtagcgg tggttttttt gtttgcaagc agcagattac gcgcagaaaa aaggatctc       2820 aagaagatcc tttgatcttt tctacggggt ctgacgctca gtggaacgaa aactcacgtt     2880
aagggatttt ggtcatgaga ttatcaaaaa ggatcttcac ctagatcctt ttaaattaaa     2940
aatgaagttt taaatcaatc taaagtatat atgagtaaac ttggtctgac agttaccaat     3000
```

```
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
ccggaagggc cgagcgcaga agtggtcctg caactttatc cgcctccatc cagtctatta   3240
attgttgccg ggaagctaga gtaagtagtt cgccagttaa tagtttgcgc aacgttgttg   3300
ccattgctac aggcatcgtg gtgtcacgct cgtcgtttgg tatggcttca ttcagctccg   3360
gttcccaacg atcaaggcga gttacatgat cccccatgtt gtgcaaaaaa gcggttagct   3420
ccttcggtcc tccgatcgtt gtcagaagta agttggccgc agtgttatca ctcatggtta   3480
tggcagcact gcataattct cttactgtca tgccatccgt aagatgcttt tctgtgactg   3540
gtgagtactc aaccaagtca ttctgagaat agtgtatgcg gcgaccgagt tgctcttgcc   3600
cggcgtcaat acgggataat accgcgccac atagcagaac tttaaaagtg ctcatcattg   3660
gaaaacgttc ttcggggcga aaactctcaa ggatcttacc gctgttgaga tccagttcga   3720
tgtaacccac tcgtgcaccc aactgatctt cagcatcttt tactttcacc agcgtttctg   3780
ggtgagcaaa aacaggaagg caaaatgccg caaaaaaggg aataagggcg acacggaaat   3840
gttgaatact catactcttc ctttttcaat attattgaag catttatcag ggttattgtc   3900
tcatgagcgg atacatattt gaatgtattt agaaaaataa acagcgatcg cagctagctc   3960
gtcgtgttca ggaactgttc gatggttcgg agagagtcgc cgcccagaac atacgcgcac   4020
cgatgtcagc agacagcctt attacaagta tattcaagca agtatatccg tagggtgcgg   4080
gtgatttgga tctaaggttc gtactcaaca ctcacgagca gcttgcctat gttacatcct   4140
tttatcagac ataacataat tggagtttac ttacacacgg ggtgtacctg tatgagcacc   4200
acctacaatt gtagcactgg tacttgtaca aagaatttat tcgtacgaat cacagggacg   4260
gccgccctca ccgaaccagc gaatacctca gcggtcccct gcagtgactc aacaaagcga   4320
tatgaacatc ttgcgatggt atcctgctga tagttttttac tgtacaaaca cctgtgtagc   4380
tccttctagc attttttaagt tattcacacc tcaaggggag ggataaatta ataaaattcc   4440
aaaagcgaag atcgagaaac taaattaaaa ttccaaaaac gaagttggaa cacaccccc    4500 cgaaaaaaaa caacaaacaa aaacccaac aaaataaaca aaaacaaaat aaatatataa     4560
ctaccagtat ctgactaaaa gttcaaatac tcgtacttac aacaaataga aatgagccgg   4620
ccaaaattct gcagaaaaaa atttcaaaca agtactggta taattaaatt aaaaaacaca   4680
tcaaagtatc ataacgttag ttattttatt ttatttaata aaagaaaaca acaagatggg   4740
ctcaaaactt tcaacttata cgatacatac caaataacaa tttagtattt atctaagtgc   4800
ttttcgtaga taatggaata caaatggata tccagagtat acacatggat agtatacact   4860
gacacgacaa ttctgtatct ctttatgtta actactgtga ggcattaaat agagcttgat   4920
atataaaatg ttcatttca cagtctgaac ttttgcagat tacctaattt ggtaagatat    4980
taattatgaa ctgaaagttg atggcggccg catagcttca aaatgtttct actccttttt   5040
tactcttcca gattttctcg gactccgcgc atcgccgtac cacttcaaaa cacccaagca   5100
cagcatacta aatttccccct cttcttcct ctagggtgtc gttaattacc cgtactaaag    5160
gtttggaaaa gaaaaagag accgcctcgt ttcttttttct tcgtcgaaaa aggcaataaa    5220 aattttatc acgttcttt ttcttgaaaa ttttttttttt tgatttttttt ctctttcgat    5280 gacctcccat tgatatttaa gttaataaac ggtcttcaat ttctcaagtt tcagtttcat   5340
```

```
ttttcttgtt ctattacaac ttttttttact tcttgctcat tagaaagaaa gcatagcaat    5400
ctaatctaag ttttaattac aaaatgatat actcaacagt caacgctaat ccttacgctt    5460
ggccttacga tggttcaata gaccctgctc acaccgcttt aatcttaatc gattggcaaa    5520 tagactttg  tggtccaggt ggttatgtcg attccatggg ttacgactta tccttgacta    5580
gaagtggttt agaacctaca gcaagagtat tggctgcagc cagagatact ggtatgacag    5640
ttatccatac tagagaaggt cacagaccag atttggctga cttgccacct aataagagat    5700
ggagatctgc atcagccggt gctgaaatcg gttcagttgg tccatgtggt agaattttag    5760
tcagaggtga acctggttgg gaaatagtac cagaagttgc acctagagaa ggtgaaccaa    5820
ttatagataa acctggtaaa ggtgctttct acgcaacaga tttggacttg ttgttgagaa    5880
caagaggtat cacccatttg attttgaccg gtataactac agatgtttgc gtccacacca    5940
ctatgagaga agccaacgat agaggttacg aatgtttaat tttgtctgat tgcaccggtg    6000
ctactgacag aaagcatcac gaagctgcat tatctatggt caccatgcaa ggtggtgtat    6060
tcggtgcaac tgcccattca gatgacttat tggccgcttt gggtacaacc gttccagcag    6120
ccgctggtcc tagagctaga acagaataaa caggccccct ttcctttgtc gatatcatgt    6180
aattagttat gtcacgctta cattcacgcc ctcctcccac atccgctcta accgaaaagg    6240
aaggagttag acaacctgaa gtctaggtcc ctatttattt tttttaatag ttatgttagt    6300
attaagaacg ttatttatat ttcaaatttt tctttttttt ctgtacaaac gcgtgtacgc    6360
atgtaacatt atactgaaaa ccttgcttga gaaggttttg ggacgctcga aggctttaat    6420
ttgcgggtaa taactgatat aattaaattg aagctctaat ttgtgagttt agtatacatg    6480
catttactta taatacagtt ttttagtttt gctggccgca tcttctcaaa tatgcttccc    6540
agcctgcttt tctgtaacgt tcaccctcta ccttagcatc ccttcccttt gcaaatagtc    6600
ctcttccaac aataataatg tcagatcctg tagagaccac atcatccacg gttctatact    6660
gttgacccaa tgcgtctccc ttgtcatcta aacccacacc gggtgtcata atcaaccaat    6720
cgtaaccttc atctcttcca cccatgtctc tttgagcaat aaagccgata acaaaatctt    6780
tgtcgctctt cgcaatgtca acagtaccct tagtatattc tccagtagct agggagccct    6840
tgcatgacaa ttctgctaac atcaaaaggc ctctaggttc cttttgttact tcttccgccg    6900 cctgcttcaa accgctaaca ataccctggg ccaccacacc gtgtgcattc gtaatgtctg    6960
cccattctgc tattctgtat acacccgcag agtactgcaa tttgactgta ttaccaatgt    7020
cagcaaattt tctgtcttcg aagagtaaaa aattgtactt ggcggataat gcctttagcg    7080
gcttaactgt gccctccatg gaaaaatcag tcaagatatc cacatgtgtt tttagtaaac    7140
aaattttggg acctaatgct tcaactaact ccagtaattc cttggtggta cgaacatcca    7200
atgaagcaca caagtttgtt tgcttttcgt gcatgatatt aaatagcttg gcagcaacag    7260
gactaggatg agtagcagca cgttccttat atgtagcttt cgacatgatt tatcttcgtt    7320
tcctgcaggt ttttgttctg tgcagttggg ttaagaatac tgggcaattt catgtttctt    7380
caacaccaca tatgcgtata tataccaatc taagtctgtg ctccttcctt cgttcttcct    7440
tctgctcgga gattaccgaa tcaaagctag cttatcgatg ataagctgtc aaagatgaga    7500
attaattcca cggactatag actatactag atactccgtc tactgtacga tacacttccg    7560
ctcaggtcct tgtcctttaa cgaggcctta ccactctttt gttactctat tgatccagct    7620
cagcaaaggc agtgtgatct aagattctat cttcgcgatg tagtaaaact agctagaccg    7680
agaaagagac tagaaatgca aaaggcactt ctacaatggc tgccatcatt attatccgat    7740
```

```
gtgacgctgc agcttctcaa tgatattcga atacgctttg aggagataca gcctaatatc    7800
cgacaaactg ttttacagat ttacgatcgt acttgttacc catcattgaa ttttgaacat    7860
ccgaacctgg gagttttccc tgaaacagat agtatatttg aacctgtata ataatatata    7920
gtctagcgct ttacggaaga caatgtatgt atttcggttc ctggagaaac tattgcatct    7980
attgcatagg taatcttgca cgtcgcatcc ccggttcatt ttctgcgttt ccatcttgca    8040
cttcaatagc atatctttgt taacgaagca tctgtgcttc atttgtaga acaaaaatgc     8100 aacgcgagag cgctaatttt tcaaacaaag aatctgagct gcatttttac agaacagaaa    8160
tgcaacgcga aagcgctatt ttaccaacga agaatctgtg cttcattttt gtaaaacaaa    8220
aatgcaacgc gacgagagcg ctaatttttc aaacaaagaa tctgagctgc attttacag    8280 aacagaaatg caacgcgaga gcgctatttt accaacaaag aatctatact tcttttttgt    8340
tctacaaaaa tgcatcccga gagcgctatt tttctaacaa agcatcttag attactttt    8400 ttctcctttg tgcgctctat aatgcagtct cttgataact ttttgcactg taggtccgtt    8460
aaggttagaa gaaggctact ttggtgtcta ttttctcttc cataaaaaaa gcctgactcc    8520
acttcccgcg tttactgatt actagcgaag ctgcgggtgc attttttcaa gataaaggca    8580
tccccgatta tattctatac cgatgtggat tgcgcatact ttgtgaacag aaagtgatag    8640
cgttgatgat tcttcattgg tcagaaaatt atgaacggtt tcttctattt tgtctctata    8700
tactacgtat aggaaatgtt tacattttcg tattgttttc gattcactct atgaatagtt    8760
cttactacaa ttttttttgtc taaagagtaa tactagagat aaacataaaa aatgtagagg    8820
tcgagtttag atgcaagttc aaggagcgaa aggtggatgg gtaggttata tagggatata    8880
gcacagagat atatagcaaa gagatacttt tgagcaat                           8918

<210> SEQ ID NO 63
<211> LENGTH: 8894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gtttgtggaa gcggtattcg caatcattta gtcgtgcaat gtatgacttt aagatttgtg      60
agcaggaaga aaagggagaa tcttctaacg ataaaccctt gaaaaactgg gtagactacg     120
ctatgttgag ttgctacgca ggctgcacaa ttacacgaga atgctcccgc ctaggattta     180
aggctaaggg acgtgcaatg cagacgacag atctaaatga ccgtgtcggt gaagtgttcg     240
ccaaactttt cggttaacac atgcagtgat gcacgcgcga tggtgctaag ttacatatat     300
atatatatat atatatatat atatatatag ccatagtgat gtctaagtaa cctttatggt     360
atatttctta atgtggaaag atactagcgc gcgcacccac acacaagctt cgtcttttct     420
tgaagaaaag aggaagctcg ctaaatggga ttccactttc cgttccctgc cagctgatgg     480
aaaaaggtta gtggaacgat gaagaataaa agagagatc cactgaggtg aaatttcagc      540
tgacagcgag tttcatgatc gtgatgaaca atggtaacga gttgtggctg ttgccaggga     600
gggtggttct caacttttaa tgtatggcca aatcgctact tgggtttgtt atataacaaa     660
gaagaaataa tgaactgatt ctcttcctcc ttcttgtcct ttcttaattc tgttgtaatt     720
accttccttt gtaattttttt ttgtaattat tcttcttaat aatccaaaca aacacacata    780
ttacaataat gaagaagccc gagctgaccg ctacctctgt tgagaagttc ctgattgaga    840
```

```
agtttgattc cgtttccgac ctgatgcagc tgtccgaggg cgaggagtct cgagccttct    900
cctttgacgt gggcggacga ggttacgttc tgcgagtgaa ctcgtgtgcc gacggcttct    960
acaaggatcg atacgtctac cgacactttg cttctgccgc tctgcccatc cctgaggttc   1020
tcgacattgg cgagttctct gagtccctca cctactgcat ctctcgacga gctcagggag   1080
tcaccctgca ggacctccct gagactgagc tgcctgctgt cctccagcct gttgctgagg   1140
ccatggacgc tatcgctgct gctgatctgt cccagacctc gggtttcggc cccttTggac   1200
ctcagggaat tggacagtac accacttggc gagacttcat ctgtgctatt gccgatcctc   1260
acgtctacca ttggcagacc gttatggacg atactgtgtc ggcttctgtc gctcaggctc   1320
tggacgagct gatgctctgg gccgaggatt gccccgaggt tcgacacctg gtgcatgctg   1380
acttcggttc caacaacgtt ctcaccgaca acggccgaat cactgccgtg attgactggt   1440
ccgaggctat gtttggcgac tcgcagtacg aggtggccaa catcttcttt tggcgaccct   1500
ggctggcttg tatggagcag cagacccgat acttcgagcg acgacatcct gagctcgctg   1560
gatcccctcg actgcgagct tacatgctcc gaattggtct ggaccagctc taccagtcgc   1620
tggtggatgg caactttgac gatgctgcct gggctcaggg acgatgtgac gccatcgtgc   1680
gatctggcgc tggaaccgtc ggacgaactc agattgcccg acgatccgct gctgtctgga   1740
ccgacggatg cgtggaggtc ctggctgatt cgggtaaccg acgaccctct actcgacctc   1800
gagctaagga gtaataaacg gcgcgccgtc tgaagaatga atgatttgat gatttctttt   1860
tccctccatt tttcttactg aatatatcaa tgatatagac ttgtatagtt tattatttca   1920
aattaagtag ctatatatag tcaagataac gtttgtttga cacgattaca ttattcgtcg   1980
acatcttttt tcagcctgtc gtggtagcaa tttgaggagt attattaatt gaataggttc   2040
attttgcgct cgcataaaca gttttcgtca gggacagtat gttggaatga gtggtaatta   2100
atggtgacat gacatgttat agcaataacc ttgatgttta catcgtagtt taatgtacac   2160
cccgcgaatt cgttcaagta ggagtgcacc aattgcaaag ggaaaagctg aatgggcagt   2220
tcgaatagta cttttTccat aggctccgcc cccctgacga gcatcacaaa aatcgacgct   2280
caagtcagag gtggcgaaac ccgacaggac tataaagata ccaggcgttt cccccTggaa   2340
gctccctcgt gcgctctcct gttccgaccc tgccgcttac cggatacctg tccgcctttc   2400
tcccttcggg aagcgtggcg ctttctcata gctcacgctg taggtatctc agttcggtgt   2460
aggtcgttcg ctccaagctg ggctgtgtgc acgaaccccc cgttcagccc gaccgctgcg   2520
ccttatccgg taactatcgt cttgagtcca acccggtaag acacgactta tcgccactgg   2580
cagcagccac tggtaacagg attagcagag cgaggtatgt aggcggtgct acagagttct   2640
tgaagtggtg gcctaactac ggctacacta agaacagt  atttggtatc tgcgctctgc   2700
tgaagccagt taccttcgga aaaagagttg gtagctcttg atccggcaaa caaaccaccg   2760
ctggtagcgg tggttttttt gtttgcaagc agcagattac gcgcagaaaa aaaggatctc   2820
aagaagatcc tttgatcttt tctacggggt ctgacgctca gtggaacgaa aactcacgtt   2880
aagggatttt ggtcatgaga ttatcaaaaa ggatcttcac ctagatcctt ttaaattaaa   2940
aatgaagttt taaatcaatc taagtatat  atgagtaaac ttggtctgac agttaccaat   3000
gcttaatcag tgaggcacct atctcagcga tctgtctatt tcgttcatcc atagttgcct   3060
gactccccgt cgtgtagata actacgatac gggagggctt accatctggc cccagtgctg   3120
caatgatacc gcgagaccca cgctcaccgg ctccagattt atcagcaata aaccagccag   3180
```

```
ccggaagggc cgagcgcaga agtggtcctg caactttatc cgcctccatc cagtctatta    3240
attgttgccg ggaagctaga gtaagtagtt cgccagttaa tagtttgcgc aacgttgttg    3300
ccattgctac aggcatcgtg gtgtcacgct cgtcgtttgg tatggcttca ttcagctccg    3360
gttcccaacg atcaaggcga gttacatgat cccccatgtt gtgcaaaaaa gcggttagct    3420
ccttcggtcc tccgatcgtt gtcagaagta agttggccgc agtgttatca ctcatggtta    3480
tggcagcact gcataattct cttactgtca tgccatccgt aagatgcttt tctgtgactg    3540
gtgagtactc aaccaagtca ttctgagaat agtgtatgcg gcgaccgagt tgctcttgcc    3600
cggcgtcaat acgggataat accgcgccac atagcagaac tttaaaagtg ctcatcattg    3660
gaaaacgttc ttcggggcga aaactctcaa ggatcttacc gctgttgaga tccagttcga    3720
tgtaacccac tcgtgcaccc aactgatctt cagcatcttt tactttcacc agcgtttctg    3780
ggtgagcaaa acaggaagg caaaatgccg caaaaaaggg aataagggcg acacggaaat    3840
gttgaatact catactcttc ctttttcaat attattgaag catttatcag gttattgtc    3900
tcatgagcgg atacatattt gaatgtattt agaaaaataa acagcgatcg cagctagctc    3960
gtcgtgttca ggaactgttc gatggttcgg agagagtcgc cgcccagaac atacgcgcac    4020
cgatgtcagc agacagcctt attacaagta tattcaagca agtatatccg tagggtgcgg    4080
gtgatttgga tctaaggttc gtactcaaca ctcacgagca gcttgcctat gttacatcct    4140
tttatcagac ataacataat tggagtttac ttacacacgg ggtgtacctg tatgagcacc    4200
acctacaatt gtagcactgg tacttgtaca aagaatttat tcgtacgaat cacagggacg    4260
gccgccctca ccgaaccagc gaatacctca gcggtcccct gcagtgactc aacaaagcga    4320
tatgaacatc ttgcgatggt atcctgctga tagttttttac tgtacaaaca cctgtgtagc    4380
tccttctagc atttttaagt tattcacacc tcaggggag ggataaatta aataaattcc    4440
aaaagcgaag atcgagaaac taaattaaaa ttccaaaaac gaagttggaa cacaaccccc    4500
cgaaaaaaaa caacaaacaa aaacccaac aaaataaaca aaaacaaaat aaatatataa    4560
ctaccagtat ctgactaaaa gttcaaatac tcgtacttac aacaaataga aatgagccgg    4620
ccaaaattct gcagaaaaaa atttcaaaca agtactggta taattaaatt aaaaaacaca    4680
tcaaagtatc ataacgttag ttattttatt ttatttaata aaagaaaaca acaagatggg    4740
ctcaaaactt tcaacttata cgatacatac caaataacaa tttagtattt atctaagtgc    4800
ttttcgtaga taatggaata caaatggata tccagagtat acacatggat agtatacact    4860
gacacgacaa ttctgtatct ctttatgtta actactgtga ggcattaaat agagcttgat    4920
atataaaatg ttacatttca cagtctgaac ttttgcagat tacctaattt ggtaagatat    4980
taattatgaa ctgaaagttg atggcggccg catagcttca aaatgtttct actccttttt    5040
tactcttcca gattttctcg gactccgcgc atcgccgtac cacttcaaaa cacccaagca    5100
cagcatacta aatttcccct ctttcttcct ctagggtgtc gttaattacc cgtactaaag    5160
gtttggaaaa gaaaaagag accgcctcgt ttctttttct tcgtcgaaaa aggcaataaa    5220
aattttatc acgtttcttt ttcttgaaaa tttttttttt tgatttttt ctctttcgat    5280
gacctcccat tgatatttaa gttaataaac ggtcttcaat ttctcaagtt tcagtttcat    5340
ttttcttgtt ctattacaac tttttttact tcttgctcat tagaaagaaa gcatagcaat    5400
ctaatctaag ttttaattac aaaatggacg caatggtaga aacaaataga cacttcatag    5460
atgccgaccc ttacccttgg ccttacaacg gtgccttgag acctgataac acagccttga    5520
ttataatcga tatgcaaacc gacttttgtg gtaaaggtgg ttatgtcgat catatgggtt    5580
```

```
acgacttatc attggtacaa gccccaatcg aacctattaa aagagtttta gctgcaatga    5640
gagctaaggg ttatcatatt atacacacaa gagaaggtca cagaccagat ttggctgact    5700
tacctgcaaa caagagatgg agatctcaaa gaataggtgc tggtatcggt gacccaggtc    5760
cttgtggtag aattttgacc agaggtgaac caggttggga tatcattcca gaattgtacc    5820
ctatagaagg tgaaactatc atcgataaac ctggtaaagg tagttttgc gcaacagact     5880 tagaattggt tttgaaccaa aagagaatcg aaaacatcat cttgaccggt atcactacag    5940
atgtttgtgt ctctaccact atgagagaag caaacgatag aggttacgaa tgcttgttgt    6000
tggaagattg ttgcggtgcc actgactacg gtaaccattt ggccgctatt aaaatggtca    6060
agatgcaagg tggtgtattc ggttctgttt caaattccgc agccttggtt gaagcattac    6120
cataaacagg ccccttttcc tttgtcgata tcatgtaatt agttatgtca cgcttacatt    6180
cacgccctcc tcccacatcc gctctaaccg aaaaggaagg agttagacaa cctgaagtct    6240
aggtccctat ttattttttt taatagttat gttagtatta agaacgttat ttatatttca    6300
aattttcctt ttttttctgt acaaacgcgt gtacgcatgt aacattatac tgaaaacctt    6360
gcttgagaag gttttgggac gctcgaaggc tttaatttgc gggtaataac tgatataatt    6420
aaattgaagc tctaatttgt gagtttagta tacatgcatt tacttataat acagtttttt    6480
agttttgctg gccgcatctt ctcaaatatg cttcccagcc tgcttttctg taacgttcac    6540
cctctacctt agcatccctt cccttgcaa atagtcctct tccaacaata ataatgtcag    6600
atcctgtaga gaccacatca tccacggttc tatactgttg acccaatgcg tctcccttgt    6660
catctaaacc cacaccgggt gtcataatca accaatcgta accttcatct cttccaccca    6720
tgtctctttg agcaataaag ccgataacaa aatctttgtc gctcttcgca atgtcaacag    6780 taccccttagt atattctcca gtagctaggg agcccttgca tgacaattct gctaacatca   6840
aaaggcctct aggttccttt gttacttctt ccgccgcctg cttcaaaccg ctaacaatac    6900
ctgggcccac cacaccgtgt gcattcgtaa tgtctgccca ttctgctatt ctgtatacac    6960
ccgcagagta ctgcaatttg actgtattac caatgtcagc aaatttttctg tcttcgaaga   7020 gtaaaaaatt gtacttggcg gataatgcct ttagcggctt aactgtgccc tccatggaaa    7080
aatcagtcaa gatatccaca tgtgttttta gtaaacaaat tttgggacct aatgcttcaa    7140
ctaactccag taattccttg gtggtacgaa catccaatga agcacacaag tttgtttgct    7200
tttcgtgcat gatattaaat agcttggcag caacaggact aggatgagta gcagcacgtt    7260
ccttatatgt agctttcgac atgatttatc ttcgtttcct gcaggttttt gttctgtgca    7320
gttgggttaa gaatactggg caatttcatg tttcttcaac accacatatg cgtatatata    7380
ccaatctaag tctgtgctcc ttccttcgtt cttccttctg ctcggagatt accgaatcaa    7440
agctagctta tcgatgataa gctgtcaaag atgagaatta attccacgga ctatagacta    7500
tactagatac tccgtctact gtacgataca cttccgctca ggtccttgtc ctttaacgag    7560
gccttaccac tcttttgtta ctctattgat ccagctcagc aaaggcagtg tgatctaaga    7620
ttctatcttc gcgatgtagt aaaactagct agaccgagaa agagactaga atgcaaaaag    7680
gcacttctac aatggctgcc atcattatta tccgatgtga cgctgcagct tctcaatgat    7740
attcgaatac gctttgagga gatacagcct aatatccgac aaactgtttt acagatttac    7800
gatcgtactt gttacccatc attgaatttt gaacatccga acctgggagt tttccctgaa    7860
acagatagta tatttgaacc tgtataataa tatatagtct agcgctttac ggaagacaat    7920
```

| | |
|---|---|
| gtatgtattt cggttcctgg agaaactatt gcatctattg cataggtaat cttgcacgtc | 7980 |
| gcatccccgg ttcattttct gcgtttccat cttgcacttc aatagcatat ctttgttaac | 8040 |
| gaagcatctg tgcttcattt tgtagaacaa aaatgcaacg cgagagcgct aattttcaa | 8100 |
| acaaagaatc tgagctgcat ttttacagaa cagaaatgca acgcgaaagc gctattttac | 8160 |
| caacgaagaa tctgtgcttc attttgtaa aacaaaaatg caacgcgacg agagcgctaa | 8220 |
| tttttcaaac aaagaatctg agctgcattt ttacagaaca gaaatgcaac gcgagagcgc | 8280 |
| tattttacca caaagaatc tatacttctt ttttgttcta caaaaatgca tcccgagagc | 8340 |
| gctattttc taacaaagca tcttagatta ctttttttct cctttgtgcg ctctataatg | 8400 |
| cagtctcttg ataacttttt gcactgtagg tccgttaagg ttagaagaag gctactttgg | 8460 |
| tgtctatttt ctcttccata aaaaagcct gactccactt cccgcgttta ctgattacta | 8520 |
| gcgaagctgc gggtgcattt tttcaagata aaggcatccc cgattatatt ctataccgat | 8580 |
| gtggattgcg catactttgt gaacagaaag tgatagcgtt gatgattctt cattggtcag | 8640 |
| aaaattatga acgtttctt ctattttgtc tctatatact acgtatagga aatgtttaca | 8700 |
| ttttcgtatt gttttcgatt cactctatga atagttctta ctacaatttt tttgtctaaa | 8760 |
| gagtaatact agagataaac ataaaaatg tagaggtcga gtttagatgc aagttcaagg | 8820 |
| agcgaaaggt ggatgggtag gttatatagg gatatagcac agagatatat agcaaagaga | 8880 |
| tacttttgag caat | 8894 |

<210> SEQ ID NO 64
<211> LENGTH: 8395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

| | |
|---|---|
| gtttgtggaa gcggtattcg caatttaatt aaagctggtg acaattaatc atcggctcgt | 60 |
| ataatgtgtg gaattgaatc gatataagga ggttaatcat atgtcaatgg aaacccatag | 120 |
| ttatgtagac gtcgcaattc gtaacgcgcg tcttgccgat acgagggaa ttgtcgatat | 180 |
| tcttattcac gatgggcgca ttgcgtccat cgtgaagtcg acaaaaacaa aaggatcggt | 240 |
| ggagatcgat gctcatgagg gtctggtcac ttccggcctg gtagagcctc acatccatct | 300 |
| cgataaggcc ctgacggcag atcgggttcc cgcaggaagc attggcgacc ttcgaacgcg | 360 |
| acgaggcctt gagatggcaa ttcgggccac ccgtgatatc aagcgtacgt tcacggttga | 420 |
| agatgttcga gaacgggcca tacgtgcggc cctgatggca tcccgtgcgg gaaccaccgc | 480 |
| attgcggaca cacgtcgatg tcgacccgat tgtcggcctc gcaggtatcc gtggtgtcct | 540 |
| tgaggcgcgt gaagtctgcg cgggattgat cgatatccag atcgtcgcct ccctcagga | 600 |
| gggactcttc tgctctgcgg gggccgtgga cctcatgcgg gaggcgatca actgggcgc | 660 |
| ggatgccgtc ggcggcgcac ccgcgctgga tgatcgcccg caggaccatg tccgagccgt | 720 |
| ttttgacctt gctgctgagt tcggcctgcc cgtagacatg cacgtcgatg agtccgaccg | 780 |
| gcgggaagac tttacgcttc cctttgtgat tgaagctgcc cgtgaacggc gtgtgcccaa | 840 |
| tgtgaccgtc gcgcacatca gctcgctgtc cgtacagacg gatgacgtag cacggtcgac | 900 |
| cattgccgcc cttgcggacg ccgatgttaa tgtcgtggtt aatccgatca ttgtcaaaat | 960 |
| tacgcggctg agtgaattac tcgatgccgg agtctccgta atgtttggct cggacaacct | 1020 |

-continued

```
gcgggatccg ttctatccgc tcggagcggc gaatcccctt ggatcagcca ttttttgcctg    1080 tcaaattgcc gcgctgggaa caccgcaaga tctcagacgg gtattcgatg cggtcaccat    1140
caacgctgcc cgcatgctgg gattcccctc acttttaggc gtcgtggaag gggcagtcgc    1200
ggatctcgca gtattcccat cggcgacgcc cgaggaggtt gttctggatc aacagtctcc    1260
gctcttcgta ctcaagggcg gacgtgtcgt tgccatgcga ttggccgctg gatcaacgtc    1320
gttccgcgac tactcatgag gaaatccatt atgatgtcag gagaacacac gttaaaagcg    1380
gtacgaggca gttttattga tgtcacccgt acgatcgata acccggaaga gattgcctct    1440
gcgctgcggt ttattgagga tggtttatta ctcattaaac agggaaaagt ggaatggttt    1500
ggcgaatggg aaaacggaaa gcatcaaatt cctgacacca ttcgcgtgcg cgactatcgc    1560
ggcaaactga tagtaccggg cttttgtcgat acacatatcc attatccgca aagtgaaatg    1620
gtgggggcct atggtgagca attgctggag tggttgaata acacaccttt ccctactgaa    1680
cgtcgttatg aggatttaga gtacgcccgc gaaatgtcgg cgttcttcat caagcagctt    1740
ttacgtaacg gaaccaccac ggcgctggtg tttggcactg ttcatccgca atctgttgat    1800
gcgctgtttg aagccgccag tcatatcaat atgcgtatga ttgccggtaa ggtgatgatg    1860
gaccgcaacg caccggatta tctgctcgac actgccgaaa gcagctatca ccaaagcaaa    1920
gaactgatcg aacgctggca caaaaatggt cgtctgctat atgcgattac gccacgcttc    1980
gccccgacct catctcctga acagatgcg atggcgcaac gctgaaaga gaatatccg    2040 gatacgtggg tacataccca tctctgtgaa acaaagatg aaattgcctg ggtgaaatcg    2100
ctttatcctg accatgatgg ttatctggat gtttaccatc agtacggcct gaccggtaaa    2160
aactgtgtct tgctcactg cgtccatctc gaagaaaaag agtgggatcg tctcagcgaa    2220
accaaatcca gcattgcttt ctgtccgacc tccaaccttt acctcggcag cggcttattc    2280
aacttgaaaa aagcatggca gaagaaagtt aaagtgggca tgggaacgga tatcggtgcc    2340
ggaaccactt tcaacatgct gcaaacgctg aacgaagcct acaaagtatt gcaattacaa    2400
ggctatcgcc tctcggcata tgaagcgttt tacctggcca cgctcggcgg agcgaaatct    2460
ctgggccttg acgatttgat tggcaacttt ttacctggca aagaggctga tttcgtggtg    2520
atggaaccca ccgccactcc gctacagcag ctgcgctatg caactctgt ttctttagtc    2580 gacaaattgt tcgtgatgat gacgttgggc gatgaccgtt cgatctaccg cacctacgtt    2640
gatggtcgtc tggtgtacga acgcaactaa ggaacgacca tgcaaacgct cagcatccag    2700
cacggtaccc tcgtcacgat ggatcagtac cgcagagtcc ttggggatag ctgggttcac    2760
gtgcaggatg gacggatcgt cgcgctcgga gtgcacgccg agtcggtgcc tccgccagcg    2820
gatcgggtga tcgatgcacg cggcaaggtc gtgttacccg gtttcatcaa tgcccacacc    2880
catgtgaacc agatcctcct gcgcggaggg ccctcgcacg gcgtcaact ctatgactgg    2940 ctgttcaacg ttttgtatcc gggacaaaag gcgatgagac cggaggacgt agcggtggcg    3000
gtgaggttgt attgtgcgga agctgtgcgc agcgggatta cgacgatcaa cgacaacgcc    3060
gattcggcca tctacccagg caacatcgag gccgcgatgg cggtctatgg tgaggtgggt    3120
gtgagggtcg tctacgcccg catgttcttt gatcggatgg acgggcgcat tcaagggtat    3180
gtggacgcct tgaaggctcg ctctccccaa gtcgaactgt gctcgatcat ggaggaaacg    3240
gctgtggcca agatcggat cacagccctg tcagatcagt atcatggcac ggcaggaggt    3300
cgtatatcag tttggcccgc tcctgccatt acccccggcgg tgacagttga aggaatgcga    3360
tgggcacaag ccttcgcccg tgatcgggcg gtaatgtgga cgcttcacat ggcggagagc    3420
```

```
gatcatgatg agcggcttca ttggatgagt cccgccgagt acatggagtg ttacggactc    3480
ttggatgagc gtctgcaggt cgcgcattgc gtgtactttg accggaagga tgttcggctg    3540
ctgcaccgcc acaatgtgaa ggtcgcgtcg caggttgtga gcaatgccta cctcggctca    3600
ggggtggccc ccgtgccaga gatggtggag cgcggcatgg ccgtgggcat tggaacagat    3660
gacgggaatt gtaatgactc cgtaaacatg atcggagaca tgaagtttat ggcccatatt    3720
caccgcgcgg tgcatcggga tgcggacgtg ctgaccccag agaagattct tgaaatggcg    3780
acgatcgatg gggcgcgttc gttgggaatg gaccacgaga ttggttccat cgaaaccggc    3840
aagcgcgcgg accttatcct gcttgacctg cgtcaccctc agacgactcc tcaccatcat    3900
ttggcggcca cgatcgtgtt tcaggcttac ggcaatgagg tggacactgt cctgattgac    3960
ggaaacgttg tgatggagaa ccgccgcttg agctttcttc ccctgaacg tgagttggcg    4020
ttccttgagg aagcgcagag ccgcgccaca gctattttgc agcgggcgaa catggtggct    4080
aacccagctt ggcgcagcct ctagcctcaa aatatatttt ccctctatct tctcgttgcg    4140
cttaatttga ctaattctca ttagcgaggc gcgccttttcc ataggctccg ccccctgac    4200
gagcatcaca aaaatcgacg ctcaagtcag aggtggcgaa acccgacagg actataaaga    4260
taccaggcgt ttccccctgg aagctccctc gtgcgctctc ctgttccgac cctgccgctt    4320
accggatacc tgtccgcctt tctcccttcg ggaagcgtgg cgctttctca tagctcacgc    4380
tgtaggtatc tcagttcggt gtaggtcgtt cgctccaagc tgggctgtgt gcacgaaccc    4440
cccgttcagc ccgaccgctg cgccttatcc ggtaactatc gtcttgagtc aacccggta    4500
agacacgact tatcgccact ggcagcagcc actggtaaca ggattagcag agcgaggtat    4560
gtaggcggtg ctacagagtt cttgaagtgg tggcctaact acggctacac tagaagaaca    4620
gtatttggta tctgcgctct gctgaagcca gttaccttcg aaaaagagt tggtagctct    4680
tgatccggca acaaaccac cgctggtagc ggtggttttt ttgtttgcaa gcagcagatt    4740
acgcgcagaa aaaaggatc tcaagaagat cctttgatct tttctacggg gtctgacgct    4800
cagtggaacg aaaactcacg ttaagggatt ttggtcatga gattatcaaa aaggatcttc    4860
acctagatcc ttttaaatta aaaatgaagt tttaaatcaa tctaaagtat atatgagtaa    4920
acttggtctg acagttacca atgcttaatc agtgaggcac ctatctcagc gatctgtcta    4980
tttcgttcat ccatagttgc ctgactcccc gtcgtgtaga taactacgat acgggagggc    5040
ttaccatctg gccccagtgc tgcaatgata ccgcgagacc cacgctcacc ggctccagat    5100
ttatcagcaa taaaccagcc agccggaagg gccgagcgca gaagtggtcc tgcaacttta    5160
tccgcctcca tccagtctat taattgttgc cgggaagcta gagtaagtag ttcgccagtt    5220
aatagtttgc gcaacgttgt tgccattgct acaggcatcg tggtgtcacg ctcgtcgttt    5280
ggtatggctt cattcagctc cggttcccaa cgatcaaggc gagttacatg atcccccatg    5340
ttgtgcaaaa aagcggttag ctccttcggt cctccgatcg ttgtcagaag taagttggcc    5400
gcagtgttat cactcatggt tatggcagca ctgcataatt ctcttactgt catgccatcc    5460
gtaagatgct tttctgtgac tggtgagtac tcaaccaagt cattctgaga atagtgtatg    5520
cggcgaccga gttgctcttg cccggcgtca atacgggata ataccgcgcc acatagcaga    5580
actttaaaag tgctcatcat tggaaaacgt tcttcgggc gaaaactctc aaggatctta    5640
ccgctgttga tccagttc gatgtaaccc actcgtgcac ccaactgatc ttcagcatct    5700
tttactttca ccagcgtttc tgggtgagca aaaacaggaa ggcaaaatgc cgcaaaaaag    5760
```

```
ggaataaggg cgacacggaa atgttgaata ctcatactct tccttttca atattattga    5820
agcatttatc agggttattg tctcatgagc ggatacatat ttgaatgtat ttagaaaaat   5880
aaacagcgat cgcgcggccg cgggtaataa ctgatataat taaattgaag ctctaatttg   5940
tgagtttagt atacatgcat ttacttataa tacagttttt tagttttgct ggccgcatct   6000
tctcaaatat gcttcccagc ctgctttct gtaacgttca ccctctacct tagcatccct    6060
tccctttgca aatagtcctc ttccaacaat aataatgtca gatcctgtag agaccacatc   6120
atccacggtt ctatactgtt gacccaatgc gtctcccttg tcatctaaac ccacaccggg   6180
tgtcataatc aaccaatcgt aaccttcatc tcttccaccc atgtctcttt gagcaataaa   6240
gccgataaca aaatctttgt cgctcttcgc aatgtcaaca gtacccttag tatattctcc   6300
agtagctagg gagcccttgc atgacaattc tgctaacatc aaaaggcctc taggttcctt   6360
tgttacttct tccgccgcct gcttcaaacc gctaacaata cctgggccca ccacaccgtg   6420
tgcattcgta atgtctgccc attctgctat tctgtataca cccgcagagt actgcaattt   6480
gactgtatta ccaatgtcag caaattttct gtcttcgaag agtaaaaaat tgtacttggc   6540
ggataatgcc tttagcggct taactgtgcc ctccatggaa aaatcagtca agatatccac   6600
atgtgttttt agtaaacaaa ttttgggacc taatgcttca actaactcca gtaattcctt   6660
ggtggtacga acatccaatg aagcacacaa gtttgtttgc ttttcgtgca tgatattaaa   6720
tagcttggca gcaacaggac taggatgagt agcagcacgt tccttatatg tagctttcga   6780
catgatttat cttcgttcc tgcaggtttt tgttctgtgc agttgggtta agaatactgg    6840
gcaatttcat gtttcttcaa caccacatat gcgtatatat accaatctaa gtctgtgctc   6900
cttccttcgt tcttccttct gctcggagat taccgaatca agctagctt atcgatgata    6960
agctgtcaaa gatgagaatt aattccacgg actatagact atactagata ctccgtctac   7020
tgtacgatac acttccgctc aggtccttgt cctttaacga ggccttacca ctcttttgtt   7080
actctattga tccagctcag caaaggcagt gtgatctaag attctatctt cgcgatgtag   7140
taaaactagc tagaccgaga aagagactag aaatgcaaaa ggcacttcta caatggctgc   7200
catcattatt atccgatgtg acgctgcagc ttctcaatga tattcgaata cgctttgagg   7260
agatacagcc taatatccga caaactgttt tacagattta cgatcgtact tgttacccat   7320
cattgaattt tgaacatccg aacctgggag ttttccctga aacagatagt atatttgaac   7380
ctgtataata atatatagtc tagcgcttta cggaagacaa tgtatgtatt tcggttcctg   7440
gagaaactat tgcatctatt gcataggtaa tcttgcacgt cgcatccccg gttcattttc   7500
tgcgtttcca tcttgcactt caatagcata tctttgttaa cgaagcatct gtgcttcatt   7560
ttgtagaaca aaaatgcaac gcgagagcgc taatttttca aacaaagaat ctgagctgca   7620
ttttttacaga acagaaatgc aacgcgaaag cgctatttta ccaacgaaga atctgtgctt   7680
cattttgta aaacaaaaat gcaacgcgac gagagcgcta atttttcaaa caaagaatct   7740
gagctgcatt tttacagaac agaaatgcaa cgcgagagcg ctattttacc aacaaagaat   7800
ctatacttct ttttgttct acaaaaatgc atcccgagag cgctattttt ctaacaaagc    7860
atcttagatt acttttttc tcctttgtgc gctctataat gcagtctctt gataactttt    7920
tgcactgtag gtccgttaag gttagaagaa ggctactttg gtgtctattt tctcttccat   7980
aaaaaaagcc tgactccact tcccgcgttt actgattact agcgaagctg cgggtgcatt   8040
ttttcaagat aaaggcatcc ccgattatat tctataccga tgtggattgc gcatactttg   8100
tgaacagaaa gtgatagcgt tgatgattct tcattggtca gaaaattatg aacggtttct   8160
```

```
tctattttgt ctctatatac tacgtatagg aaatgtttac attttcgtat tgttttcgat    8220
tcactctatg aatagttctt actacaattt ttttgtctaa agagtaatac tagagataaa    8280
cataaaaaat gtagaggtcg agtttagatg caagttcaag gagcgaaagg tggatgggta    8340
ggttatatag ggatatagca cagagatata tagcaaagag atactttgta gcaat         8395

<210> SEQ ID NO 65
<211> LENGTH: 12133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gtttgtggaa gcggtattcg caatttaatt aaagctggtg acaattaatc atcggctcgt      60
ataatgtgtg gaattgaatc gatataagga ggttaatcat atgcaagcgc aagttttcg     120 agttccaatg agtaatccag ccgatgttag tggcgtagcc aagctcatcg atgagggagt    180
gatccgtgcc gaagaggtcg tctgcgttct cggcaagacc gaaggcaacg gctgtgtcaa    240
tgacttcacg cgtggctaca ccaccctcgc gttcaaggtc tacttctccg agaaactggg    300
cgtgtcccgg caagaggtcg gcgagcgcat cgctttcatc atgtccggcg gtaccgaagg    360
cgtcatggcg cctcactgca ccatcttcac cgtgcagaag acgacaaca agcagaagac     420 cgccgctgaa ggcaagcgac ttgccgttca gcagatcttt acccgcgagt tcctgccgga    480
ggagatcggc cgcatgccgc aggtcacgga aacagccgac gctgttcgcc gcgccatgcg    540
cgaagccggc atcgcggatg catccgatgt ccacttcgtt caggtcaagt gcccactgct    600
cactgccggc gcatgcatg acgctgtcga gcgcgggcat acggttgcca ccgaagatac    660
ctatgagtcc atgggctact cccgcggcgc atccgcgctt ggtatcgccc tggccctcgg    720
ggaagtcgag aaggccaacc tcagtgatga agttattacc gcagactaca gtctctactc    780
ctcggttgcc tcaacttcgg cgggtatcga gttgatgaac aacgagatca tcgtcatggg    840
caacagccgc gcatggggtg gtgacctcgt catcggccac gccgagatga aggacgccat    900
cgacggtgca gcggtccggc aggccctgcg cgacgtcggg tgctgcgaga acgacctgcc    960
gaccgtcgac gagctcggcc gcgtggtcaa tgtatttgcc aaggctgaag cctccccgga    1020
cggtgaggtt cgtaaccgcc gccacacgat gctggacgat tcggacatta acagcacgcg    1080
ccatgcgcga gcggtcgtca atgcagttat cgcttcgatc gtgggagatc ccatggttta    1140
tgtctccggc ggctccgagc atcagggccc cgccggtggc ggtcccgttg cagttatcgc    1200
gcgcacagct taaggaaatc cattatgata tactcaacag tcaacgctaa tccttacgct    1260
tggccttacg atggttcaat agaccctgct cacaccgctt taatcttaat cgattggcaa    1320
atagactttt gtggtccagg tggttatgtc gattccatgg gttacgactt atccttgact    1380
agaagtggtt tagaacctac agcaagagta ttggctgcag ccagagatac tggtatgaca    1440
gttatccata ctagagaagg tcacagacca gatttggctg acttgccacc taataagaga    1500
tggagatctg catcagccgg tgctgaaatc ggttcagttg gtccatgtgg tagaattta     1560 gtcagaggtg aacctggttg ggaaatagta ccagaagttg cacctagaga aggtgaacca    1620
attatagata aacctggtaa aggtgctttc tacgcaacag atttggactt gttgttgaga    1680
acaagaggta tcacccattt gattttgacc ggtataacta cagatgtttg cgtccacacc    1740
actatgagag aagccaacga tagaggttac gaatgtttaa ttttgtctga ttgcaccggt    1800
```

```
gctactgaca gaaagcatca cgaagctgca ttatctatgg tcaccatgca aggtggtgta  1860
ttcggtgcaa ctgcccattc agatgactta ttggccgctt tgggtacaac cgttccagca  1920
gccgctggtc ctagagctag aacagaataa ggaacgacca tgacagttag ttccgataca  1980
actgctgaaa tatcgttagg ttggtcaatc caagactgga ttgatttcca caagtcatca  2040
agctcccagg cttcactaag gcttcttgaa tcactactag actctcaaaa tgttgcgcca  2100
gtcgataatg cgtggatatc gctaatttca aggaaaatt tactgcacca attccaaatt  2160
ttaaagagca gagaaaataa agaaactcta cctctctacg gtgtccctat gctgttaag  2220
gacaacatcg acgttagagg tctacccacc accgctgcat gtccatcctt tgcatatgag  2280
ccttccaaag actctaaagt agtagaacta ctaagaaatg caggtgcgat aatcgtgggt  2340
aagacaaact tggaccaatt tgccacagga ttagtcggca cacggtctcc atatgggaaa  2400
acaccttgcg cttttagcaa agagcatgta tctggtggtt cctccgctgg gtcagcatcg  2460
gtggtcgcca gaggtatcgt accaattgca ttgggtactg atacagcagg ttctggtaga  2520
gtcccagccg ccttgaacaa cctgattggc ctaaagccaa caagggcgt cttttcctgt  2580
caaggtgtag ttcccgcttg taaatcttta gactgcgtct ccatctttgc attaaaccta  2640
agtgatgctg aacgctgctt ccgcatcatg tgccagccag atcctgataa tgatgaatat  2700
tctagaccct atgtttccaa ccctttgaaa aaattttcaa gcaatgtaac gattgctatt  2760
cctaaaaata tcccatggta tggtgaaacc aagaatcctg tactgttttc caatgctgtc  2820
gaaaatctat caagaacggg cgctaacgtc atagaaattg atttgagcc tcttttagag  2880
ttagctcgct gtttatacga aggtacttgg gtggccgagc gttatcaagc tattcaatcg  2940
ttttggaca gtaaaccacc aaaggaatct ttggaccta ctgttatttc aattatagaa  3000
ggggccaaga aatacagtgc agtagactgc ttcagttttg aatacaaaag acaaggcatc  3060
ttgcaaaag tgagacgact tctcgaatca gtcgatgtat tgtgtgtgcc cacatgtcct  3120
ttaaatccta ctatgcaaca agttgcggat gaaccagtcc tagtcaattc aagacaaggc  3180
acatggacta attttgtcaa cttggcagat ttggcagccc ttgctgttcc cgcagggttc  3240
cgagacgatg gtttgccaaa tggtattact ttaatcggta aaaaattcac agattacgca  3300
ctattagagt tggctaaccg ctatttccaa aatatattcc ccaacggttc cagaacatac  3360
ggtactttta cctcttcttc agtaaagcca gcaaacgatc aattagtggg accagactat  3420
gacccatcta cgtccataaa attggctgtt gtcggtgcac atcttaaggg tctgcctcta  3480
cattggcaat tggaaaaggt caatgcaaca tatttatgta caacaaaaac atcaaaagct  3540
taccagcttt ttgctttgcc caaaaatgga ccagttttaa aacctggttt gagaagagtt  3600
caagatagca atggctctca aatcgaatta gaagtgtaca gtgttccaaa agaactgttc  3660
ggtgctttta tttccatggt tcctgaacca ttaggaatag gttcagtgga gttagaatct  3720
ggtgaatgga tcaaatcctt tatttgtgaa gaatctggtt acaaagccaa aggtacagtt  3780
gatatcacaa agtatggtgg atttagagca tattttgaaa tgttgtaagg acacgataat  3840
gtcaatggaa acccatagtt atgtagacgt cgcaattcgt aacgcgcgtc ttgccgatac  3900
ggagggaatt gtcgatattc ttattcacga tgggcgcatt gcgtccatcg tgaagtcgac  3960
aaaaacaaaa ggatcggtgg agatcgatgc tcatgagggt ctggtcactt ccggcctggt  4020
agagcctcac atccatctcg ataaggccct gacggcagat cgggttcccg caggaagcat  4080
tggcgaccct cgaacgcgac gaggccttga gatggcaatt cgggccaccc gtgatatcaa  4140
```

```
gcgtacgttc acggttgaag atgttcgaga acgggccata cgtgcggccc tgatggcatc    4200
ccgtgcggga accaccgcat tgcggacaca cgtcgatgtc gacccgattg tcggcctcgc    4260
aggtatccgt ggtgtccttg aggcgcgtga agtctgcgcg ggattgatcg atatccagat    4320
cgtcgccttc cctcaggagg gactcttctg ctctgcgggg gccgtggacc tcatgcggga    4380
ggcgatcaaa ctgggcgcgg atgccgtcgg cggcgcaccc gcgctggatg atcgcccgca    4440
ggaccatgtc cgagccgttt ttgaccttgc tgctgagttc ggcctgcccg tagacatgca    4500
cgtcgatgag tccgaccggc gggaagactt tacgcttccc tttgtgattg aagctgcccg    4560
tgaacggcgt gtgcccaatg tgaccgtcgc gcacatcagc tcgctgtccg tacagacgga    4620
tgacgtagca cggtcgacca ttgccgccct tgcggacgcc gatgttaatg tcgtggttaa    4680
tccgatcatt gtcaaaatta cgcggctgag tgaattactc gatgccggag tctccgtaat    4740
gtttggctcg acaacctgcg ggatccgtt ctatccgctc ggagcggcga atcccttgg     4800
atcagccatt tttgcctgtc aaattgccgc gctgggaaca ccgcaagatc tcagacgggt    4860
attcgatgcg gtcaccatca acgctgcccg catgctggga ttcccctcac ttttaggcgt    4920
cgtggaaggg gcagtcgcgg atctcgcagt attcccatcg gcgacgcccg aggaggttgt    4980
tctggatcaa cagtctccgc tcttcgtact caagggcgga cgtgtcgttg ccatgcgatt    5040
ggccgctgga tcaacgtcgt tccgcgacta ctcatgagga aatccattat gatgtcagga    5100
gaacacacgt taaagcggt acgaggcagt tttattgatg tcacccgtac gatcgataac     5160
ccggaagaga ttgcctctgc gctgcggttt attgaggatg gtttattact cattaaacag    5220
ggaaaagtgg aatggtttgg cgaatgggaa aacggaaagc atcaaattcc tgacaccatt    5280
cgcgtgcgcg actatcgcgg caaactgata gtaccgggct tgtcgatac acatatccat     5340
tatccgcaaa gtgaaatggt gggggcctat ggtgagcaat tgctggagtg gttgaataaa    5400
cacaccttcc ctactgaacg tcgttatgag gatttagagt acgcccgcga aatgtcggcg    5460
ttcttcatca agcagctttt acgtaacgga accaccacgg cgctggtgtt tggcactgtt    5520
catccgcaat ctgttgatgc gctgtttgaa gccgccagtc atatcaatat gcgtatgatt    5580
gccggtaagg tgatgatgga ccgcaacgca ccggattatc tgctcgacac tgccgaaagc    5640
agctatcacc aaagcaaaga actgatcgaa cgctggcaca aaaatggtcg tctgctatat    5700
gcgattacgc cacgcttcgc cccgacctca tctcctgaac agatggcgat ggcgcaacgc    5760
ctgaaagaag aatatccgga tacgtgggta catacccatc tctgtgaaaa caaagatgaa    5820
attgcctggg tgaaatcgct ttatcctgac catgatggtt atctggatgt ttaccatcag    5880
tacggcctga ccggtaaaaa ctgtgtcttt gctcactgcg tccatctcga agaaaagag    5940
tgggatcgtc tcagcgaaac caaatccagc attgctttct gtccgacctc caacctttac    6000
ctcggcagcg gcttattcaa cttgaaaaaa gcatggcaga agaaagttaa agtgggcatg    6060
ggaacggata tcggtgccgg aaccactttc aacatgctgc aaacgctgaa cgaagcctac    6120
aaagtattgc aattacaagg ctatcgcctc tcggcatatg aagcgttta cctgccacg     6180
ctcggcggag cgaaatctct gggccttgac gatttgattg caacttttt acctggcaaa    6240
gaggctgatt tcgtggtgat ggaacccacc gccactccgc tacagcagct cgcctatgac    6300
aactctgttt ctttagtcga caaattgttc gtgatgatga cgttgggcga tgaccgttcg    6360
atctaccgca cctacgttga tggtcgtctg gtgtacgaac gcaactaagg aacgaccatg    6420
caaacgctca gcatccagca cggtaccctc gtcacgatgg atcagtaccg cagagtcctt    6480
ggggatagct gggttcacgt gcaggatgga cggatcgtcg cgctcggagt gcacgccgag    6540
```

```
tcggtgcctc cgccagcgga tcgggtgatc gatgcacgcg gcaaggtcgt gttacccggt    6600
ttcatcaatg cccacaccca tgtgaaccag atcctcctgc gcggagggcc ctcgcacggg    6660
cgtcaactct atgactggct gttcaacgtt ttgtatccgg gacaaaaggc gatgagaccg    6720
gaggacgtag cggtggcggt gaggttgtat tgtgcgcaag ctgtgcgcag cgggattacg    6780
acgatcaacg acaacgccga ttcggccatc tacccaggca acatcgaggc cgcgatggcg    6840
gtctatggtg aggtgggtgt gagggtcgtc tacgcccgca tgttctttga tcggatggac    6900
gggcgcattc aagggtatgt ggacgccttg aaggctcgct ctccccaagt cgaactgtgc    6960
tcgatcatgg aggaaacggc tgtggccaaa gatcggatca cagccctgtc agatcagtat    7020
catggcacgg caggaggtcg tatatcagtt tggcccgctc ctgccattac cccggcggtg    7080
acagttgaag gaatgcgatg ggcacaagcc ttcgcccgtg atcgggcggt aatgtggacg    7140
cttcacatgg cggagagcga tcatgatgag cggcttcatt ggatgagtcc cgccgagtac    7200
atggagtgtt acggactctt ggatgagcgt ctgcaggtcg cgcattgcgt gtactttgac    7260
cggaaggatg ttcggctgct gcaccgccac aatgtgaagg tcgcgtcgca ggttgtgagc    7320
aatgcctacc tcggctcagg ggtggccccc gtgccagaga tggtggagcg cggcatggcc    7380
gtgggcattg aacagatgac gggaattgt aatgactccg taaacatgat cggagacatg    7440
aagtttatgg cccatattca ccgcgcggtg catcggatg cggacgtgct gaccccagag    7500
aagattcttg aaatggcgac gatcgatggg gcgcgttcgt tgggaatgga ccacgagatt    7560
ggttccatcg aaaccggcaa gcgcgcggac cttatcctgc ttgacctgcg tcaccctcag    7620
acgactcctc accatcattt ggcggccacg atcgtgtttc aggcttacgg caatgaggtg    7680
gacactgtcc tgattgacgg aaacgttgtg atggagaacc gccgcttgag ctttcttccc    7740
cctgaacgtg agttggcgtt ccttgaggaa gcgcagagcc gcgccacagc tattttgcag    7800
cgggcgaaca tggtggctaa cccagcttgg cgcagcctct agcctcaaaa tatattttcc    7860
ctctatcttc tcgttgcgct taatttgact aattctcatt agcgaggcgc gccttccat    7920 aggctccgcc cccctgacga gcatcacaaa atcgacgct caagtcagag gtggcgaaac    7980
ccgacaggac tataaagata ccaggcgttt cccctggaa gctccctcgt gcgctctcct    8040
gttccgaccc tgccgcttac cggatacctg tccgccttc tcccttcggg aagcgtggcg    8100
ctttctcata gctcacgctg taggtatctc agttcggtgt aggtcgttcg ctccaagctg    8160
ggctgtgtgc acgaaccccc cgttcagccc gaccgctgcg ccttatccgg taactatcgt    8220
cttgagtcca acccggtaag acacgactta tcgccactgg cagcagccac tggtaacagg    8280
attagcagag cgaggtatgt aggcggtgct acagagttct tgaagtggtg gcctaactac    8340
ggctacacta agaacagt atttggtatc tgcgctctgc tgaagccagt taccttcgga    8400
aaaagagttg gtagctcttg atccggcaaa caaaccaccg ctggtagcgg tggtttttt    8460 gtttgcaagc agcagattac gcgcagaaaa aaaggatctc aagaagatcc tttgatcttt    8520
tctacggggt ctgacgctca gtggaacgaa aactcacgtt aagggatttt ggtcatgaga    8580
ttatcaaaaa ggatcttcac ctagatcctt ttaaattaaa aatgaagttt taaatcaatc    8640
taaagtatat atgagtaaac ttggtctgac agttaccaat gcttaatcag tgaggcacct    8700
atctcagcga tctgtctatt tcgttcatcc atagttgcct gactccccgt cgtgtagata    8760
actacgatac gggagggctt accatctggc cccagtgctg caatgatacc gcagaccca    8820 cgctcaccgg ctccagattt atcagcaata aaccagccag ccggaagggc cgagcgcaga    8880
```

```
agtggtcctg caactttatc cgcctccatc cagtctatta attgttgccg ggaagctaga    8940
gtaagtagtt cgccagttaa tagtttgcgc aacgttgttg ccattgctac aggcatcgtg    9000
gtgtcacgct cgtcgtttgg tatggcttca ttcagctccg gttcccaacg atcaaggcga    9060
gttacatgat cccccatgtt gtgcaaaaaa gcggttagct ccttcggtcc tccgatcgtt    9120
gtcagaagta agttggccgc agtgttatca ctcatggtta tggcagcact gcataattct    9180
cttactgtca tgccatccgt aagatgcttt tctgtgactg gtgagtactc aaccaagtca    9240
ttctgagaat agtgtatgcg gcgaccgagt tgctcttgcc cggcgtcaat acgggataat    9300
accgcgccac atagcagaac tttaaaagtg ctcatcattg gaaaacgttc ttcggggcga    9360
aaactctcaa ggatcttacc gctgttgaga tccagttcga tgtaacccac tcgtgcaccc    9420
aactgatctt cagcatcttt tactttcacc agcgtttctg ggtgagcaaa acaggaagg    9480
caaaatgccg caaaaaaggg aataagggcg acacggaaat gttgaatact catactcttc    9540
ctttttcaat attattgaag catttatcag ggttattgtc tcatgagcgg atacatattt    9600
gaatgtattt agaaaaataa acagcgatcg cgcggccgcg gtaataact gatataatta    9660
aattgaagct ctaatttgtg agtttagtat acatgcattt acttataata cagtttttta    9720
gttttgctgg ccgcatcttc tcaaatatgc ttcccagcct gcttttctgt aacgttcacc    9780
ctctaccta gcatcccttc cctttgcaaa tagtcctctt ccaacaataa taatgtcaga    9840
tcctgtagag accacatcat ccacggttct atactgttga cccaatgcgt ctcccttgtc    9900
atctaaaccc acaccgggtg tcataatcaa ccaatcgtaa ccttcatctc ttccacccat    9960
gtctctttga gcaataaagc cgataacaaa atctttgtcg ctcttcgcaa tgtcaacagt    10020
acccttagta tattctccag tagctaggga gcccttgcat gacaattctg ctaacatcaa    10080
aaggcctcta ggttccttg ttacttcttc cgccgcctgc ttcaaaccgc taacaatacc    10140
tgggcccacc acaccgtgtg cattcgtaat gtctgcccat tctgctattc tgtatacacc    10200
cgcagagtac tgcaatttga ctgtattacc aatgtcagca aattttctgt cttcgaagag    10260
taaaaaattg tacttggcgg ataatgcctt tagcggctta actgtgccct ccatggaaaa    10320
atcagtcaag atatccacat gtgtttttag taaacaaatt ttgggaccta atgcttcaac    10380
taactccagt aattccttgg tggtacgaac atccaatgaa gcacacaagt tgtttgctt    10440
ttcgtgcatg atattaaata gcttggcagc aacaggacta ggatgagtag cagcacgttc    10500
cttatatgta gctttcgaca tgatttatct tcgtttcctg caggttttg ttctgtgcag    10560
ttgggttaag aatactgggc aatttcatgt ttccttcaaca ccacatatgc gtatatatac    10620
caatctaagt ctgtgctcct tccttcgttc ttccttctgc tcggagatta ccgaatcaaa    10680
gctagcttat cgatgataag ctgtcaaaga tgagaattaa ttccacggac tatagactat    10740
actagatact ccgtctactg tacgatacac ttccgctcag gtccttgtcc tttaacgagg    10800
ccttaccact cttttgttac tctattgatc cagctcagca aaggcagtgt gatctaagat    10860
tctatcttcg cgatgtagta aaactagcta gaccgagaaa gagactagaa atgcaaaagg    10920
cacttctaca atggctgcca tcattattat ccgatgtgac gctgcagctt ctcaatgata    10980
ttcgaatacg ctttgaggag atacagccta atatccgaca aactgtttta cagatttacg    11040
atcgtacttg ttacccatca ttgaattttg aacatccgaa cctgggagtt ttccctgaaa    11100
cagatagtat atttgaacct gtataataat atatagtcta gcgctttacg gaagacaatg    11160
tatgtatttc ggttcctgga gaaactattg catctattgc ataggtaatc ttgcacgtcg    11220
catccccggt tcattttctg cgtttccatc ttgcacttca atagcatatc tttgttaacg    11280
```

```
aagcatctgt gcttcatttt gtagaacaaa aatgcaacgc gagagcgcta attttttcaaa    11340 caaagaatct gagctgcatt tttacagaac agaaatgcaa cgcgaaagcg ctattttacc    11400
aacgaagaat ctgtgcttca tttttgtaaa acaaaaatgc aacgcgacga gagcgctaat    11460
ttttcaaaca aagaatctga gctgcatttt tacagaacag aaatgcaacg cgagagcgct    11520
attttaccaa caaagaatct atacttcttt tttgttctac aaaaatgcat cccgagagcg    11580
ctatttttct aacaaagcat cttagattac ttttttttctc ctttgtgcgc tctataatgc    11640
agtctcttga taacttttg cactgtaggt ccgttaaggt tagaagaagg ctactttggt    11700 gtctatttc tcttccataa aaaaagcctg actccacttc ccgcgtttac tgattactag    11760
cgaagctgcg ggtgcatttt ttcaagataa aggcatcccc gattatattc tataccgatg    11820
tggattgcgc atactttgtg aacagaaagt gatagcgttg atgattcttc attggtcaga    11880
aaattatgaa cggtttcttc tattttgtct ctatatacta cgtataggaa atgtttacat    11940
tttcgtattt ttttcgattc actctatgaa tagttcttac tacaatttt ttgtctaaag    12000 agtaatacta gagataaaca taaaaaatgt agaggtcgag tttagatgca agttcaagga    12060
gcgaaaggtg gatgggtagg ttatataggg atatagcaca gagatatata gcaaagagat    12120
acttttgagc aat                                                       12133

<210> SEQ ID NO 66
<211> LENGTH: 12112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gtttgtggaa gcggtattcg caatttaatt aaagctggtg acaattaatc atcggctcgt       60
ataatgtgtg gaattgaatc gatataagga ggttaatcat atgtaccata tagatgtatt      120
cagaatccct tgccatagtc caggtgacac ttcaggttta aagatttga tagaaacagg      180 tagagtcgct ccagcagata ttgttgctgt catgggtaaa acagagggta atggttgtgt      240
taacgactat acaagagaat acgccaccgc tatgttggct gcatgcttag gtagacattt      300
gcaattacca cctcacgaag ttgaaaagag agtagctttt gttatgtccg gtggtacaga      360
aggtgtattg tctccacatc acccgttttt cgctagaaga ccagcaatag atgcccatag      420
acctgcaggt aaaagattga ctttaggtat cgcttttaca agagatttct tgcctgaaga      480
aattggtaga catgcacaaa taaccgaaac tgcaggtgcc gttaagagag ctatgagaga      540
tgctggtatc gcatcaatag atgacttaca tttcgtacag gttaagtgtc cattgttgac      600
tcctgcaaag atcgcttcag caagatccag aggttgcgct ccagtcacta cagatacata      660
tgaaagtatg ggttactcta gaggtgcctc agctttgggt attgcattag ccaccgaaga      720
agttccttct tcaatgttgg tcgatgaatc cgtattaaat gactgagagtt tgtccagttc      780 tttagcttca gcatccgccg gtatagaatt ggaacataac gttgtcattg ccataggcat      840
gtccgaacaa gctacaagtg aattagttat cgcacacggt gtcatgtctg atgccattga      900
cgccgcttca gttagaagaa ctatagaatc tttgggtatc agatcagatg acgaaatgga      960
tagaatagtc aacgtattcg ctaaagcaga agcctctcca gacggtgtag ttagaggcat     1020
gagacatact atgttgagtg attctgacat caactctacc agacacgcta gagcagttac     1080
tggtgcagcc atagcttctg tcgtaggtca tggtatggtt tatgtctcag gtggtgccga     1140
```

-continued

```
acaccaaggt ccagctggtg gtggtccttt cgcagttatt gccagagctt aaggaaatcc   1200
attatgatat actcaacagt caacgctaat ccttacgctt ggccttacga tggttcaata   1260
gaccctgctc acaccgcttt aatcttaatc gattggcaaa tagacttttg tggtccaggt   1320
ggttatgtcg attccatggg ttacgactta tccttgacta gaagtggttt agaacctaca   1380
gcaagagtat tggctgcagc cagagatact ggtatgacag ttatccatac tagagaaggt   1440
cacagaccag atttggctga cttgccacct aataagagat ggagatctgc atcagccggt   1500
gctgaaatcg gttcagttgg tccatgtggt agaatttttag tcagaggtga acctggttgg   1560
gaaatagtac cagaagttgc acctagagaa ggtgaaccaa ttatagataa acctggtaaa   1620
ggtgctttct acgcaacaga tttggacttg ttgttgagaa caagaggtat cacccatttg   1680
attttgaccg gtataactac agatgtttgc gtccacacca ctatgagaga agccaacgat   1740
agaggttacg aatgtttaat tttgtctgat tgcaccggtg ctactgacag aaagcatcac   1800
gaagctgcat tatctatggt caccatgcaa ggtggtgtat tcggtgcaac tgcccattca   1860
gatgacttat tggccgcttt gggtacaacc gttccagcag ccgctggtcc tagagctaga   1920
acagaataag gaacgaccat gacagttagt tccgatacaa ctgctgaaat atcgttaggt   1980
tggtcaatcc aagactggat tgatttccac aagtcatcaa gctcccaggc ttcactaagg   2040
cttcttgaat cactactaga ctctcaaaat gttgcgccag tcgataatgc gtggatatcg   2100
ctaatttcaa aggaaaattt actgcaccaa ttccaaattt taaagagcag agaaaataaa   2160
gaaactctac ctctctacgg tgtccctatt gctgttaagg acaacatcga cgttagaggt   2220
ctacccacca ccgctgcatg tccatccttt gcatatgagc cttccaaaga ctctaaagta   2280
gtagaactac taagaaatgc aggtgcgata atcgtgggta agacaaactt ggaccaattt   2340
gccacaggat tagtcggcac acggtctcca tatgggaaaa caccttgcgc tttttagcaaa   2400 gagcatgtat ctggtggttc ctccgctggg tcagcatcgg tggtcgccag aggtatcgta   2460
ccaattgcat tgggtactga tacagcaggt tctggtagag tcccagccgc cttgaacaac   2520
ctgattggcc taaagccaac aaagggcgtc ttttcctgtc aaggtgtagt tcccgcttgt   2580
aaatctttag actgcgtctc catctttgca ttaaacctaa gtgatgctga acgctgcttc   2640
cgcatcatgt gccagccaga tcctgataat gatgaatatt ctagacccta tgtttccaac   2700
cctttgaaaa aattttcaag caatgtaacg attgctattc ctaaaatat cccatggtat   2760 ggtgaaacca agaatcctgt actgttttcc aatgctgtcg aaaatctatc aagaacgggc   2820
gctaacgtca tagaaattga ttttgagcct cttttagagt tagctcgctg tttatacgaa   2880
ggtacttggg tggccgagcg ttatcaagct attcaatcgt ttttggacag taaaccacca   2940
aaggaatctt tggaccctac tgttatttca attatagaag gggccaagaa atacagtgca   3000
gtagactgct tcagtttga atacaaaaga caaggcatct tgcaaaaagt gagacgactt   3060
ctcgaatcag tcgatgtatt gtgtgtgccc acatgtcctt taaatcctac tatgcaacaa   3120
gttgcggatg aaccagtcct agtcaattca agacaaggca catggactaa ttttgtcaac   3180
ttggcagatt tggcagccct tgctgttccc gcagggttcc gagacgatgg tttgccaaat   3240
ggtattactt taatcggtaa aaaattcaca gattacgcac tattagagtt ggctaaccgc   3300
tatttccaaa atatattccc caacggttcc agaacatacg gtacttttac ctcttcttca   3360
gtaaagccag caaacgatca attagtggga ccagactatg acccatctac gtccataaaa   3420
ttggctgttg tcggtgcaca tcttaagggt ctgcctctac attggcaatt ggaaaaggtc   3480
```

```
aatgcaacat atttatgtac aacaaaaaca tcaaaagctt accagctttt tgctttgccc    3540
aaaaatggac cagttttaaa acctggtttg agaagagttc aagatagcaa tggctctcaa    3600
atcgaattag aagtgtacag tgttccaaaa gaactgttcg gtgcttttat ttccatggtt    3660
cctgaaccat taggaatagg ttcagtggag ttagaatctg gtgaatggat caaatccttt    3720
atttgtgaag aatctggtta caaagccaaa ggtacagttg atatcacaaa gtatggtgga    3780
tttagagcat attttgaaat gttgtaagga cacgataatg tcaatggaaa cccatagtta    3840
tgtagacgtc gcaattcgta acgcgcgtct tgccgatacg gagggaattg tcgatattct    3900
tattcacgat gggcgcattg cgtccatcgt gaagtcgaca aaaacaaaag gatcggtgga    3960
gatcgatgct catgagggtc tggtcacttc cggcctggta gagcctcaca tccatctcga    4020
taaggccctg acggcagatc gggttcccgc aggaagcatt ggcgaccttc gaacgcgacg    4080
aggccttgag atggcaattc gggccacccg tgatatcaag cgtacgttca cggttgaaga    4140
tgttcgagaa cgggccatac gtgcggccct gatggcatcc cgtgcgggaa ccaccgcatt    4200
gcggacacac gtcgatgtcg acccgattgt cggcctcgca ggtatccgtg gtgtccttga    4260
ggcgcgtgaa gtctgcgcgg gattgatcga tatccagatc gtcgccttcc ctcaggaggg    4320
actcttctgc tctgcggggg ccgtggacct catgcgggag gcgatcaaac tgggcgcgga    4380
tgccgtcggc ggcgcacccg cgctggatga tcgcccgcag gaccatgtcc gagccgtttt    4440
tgaccttgct gctgagttcg gcctgcccgt agacatgcac gtcgatgagt ccgaccggcg    4500
ggaagacttt acgcttccct ttgtgattga agctgcccgt gaacggcgtg tgcccaatgt    4560
gaccgtcgcg cacatcagct cgctgtccgt acagacggat gacgtagcac ggtcgaccat    4620
tgccgccctt gcggacgccg atgttaatgt cgtggttaat ccgatcattg tcaaaattac    4680
gcggctgagt gaattactcg atgccggagt ctccgtaatg tttggctcgg acaacctgcg    4740
ggatccgttc tatccgctcg gagcggcgaa tccccttgga tcagccattt ttgcctgtca    4800
aattgccgcg ctgggaacac cgcaagatct cagacgggta ttcgatgcgg tcaccatcaa    4860
cgctgcccgc atgctgggat tcccctcact tttaggcgtc gtggaagggg cagtcgcgga    4920
tctcgcagta ttcccatcgg cgacgcccga ggaggttgtt ctggatcaac agtctccgct    4980
cttcgtactc aagggcggac gtgtcgttgc catgcgattg gccgctggat caacgtcgtt    5040
ccgcgactac tcatgaggaa atccattatg atgtcaggag aacacacgtt aaaagcggta    5100
cgaggcagtt ttattgatgt cacccgtacg atcgataacc cggaagagat tgcctctgcg    5160
ctgcggttta ttgaggatgg tttattactc attaaacagg gaaaagtgga atggtttggc    5220
gaatgggaaa acgaaaagca tcaaattcct gacaccattc gcgtgcgcga ctatcgcggc    5280
aaactgatag taccgggctt tgtcgataca catatccatt atccgcaaag tgaaatggtg    5340
ggggcctatg gtgagcaatt gctggagtgg ttgaataaac acaccttccc tactgaacgt    5400
cgttatgagg atttagagta cgcccgcgaa atgtcggcgt tcttcatcaa gcagctttta    5460
cgtaacggaa ccaccacggc gctggtgttt ggcactgttc atccgcaatc tgttgatgcg    5520
ctgtttgaag ccgccagtca tatcaatatg cgtatgattg ccggtaaggt gatgatggac    5580
cgcaacgcac cggattatct gctcgacact gccgaaagca gctatcacca aagcaaagaa    5640
ctgatcgaac gctggcacaa aaatggtcgt ctgctatatg cgattacgcc acgcttcgcc    5700
ccgacctcat ctcctgaaca gatggcgatg gcgcaacgcc tgaaagaaga atatccggat    5760
acgtgggtac atacccatct ctgtgaaaac aaagatgaaa ttgcctgggt gaaatcgctt    5820
tatcctgacc atgatggtta tctggatgtt taccatcagt acggcctgac cggtaaaaac    5880
```

```
tgtgtctttg ctcactgcgt ccatctcgaa gaaaaagagt gggatcgtct cagcgaaacc    5940
aaatccagca ttgctttctg tccgacctcc aaccttacc tcggcagcgg cttattcaac     6000
ttgaaaaaag catggcagaa gaaagttaaa gtgggcatgg aacggatat cggtgccgga     6060 accactttca acatgctgca aacgctgaac gaagcctaca agtattgca attacaaggc     6120 tatcgcctct cggcatatga agcgttttac ctggccacgc tcggcggagc gaaatctctg    6180
ggccttgacg atttgattgg caactttta cctggcaaag aggctgattt cgtggtgatg      6240
gaacccaccg ccactccgct acagcagctg cgctatgaca actctgtttc tttagtcgac    6300
aaattgttcg tgatgatgac gttgggcgat gaccgttcga tctaccgcac ctacgttgat    6360
ggtcgtctgg tgtacgaacg caactaagga acgaccatgc aaacgctcag catccagcac    6420
ggtaccctcg tcacgatgga tcagtaccgc agagtccttg gggatagctg ggttcacgtg    6480
caggatggac ggatcgtcgc gctcggagtg cacgccgagt cggtgcctcc gccagcggat    6540
cgggtgatcg atgcacgcgg caaggtcgtg ttacccggtt tcatcaatgc ccacacccat    6600
gtgaaccaga tcctcctgcg cggagggccc tcgcacgggc gtcaactcta tgactggctg    6660
ttcaacgttt tgtatccggg acaaaaggcg atgagaccgg aggacgtagc ggtggcggtg    6720
aggttgtatt gtgcggaagc tgtgcgcagc gggattacga cgatcaacga caacgccgat    6780
tcggccatct acccaggcaa catcgaggcc gcgatggcgg tctatggtga ggtgggtgtg    6840
agggtcgtct acgcccgcat gttctttgat cggatggacg gcgcattca agggtatgtg    6900 gacgccttga aggctcgctc tccccaagtc gaactgtgct cgatcatgga ggaaacggct    6960
gtggccaaag atcggatcac agccctgtca gatcagtatc atggcacggc aggaggtcgt    7020
atatcagttt ggcccgctcc tgccattacc ccggcggtga cagttgaagg aatgcgatgg    7080
gcacaagcct tcgcccgtga tcgggcggta atgtggacgc ttcacatggc ggagagcgat    7140
catgatgagc ggcttcattg gatgagtccc gccgagtaca tggagtgtta cggactcttg    7200
gatgagcgtc tgcaggtcgc gcattgcgtg tactttgacc ggaaggatgt tcggctgctg    7260
caccgccaca atgtgaaggt cgcgtcgcag gttgtgagca atgcctacct cggctcaggg    7320 gtggccccg tgccagagat ggtggagcgc ggcatggccg tgggcattgg aacagatgac     7380
gggaattgta atgactccgt aaacatgatc ggagacatga agtttatggc ccatattcac    7440
cgcgcggtgc atcgggatgc ggacgtgctg accccagaga agattcttga aatggcgacg    7500
atcgatgggg cgcgttcgtt gggaatggac cacgagattg gttccatcga aaccggcaag    7560
cgcgcggacc ttatcctgct tgacctgcgt caccctcaga cgactcctca ccatcatttg    7620
gcggccacga tcgtgtttca ggcttacggc aatgaggtgg acactgtcct gattgacgga    7680
aacgttgtga tggagaaccg ccgcttgagc tttcttcccc ctgaacgtga gttggcgttc    7740
cttgaggaag cgcagagccg cgccacagct attttgcagc gggcgaacat ggtggctaac    7800
ccagcttggc gcagcctcta gcctcaaaat atattttccc tctatcttct cgttgcgctt    7860
aatttgacta attctcatta gcgaggcgcg cctttccata ggctccgccc ccctgacgag    7920
catcacaaaa atcgacgctc aagtcagagg tggcgaaacc cgacaggact ataaagatac    7980
caggcgtttc cccctggaag ctccctcgtg cgctctcctg ttccgaccct gccgcttacc    8040
ggatacctgt ccgcctttct cccttcggga agcgtggcgc tttctcatag ctcacgctgt    8100
aggtatctca gttcggtgta ggtcgttcgc tccaagctgg gctgtgtgca cgaacccccc    8160
gttcagcccg accgctgcgc cttatccggt aactatcgtc ttgagtccaa cccggtaaga    8220
```

```
cacgacttat cgccactggc agcagccact ggtaacagga ttagcagagc gaggtatgta    8280
ggcggtgcta cagagttctt gaagtggtgg cctaactacg gctacactag aagaacagta    8340
tttggtatct gcgctctgct gaagccagtt accttcggaa aaagagttgg tagctcttga    8400
tccggcaaac aaaccaccgc tggtagcggt ggttttttg tttgcaagca gcagattacg     8460
cgcagaaaaa aaggatctca agaagatcct ttgatctttt ctacggggtc tgacgctcag    8520
tggaacgaaa actcacgtta agggattttg gtcatgagat tatcaaaaag gatcttcacc    8580
tagatccttt taaattaaaa atgaagtttt aaatcaatct aaagtatata tgagtaaact    8640
tggtctgaca gttaccaatg cttaatcagt gaggcaccta tctcagcgat ctgtctattt    8700
cgttcatcca tagttgcctg actccccgtc gtgtagataa ctacgatacg ggagggctta    8760
ccatctggcc ccagtgctgc aatgataccg cgagacccac gctcaccggc tccagattta    8820
tcagcaataa accagccagc cggaagggcc gagcgcagaa gtggtcctgc aactttatcc    8880
gcctccatcc agtctattaa ttgttgccgg gaagctagag taagtagttc gccagttaat    8940
agtttgcgca acgttgttgc cattgctaca ggcatcgtgg tgtcacgctc gtcgtttggt    9000
atggcttcat tcagctccgg ttcccaacga tcaaggcgag ttacatgatc ccccatgttg    9060
tgcaaaaaag cggttagctc cttcggtcct ccgatcgttg tcagaagtaa gttggccgca    9120
gtgttatcac tcatggttat ggcagcactg cataattctc ttactgtcat gccatccgta    9180
agatgctttt ctgtgactgg tgagtactca accaagtcat tctgagaata gtgtatgcgg    9240
cgaccgagtt gctcttgccc ggcgtcaata cgggataata ccgcgccaca tagcagaact    9300
ttaaaagtgc tcatcattgg aaaacgttct cggggcgaaa actctcaag gatcttaccg      9360 ctgttgagat ccagttcgat gtaacccact cgtgcaccca actgatcttc agcatctttt    9420
actttcacca gcgtttctgg gtgagcaaaa acaggaaggc aaaatgccgc aaaaaaggga    9480
ataagggcga cacggaaatg ttgaatactc atactcttcc ttttcaata ttattgaagc     9540 atttatcagg gttattgtct catgagcgga tacatatttg aatgtattta gaaaaataaa    9600
cagcgatcgc gcggccgcgg gtaataactg atataattaa attgaagctc taatttgtga    9660
gtttagtata catgcattta cttataatac agttttttag ttttgctggc cgcatcttct    9720
caaatatgct tcccagcctg cttttctgta acgttcaccc tctaccttag catcccttcc    9780
ctttgcaaat agtcctcttc aacaataat aatgtcagat cctgtagaga ccacatcatc     9840
cacggttcta tactgttgac ccaatgcgtc tcccttgtca tctaaaccca caccgggtgt    9900
cataatcaac caatcgtaac cttcatctct tccacccatg tctctttgag caataaagcc    9960
gataacaaaa tctttgtcgc tcttcgcaat gtcaacagta cccttagtat attctccagt   10020
agctagggag cccttgcatg acaattctgc taacatcaaa aggcctctag gttcctttgt    10080
tacttcttcc gccgcctgct tcaaaccgct aacaatacct gggcccacca caccgtgtgc    10140
attcgtaatg tctgcccatt ctgctattct gtatacaccc gcagagtact gcaatttgac    10200
tgtattacca atgtcagcaa atttttctgtc ttcgaagagt aaaaaattgt acttggcgga   10260
taatgccttt agcggcttaa ctgtgccctc catggaaaaa tcagtcaaga tatccacatg    10320
tgtttttagt aaacaaattt tgggacctaa tgcttcaact aactccagta attccttggt    10380
ggtacgaaca tccaatgaag cacacaagtt tgtttgcttt tcgtgcatga tattaaatag    10440
cttggcagca acaggactag gatgagtagc agcacgttcc ttatatgtag ctttcgacat    10500
gatttatctt cgtttcctgc aggttttgt tctgtgcagt tgggttaaga atactgggca    10560
atttcatgtt tcttcaacac cacatatgcg tatatatacc aatctaagtc tgtgctcctt    10620
```

```
ccttcgttct tccttctgct cggagattac cgaatcaaag ctagcttatc gatgataagc    10680
tgtcaaagat gagaattaat tccacggact atagactata ctagatactc cgtctactgt    10740
acgatacact tccgctcagg tccttgtcct ttaacgaggc cttaccactc ttttgttact    10800
ctattgatcc agctcagcaa aggcagtgtg atctaagatt ctatcttcgc gatgtagtaa    10860
aactagctag accgagaaag agactagaaa tgcaaaaggc acttctacaa tggctgccat    10920
cattattatc cgatgtgacg ctgcagcttc tcaatgatat tcgaatacgc tttgaggaga    10980
tacagcctaa tatccgacaa actgttttac agatttacga tcgtacttgt tacccatcat    11040
tgaattttga acatccgaac ctgggagttt tccctgaaac agatagtata tttgaacctg    11100
tataataata tatagtctag cgctttacgg aagacaatgt atgtatttcg gttcctggag    11160
aaactattgc atctattgca taggtaatct tgcacgtcgc atccccggtt cattttctgc    11220
gtttccatct tgcacttcaa tagcatatct ttgttaacga agcatctgtg cttcattttg    11280
tagaacaaaa atgcaacgcg agagcgctaa ttttcaaac aaagaatctg agctgcattt    11340
ttacagaaca gaaatgcaac gcgaaagcgc tattttacca acgaagaatc tgtgcttcat    11400
ttttgtaaaa caaaaatgca acgcgacgag agcgctaatt tttcaaacaa agaatctgag    11460
ctgcattttt acagaacaga atgcaacgc gagagcgcta ttttaccaac aaagaatcta    11520
tacttctttt tgttctaca aaatgcatc ccgagagcgc tatttttcta acaaagcatc    11580
ttagattact ttttttctcc tttgtgcgct ctataatgca gtctcttgat aacttttgc    11640 actgtaggtc cgttaaggtt agaagaaggc tactttggtg tctatttct cttccataaa    11700 aaaagcctga ctccacttcc cgcgtttact gattactagc gaagctgcgg gtgcattttt    11760
tcaagataaa ggcatccccg attatattct ataccgatgt ggattgcgca tactttgtga    11820
acagaaagtg atagcgttga tgattcttca ttggtcagaa aattatgaac ggtttcttct    11880
attttgtctc tatatactac gtataggaaa tgtttacatt ttcgtattgt tttcgattca    11940
ctctatgaat agttcttact acaattttt tgtctaaaga gtaatactag agataaacat    12000
aaaaaatgta gaggtcgagt ttagatgcaa gttcaaggag cgaaaggtgg atgggtaggt    12060
tatataggga tatagcacag agatatatag caaagagata cttttgagca at            12112
```

<210> SEQ ID NO 67
<211> LENGTH: 252
<212> TYPE: DNA
<213> ORGANISM: Unknown
<220> FEATURE:
<223> OTHER INFORMATION: Description of Unknown: imm
      sequence

<400> SEQUENCE: 67

```
atggaaactt tagtagcagg ttcaattttt atggtttag tttcaggcgt gttggctatt      60
attatataca tgcttccatg gtttatcgcc ttgatgcgtg ggtcaaaatc gacagtagga     120
atctttttcg catctttact gtttaactgg tcaattattg gttggtttat tacatttatt     180
tggtcaattg caggtgaaac taaaaagtct gcgcagccaa atcaggtaat tatcatcaga     240
gagaaggaat ga                                                        252
```

<210> SEQ ID NO 68
<211> LENGTH: 294
<212> TYPE: DNA
<213> ORGANISM: Unknown
<220> FEATURE:
<223> OTHER INFORMATION: Description of Unknown: sp sequence

<400> SEQUENCE: 68

| atgaaaaaat tcatctttgc tacaattttt gctttagctt cttgtgctgc tcagcctgct | 60 |
| atggcaggtt atgataaaga tttgtgcgaa tggtctatga ctgcggatca gactgaggtt | 120 |
| gaaactcaaa ttgaagcaga tattatgaat atcgttaagc gtgatcgtcc tgaaatgaaa | 180 |
| gctgaagtgc aaaaacagct taagtctggt ggtgtaatgc agtataatta tgttctgtat | 240 |
| tgcgataaaa actttaataa caaaaatatc atcgctgaag tggtaggtga ataa | 294 |

<210> SEQ ID NO 69
<211> LENGTH: 738
<212> TYPE: DNA
<213> ORGANISM: Unknown
<220> FEATURE:
<223> OTHER INFORMATION: Description of Unknown: traT
      sequence

<400> SEQUENCE: 69

| atgaaacata acgttaagct gatggcaatg actgccgttt atcctctgt cctcgtgctc | 60 |
| tccgggtgtg gcgcgatgag cacagcgatt aagaaacgta acctcgaagt caaaactcag | 120 |
| atgagtgaaa ccatctggct ggagccgtcc tcacagaaaa ccgtgtatct ccagataaaa | 180 |
| aatacctctg acaaagacat gtctggcctg caggcgaaag taaccaaagc ggttcaggat | 240 |
| aagggctata ccatcacgtc atcgccggac agcgcacact actggattca ggccaatgtc | 300 |
| ctgaaagccg ataaaatgga cctgcgtacc gcccagggt tcctgagcca gggctacgaa | 360 |
| ggcgcgatag cgggtgctgc attaggtgcg gggatcaccg ttataactc cagttctgcc | 420 |
| ggcgcgacat taggtgttgg cctggcggcg ggcctggtgg aatggccgc tgacgcgatg | 480 |
| gtggaagata tcaactatac gatggtgacg gatattcaga tttctgaaaa aaccaccgca | 540 |
| agcgtgcaga ctgataatgt cgccgccctg aaacagggta cttccggata taaagtgcag | 600 |
| accagcacgc agaccggtaa tcagcataaa taccagaccc gcatcgtgtc atctgccaat | 660 |
| aaagttaacc tgaaattcga agaagcaaaa cctgtcctcg aagatcagtt ggcgaaatct | 720 |
| gtcgccaata ttctgtaa | 738 |

<210> SEQ ID NO 70
<211> LENGTH: 234
<212> TYPE: DNA
<213> ORGANISM: Escherichia phage T5

<400> SEQUENCE: 70

| atgaaaaaat tatttttagc tatggcagtg gtacttcttt cggcttgctc tacttttgga | 60 |
| cctaaagata ttaaatgtga ggcatactat atgcaggatc atgtgaaata taaggctaat | 120 |
| gtttttgata ggaaagggga tatgttttg gtgtcaccaa ttatggccta tggatctttc | 180 |
| tgggcccccg taagctactt taccgaagga aatacatgcg agggagtttt ctaa | 234 |

<210> SEQ ID NO 71
<211> LENGTH: 495
<212> TYPE: DNA
<213> ORGANISM: Unknown
<220> FEATURE:
<223> OTHER INFORMATION: Description of Unknown: SieA
      sequence

<400> SEQUENCE: 71

| gtgtctgatt ctatgagtta tgctgtgcta gttgccgcaa ctctatttct ggggatagga | 60 |

-continued

```
ttgcagattg cgtggttgtt tttttctaat tttattaaac gtaaaagact tgaatcaagg      120
atatctgagg tttctattgc aatagggaaa atgctaaaa atccagagaa tgaggcctac       180
gtactcaatt accttaaaga aaagttttcc cctgaaagat ttgaaaacag aattactgat      240
gcccttggat tgataatatc agtaattcat ataccactaa gtttgctgat aacagtgtgg      300
tactttgcca tgatcgcagg aagaatattt ggtttcatga atatagagcc tgttgttctt     360
tgggttccaa tgatactgca attgttgtta agcattgcta tctttatttt ttctgttttt     420
ataaaaattg tctttggaag ataccccgga gaagcgaatg gatttaataa agaattcata    480
aaaactataa aataa                                                      495
```

<210> SEQ ID NO 72
<211> LENGTH: 164
<212> TYPE: PRT
<213> ORGANISM: Unknown
<220> FEATURE:
<223> OTHER INFORMATION: Description of Unknown: SieA
      sequence

<400> SEQUENCE: 72

```
Met Ser Asp Ser Met Ser Tyr Ala Val Leu Val Ala Ala Thr Leu Phe
1               5                   10                  15

Leu Gly Ile Gly Leu Gln Ile Ala Trp Leu Phe Phe Ser Asn Phe Ile
            20                  25                  30

Lys Arg Lys Arg Leu Glu Ser Arg Ile Ser Glu Val Ser Ile Ala Ile
        35                  40                  45

Gly Lys Asn Ala Lys Asn Pro Glu Asn Glu Ala Tyr Val Leu Asn Tyr
    50                  55                  60

Leu Lys Glu Lys Phe Ser Pro Glu Arg Phe Glu Asn Arg Ile Thr Asp
65                  70                  75                  80

Ala Leu Gly Leu Ile Ile Ser Val Ile His Ile Pro Leu Ser Leu Leu
                85                  90                  95

Ile Thr Val Trp Tyr Phe Ala Met Ile Ala Gly Arg Ile Phe Gly Phe
            100                 105                 110

Met Asn Ile Glu Pro Val Val Leu Trp Val Pro Met Ile Leu Gln Leu
        115                 120                 125

Leu Leu Ser Ile Ala Ile Phe Ile Phe Ser Val Phe Ile Lys Ile Val
    130                 135                 140

Phe Gly Arg Tyr Pro Gly Glu Ala Asn Gly Phe Asn Lys Glu Phe Ile
145                 150                 155                 160

Lys Thr Ile Lys
```

<210> SEQ ID NO 73
<211> LENGTH: 249
<212> TYPE: DNA
<213> ORGANISM: Enterobacteria phage P1

<400> SEQUENCE: 73

```
atgctgattc gtttgttttt agtgctttcc tttttaacat ttaatgtttt tgctgatgaa     60
gttgactttt cgaaggtaga ttgcaattca gtggaaacaa gaaaagctct tattgaagaa    120
tataacgaaa tattatcgtc atatggaata acagtggttg attcttataa tcaaaaaact   180
attcagaaag gaataaataa actggtctgt tatggggttt accaatattc agatggctct  240
tcggagtag                                                           249
```

<210> SEQ ID NO 74
<211> LENGTH: 82
<212> TYPE: PRT
<213> ORGANISM: Enterobacteria phage P1

<400> SEQUENCE: 74

Met Leu Ile Arg Leu Phe Leu Val Leu Ser Phe Leu Thr Phe Asn Val
1               5                   10                  15

Phe Ala Asp Glu Val Asp Phe Ser Lys Val Asp Cys Asn Ser Val Glu
                20                  25                  30

Thr Arg Lys Ala Leu Ile Glu Glu Tyr Asn Glu Ile Leu Ser Ser Tyr
            35                  40                  45

Gly Ile Thr Val Val Asp Ser Tyr Asn Gln Lys Thr Ile Gln Lys Gly
        50                  55                  60

Ile Asn Lys Leu Val Cys Tyr Gly Val Tyr Gln Tyr Ser Asp Gly Ser
65                  70                  75                  80

Ser Glu

<210> SEQ ID NO 75
<211> LENGTH: 780
<212> TYPE: DNA
<213> ORGANISM: Enterobacteria phage P1

<400> SEQUENCE: 75
atgaaattat ttaatgtaat aacattttgt tgtgctattt ttgctggaag cgcgatagct      60
gataataaat tgccagattg gctttctacc tcaaagaaag attatgattt agtaagggca     120
ttctatttgt ctggatttgc ttcgaaagca atgaacaatc aatttggtta tcatttgcca     180
tctgagttgg ttaatgattt taagataat gaatttgctg ctcaggaaaa atggaacaca     240
attccaattg tgtatggtga ataaaatcc ataagaatgg tgataataa accaattgta     300 gaattattta ctccagggga aaatgcaacg cctataaatt atatcaaatt gaaaatattg     360
gattcaaagc aagactctct gttaaaacta aaaaaggggg atgatatata tgcagtgtgc     420
tccggtgcta atttagcctt agtgccaatt ctgagcaact gcactccagc aacagacgtc     480
attgatgctg cactctcttt ttctggtgaa tatatgttcc ctgcttttga ttctttttca     540
cctactaagc aaaacgtcaa atatatattc acaaatcaag atcctgttca gatgatgaat     600
tttatagggt acctatcctt agtcgataca acgaaggata agaataaaat ggatatggtt     660
cgtaagtgta cgccttggaa gccggaatgt tcacaacaat tcgttgatgt aatggaagga     720
tttgatagca tcatgtataa atatgaggga gaatttaaaa actacataga attaaaatag     780

<210> SEQ ID NO 76
<211> LENGTH: 259
<212> TYPE: PRT
<213> ORGANISM: Enterobacteria phage P1

<400> SEQUENCE: 76

Met Lys Leu Phe Asn Val Ile Thr Phe Cys Cys Ala Ile Phe Ala Gly
1               5                   10                  15

Ser Ala Ile Ala Asp Asn Lys Leu Pro Asp Trp Leu Ser Thr Ser Lys
                20                  25                  30

Lys Asp Tyr Asp Leu Val Arg Ala Phe Tyr Leu Ser Gly Phe Ala Ser
            35                  40                  45

Lys Ala Met Asn Asn Gln Phe Gly Tyr His Leu Pro Ser Glu Leu Val
        50                  55                  60

Asn Asp Phe Lys Asp Asn Glu Phe Ala Ala Gln Glu Lys Trp Asn Thr

| | | | | | | | | | | | | | | | |
|---|---|---|---|---|---|---|---|---|---|---|---|---|---|---|---|

```
                65                  70                  75                  80
Ile Pro Ile Val Tyr Gly Glu Ile Lys Ser Ile Arg Met Val Asn Asn
                    85                  90                  95
Lys Pro Ile Val Glu Leu Phe Thr Pro Gly Glu Asn Ala Thr Pro Ile
                    100                 105                 110
Asn Tyr Ile Lys Leu Lys Ile Leu Asp Ser Lys Gln Asp Ser Leu Leu
                    115                 120                 125
Lys Leu Lys Lys Gly Asp Asp Ile Tyr Ala Val Cys Ser Gly Ala Asn
                130                 135                 140
Phe Ser Leu Val Pro Ile Leu Ser Asn Cys Thr Pro Ala Thr Asp Val
145                 150                 155                 160
Ile Asp Ala Ala Leu Ser Phe Ser Gly Glu Tyr Met Phe Pro Ala Phe
                    165                 170                 175
Asp Ser Phe Ser Pro Thr Lys Gln Asn Val Lys Tyr Ile Phe Thr Asn
                    180                 185                 190
Gln Asp Pro Val Gln Met Met Asn Phe Ile Gly Tyr Leu Ser Leu Val
                    195                 200                 205
Asp Thr Thr Lys Asp Lys Asn Lys Met Asp Met Val Arg Lys Cys Thr
                210                 215                 220
Pro Trp Lys Pro Glu Cys Ser Gln Gln Phe Val Asp Val Met Glu Gly
225                 230                 235                 240
Phe Asp Ser Ile Met Tyr Lys Tyr Glu Gly Glu Phe Lys Asn Tyr Ile
                    245                 250                 255
Glu Leu Lys
```

<210> SEQ ID NO 77
<211> LENGTH: 840
<212> TYPE: DNA
<213> ORGANISM: Unknown
<220> FEATURE:
<223> OTHER INFORMATION: Description of Unknown: rexA
      sequence

<400> SEQUENCE: 77

```
atgaagaatg gtttttatgc gacttaccgc agcaaaaata aagggaaaga taagcgctca      60
ataaacctgt ctgttttcct taattctctg ctggctgata atcatcacct gcaggttggc     120
tccaattatt tgtatattca taaaatcgat ggaaaaactt ttctctttac caaaacaaat     180
gacaagagtc tggttcagaa gataaatcgc tctaaagctt cagttgaaga tattaagaac     240
agcctcgcag atgacgaatc attgggattc catctttttt tgtttgttga aggcgacacc     300
attggttttg ccagaactgt tttcgggccg accacatccg atctgacaga ttttttaatc     360
gggaaaggaa tgtcattaag cagtggagag cgcgttcaga tagagccact gatgagggga     420
accaccaaag acgatgttat gcatatgcat ttcatcggcc gaacaacggt gaaggtagaa     480
gccaagctac ctgtatttgg cgatatatta aaggtcttag ggcaacaga tattgaaggg     540
gagcttttg actcattgga tatagtcatt aagccaaaat ttaaaaggga tataaaaaag     600
gttgccaagg atattatttt taacccgtca cctcaatttt cagacattag cctgcgggca     660
aaagatgagg ccggagatat tttaacagaa cattatctat cagaaaaagg ccatctctca     720
gcgcctctga acaaggtcac caatgctgag atagctgaag atggcata ttgctacgca     780
agaatgaaaa gtgatatact ggaatgtttt aaaaggcagg tgggcaaagt taaggattaa     840
```

<210> SEQ ID NO 78
<211> LENGTH: 279

```
<212> TYPE: PRT
<213> ORGANISM: Unknown
<220> FEATURE:
<223> OTHER INFORMATION: Description of Unknown: rexA
      sequence

<400> SEQUENCE: 78

Met Lys Asn Gly Phe Tyr Ala Thr Tyr Arg Ser Lys Asn Lys Gly Lys
1               5                   10                  15

Asp Lys Arg Ser Ile Asn Leu Ser Val Phe Leu Asn Ser Leu Leu Ala
            20                  25                  30

Asp Asn His His Leu Gln Val Gly Ser Asn Tyr Leu Tyr Ile His Lys
        35                  40                  45

Ile Asp Gly Lys Thr Phe Leu Phe Thr Lys Thr Asn Asp Lys Ser Leu
    50                  55                  60

Val Gln Lys Ile Asn Arg Ser Lys Ala Ser Val Glu Asp Ile Lys Asn
65                  70                  75                  80

Ser Leu Ala Asp Asp Glu Ser Leu Gly Phe Pro Ser Phe Leu Phe Val
                85                  90                  95

Glu Gly Asp Thr Ile Gly Phe Ala Arg Thr Val Phe Gly Pro Thr Thr
            100                 105                 110

Ser Asp Leu Thr Asp Phe Leu Ile Gly Lys Gly Met Ser Leu Ser Ser
        115                 120                 125

Gly Glu Arg Val Gln Ile Glu Pro Leu Met Arg Gly Thr Thr Lys Asp
    130                 135                 140

Asp Val Met His Met His Phe Ile Gly Arg Thr Thr Val Lys Val Glu
145                 150                 155                 160

Ala Lys Leu Pro Val Phe Gly Asp Ile Leu Lys Val Leu Gly Ala Thr
                165                 170                 175

Asp Ile Glu Gly Glu Leu Phe Asp Ser Leu Asp Ile Val Ile Lys Pro
            180                 185                 190

Lys Phe Lys Arg Asp Ile Lys Lys Val Ala Lys Asp Ile Ile Phe Asn
        195                 200                 205

Pro Ser Pro Gln Phe Ser Asp Ile Ser Leu Arg Ala Lys Asp Glu Ala
    210                 215                 220

Gly Asp Ile Leu Thr Glu His Tyr Leu Ser Glu Lys Gly His Leu Ser
225                 230                 235                 240

Ala Pro Leu Asn Lys Val Thr Asn Ala Glu Ile Ala Glu Glu Met Ala
                245                 250                 255

Tyr Cys Tyr Ala Arg Met Lys Ser Asp Ile Leu Glu Cys Phe Lys Arg
            260                 265                 270

Gln Val Gly Lys Val Lys Asp
        275

<210> SEQ ID NO 79
<211> LENGTH: 435
<212> TYPE: DNA
<213> ORGANISM: Unknown
<220> FEATURE:
<223> OTHER INFORMATION: Description of Unknown: rexB
      sequence

<400> SEQUENCE: 79
atgcggaaca gaatcatgcc tggtgtttac atagtaataa ttccttacgt tatcgtaagc    60
atttgctatc tccttttccg ccactacatt cctggtgttt cttttttcagc tcatagagat   120 ggtcttgggg cgacattgtc atcatatgca ggaaccatga ttgcaatcct gattgctgcc   180
```

```
ttgacgtttc taatcggaag cagaacgcgc cgactggcca agattagaga gtatgggtat      240
atgacatcgg tagttattgt ctatgcccct agttttgttg agcttggagc tttgttttc      300 tgcgggttat tgcttctttc cagcataagc ggctacatga tacccactat cgccatcggc      360
attgcctctg catcgttcat tcatatatgc atccttgttt tccaactata taatttgacc      420
agagaacaag aataa                                                       435
```

<210> SEQ ID NO 80
<211> LENGTH: 144
<212> TYPE: PRT
<213> ORGANISM: Unknown
<220> FEATURE:
<223> OTHER INFORMATION: Description of Unknown: rexB
      sequence

<400> SEQUENCE: 80

```
Met Arg Asn Arg Ile Met Pro Gly Val Tyr Ile Val Ile Pro Tyr
1               5                   10                  15

Val Ile Val Ser Ile Cys Tyr Leu Leu Phe Arg His Tyr Ile Pro Gly
            20                  25                  30

Val Ser Phe Ser Ala His Arg Asp Gly Leu Gly Ala Thr Leu Ser Ser
        35                  40                  45

Tyr Ala Gly Thr Met Ile Ala Ile Leu Ile Ala Ala Leu Thr Phe Leu
    50                  55                  60

Ile Gly Ser Arg Thr Arg Arg Leu Ala Lys Ile Arg Glu Tyr Gly Tyr
65                  70                  75                  80

Met Thr Ser Val Val Ile Val Tyr Ala Leu Ser Phe Val Glu Leu Gly
                85                  90                  95

Ala Leu Phe Phe Cys Gly Leu Leu Leu Leu Ser Ser Ile Ser Gly Tyr
            100                 105                 110

Met Ile Pro Thr Ile Ala Ile Gly Ile Ala Ser Ala Ser Phe Ile His
        115                 120                 125

Ile Cys Ile Leu Val Phe Gln Leu Tyr Asn Leu Thr Arg Glu Gln Glu
    130                 135                 140
```

<210> SEQ ID NO 81
<211> LENGTH: 894
<212> TYPE: DNA
<213> ORGANISM: Escherichia coli

<400> SEQUENCE: 81

```
atgcgctcac caatttgtca tcttttctca gcaattaatt catcaccatt taagattgca       60
ccagagaagg agcaagatct taaaacgata gttgacgaca aaaaaattat aatttcagtt      120
gtgagtgaac ctggttttaa tatccgagtc aggaagaatg agagtaataa ttcacatgaa      180
atagttctaa cagtagcttc acttgaatat atttgggcat tttccaattt cttttgggtt      240
tttacgcaag agtactccaa atctcagaaa aataatgatg agcactttga tttaacagga      300
aaaaatagcc ttaaaaagtc tgatgaactt cttaaatggg caaggaaaaa cttgcaaaca      360
caggttgcga atcatggcct aaaaaatgtc ccaagccaga agcattattt acaaggaagc      420
gaagactcac aagttgctag cgagatattt ctttgtgcta ttgcttggat tcttcatcat      480
gaaataagtc atgttgtttt acagcatcca ttggtcacta cagcattctc cactcaagag      540
gagcgtgaag cagattcaca tgctacaaaa tggatattag caacctgta tgaatccgct      600 cctgaattaa agaaacgtgc acttggcatt gctacggcag tgctttgtat acaaagctta      660
gaagttgaaa attacttctg tttacaaaat acacacccag ctgcatatga gcgtatatat      720
```

```
tcgaatattt catgctaccc tgtcggaaat gaagagttga ttgaagctct atgtacagtg    780
atgcttcaat atcttttcca tggcaaaaat atcaatgtga atctagatgg ggagtccttt    840
tcatcgattt taggtgatct tctctgtgat atttcacgtc ttaccagtaa ctga          894
```

<210> SEQ ID NO 82
<211> LENGTH: 297
<212> TYPE: PRT
<213> ORGANISM: Escherichia coli

<400> SEQUENCE: 82

```
Met Arg Ser Pro Ile Cys His Leu Phe Ser Ala Ile Asn Ser Ser Pro
1               5                   10                  15

Phe Lys Ile Ala Pro Glu Lys Glu Gln Asp Leu Lys Thr Ile Val Asp
            20                  25                  30

Asp Lys Lys Ile Ile Ile Ser Val Ser Glu Pro Gly Phe Asn Ile
        35                  40                  45

Arg Val Arg Lys Asn Glu Ser Asn Asn Ser His Glu Ile Val Leu Thr
    50                  55                  60

Val Ala Ser Leu Glu Tyr Ile Trp Ala Phe Ser Asn Phe Phe Trp Val
65                  70                  75                  80

Phe Thr Gln Glu Tyr Ser Lys Ser Gln Lys Asn Asn Asp Glu His Phe
                85                  90                  95

Asp Leu Thr Gly Lys Asn Arg Leu Lys Lys Ser Asp Glu Leu Leu Lys
            100                 105                 110

Trp Ala Arg Lys Asn Leu Gln Thr Gln Val Ala Asn His Gly Leu Lys
        115                 120                 125

Asn Val Pro Ser Gln Lys His Tyr Leu Gln Gly Ser Glu Asp Ser Gln
    130                 135                 140

Val Ala Ser Glu Ile Phe Leu Cys Ala Ile Ala Trp Ile Leu His His
145                 150                 155                 160

Glu Ile Ser His Val Val Leu Gln His Pro Leu Val Thr Thr Ala Phe
                165                 170                 175

Ser Thr Gln Glu Glu Arg Glu Ala Asp Ser His Ala Thr Lys Trp Ile
            180                 185                 190

Leu Gly Asn Leu Tyr Glu Ser Ala Pro Glu Leu Lys Lys Arg Ala Leu
        195                 200                 205

Gly Ile Ala Thr Ala Val Leu Cys Ile Gln Ser Leu Glu Val Glu Asn
    210                 215                 220

Tyr Phe Cys Leu Gln Asn Thr His Pro Ala Ala Tyr Glu Arg Ile Tyr
225                 230                 235                 240

Ser Asn Ile Ser Cys Tyr Pro Val Gly Asn Glu Glu Leu Ile Glu Ala
                245                 250                 255

Leu Cys Thr Val Met Leu Gln Tyr Leu Phe His Gly Lys Asn Ile Asn
            260                 265                 270

Val Asn Leu Asp Gly Glu Ser Phe Ser Ser Ile Leu Gly Asp Leu Leu
        275                 280                 285

Cys Asp Ile Ser Arg Leu Thr Ser Asn
    290                 295
```

<210> SEQ ID NO 83
<211> LENGTH: 1191
<212> TYPE: DNA
<213> ORGANISM: Escherichia coli

<400> SEQUENCE: 83

```
atgggcaaga cactctcgga aatagctcaa cagcttagta cgcctcagaa agtcaagaag      60
actgtccata aagaagttga agcgaccagg gccgtgccaa aggtgcagtt aatctacgct     120
ttcaatggca cggggaaaac gcgtctttcc cgggatttca agcaactgct tgagtccaaa     180
gttcatgacg agaaggtgaa agacgaagct gaacagtccg cgttgtcgcg caaaaaaatc     240
ctctattata atgccttcac cgaggacttg ttctattggg ataacgatct gcaagaagac     300
gcagaaccga agctgaaggt gcagcctaac tcctatacaa actggttgct gaccttgcta     360
aaagatttgg acaggatag caatatcgtc cgttatttcc agcgctatgc gaacgacaag     420
ctaacgccac acttcaatcc agattttacc gaaatcactt tttccatgga gcgcggtaac     480
gatgagcgtt ccgcccacat caagttatcc aaaggtgaag agagcaactt catctggagt     540
gtgttttaca ccctactgga tcaagtggta acaattctca atgtcgctga cccggatgcg     600
cgcgagaccc acgcatttga tcaactgaaa tatgtattca ttgatgatcc cgttagctcc     660
cttgatgata accatttgat tgaactggcg gttaatcttg cagggctgat caaatccagc     720
gaatccgatt tgaagttcat tatcacgaca catagtccaa tattttataa tgtactttc      780
aatgagttga acggtaaagt ttgctacatg ttggaaagtt ttgaggatgg tacatttgcc     840
ctcacagaaa aatatggcga ctctaacaag agttttcct accatctcca cctaaagcaa      900
acaatcgaac aggcaattgc tgacaacaac gttgaaagat atcatttcac gttactgcgc     960
aatctttatg agaaaacggc cagctttctg ggctacccta aatggtctga actcttgcct    1020
gacgacaagc agctttatct gagcagaatc atcaatttca caagccacag cacgctatcg    1080
aatgaggccg ttgcagagcc aacgccagcg gagaaagcga ctgtcaaact gttgctcgat    1140
cacttgaaga caactgtgg cttctggcag caggaacaaa aaaatggttg a              1191
```

<210> SEQ ID NO 84
<211> LENGTH: 313
<212> TYPE: PRT
<213> ORGANISM: Escherichia coli

<400> SEQUENCE: 84

```
Met Val Asp Cys Thr Lys Pro Ile Ala Glu Ser Asn Asn Phe Ile Ile
1               5                   10                  15

Leu Asp Lys Tyr Asn Pro Asp Trp Lys Ile Thr Glu Ser Tyr Gln Ser
            20                  25                  30

Glu Gly Asp Leu Glu Arg Glu Leu Ile Gln Asp Leu Val Asn Gln Gly
        35                  40                  45

Tyr Glu Tyr Leu Pro Thr Leu Asn Asn Thr Lys Ala Met Leu Ala Asn
    50                  55                  60

Val Arg Glu Gln Leu Gln Asn Leu Asn Asn Val Glu Phe Leu Glu Ala
65                  70                  75                  80

Glu Trp Arg Arg Phe Val Glu Thr Trp Met Asp Lys Pro Ser Asp Gly
                85                  90                  95

Val Val Glu Lys Ala Arg Lys Ile His Asp Asp Tyr Val His Asp Phe
            100                 105                 110

Val Phe Asp Asp Gly Arg Ile Gln Asn Ile Tyr Leu Leu Asp Arg Lys
        115                 120                 125

Asn Ile Leu Arg Asn Lys Val Gln Val Ile Lys Gln Phe Glu Gln Ala
    130                 135                 140

Gly Thr His Ala Asn Arg Tyr Asp Val Thr Ile Leu Val Asn Gly Leu
145                 150                 155                 160
```

```
Pro Leu Val Gln Ile Glu Leu Lys Lys Arg Gly Val Ala Ile Arg Glu
            165                 170                 175

Ala Phe Asn Gln Ile His Arg Tyr Ser Lys Glu Ser Phe Asn Ser Glu
        180                 185                 190

Asn Ser Leu Phe Lys Tyr Leu Gln Leu Phe Val Ile Ser Asn Gly Thr
    195                 200                 205

Asp Thr Arg Tyr Phe Ala Asn Thr Thr Lys Arg Asp Lys Asn Ser Phe
    210                 215                 220

Asp Phe Thr Met Asn Trp Ala Lys Ser Asp Asn Thr Leu Ile Lys Asp
225                 230                 235                 240

Leu Lys Asp Phe Thr Ala Thr Phe Phe Gln Lys His Thr Leu Leu Asn
                245                 250                 255

Val Leu Val Asn Tyr Ser Val Phe Asp Ser Ser Gln Thr Leu Leu Val
                260                 265                 270

Met Arg Pro Tyr Gln Ile Ala Ala Thr Glu Arg Ile Leu Trp Lys Ile
                275                 280                 285

Lys Ser Ser Phe Thr Ser Glu Glu Leu Val Lys Thr Gly Lys Arg Trp
    290                 295                 300

Val Tyr Leu Ala His Tyr Arg Phe Trp
305                 310
```

<210> SEQ ID NO 85
<211> LENGTH: 942
<212> TYPE: DNA
<213> ORGANISM: Escherichia coli

<400> SEQUENCE: 85

```
atggttgatt gcaccaaacc aattgctgag tccaataatt ttatcatttt ggacaaatac    60
aacccggact ggaagattac cgagagctac cagagcgaag gtgatctgga gcgtgagctg   120
attcaggatt tggttaacca gggctatgaa tacctgccaa ccctgaacaa caccaaggct   180
atgctcgcta atgtcaggga acagttgcaa aaccttaaca atgtagagtt cctggaggct   240
gaatggcgtc gctttgtgga aacctggatg acaagcccag cgatggcgt tgttgaaaag   300
gcccgcaaga ttcatgatga ttatgttcat gatttcgtct tcgacgatgg ccgtattcag   360
aatatctatc tgctggatag aaaaaacatc cttcgcaata agtgcaggt catcaagcag   420
tttgaacaag caggcacgca cgccaatcgc tacgatgtca ccattctggt caatggcctg   480
ccgctggtac aaattgaatt gaaaaaacgt ggtgtagcga ttcgtgaggc tttcaaccag   540
atacatcgtt acagtaaaga gagttttaac agcgaaaatt ccctgtttaa gtatctgcag   600
ctgttcgtca tttccaacgg cactgatacc cgttattttg ccaacaccac aaagcgcgat   660
aaaaacagtt ttgacttcac catgaactgg gctaaatcag acaatacact gattaaagac   720
ctcaaagact ttaccgctac cttttttccag aaacatactc tgcttaatgt tctggtgaac   780
tacagcgttt ttgacagcag tcagacgcta ctggtaatgc gaccgtacca gattgccgcc   840
accgagcgca ttctgtggaa aattaagagt tcctttacca gcgaagaact ggtcaaaacc   900
ggaaagcggt gggtatatct ggcacactac cggttctggt aa                      942
```

<210> SEQ ID NO 86
<211> LENGTH: 313
<212> TYPE: PRT
<213> ORGANISM: Escherichia coli

<400> SEQUENCE: 86

Met Val Asp Cys Thr Lys Pro Ile Ala Glu Ser Asn Asn Phe Ile Ile

|    | 1   |     |     |     | 5   |     |     |     |     | 10  |     |     |     |     | 15  |     |
|----|-----|-----|-----|-----|-----|-----|-----|-----|-----|-----|-----|-----|-----|-----|-----|-----|

Leu Asp Lys Tyr Asn Pro Asp Trp Lys Ile Thr Glu Ser Tyr Gln Ser
            20                      25                      30

Glu Gly Asp Leu Glu Arg Glu Leu Ile Gln Asp Leu Val Asn Gln Gly
            35                      40                      45

Tyr Glu Tyr Leu Pro Thr Leu Asn Asn Thr Lys Ala Met Leu Ala Asn
50                      55                      60

Val Arg Glu Gln Leu Gln Asn Leu Asn Asn Val Glu Phe Leu Glu Ala
65                      70                      75                      80

Glu Trp Arg Arg Phe Val Glu Thr Trp Met Asp Lys Pro Ser Asp Gly
                    85                      90                      95

Val Val Glu Lys Ala Arg Lys Ile His Asp Asp Tyr Val His Asp Phe
            100                     105                     110

Val Phe Asp Asp Gly Arg Ile Gln Asn Ile Tyr Leu Leu Asp Arg Lys
            115                     120                     125

Asn Ile Leu Arg Asn Lys Val Gln Val Ile Lys Gln Phe Glu Gln Ala
130                     135                     140

Gly Thr His Ala Asn Arg Tyr Asp Val Thr Ile Leu Val Asn Gly Leu
145                     150                     155                     160

Pro Leu Val Gln Ile Glu Leu Lys Lys Arg Gly Val Ala Ile Arg Glu
                    165                     170                     175

Ala Phe Asn Gln Ile His Arg Tyr Ser Lys Glu Ser Phe Asn Ser Glu
            180                     185                     190

Asn Ser Leu Phe Lys Tyr Leu Gln Leu Phe Val Ile Ser Asn Gly Thr
            195                     200                     205

Asp Thr Arg Tyr Phe Ala Asn Thr Thr Lys Arg Asp Lys Asn Ser Phe
            210                     215                     220

Asp Phe Thr Met Asn Trp Ala Lys Ser Asp Asn Thr Leu Ile Lys Asp
225                     230                     235                     240

Leu Lys Asp Phe Thr Ala Thr Phe Phe Gln Lys His Thr Leu Leu Asn
                    245                     250                     255

Val Leu Val Asn Tyr Ser Val Phe Asp Ser Ser Gln Thr Leu Leu Val
            260                     265                     270

Met Arg Pro Tyr Gln Ile Ala Ala Thr Glu Arg Ile Leu Trp Lys Ile
            275                     280                     285

Lys Ser Ser Phe Thr Ser Glu Glu Leu Val Lys Thr Gly Lys Arg Trp
            290                     295                     300

Val Tyr Leu Ala His Tyr Arg Phe Trp
305                     310

<210> SEQ ID NO 87
<211> LENGTH: 2226
<212> TYPE: DNA
<213> ORGANISM: Unknown
<220> FEATURE:
<223> OTHER INFORMATION: Description of Unknown: pifA
      sequence

<400> SEQUENCE: 87

```
atgaagatac tgaggcagct gtggaaccag aaagggcttg atgcggcagt tgaagatgta      60
cctgaggatc gatacggttt cggtaatatc gcagaaaata tatcccgttc catccttact     120
cttcctctgg aggcttcaaa tgttgtcgga atagaaggtg catggggatc gggtaaaaca     180
agcctcctta atctgatcct gagaaacctt gccctgaaaa aagatgctca cacacatgtg     240
ctgcatattt ctccctggct gagtggcggc agtccggttg aagcgctctt tcttccggtt     300
```

-continued

```
gccacggtta tccagcagga aatggaaata cgctatcccc cgaagggctt caaaaagctc      360
tggcgtaaat atctgttgtc accggaagct caaaaagtga ttgagtatgc tcaggatact      420
tcatcgcgcg tccttccact ggttcaatat atcggacagt tttccagcat tattaactgg      480
atagcaggcg aataaaggt attttcagac agccgtctgg ctgttgatca aaaaccacg       540 acaaagcttc gggctgaaat tgcaggacaa ctggtgagtc tggatctgaa gttcattgtt      600
gtcatggatg atctggaccg actggagcca tcccaggtgg cggaagtgtt caggcttgtg      660
cgtgcagtag ccgatctgcc ccgctttacc catattctct gttatgacag gcagattatc      720
actcatgccg ttgaacatgc gctgaatatc gaagatggca gccgttatct ccagaaaatc      780
attcagctta gttttaaatt accccgacct gaagcctttg atttacgtaa tgaatttcgc      840
cagcgggctg aggctctata tcagcaaatt aataatcaac cgccagactc tggaatggta      900
agggatctca tcgcggtgac tgatacctat ggtgccgcac tttcgacgcc acgggaaatc      960
catcaggcca ttaattccct gatttttctt tatccgggga tgcgggattt tgtttatttc      1020
cctgatttgt gcctgcttca gcttatacgg gtgacaaacc cggctctgta tgactggaca      1080
gagcattacc tgacagaacg gtccgtgatt gaaaccggtc agggtatgct ttctgacgga      1140
gagaaagcag acttccggga ggggcttatc agatgtatga agacgttcag ggcatcaaat      1200
gcagactcgt ttctgacact tgcagactgg atcccaggta tcagtggaca taatgatgaa      1260
tatctgaatc ttttttgagcc cgtcagtgag gattttcgtc atatccagac gaccggtaaa      1320
cgactcagca gcctgacgca ctggcgatat tattttgcct tctcctcacc acagaatgtt      1380
ctgccacctg aattcttcag acagctttt gaacaggctg gcgtatcgga aaaacagcag      1440
cagctttctg aattgctgct ctcaaaaatc aacagtgtgg gcagtctgtc cggaaccctgg     1500 tttgaacata tactgagcag actgactcca ggcctgataa gagaacgtaa tttcgaagag      1560
tgcgcaggac tggttcattt tttcttcgat cacaccgatg aggtgagcac tcgcttcagt      1620
atccgtaacc catggttttc cctgcgtgaa atggccatta atgaggttgt acggcatctg      1680
ctgaagcata tgcaggatat tgatgagacc agaacgatca cgcttatgga aaaactgatc      1740
gttacgggtg cttcgccgtt ctggatagcc gattttatgc gggatcttat ctgggaacat      1800
ggacttgctc agaatgcagt accttcgcct tcagacgctc ttttcagtcg cgatattacg      1860
gaacggttgc gtgacaggtt tgcggaacgt atgaatcaac cagaacttca gcaacagctt      1920
ctcctgcgca agtctcttct cgggtatctc tacgcctgga gagacatgag ttcaggtgaa      1980
accgtgaagc aatgggtcag agaagttact accactgatg aaggccttgt taacctgttg      2040
atacgattac agaccagtgt cttcagctcc caccgagggg catatcgccg gattgcgcgt      2100
gaccaggtca gtccgttctt tgatgactgg ccagcagtcg aagagaagtt gaaggttatg      2160
ctgtccggca acgagctgac tccggagcag gaagcgctca aacagcgct ggaaaatgac       2220 gactga                                                                2226
```

<210> SEQ ID NO 88
<211> LENGTH: 741
<212> TYPE: PRT
<213> ORGANISM: Unknown
<220> FEATURE:
<223> OTHER INFORMATION: Description of Unknown: pifA
      sequence

<400> SEQUENCE: 88

Met Lys Ile Leu Arg Gln Leu Trp Asn Gln Lys Gly Leu Asp Ala Ala

```
1               5                   10                  15
Val Glu Asp Val Pro Glu Asp Arg Tyr Gly Phe Gly Asn Ile Ala Glu
                20                  25                  30

Asn Ile Ser Arg Ser Ile Leu Thr Leu Pro Leu Glu Ala Ser Asn Val
                35                  40                  45

Val Gly Ile Glu Gly Ala Trp Gly Ser Gly Lys Thr Ser Leu Leu Asn
                50                  55                  60

Leu Ile Leu Arg Asn Leu Ala Leu Lys Lys Asp Ala His Thr His Val
65                  70                  75                  80

Leu His Ile Ser Pro Trp Leu Ser Gly Gly Ser Pro Val Glu Ala Leu
                    85                  90                  95

Phe Leu Pro Val Ala Thr Val Ile Gln Gln Glu Met Glu Ile Arg Tyr
                100                 105                 110

Pro Pro Lys Gly Phe Lys Lys Leu Trp Arg Lys Tyr Leu Leu Ser Pro
                115                 120                 125

Glu Ala Gln Lys Val Ile Glu Tyr Ala Gln Asp Thr Ser Ser Arg Val
                130                 135                 140

Leu Pro Leu Val Gln Tyr Ile Gly Gln Phe Ser Ser Ile Ile Asn Trp
145                 150                 155                 160

Ile Ala Gly Gly Ile Lys Val Phe Ser Asp Ser Arg Leu Ala Val Asp
                    165                 170                 175

Gln Lys Thr Thr Thr Lys Leu Arg Ala Glu Ile Ala Gly Gln Leu Val
                180                 185                 190

Ser Leu Asp Leu Lys Phe Ile Val Val Met Asp Asp Leu Asp Arg Leu
                195                 200                 205

Glu Pro Ser Gln Val Ala Glu Val Phe Arg Leu Val Arg Ala Val Ala
                210                 215                 220

Asp Leu Pro Arg Phe Thr His Ile Leu Cys Tyr Asp Arg Gln Ile Ile
225                 230                 235                 240

Thr His Ala Val Glu His Ala Leu Asn Ile Glu Asp Gly Ser Arg Tyr
                    245                 250                 255

Leu Gln Lys Ile Ile Gln Leu Ser Phe Lys Leu Pro Arg Pro Glu Ala
                260                 265                 270

Phe Asp Leu Arg Asn Glu Phe Arg Gln Arg Ala Glu Ala Leu Tyr Gln
                275                 280                 285

Gln Ile Asn Asn Gln Pro Pro Asp Ser Gly Met Val Arg Asp Leu Ile
                290                 295                 300

Ala Val Thr Asp Thr Tyr Gly Ala Ala Leu Ser Thr Pro Arg Glu Ile
305                 310                 315                 320

His Gln Ala Ile Asn Ser Leu Ile Phe Leu Tyr Pro Gly Met Arg Asp
                    325                 330                 335

Phe Val Tyr Phe Pro Asp Leu Cys Leu Leu Gln Leu Ile Arg Val Thr
                340                 345                 350

Asn Pro Ala Leu Tyr Asp Trp Thr His Tyr Leu Thr Glu Arg Ser
                355                 360                 365

Val Ile Glu Thr Gly Gln Gly Met Leu Ser Asp Gly Glu Lys Ala Asp
                370                 375                 380

Phe Arg Glu Gly Leu Ile Arg Cys Met Lys Thr Phe Arg Ala Ser Asn
385                 390                 395                 400

Ala Asp Ser Phe Leu Thr Leu Ala Asp Trp Ile Pro Gly Ile Ser Gly
                    405                 410                 415

His Asn Asp Glu Tyr Leu Asn Leu Phe Glu Pro Val Ser Glu Asp Phe
                420                 425                 430
```

| | | | | | | | | | | | | |
|---|---|---|---|---|---|---|---|---|---|---|---|---|
|Arg|His|Ile|Gln|Thr|Thr|Gly|Lys|Arg|Leu|Ser|Ser|Leu|Thr|His|Trp|
| | |435| | | |440| | | |445| | | | | |

Arg Tyr Tyr Phe Ala Phe Ser Ser Pro Gln Asn Val Leu Pro Pro Glu
        450                 455                 460

Phe Phe Arg Gln Leu Phe Glu Gln Ala Gly Val Ser Glu Lys Gln Gln
465             470                 475                 480

Gln Leu Ser Glu Leu Leu Ser Lys Ile Asn Ser Val Gly Ser Leu
                485                 490                 495

Ser Gly Thr Trp Phe Glu His Ile Leu Ser Arg Leu Thr Pro Gly Leu
                500                 505                 510

Ile Arg Glu Arg Asn Phe Glu Cys Ala Gly Leu Val His Phe Phe
                515                 520                 525

Phe Asp His Thr Asp Glu Val Ser Thr Arg Phe Ser Ile Arg Asn Pro
        530                 535                 540

Trp Phe Ser Leu Arg Glu Met Ala Ile Asn Glu Val Val Arg His Leu
545             550                 555                 560

Leu Lys His Met Gln Asp Ile Asp Glu Thr Arg Thr Ile Thr Leu Met
                565                 570                 575

Glu Lys Leu Ile Val Thr Gly Ala Ser Pro Phe Trp Ile Ala Asp Phe
                580                 585                 590

Met Arg Asp Leu Ile Trp Glu His Gly Leu Ala Gln Asn Ala Val Pro
        595                 600                 605

Ser Pro Ser Asp Ala Leu Phe Ser Arg Asp Ile Thr Glu Arg Leu Arg
        610                 615                 620

Asp Arg Phe Ala Glu Arg Met Asn Gln Pro Glu Leu Gln Gln Gln Leu
625             630                 635                 640

Leu Leu Arg Lys Ser Leu Leu Gly Tyr Leu Tyr Ala Trp Arg Asp Met
                645                 650                 655

Ser Ser Gly Glu Thr Val Lys Gln Trp Val Arg Glu Val Thr Thr Thr
                660                 665                 670

Asp Glu Gly Leu Val Asn Leu Leu Ile Arg Leu Gln Thr Ser Val Phe
        675                 680                 685

Ser Ser His Arg Gly Ala Tyr Arg Arg Ile Ala Arg Asp Gln Val Ser
        690                 695                 700

Pro Phe Phe Asp Asp Trp Pro Ala Val Glu Glu Lys Leu Lys Val Met
705             710                 715                 720

Leu Ser Gly Asn Glu Leu Thr Pro Gln Glu Ala Leu Lys Thr Ala
                725                 730                 735

Leu Glu Asn Asp Asp
            740

<210> SEQ ID NO 89
<211> LENGTH: 423
<212> TYPE: DNA
<213> ORGANISM: Saccharomyces cerevisiae

<400> SEQUENCE: 89
aggaacccat caggttggtg gaagattacc cgttctaaga cttttcagct tcctctattg      60
atgttacacc tggacacccc ttttctggca tccagttttt aatcttcagt ggcatgtgag     120
attctccgaa attaattaaa gcaatcacac aattctctcg gataccacct cggttgaaac     180
tgacaggtgg tttgttacgc atgctaatgc aaaggagcct atatcctttt ggctcggctg     240
ctgtaacagg gaatataaag ggcagcataa tttaggagtt tagtgaactt gcaacattta     300

```
ctattttccc ttccttacgta aatattttc tttttaattc taaatcaatc ttttcaatt    360 ttttgtttgt attcttttct tgcttaaatc tataactaca aaaacacat acataaacta    420 aaa                                                                 423
```

<210> SEQ ID NO 90
<211> LENGTH: 658
<212> TYPE: DNA
<213> ORGANISM: Saccharomyces cerevisiae

<400> SEQUENCE: 90

```
ttgctacgca ggctgcacaa ttacacgaga atgctcccgc ctaggattta aggctaaggg     60
acgtgcaatg cagacgacag atctaaatga ccgtgtcggt gaagtgttcg ccaaactttt    120
cggttaacac atgcagtgat gcacgcgcga tggtgctaag ttacatatat atatatatat    180
atatatatat atatatatag ccatagtgat gtctaagtaa cctttatggt atatttctta    240
atgtggaaag atactagcgc gcgcacccac acacaagctt cgtctttct tgaagaaaag     300 aggaagctcg ctaaatggga ttccactttc cgttccctgc cagctgatgg aaaaaggtta    360
gtggaacgat gaagaataaa aagagagatc cactgaggtg aaatttcagc tgacagcgag    420
tttcatgatc gtgatgaaca atggtaacga gttgtggctg ttgccaggga gggtggttct    480
caacttttaa tgtatggcca aatcgctact tgggtttgtt atataacaaa gaagaaataa    540
tgaactgatt ctcttcctcc ttcttgtcct ttcttaattc tgttgtaatt accttccttt    600 gtaattttt ttgtaattat tcttcttaat aatccaaaca aacacacata ttacaata      658
```

<210> SEQ ID NO 91
<211> LENGTH: 573
<212> TYPE: DNA
<213> ORGANISM: Saccharomyces cerevisiae

<400> SEQUENCE: 91

```
tgctgtaacc cgtacatgcc caaaataggg ggcgggttac acagaatata taacatcgta     60
ggtgtctggg tgaacagttt attcctggca tccactaaat ataatggagc ccgcttttta    120
agctggcatc cagaaaaaaa aagaatccca gcaccaaaat attgttttct tcaccaacca    180
tcagttcata ggtccattct cttagcgcaa ctacagagaa caggggcaca aacaggcaaa    240
aaacgggcac aacctcaatg gagtgatgca acctgcctgg agtaaatgat gacacaaggc    300
aattgaccca cgcatgtatc tatctcattt tcttacacct tctattacct tctgctctct    360
ctgatttgga aaaagctgaa aaaaaaggtt gaaaccagtt ccctgaaatt attcccctac    420
ttgactaata agtatataaa gacggtaggt attgattgta attctgtaaa tctatttctt    480
aaacttctta aattctactt ttatagttag tcttttttt agttttaaaa caccaagaac     540
ttagtttcga ataaacacac ataaacaaac aaa                                 573
```

<210> SEQ ID NO 92
<211> LENGTH: 812
<212> TYPE: DNA
<213> ORGANISM: Saccharomyces cerevisiae

<400> SEQUENCE: 92

```
gcaccgctgg cttgaacaac aataccagcc ttccaacttc tgtaaataac ggcggtacgc     60
cagtgccacc agtaccgtta cctttcggta tacctccttt ccccatgttt ccaatgccct    120
tcatgcctcc aacggctact atcacaaatc ctcatcaagc tgacgcaagc cctaagaaat    180
gaataacaat actgacagta ctaaataatt gcctacttgg cttcacatac gttgcatacg    240
```

```
tcgatatga taataatgat aatgacagca ggattatcgt aatacgtaat agttgaaaat    300
ctcaaaaatg tgtgggtcat tacgtaaata atgataggaa tgggattctt ctattttcc    360 tttttccatt ctagcagccg tcgggaaaac gtggcatcct ctctttcggg ctcaattgga    420
gtcacgctgc cgtgagcatc ctctctttcc atatctaaca actgagcacg taaccaatgg    480
aaaagcatga gcttagcgtt gctccaaaaa agtattggat ggttaatacc atttgtctgt    540
tctcttctga ctttgactcc tcaaaaaaaa aaatctaca atcaacagat cgcttcaatt    600
acgccctcac aaaaactttt ttccttcttc ttcgcccacg ttaaatttta tccctcatgt    660
tgtctaacgg atttctgcac ttgatttatt ataaaaagac aaagacataa tacttctcta    720
tcaatttcag ttattgttct tccttgcgtt attcttctgt tcttctttt ctttttgtcat    780 atataaccat aaccaagtaa tacatattca aa                                  812
```

<210> SEQ ID NO 93
<211> LENGTH: 625
<212> TYPE: DNA
<213> ORGANISM: Yarrowia lipolytica

<400> SEQUENCE: 93

```
tataaacggt attttcacaa ttgcaccca gccagaccga tagccggtcg caatccgcca    60
cccacaaccg tctacctccc acagaacccc gtcacttcca ccctttttcca ccagatcata   120 tgtcccaact tgccaaatta aaaccgtgcg aattttcaaa ataaactttg gcaaagaggc   180
tgcaaaggag gggctggtga gggcgtctgg aagtcgacca gagaccgggt tggcggcgca   240
tttgtgtccc aaaaaacagc cccaattgcc ccaattgacc ccaaattgac ccagtagcgg   300
gcccaacccc ggcgagagcc cccttctccc cacatatcaa acctccccg gttcccacac    360 ttgccgttaa gggcgtaggg tactgcagtc tggaatctac gcttgttcag actttgtact   420
agtttctttg tctggccatc cgggtaaccc atgccggacg caaatagac tactgaaaat     480 tttttttgctt tgtggttggg actttagcca agggtataaa agaccaccgt ccccgaatta   540
cctttcctct tcttttctct ctctccttgt caactcacac ccgaaatcgt taagcatttc   600
cttctgagta taagaatcat tcaaa                                          625
```

<210> SEQ ID NO 94
<211> LENGTH: 318
<212> TYPE: DNA
<213> ORGANISM: Saccharomyces cerevisiae

<400> SEQUENCE: 94

```
gcataatatt gtccgctgcc cgttttcctg ttagacggtg tcttgatcta cttgctatcg    60
ttcaacacca ccttatttc taactatttt ttttttagct catttgaatc agcttatggt    120
gatggcacat ttttgcataa acctagctgt cctcgttgaa cataggaaaa aaaaatatat   180
aaacaaggct ctttcactct ccttggaatc agatttggg ttgttccctt tatttttcata    240 tttcttgtca tattctttc tcaattatta tcttctactc ataacctcac gcaaaataac     300
acagtcaaat caatcaaa                                                   318
```

<210> SEQ ID NO 95
<211> LENGTH: 413
<212> TYPE: DNA
<213> ORGANISM: Saccharomyces cerevisiae

<400> SEQUENCE: 95
catagcttca aaatgtttct actccttttt tactcttcca gattttctcg gactccgcgc    60
atcgccgtac cacttcaaaa cacccaagca cagcatacta aatttcccct ctttcttcct    120
ctagggtgtc gttaattacc cgtactaaag gtttggaaaa gaaaaaagag accgcctcgt    180
ttctttttct tcgtcgaaaa aggcaataaa aatttttatc acgttctttt tcttgaaaa     240 ttttttttt tgattttttt ctctttcgat gacctcccat tgatatttaa gttaataaac     300
ggtcttcaat ttctcaagtt tcagtttcat tttcttgtt ctattacaac tttttttact     360
tcttgctcat tagaaagaaa gcatagcaat ctaatctaag ttttaattac aaa            413

```
<210> SEQ ID NO 96
<211> LENGTH: 330
<212> TYPE: DNA
<213> ORGANISM: Saccharomyces cerevisiae

<400> SEQUENCE: 96
```
taagattaat ataattatat aaaaatatta tcttcttttc tttatatcta gtgttatgta    60
aaataaattg atgactacgg aaagcttttt tatattgttc cttttcatt ctgagccact     120 taaatttcgt gaatgttctt gtaagggacg gtagatttac aagtgataca acaaaaagca    180
aggcgctttt tctaataaaa agaagaaaag catttaacaa ttgaacacct ctatatcaac    240
gaagaatatt actttgtctc taaatccttg taaaatgtgt acgatctcta tatgggttac    300
tcataagtgt accgaagact gcattgaaag                                      330

```
<210> SEQ ID NO 97
<211> LENGTH: 377
<212> TYPE: DNA
<213> ORGANISM: Saccharomyces cerevisiae

<400> SEQUENCE: 97
```
gtctgaagaa tgaatgattt gatgatttct ttttccctcc attttcttta ctgaatatat    60
caatgatata gacttgtata gtttattatt tcaaattaag tagctatata tagtcaagat    120
aacgtttgtt tgacacgatt acattattcg tcgacatctt ttttcagcct gtcgtggtag    180
caatttgagg agtattatta attgaatagg ttcattttgc gctcgcataa acagttttcg    240
tcagggacag tatgttggaa tgagtggtaa ttaatggtga catgacatgt tatagcaata    300
accttgatgt ttcatcgta gtttaatgta caccccgcga attcgttcaa gtaggagtgc    360
accaattgca aagggaa                                                    377

```
<210> SEQ ID NO 98
<211> LENGTH: 506
<212> TYPE: DNA
<213> ORGANISM: Saccharomyces cerevisiae

<400> SEQUENCE: 98
```
gtgaatttac tttaaatctt gcatttaaat aaatttctt tttatagctt tatgacttag     60
tttcaattta tatactattt taatgacatt ttcgattcat tgattgaaag ctttgtgttt    120
tttcttgatg cgctattgca ttgttcttgt cttttcgcc acatgtaata tctgtagtag     180
atacctgata cattgtggat gctgagtgaa attttagtta ataatggagg cgctcttaat    240
aattttgggg atattggctt ttttttttaa agtttacaaa tgaatttttt ccgccaggat    300
aacgattctg aagttactct tagcgttcct atcggtacag ccatcaaatc atgcctataa    360
atcatgccta tatttgcgtg cagtcagtat catctacatg aaaaaaactc ccgcaatttc    420
ttatagaata cgttgaaaat taaatgtacg cgccaagata agataacata tatctagatg    480
cagtaatata cacagattcc cgcgga    506

<210> SEQ ID NO 99
<211> LENGTH: 199
<212> TYPE: DNA
<213> ORGANISM: Saccharomyces cerevisiae

<400> SEQUENCE: 99
gttaattcaa attaattgat atagttttt aatgagtatt gaatctgttt agaaataatg    60
gaatattatt tttatttatt tatttatatt attggtcggc tcttttcttc tgaaggtcaa   120
tgacaaaatg atatgaagga ataatgatt tctaaaattt tacaacgtaa gatattttta   180
caaaagccta gctcatctt    199

<210> SEQ ID NO 100
<211> LENGTH: 400
<212> TYPE: DNA
<213> ORGANISM: Yarrowia lipolytica

<400> SEQUENCE: 100
gctgcttgta cctagtgcaa ccccagtttg ttaaaaatta gtagtcaaaa acttctgagt    60
tagaaatttg tgagtgtagt gagattgtag agtatcatgt gtgtccgtaa gtgaagtgtt   120
attgactctt agttagttta tctagtactc gtttagttga cactgatcta gtattttacg   180
aggcgtatga ctttagccaa gtgttgtact tagtcttctc tccaaacatg agagggctct   240
gtcactcagt cggcctatgg gtgagatggc ttggtgagat ctttcgatag tctcgtcaag   300
atggtaggat gatgggggaa tacattactg ctctcgtcaa ggaaaccaca atcagatcac   360
accatcctcc atggtatccg atgactctct tctccacagt                         400

<210> SEQ ID NO 101
<211> LENGTH: 203
<212> TYPE: DNA
<213> ORGANISM: Saccharomyces cerevisiae

<400> SEQUENCE: 101
acaagctaag ttgactgctg ctaccaacgc taagcaataa gcgatttaat ctctaattat    60
tagttaaagt tttataagca tttttatgta acgaaaaata aattggttca tattattact   120
gcactgtcac ttaccatgga aagaccagac aagaagttgc cgacacgaca gtctgttgaa   180
ttggcttaag tctgggtccg ctt    203

<210> SEQ ID NO 102
<211> LENGTH: 274
<212> TYPE: DNA
<213> ORGANISM: Saccharomyces cerevisiae

<400> SEQUENCE: 102 caggccccctt ttcctttgtc gatatcatgt aattagttat gtcacgctta cattcacgcc    60
ctcctcccac atccgctcta accgaaaagg aaggagttag acaacctgaa gtctaggtcc   120
ctatttattt tttttaatag ttatgttagt attaagaacg ttatttatat ttcaaatttt   180 tcttttttt ctgtacaaac gcgtgtacgc atgtaacatt atactgaaaa ccttgcttga   240
gaaggttttg ggacgctcga aggctttaat ttgc    274

<210> SEQ ID NO 103
<211> LENGTH: 474
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 103

Met Gln Thr Leu Ser Ile Gln His Gly Thr Leu Val Thr Met Asp Gln
1               5                   10                  15

Tyr Arg Arg Val Leu Gly Asp Ser Trp Val His Val Gln Asp Gly Arg
            20                  25                  30

Ile Val Ala Leu Gly Val His Ala Glu Ser Val Pro Pro Pro Ala Asp
        35                  40                  45

Arg Val Ile Asp Ala Arg Gly Lys Val Val Leu Pro Gly Phe Ile Asn
    50                  55                  60

Ala His Thr His Val Asn Gln Ile Leu Leu Arg Gly Gly Pro Ser His
65                  70                  75                  80

Gly Arg Gln Leu Tyr Asp Trp Leu Phe Asn Val Leu Tyr Pro Gly Gln
                85                  90                  95

Lys Ala Met Arg Pro Glu Asp Val Ala Val Ala Val Arg Leu Tyr Cys
            100                 105                 110

Ala Glu Ala Val Arg Ser Gly Ile Thr Thr Ile Asn Asp Asn Ala Asp
        115                 120                 125

Ser Ala Ile Tyr Pro Gly Asn Ile Glu Ala Ala Met Ala Val Tyr Gly
130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Ile Thr Pro Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Leu His Trp Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asp Gly Asn Cys Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

```
Glu Thr Gly Lys Arg Ala Asp Leu Ile Leu Leu Asp Leu Arg His Pro
385             390                 395                 400

Gln Thr Thr Pro His His His Leu Ala Ala Thr Ile Val Phe Gln Ala
                405             410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
        435             440                 445

Leu Glu Glu Ala Gln Ser Arg Ala Thr Ala Ile Leu Gln Arg Ala Asn
    450                 455                 460

Met Val Ala Asn Pro Ala Trp Arg Ser Leu
465                 470
```

SELECTIVE ADVANTAGE IN FERMENTATION

RELATED APPLICATIONS

This application is a § 371 national stage application based on PCT/US2015/024943, filed Apr. 8, 2015, which claims the benefit of priority to U.S. Provisional Patent Application No. 61/976,672, filed Apr. 8, 2014; and U.S. Provisional Patent Application No. 62/083,540, filed Nov. 24, 2014.

SEQUENCE LISTING

The instant application contains a Sequence Listing which has been submitted via EFS-Web and is hereby incorporated by reference in its entirety. Said ASCII copy is named NGX-027.01.txt and is 354 kilobytes in size.

BACKGROUND

Due to environmental concerns and the projected future depletion of fossil fuels, fuels and chemicals traditionally made in petrochemical processes are increasingly produced biologically via fermentation. Commodity chemicals that can be produced via anaerobic fermentation have been successfully introduced to the marketplace, in large part because they can be prepared from inexpensive sugars, such as corn starch. The production of other chemicals (e.g., lipids, triacylglycerides, fatty alcohols, fatty acids, alkanes, alkenes, isoprenoids, isoprene, squalene, farnasene, alcohols, isopropanol, n-propanol, n-butanol, isobutanol, 2-butanol, butadiene, diols, 1,3 propanediol, 1,4 propanediol, succinic acid, adipic acid, nylon precursors, citric acid, malic acid, polyols, erythritol) requires an aerobic or microaerobic fermentation environment, but in traditional corn ethanol fermentation, the viscosity of the fermentation broth reduces oxygen transfer to such an extent that it cannot support sufficient aerobic productivity for an economically viable process. Thus, aerobic and microaerobic processes typically use expensive carbon sources, such as dextrose.

Additionally, as with any fermentation process, aerobic and microaerobic fermentation require methods for controlling contamination, such as contaminating bacteria. The addition of selective growth inhibitors, such as bacterial antibiotics, provides a selective advantage for transformed cells that are resistant to the growth inhibitor; however, antibiotics are often undesirable or infeasible, and spontaneously resistant contaminations frequently occur. Additionally, bacteriophage may also contaminate a fermentation, and selective growth inhibitors are ineffective at combatting bacteriophage contamination.

SUMMARY

In some embodiments, the invention relates to a method of fermentation, comprising incubating a transformed cell in a fermentation mixture. The fermentation may be an aerobic or microaerobic fermentation. The fermentation mixture may comprise a first fraction and a second fraction, as described infra. The first fraction may comprise a fraction of a fractionated grain, such as an endosperm fraction. The first fraction may consist essentially of a fraction of a fractionated grain, such as an endosperm fraction. The second fraction may comprise one or more compounds selected from the group consisting of nitrogen-containing compounds, phosphorus-containing compounds, and sulfur-containing compounds, as described infra. The transformed cell may be selected from the group consisting of algae, bacteria, molds, fungi, plants, and yeasts. In some embodiments, the transformed cell can metabolize the one or more compounds (i.e., use the one or more nitrogen-, phosphorous-, and/or sulfur-containing compounds as a source of nitrogen, phosphorous, and/or sulfur, respectively). In some embodiments, a native cell of the same species as the transformed cell cannot metabolize the one or more compounds. The transformed cell may comprise a genetic modification that enables the cell to metabolize the one or more compounds. In some embodiments, the transformed cell comprises a genetic modification that confers resistance to a bacteriophage. In some embodiments, the fermentation mixture does not comprise an antibiotic.

In some embodiments, a selective advantage results from transformation of a cell with a nucleic acid that allows a transformed cell to metabolize one or more nitrogen-, phosphorous-, and/or sulfur-containing compounds that a native cell of the same species as the transformed cell cannot metabolize, and from fermentation of the transformed cell using one or more feedstocks, such as fractioned grain, which are depleted in or free of conventional nitrogen-, phosphorous-, and/or sulfur-containing compounds that a native cell of the same species as the transformed cell can metabolize. Such selective advantages of the transformed cells over the native cells allow reductions in contamination by the native cells and other organisms.

DETAILED DESCRIPTION

Definitions

Figure 1:
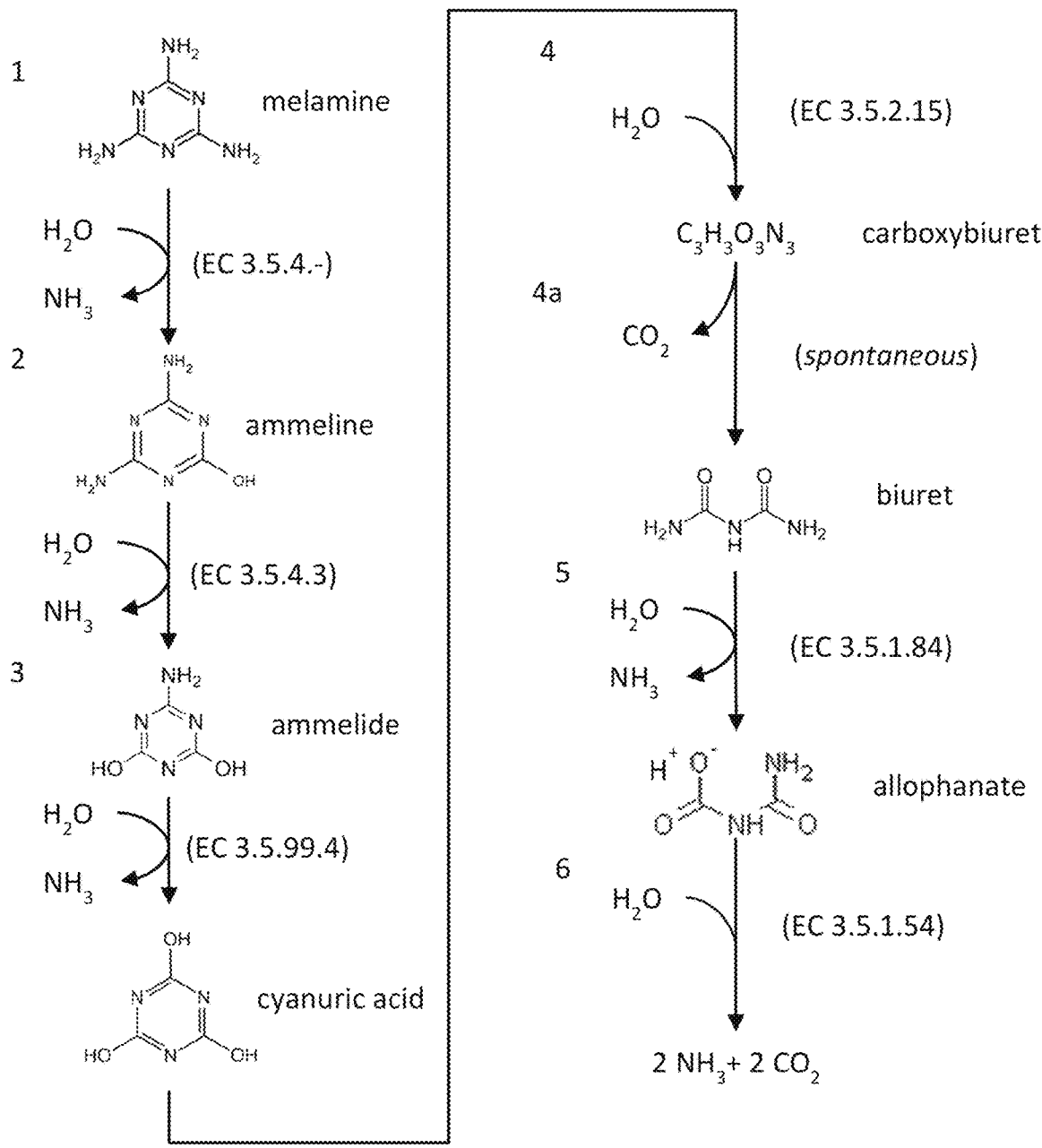
FIG. 1 depicts a schematic representation of the melamine degradation pathway. 1—Melamine deaminase (tzrA) (EC 3.5.4.-); 2—Ammeline deaminase (guanine deaminase) (EC 3.5.4.3); 3—N-isopropylammelide isopropylamino (Ammelide) hydrolyase (EC 3.5.99.4); 4—Cyanuric acid hydrolyase (EC 3.5.2.15); 4a—Carboxybiuret decarboxylase, spontaneous reaction; 5—Biuret amidohydrolase (EC 3.5.1.84); 6—Allophanate hydrolyase (EC 3.5.1.54). Nitrogen can be assimilated (as $NH_3$) by the action of the complete pathway acting on melamine, liberating 6 mol $NH_3$ per mol melamine, or via a subset of enzymes acting on pathway intermediates (e.g., steps 4, 4a, 5, and 6 acting on cyanuric acid releasing 3 mol $NH_3$ per mol cyanuric acid).
Figure 2:
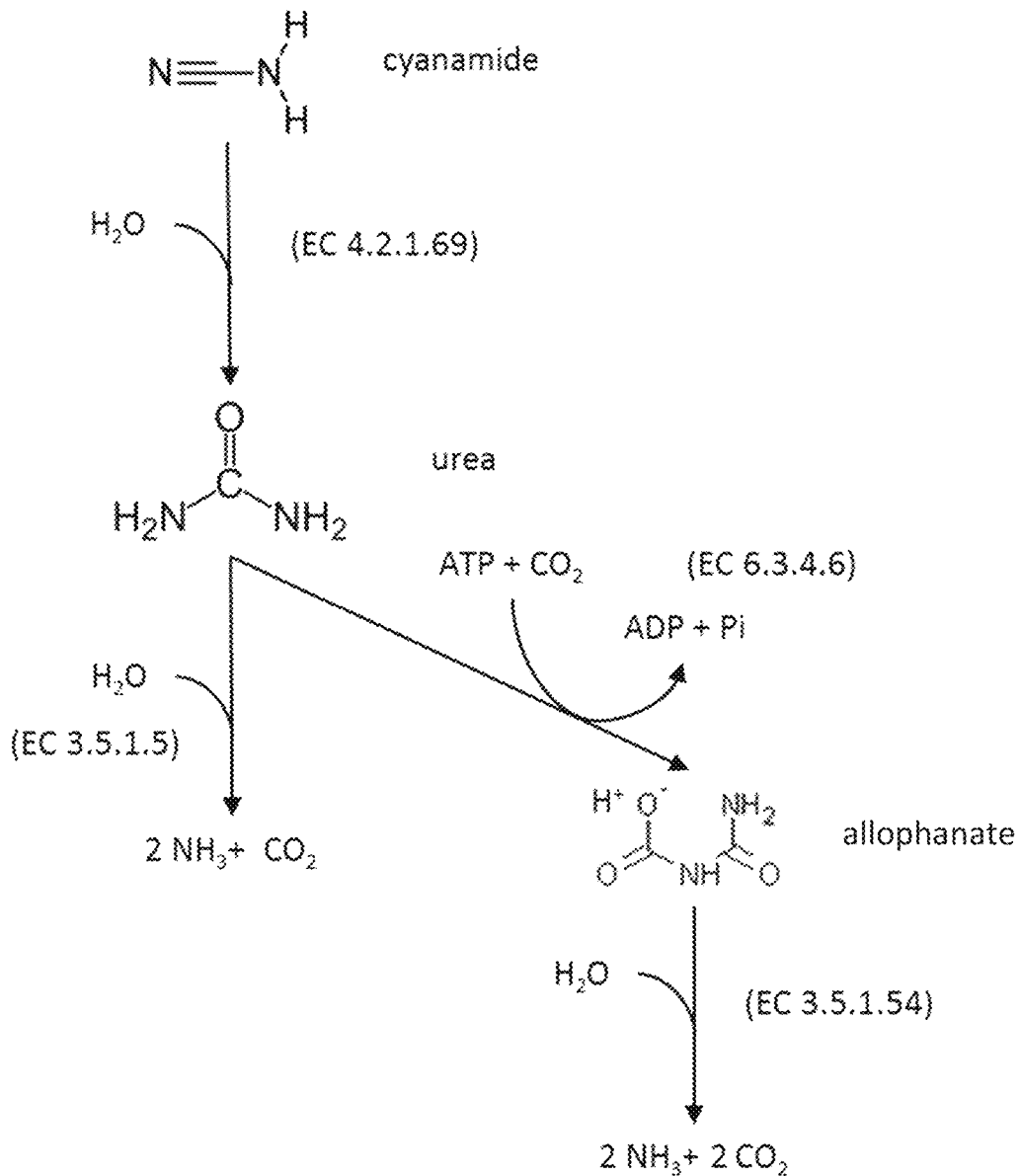
FIG. 2 depicts a schematic representation of the cyanamide assimilation pathway. After conversion of cyanamide to urea by cyanamide hydratase (EC 4.2.1.69), urea can be degraded either via urease (EC 3.5.1.5) or by urea carboxylase (EC 6.3.4.6) and allophanate hydrolyase (EC 3.5.1.54).

The articles "a" and "an" are used herein to refer to one or to more than one (i.e., to at least one) of the grammatical object of the article. By way of example, "an element" means one element or more than one element.

The term "bacteriophage" or "phage" refers to a virus that selectively infects one or more bacterial species. In some embodiments, the phage is lytic, while in other embodiments, the phage is lysogenic. A lytic bacteriophage is a phage that follows the lytic pathway through completion of a lytic cycle, rather than entering the lysogenic pathway. A lytic bacteriophage undergoes viral replication leading to lysis of the cell membrane, destruction of the cell, and release of progeny bacteriophage particles capable of infecting other cells. A lysogenic bacteriophage is a phage capable of entering the lysogenic pathway, in which the bacteriophage becomes a dormant, passive part of the cell's genome prior to the completion of a lytic cycle. Bacteriophages useful in the present invention include, but are not limited to bacteriophages that belong to any of the following virus families: Corticoviridae, Cystoviridae, Inoviridae, Leviviridae, Microviridae, Myoviridae, Podoviridae, Siphoviridae, and Tectiviridae.

The term "encode" refers to nucleic acids that comprise a coding region, portion of a coding region, or compliments thereof. Both DNA and RNA may encode a gene. Both DNA and RNA may encode a protein.

The terms "fractionated grain" and "fractionated grain mash" refer to grains that have been separated into portions that are substantially devoid of germ, bran, endosperm, or two of the foregoing (i.e., germ and bran, germ and endosperm, or bran and endosperm). In some embodiments of the invention, a fractionated grain or fractionated grain mash consists essentially of endosperm. A fractionated grain mash is a fractionated grain that has been processed to break down the starches of the grain into sugars. Unless otherwise noted, the terms "fractionated grain" and "fractionated grain mash" are used interchangeably.

The term "gene," as used herein, may encompass genomic sequences that contain introns, particularly polynucleotide sequences encoding polypeptide sequences involved in a specific activity. The term further encompasses synthetic nucleic acids that did not derive from genomic sequence. In certain embodiments, the genes lack introns, as they are synthesized based on the known DNA sequence of cDNA and protein sequence. In other embodiments, the genes are synthesized, non-native cDNA wherein the codons have been optimized for expression in *E. coli* or other organism, e.g., based on codon usage. The term can further include nucleic acid molecules comprising upstream, downstream, and/or intron nucleotide sequences.

The term "genetic modification" refers to the result of a transformation. Every transformation causes a genetic modification by definition.

The term "inducible promoter" refers to a promoter that mediates the transcription of an operably-linked gene in response to a particular stimulus.

The term "integrated" refers to a nucleic acid that is maintained in a cell as an insertion into the cell's genome, such as insertion into a chromosome, including insertions into a plastid genome.

The terms "operable linkage" or "in operable linkage" mean a functional linkage between two nucleotide sequences, such a control sequence (typically a promoter) and the linked sequence (typically a sequence that encodes a protein, also called a coding sequence). A promoter is in operable linkage with a gene if it can mediate transcription of the gene.

The term "native" refers to the composition of a cell or parent cell prior to a transformation event.

The term "nucleic acid" refers to a polymeric form of nucleotides of any length, either deoxyribonucleotides or ribonucleotides, or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleotide sequences provided herein, U nucleotides are interchangeable with T nucleotides.

The term "parent cell" refers to every cell from which a cell descended. A cell's genome is comprised of the parent cell's genome and any subsequent genetic modifications to the parent cell's genome.

As used herein, the term "plasmid" refers to a circular DNA molecule that is physically separate from an organism's genomic DNA. Plasmids may be linearized before being introduced into a host cell (referred to herein as a linearized plasmid). Linearized plasmids may not be self-replicating, but may integrate into and be replicated with the genomic DNA of an organism.

A "promoter" is a nucleic acid control sequence that directs transcription of a nucleic acid. As used herein, a promoter includes necessary nucleotide sequences near the start site of transcription. A promoter also optionally includes distal enhancer or repressor elements, which can be located as much as several thousand base pairs from the start site of transcription.

"Recombinant" refers to a cell, nucleic acid, protein, or vector, which has been modified due to the introduction of an exogenous nucleic acid or the alteration of a native nucleic acid. Thus, e.g., recombinant cells can express genes that are not found within the native (non-recombinant) form of the cell or express native genes differently than those genes are expressed by a non-recombinant cell. Recombinant cells can, without limitation, include recombinant nucleic acids that encode for a gene product or for suppression elements such as mutations, knockouts, antisense, interfering RNA (RNAi), or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, or otherwise is in a form not normally found in nature. Recombinant nucleic acids may be produced, for example, to place two or more nucleic acids in operable linkage. Thus, an isolated nucleic acid or an expression vector formed in vitro by ligating DNA molecules that are not normally joined in nature, are both considered recombinant for the purposes of this invention. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

The terms "resistant" and "resistance" as used herein refer to resistance to a bacteriophage. In some embodiments, a transformed cell is resistant to a bacteriophage because the cell has a reduced susceptibility to bacteriophage multiplication or infection relative to a native cell of the same species as the transformed cell. In some embodiments, a transformed cell is resistant to a bacteriophage because the cell has low susceptibility to bacteriophage multiplication relative to a native cell of the same species as the transformed cell. For example, the transformed cell may have a susceptibility to bacteriophage multiplication that is at least 2, 3, 4, 5, 6, 7, 8, 9, 10, 20, 30, 40, 50, 60, 70, 80, 90, 100, 200, 300, 400, 500, 600, 700, 800, 900, 1000, 10,000, or 100,000 times lower than a native cell of the same species. In some embodiments, resistance refers to a genetic modification that leads to the death of an infective cell before the bacteriophage has exhausted the cell's metabolic resources (e.g., the genetic modification confers resistance through an abortive infection system). For example, the transformed cell may produce less progeny of the bacteriophage relative to a native cell of the same species as the transformed cell, such as at least 2, 3, 4, 5, 6, 7, 8, 9, 10, 20, 30, 40, 50, 60, 70, 80, 90, 100, 200, 300, 400, 500, 600, 700, 800, 900, 1000, 10,000, or 100,000 times less progeny.

"Transformation" refers to the transfer of a nucleic acid into a host organism or the genome of a host organism, resulting in genetically stable inheritance. Host organisms containing the transformed nucleic acid fragments are referred to as "recombinant", "transgenic", or "transformed" organisms. Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region (e.g., a regulatory region controlling inducible or constitutive, environmentally- or developmentally-regulated, or location-specific expression), a transcription initiation start site, a ribosome binding site, a transcription termination site, and/or a polyadenylation signal.

The term "transformed cell" refers to a cell that has undergone a transformation. Thus, a transformed cell comprises the parent's genome and an inheritable genetic modification.

The term "vector" refers to the means by which a nucleic acid can be propagated and/or transferred between organisms, cells, or cellular components. Vectors include plasmids, linear DNA fragments, viruses, bacteriophage, proviruses, phagemids, transposons, and artificial chromosomes, and the like, that may or may not be able to replicate autonomously or integrate into a chromosome of a host cell.

MICROBE ENGINEERING

A. Overview

Genes and gene products may be introduced into microbial host cells. Suitable host cells for expression of genes and nucleic acid molecules according to various embodiments of the instant invention comprise microbial hosts that can be found broadly within the algae, bacteria, mold, fungi, plant, and yeast families.

Examples of suitable yeast include *Arxula, Aspegillus, Aurantiochytrium, Candida, Claviceps, Cryptococcus, Cun-*

*ninghamella, Geotrichum, Hansenula, Kluyveromyces, Kodamaea, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Wickerhamomyces,* and *Yarrowia*, For example, a yeast cell may be selected from the group consisting of *Arxula adeninivorans, Aspergillus niger, Aspergillus orzyae, Aspergillus terreus, Aurantiochytrium limacinum, Candida utilis, Claviceps purpurea, Cryptococcus albidus, Cryptococcus curvatus, Cryptococcus ramirezgomezianus, Cryptococcus terreus, Cryptococcus wieringae, Cunninghamella echinulata, Cunninghamella japonica, Hansenula polymorpha, Kluyveromyces lactis, Kluyveromyces marxianus, Leucosporidiella creatinivora, Lipomyces lipofer, Lipomyces starkeyi, Lipomyces tetrasporus, Mortierella isabellina, Ogataea polymorpha, Pichia guilliermondii, Pichia pastoris, Pichia stipites, Prototheca zopfii, Rhizopus arrhizus, Rhodosporidium babjevae, Rhodosporidium toruloides, Rhodosporidium paludigenum, Rhodotorula glutinis, Rhodotorula mucilaginosa, Saccharomyces cerevisiae, Schizosaccharomyces pombe, Tremella enchepala, Trichosporon cutaneum, Trichosporon fermentans,* and *Yarrowia lipolytica.*

Examples of suitable algae include *Chlamydomonas reinhardtii, Aurantiochytrium* spp, *Nannochloropsis* spp., *Tetraselmis* spp., *Pavlova* spp., and *Isochrysis* spp. The cell may be selected from thraustochytrids (*Aurantiochytrium*) and achlorophylic unicellular algae (*Prototheca*).

Examples of suitable bacteria include *Acetobacter, Acinetobacter, Alcaligenes, Arthrobacter, Bacillus, Brevibacterium, Acidovorax, Bacillus, Clostridia, Corynebacterium, Escherichia, Lactococcus, Micrococcus, Paracoccus, Pseudomonas, Salmonella, Streptococcus, Streptomyces, Synechococcus, Thermoanaerobacter,* and *Xanthomonas*. For example, a bacterium may be selected from the group consisting of *Acetobacter, Acinetobacter calcoaceticus, Alcaligenes eutropha, Bacillus licheniforms, Bacillus methanolicus, Bacillus stearothermophilus, Bacillus subtilis, Clostridium acetobutylicum, Clostridium thermocellum, Corynebacterium glutamicum, Escherichia coli, Lactococcus lactis, Micrococcus lysodeikticus, Paracoccus denitrificans, Pseudomonas putida, Streptococcus lactis, Streptomyces, Synechococcus elongates, Thermoanaerobacter/ Thermoanaerobacterium* spp., and *Xanthomonas campestris.*

Examples of suitable fungi include *Aspergillus nidulans, Aspergillus niger, Aspergillus orzyae, Aspergillus terreus, Penicillium chrysogenum, Rhizopus* spp., and *Trichoderma reesei.*

The cell may be selected from the group consisting of *Arxula, Aspergillus, Aurantiochytrium, Candida, Claviceps, Cryptococcus, Cunninghamella, Hansenula, Kluyveromyces, Leucosporidiella, Lipomyces, Mortierella, Ogataea, Pichia, Prototheca, Rhizopus, Rhodosporidium, Rhodotorula, Saccharomyces, Schizosaccharomyces, Tremella, Trichosporon, Yarrowia, Chlamydomonas, Aurantiochytrium, Nannochloropsis, Tetraselmis, Pavlova, Isochrysis, Acetobacter, Acinetobacter, Alcaligenes, Bacillus, Clostridium, Corynebacterium, Escherichia, Lactococcus, Micrococcus, Paracoccus, Pseudomonas, Streptococcus, Streptomyces, Synechococcus, Thermoanaerobacter, Aspergillus, Penicillium, Rhizopus,* and *Trichoderma.*

In some aspects, the invention relates to a transformed cell comprising a gene comprising any one of the nucleotide sequences disclosed herein. In certain embodiments, the invention relates to a transformed cell comprising a nucleotide sequence having at least 75%, 80%, 85%, 90%, 95%, 96%, 97%, 98%, 99%, 99.5%, or 99.9% sequence homology with any one of the nucleotide sequences set forth in SEQ ID NO. 1-30, 32, 34, 36, 38, 40, 42, 44, 46, 48, 50, 52, and 54-71, 73, 75, 77, 79, 81, 83, 85, and 87-102. In some embodiments, the invention relates to a transformed cell comprising a nucleotide sequence encoding an amino acid sequence having at least 75%, 80%, 85%, 90%, 95%, 96%, 97%, 98%, 99%, 99.5%, or 99.9% sequence homology with any one of the amino acid sequences set forth in SEQ ID NO. 31, 33, 35, 37, 39, 41, 43, 45, 47, 49, 51, 72, 74, 76, 78, 80, 82, 84, and 86.

Microbial expression systems and expression vectors containing regulatory sequences that direct the expression of foreign proteins are known to those skilled in the art. Any of these could be used to construct chimeric genes to produce any one of the gene products of the instant sequences. These chimeric genes could then be introduced into appropriate microorganisms via transformation techniques to express an enzyme or phage resistance gene.

For example, a gene encoding an enzyme can be cloned in a suitable plasmid, and the aforementioned starting parent strain as a host can be transformed with the resulting plasmid. This approach can add multiple copies of each of the genes encoding the enzymes and, as a result, the activities of the enzymes can be increased. The plasmid is not particularly limited so long as it renders a desired gene inheritable to the microorganism's progeny.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene harboring transcriptional initiation controls and a region 3' of the gene which controls transcriptional termination. It is preferred when both control regions are derived from genes homologous to the transformed host cell, although it is to be understood that such control regions need not be derived from the genes native to the specific species chosen as a production host.

Promoters, cDNAs, and 3'UTRs, as well as other elements of the vectors, can be generated through cloning techniques using fragments isolated from native sources (Green & Sambrook, *Molecular Cloning: A Laboratory Manual,* (4th ed., 2012); U.S. Pat. No. 4,683,202, herein incorporated by reference). Alternatively, elements can be generated synthetically using known methods (Gene 164:49-53 (1995)).

B. Vectors and Vector Components

Vectors for the transformation of microorganisms in accordance with the present invention can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location in or outside the cell.

Thus, an exemplary vector design for expression of a gene in a microbe contains a coding sequence for a desired gene product (for example, a selectable marker, or an enzyme) in operable linkage with a promoter active in the host cell. Alternatively, if the vector does not contain a promoter in operable linkage with the coding sequence of interest, the coding sequence can be transformed into the cells such that it becomes operably linked to an endogenous promoter at the point of integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the invention. Inducible promoters useful in the invention include those that mediate the transcription of an operably linked gene in response to a stimulus, such as an exogenously provided small molecule, temperature (heat or cold), lack of nitrogen in culture media, etc. Suitable promoters can activate the transcription of an essentially silent gene or upregulate, preferably substantially, the transcription of an operably linked gene that is transcribed at a low level.

The inclusion of termination region control sequence is optional, and if employed, then the choice is primarily one of convenience, as termination regions are relatively interchangeable. The termination region may be native to the DNA sequence of interest, for example, or obtainable from another source (See, e.g., Chen & Orozco, Nucleic Acids Research 16:8411 (1988)).

2. Genes and Codon Optimization

Typically, a gene includes a promoter, coding sequence, and termination control sequences. When assembled by recombinant DNA technology, a gene may be termed an expression cassette and may be flanked by restriction sites for the convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., as an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the invention.

For the optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools may be insufficient to allow for efficient translation of the transgenic mRNA resulting in ribosomal stalling and termination and possible instability of the transgenic mRNA.

C. Expression of Two or More Exogenous Genes

Further, a transformed cell may comprise and express more than one exogenous gene. One or more genes can be expressed using an inducible promoter, which allows the relative timing of expression of these genes to be controlled. Expression of the two or more exogenous genes may be under control of the same inducible promoter or different inducible promoters. In the latter situation, expression of a first exogenous gene can be induced for a first period of time (during which expression of a second exogenous gene may or may not be induced), and expression of a second or further exogenous gene(s) can be induced for a second period of time (during which expression of a first exogenous gene may or may not be induced).

D. Transformation

Cells may be transformed by any suitable technique including, e.g., biolistics, electroporation, glass bead transformation, and silicon carbide whisker transformation. Any convenient technique for introducing a transgene into a microorganism can be employed in the present invention. Transformation can be achieved by, for example, the method of D. M. Morrison (Methods in Enzymology 68:326 (1979)), the method by increasing permeability of recipient cells for DNA with calcium chloride (Mandel & Higa, J. Molecular Biology, 53:159 (1970)), or the like. Examples for transforming bacteria such as *E. coli* are well known (see, e.g., Green & Sambrook, *Molecular Cloning: A Laboratory Manual*, (4th ed., 2012)).

Vectors for the transformation of microorganisms in accordance with the present invention can be prepared by known techniques familiar to those skilled in the art. In one embodiment, an exemplary vector design for the expression of a gene in a microorganism contains a gene encoding an enzyme in operable linkage with a promoter that is active in the microorganism. Alternatively, if the vector does not contain a promoter in operable linkage with the gene of interest, the gene can be transformed into a cell such that it becomes operably linked to a native promoter at the point of integration. The vector can also contain a second gene that encodes a protein. Optionally, one or both gene(s) is/are followed by a 3' untranslated sequence containing a polyadenylation signal. Expression cassettes encoding two or more genes can be physically linked in the vector or on separate vectors. Co-transformation of microbes can also be performed, in which distinct vector molecules are simultaneously used to transform cells (Protist 155:381-93 (2004)). The transformed cells can be optionally selected based upon the ability to grow in the presence of an antibiotic or other selectable marker under conditions in which cells lacking the resistance cassette would not grow.

E. Recombineering

Figure 28:
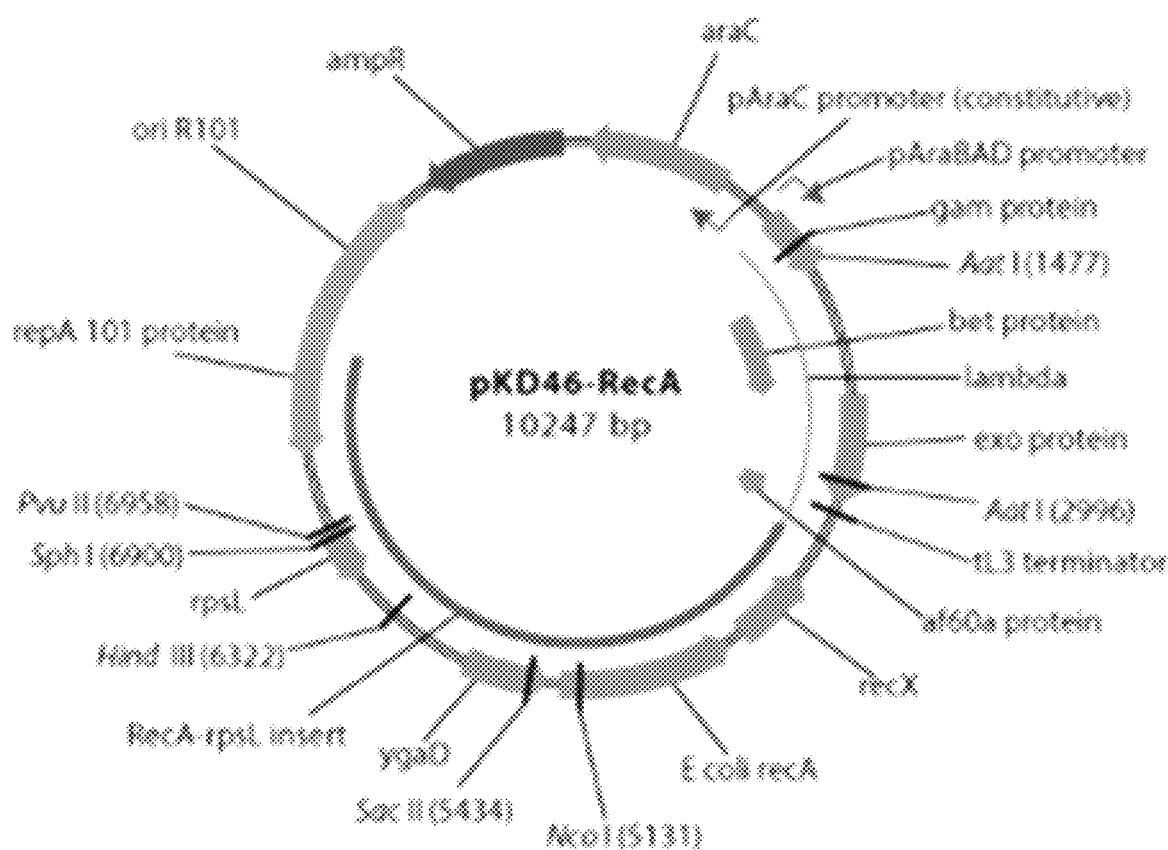
FIG. 28 shows the pKD46-recA plasmid, which encodes constitutively expressed *Escherichia coli* recA+ along with wild type rpsL.

Recombineering (recombinogenic engineering) is a homologous recombination-based technology used to modify DNA. Target DNA molecules (plasmids, BAC vectors, or the host chromosome) are precisely altered by homologous recombination in host cells which express recombineering enzymes. Recombineering in *E. coli* often utilizes the phage λ Red recombination functions (Murphy, *J Bacteriol* 1998, 180:2063-2071; Datsenko and Wanner, *Proc Natl Acad Sci USA* 2000, 97:6640-6645). The λ genes involved in Red recombination are exo, bet, and gam. The exo (Reda) gene product has 5' to 3' exonuclease activity, and the bet (Redb) gene product is a single-strand DNA binding protein that promotes annealing. The gam gene product inhibits the RecBCD nuclease preventing linear DNA (i.e., PCR product) degradation. Nature Technologies Inc. has developed two plasmids for use in recombineering: pKD46-RecA (FIG. 28) and pKD46-RecA$_{pa}$.

Figure 29:
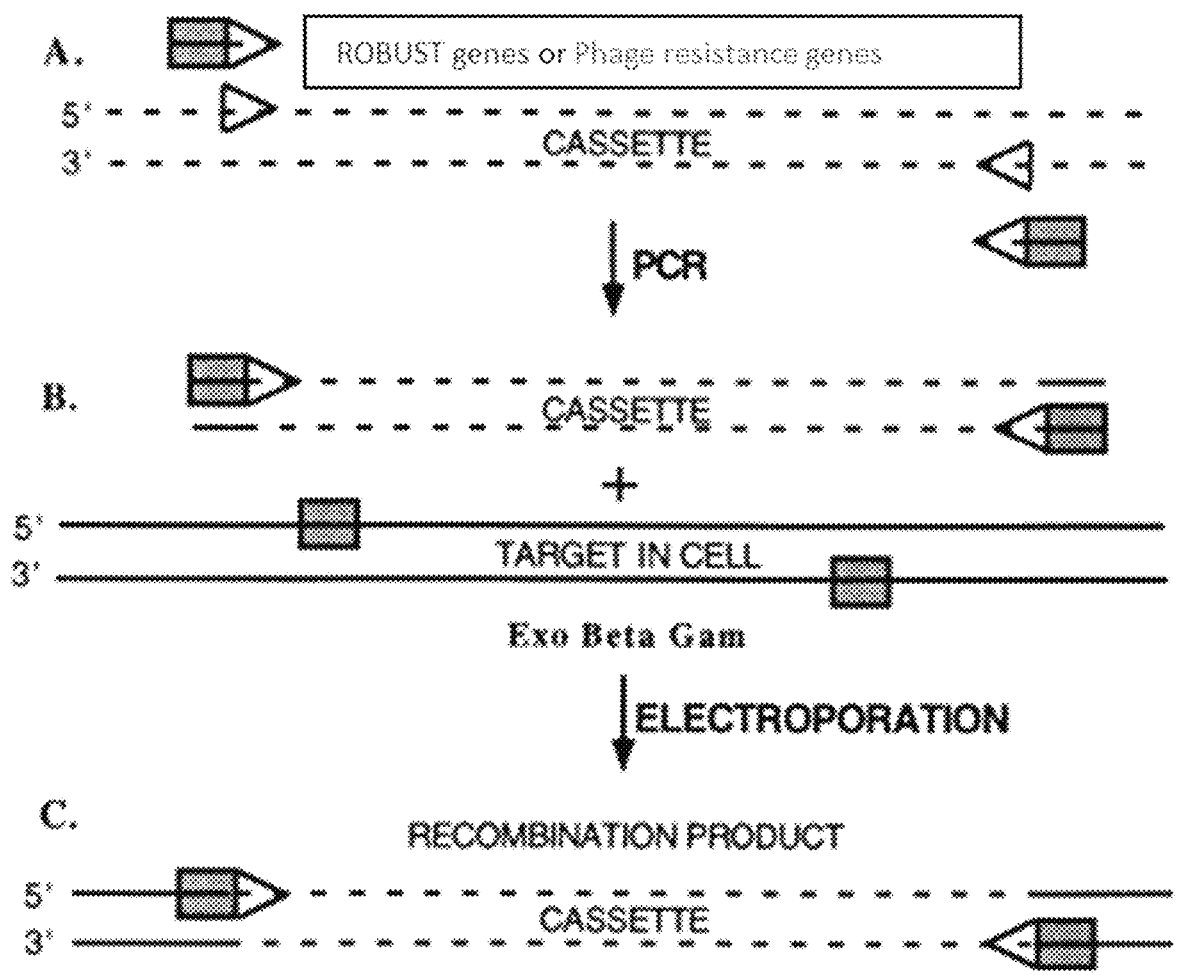
FIG. 29 shows a strategy for generating recombinant DNA molecules and gene replacement. (A) Recombinant oligonucleotides are chemically synthesized with the 5' 30-50 nt (shaded rectangles) identical to sequences at the target and the 3' 20 nt (arrowheads) homologous to the ends of the cassette to be introduced. A cassette is generated by PCR which is flanked by the 30- to 50-bp homologies present at the target. (B) Cells carrying the target DNA either on the chromosome or on a plasmid are induced for Exo, Beta, and Gam function. These cells are made competent for electroporation, and mixed with the amplified cassette. (C) After electroporation, recombination occurs between the homologous sequences on the linear cassette and the target, replacing the target segment with the cassette

The λ Red recombination system, consisting of Bet (a ssDNA annealing protein) and Exo (a 5'-3' dsDNA exonuclease) promotes gene replacement of electroporated linear DNA substrates into the *Escherichia coli* K-12 chromosome at a very high efficiency. To perform recombineering, a bacterial strain expressing a bacteriophage recombination system is required. The first step in creating a transformed *E. coli* comprising a new genetic modification is to prepare electrocompetent cells that have expressed the recombineering functions (in this case an *E. coli* strain transformed with the pKD46-RecA plasmid). pKD46-RecA contains the phage λ Red genes required for recombination. The next step is transformation with a double-stranded linear DNA, such as a gene that expresses an enzyme or a phage resistance gene. After transformation, recombination occurs between the homologous sequences on the linear DNA and a target sequence, replacing the target segment with the cassette (FIG. 29).

EXEMPLARY TRANSFORMED CELLS

1. Transformed Cells that Metabolize Nitrogen-Containing Compounds

In certain embodiments, the invention relates to a transformed cell, wherein the transformed cell comprises a genetic modification that encodes an enzyme selected from the group consisting of allophanate hydrolase, biuret amidohydrolase, cyanuric acid amidohydrolase, guanine deaminase, ammeline hydrolase, ammelide hydrolyase, melamine deaminase, isopropylammelide isopropylaminohydrolase, cyanamide hydratase, urease, and urea carboxylase. Exemplary transformed cells that can metabolize nitrogen-containing compounds according to certain embodiments of the invention are described in PCT Patent Application Publication No. WO 2014/107660, hereby incorporated by reference.

In certain embodiments, the genetic modification is transformation with a nucleic acid comprising a gene selected from the group consisting of atzF, DUR1,2 YALI0E 07271g, atzE, atzD, trzC, trzD, trzE, atzD, guaD, blr3880, GUD1/Y DL238C, YAL10E2 5740p, trzA, triA, atzC, and cah. In certain embodiments, the genetic modification is transformation with a nucleic acid comprising a gene selected from the group consisting of atzF, DUR1,2 YALI0E 07271g, atzE, atzD, trzD, atzD, guaD, blr3880, GUD1/Y DL238C, YAL10E2 5740p, trzA, triA, atzC, and cah. Any organism may be used as the source of the gene, as long as the gene has the desired enzymatic activity. The gene can be obtained from the chromosomal DNA of an organism by isolating a DNA fragment that complements the auxotrophy of a variant strain lacking the enzymatic activity. Alternatively, if the nucleotide sequence of a gene has already been elucidated, then the gene can be obtained by PCR using primers synthesized based on the known nucleotide sequences, using chromosomal DNA as a template (Biochemistry, 22:5243-49 (1983); J. Biochemistry 95:909-16 (1984); Gene 27:193-99 (1984); Microbiology 140:1817-28 (1994); Molecular Genetics & Genomics 218:330-39 (1989); Molecular Microbiology 6:317-26 (1992)).

In certain embodiments, the invention relates to a transformed cell, wherein the transformed cell comprises a genetic modification that encodes an enzyme selected from the group consisting of trzE from *Rhodococcus* sp. strain Mel, trzE from *Rhizobium leguminosarum*, trzC MEL, trzC 12227, cah from *Fusarium oxysporum* Fo5176, cah from *F. pseudograminaearum* CS3096, cah from *Gibberella zeae* PH-1, cah from *Aspergillus kawachii* IFO 4308, cah from *A. niger* CBS 513.88, cah from *A. niger* ATCC 1015, cah from *A. oryzae* 3.042, cah from *S. cerevisiae* FostersB, atzF from *Pseudomonas* sp. strain ADP, DUR1,2 from *S. cerevisiae*, YALI0E 07271g from *Y. lipolytica* CLIB122, atzE from *Pseudomonas* sp. strain ADP, atzD from *Pseudomonas* sp. strain ADP, trzD from *Pseudomonas* sp. strain NRRLB-12227, atzD from *Rhodococcus* sp. Mel, trzD from *Rhodococcus* sp. Mel, guaD from *E. coli* K12 strain MG1566, blr3880 from *Bradyrhizobium japonicum* USDA 110, GUD1/Y DL238C from *S. cerevisiae*, YAL10E2 5740p from *Y. lipolytica* CLIB122, trzA from *Williamsia* sp. NRRL B-15444R, triA from *Pseudomonas* sp. strain NRRL B-12227, atzC from *Pseudomonas* sp. strain ADP, and cah from *Myrothecium verrucaria*.

In certain embodiments, the invention relates to a transformed cell, wherein the transformed cell comprises a genetic modification that encodes one or more enzymes that can catalyze steps in the melamine degradation pathway. In certain embodiments, the invention relates to transformed cells that express enzymes that can catalyze steps in the melamine degradation pathway.

TABLE 1

DNA and protein sequences for enzymes involved in the melamine degradation pathway.

| Enzyme | Gene | Source | EC | GenBank Nucleotide | GenBank Protein or Nucleotide Region |
|---|---|---|---|---|---|
| Allophanate hydrolase | atzF | *Pseudomonas* sp. strain ADP | 3.5.1.54 | NC_004956 | REGION: 104283 . . . 106100 |
| Allophanate hydrolase | DUR1,2 | *S. cerevisiae* | 6.3.4.6/ 3.5.1.54 | YSCUAMD | |

TABLE 1-continued

DNA and protein sequences for enzymes involved in the melamine degradation pathway.

| Enzyme | Gene | Source | EC | GenBank Nucleotide | GenBank Protein or Nucleotide Region |
|---|---|---|---|---|---|
| Allophanate hydrolase | YALI0E07271g | *Y. lipolytica* CLIB122 | 6.3.4.6/ 3.5.1.54 | XM_503658 | |
| Biuret amidohydrolase | atzE | *Pseudomonas* sp. strain ADP | 3.5.1.84 | NC_004956 | REGION: 102427 . . . 103800 |
| Cyanuric acid amidohydrolase | atzD | *Pseudomonas* sp. strain ADP | 3.5.2.15 | NC_004956 | REGION: 101053 . . . 102144 |
| Cyanuric acid amidohydrolase | trzD | *Pseudomonas* sp. strain NRRLB-12227 (formerly *Acidovorax citrulli*) | 3.5.2.15 | AF086815 | |
| Cyanuric acid amidohydrolase | atzD trzD | *Rhodococcus* sp. Mel | 3.5.2.15 | JN241637 | Protein: AEX65082 |
| Guanine deaminase | guaD | *E. coli* K12 strain MG1566 | 3.5.4.3 | NC_000913 | REGION: 3023788 . . . 3025107 |
| Guanine deaminase | blr3880 | *Bradyrhizobium japonicum* USDA 110 | 3.5.4.3 | NC_004463 | REGION: 4303362 . . . 4304759 |
| Guanine deaminase | GUD1/YDL238C | *S. cerevisiae* | 3.5.4.3 | Z74286 | |
| Guanine deaminase | YALI0E25740p | *Y. lipolytica* CLIB122 | 3.5.4.3 | NC_006071 | REGION: complement (3051691 . . . 3053046) |
| Melamine deaminase | trzA | *Williamsia* sp. NRRL B-15444R (formerly *R. corallinus*) | 3.5.4.— | JN241635 | |
| Melamine deaminase | triA | *Pseudomonas* sp. strain NRRL B-12227 (formerly *Acidovorax citrulli*) | 3.5.4.— | AF312304 | |
| isopropylammelide isopropylamino-hydrolase | atzC | *Pseudomonas* sp. strain ADP | 3.5.99.4 | NC_004956 | REGION: complement (70219 . . . 71430) |

In certain embodiments, the invention relates to a transformed cell, wherein the transformed cell comprises a genetic modification that encodes one or more enzymes that can catalyze the conversion of cyanamide to urea, urea to ammonia, urea to allophanate, or allophanate to ammonia. In certain embodiments, the invention relates to transformed cells that express enzymes that catalyze the conversion of cyanamide to urea, urea to ammonia, urea to allophanate, or allophanate to ammonia.

2. Transformed Cells that Metabolize Phosphorus- and Sulfur-Containing Compounds In certain embodiments, the invention relates to a transformed cell, wherein the transformed cell comprises a genetic modification that encodes one or more enzymes selected from the group consisting of phosphite dehydrogenase, hypophosphite/2-oxoglutarate dioxygenase, glycerol-3-phosphate dehydrogenase (sn-glycerol 3-phosphate: NAD (+) oxidoreductase, EC 1.1.1.8), glyceraldehyde-3-phosphate dehydrogenase, an organophosphate degradation enzyme, a phosphodiesterase, a phospholipase, desulfurization enzyme, a dibenzothiophene-5,5-dioxide monooxygenase, a 2-hydroxybiphenyl-2-sulfinate sulfinolyase, a dibenzothiophene monooxygenase, and a NADH-FMN oxidoreductase. Exemplary transformed cells that can metabolize phosphorous- and sulfur-containing compounds according to certain embodiments of the invention are described in PCT Patent Application Publication No. WO 2015/031441, hereby incorporated by reference.

In certain embodiments, the invention relates to a transformed cell, wherein the transformed cell comprises a genetic modification that encodes one or more genes selected from the group consisting of dszABC, dszA, dsz-ABCD, dszB, dszC, dszD, gpdQ, hocA, htxA, htx-ABCDEFGHIJKLMN, htxB, htxC, htxD, htxE, htxF, htxG, htxH, htxI, htxJ, htxK, htxL, htxM, htxN, opdA, ophA, pde, pdeA, phoA, ptxABCDE, ptxD, ugpA, ugpAECB, ugpB, ugpC, ugpE, updA, updABDE, updB, updD, and updE.

In certain embodiments, the invention relates to a transformed cell, wherein the transformed cell comprises a genetic modification that encodes one or more genes selected from the group consisting of *Delftia acidoorans* phosphodiesterase pdeA, *Enterobacter aerogenes* upd-ABDE gpdQ, *Flavobacterium* opdA without periplasmic leader sequence, *Pseudomonas aeruginosa* PAO1 phoA, *Pseudomonas monteilii* C11 hocA, *Pseudomonas stutzeri* WM88 htxABCDEFHGIJKLMN, *Pseudomonas stutzeri* WM88 ptxABCDE, *Rhodococcus* dszD, and *Rhodococcus* dszABC.

3. Identifying Additional Enzymes that Metabolize Nitrogen-, Phosphorus-, and Sulfur-Containing Compounds Any organism may be used as a source of a gene, as long as the gene has the desired enzymatic activity. The gene can be obtained from the chromosomal DNA of an organism by isolating a DNA fragment that complements the auxotrophy of a variant strain lacking the enzymatic activity. Alternatively, if the nucleotide sequence of a gene has already been elucidated, then the gene can be obtained by PCR using primers synthesized based on the known nucleotide sequences, using chromosomal DNA as a template.

Nucleotide sequences may comprise conservative substitutions, deletions, or insertions while still maintaining functional activity. For example, codons may be optimized for a particular host cell, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions. Conservative substitution tables are well known in the art (Creighton, *Proteins* (2d ed., 1992)).

Amino acid substitutions, deletions, and/or insertions may readily be made using recombinant DNA manipulation. Methods for the manipulation of DNA sequences to produce substitution, insertion, or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

To determine the percent identity of two amino acid sequences or of two nucleotide sequences, the sequences can be aligned for optimal comparison purposes (e.g., gaps can be introduced in one or both of a first and a second amino acid or nucleotide sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. (As used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and the determination of a percent identity between two sequences may be accomplished using a mathematical algorithm. In one embodiment, the percent identity between two amino acid sequences can be determined using the Needleman and Wunsch algorithm (J. Molecular Biology 48:444-453 (1970)), which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, e.g., ClustalW, ClustalX, and Clustal Omega.

Sequence searches are typically carried out using the BLASTN program, when evaluating a given nucleotide sequence relative to nucleotide sequences in the GenBank DNA Sequences and other public databases. The BLASTX program is effective for searching nucleotide sequences that have been translated in all reading frames against amino acid sequences in the GenBank Protein Sequences and other public databases. An alignment of selected sequences in order to determine "% identity" between two or more sequences may be performed using, for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, the nucleotide sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands. The efficiency and strength of said hybridization depends upon the detection method.

4. Transformed Cells that are Resistant to a Bacteriophage

The ubiquitous distribution and abundance of bacteriophage have a profound impact on the industrial use of bacteria. Numerous strains of bacteria have been cultured for fermentation and biotechnology processes, but domesticated bacteria are often susceptible to phage attack. Thus, phage contamination typically must be addressed when using a bacterium such as E. coli to manufacture a product. Various strategies have been devised to combat phages based on strain diversity, bacteriophage insensitive mutants, and plasmids bearing phage-resistance mechanisms. A transformed cell according to some embodiments of the invention may contain one or more mutations that confer resistance to bacteriophage infection.

Natural bacteria have developed a variety of natural defense mechanisms that target diverse steps of the phage life cycle, for example, by blocking adsorption, preventing DNA injection, restricting the incoming DNA, and abortive infection systems. These antiviral barriers can be engineered and manipulated to better control phage populations (See e.g., Chibani-Chemoufi et al., J. Bacteriol., 186:3677 (2004); Sturino and Klaenhammer, Nat. Rev. Microbiol., 4:395 (2006)).

Bacteriophage can be distinguished from each another based on their genetic composition and/or their virion morphology. Some phage have double stranded DNA genomes, including phage of the corticoviridae, lipothrixviridae, plasmaviridae, myoviridae, siphoviridae, sulfolobus shibate, podoviridae, tectiviridae, and fuselloviridae families. Other phage have single stranded DNA genomes, including phage of the microviridae and inoviridae families. Other phage have RNA genomes, including phage of the leviviridae and cystoviridae families. Exemplary bacteriophage include phages Wphi, Mu, T1, T2, T3, T4, T5, T6, T7, P1, P2, P4, P22, fd, phi6, phi29, phi31, phiC31, phi35, phi36, phi48, phi50, phi80, phiX174, SP01, M13, MS2, PM2, SSV-1, L5, PRD1, Qbeta, lambda, UC-1, HK97, and HK022. Accordingly, in some embodiments, the transformed cell comprises a genetic modification that confers resistance to a bacteriophage selected from the group consisting of Wphi, Mu, T1, T2, T3, T4, T5, T6, T7, P1, P2, P4, P22, fd, phi6, phi29, phi31, phiC31, phi35, phi36, phi48, phi50, phi80, phiX174, SP01, M13, MS2, PM2, SSV-1, L5, PRD1, Qbeta, lambda, UC-1, HK97, and HK022.

Host and phage proteins important for bacteriophage infection are known in the art and can be subject to mutation by those of skill in the art using routine methods. Bacteria resistant to phage infection also can be obtained by the screening of mutant (spontaneous or induced) bacteria. For example, phage resistance may be accomplished by random gene inactivation as described in U.S. Pat. No. 7,435,434, hereby incorporated by reference.

Phage-resistant bacteria often have cellular properties that inhibit or substantially reduce the ability of one or more types of bacteriophage to insert their genetic material into the bacterial cell. Thus, some bacteriophage resistant bacteria have cellular properties that prevent or inhibit bacteriophage attachment to the bacterial cell surface, and/or insertion of bacteriophage genetic material into the bacterial cytoplasm. Methods of generating phage-resistant bacteria are well known in the art (U.S. Pat. Nos. 5,240,841; 5,538,864; 5,432,066; 5,538,864; 5,629,183; 5,658,770; 5,677,166; and 5,824,523, and U.S. Patent Publication Nos. 2006/0019370; 2011/0002889; and 2012/0015426, each of which is hereby incorporated by reference).

Any strategy for generating phage resistance may be utilized in an embodiment of the invention. General classes of phage resistance include (1) blocking phage receptors, (2) inhibiting phage DNA entry, (3) abortive phage infection systems, (4) extracellular matrix secretion, (5) phase variation, (6) production of competitive inhibitors, (7) restriction/modification systems, and (8) CRISPR-based systems (see Labrie, S. J. et al., Nature Review Microbiology 8:317 (2010)). In some embodiments, the transformed cell comprises a genetic modification that confers resistance to a bacteriophage by blocking one or more phage receptors; by inhibiting the entry of phage DNA into the cell; by an abortive infection system; by encoding an extracellular matrix protein that protects against infection; by triggering a new gene expression profile (phase variation); by encoding a competitive inhibitor that binds phage receptors; by digesting or modifying phage nucleic acids; or by encoding one or more components of a CRISPR locus. For example, the Rex system is an abortive infection system that requires a RexA protein (encoded by the rexA gene) that senses the beginning of a bacteriophage infection and a RexB protein (encoded by the rexB gene) that responds to activated RexA by opening a cell membrane ion channel that leads to premature cell apoptosis. In some embodiments, the transformed cell comprises a genetic modification that confers resistance to a bacteriophage by blocking a phage receptor. In some embodiments, the transformed cell comprises a genetic modification that confers resistance to a bacteriophage by preventing phage DNA from entering the cell. nucleotide sequence In some embodiments, the transformed cell comprises a genetic modification that confers resistance to a bacteriophage by an abortive phage infection system.

Representative phage-resistance genes include imm, sp, traT, llp, SieA, sim, rexA, rexB, lit, prrC, prrD, and pifA. In some aspects, the invention relates to a transformed cell comprising a genetic modification, wherein the modification is transformation with a nucleic acid comprising a gene selected from the group consisting of imm, sp, traT, llp, SieA, sim, rexA, rexB, lit, prrC, prrD, and pifA. For example, the transformed cell may comprise a rexA gene and a rexB gene. Similarly, the transformed cell may comprise a prrC gene and a prrD gene.

In some embodiments, the transformed cell has been transformed with a nucleic acid comprising a nucleotide sequence that has at least 75%, 80%, 85%, 90%, 95%, 96%, 97%, 98%, 99%, 99.5%, or 99.9% sequence homology with the nucleotide sequence set forth in SEQ ID NO: 67, SEQ ID NO: 68, SEQ ID NO: 69, SEQ ID NO: 70, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, or SEQ ID NO: 87. In certain embodiments, the transformed cell has been transformed with a nucleic acid comprising the nucleotide sequence set forth in SEQ ID NO: 67, SEQ ID NO: 68, SEQ ID NO: 69, SEQ ID NO: 70, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, or SEQ ID NO: 87. In some embodiments, the transformed cell has been transformed with a nucleic acid that encodes the amino acid sequence set forth in SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, or SEQ ID NO: 88. In some embodiments, the transformed cell has been transformed with a nucleic acid that encodes the an amino acid sequence having at least 75%, 80%, 85%, 90%, 95%, 96%, 97%, 98%, 99%, 99.5%, or 99.9% sequence homology with the sequence set forth in SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, or SEQ ID NO: 88. In some embodiments, the transformed cell comprises a nucleotide sequence that has at least 75%, 80%, 85%, 90%, 95%, 96%, 97%, 98%, 99%, 99.5%, or 99.9% sequence homology with the sequence set forth in SEQ ID NO: 73 and a nucleic acid sequence that has at least 75%, 80%, 85%, 90%, 95%, 96%, 97%, 98%, 99%, 99.5%, or 99.9% sequence homology with the sequence set forth in SEQ ID NO: 75. In some embodiments, the transformed cell comprises a nucleotide sequence that encodes an amino acid sequence that has at least 75%, 80%, 85%, 90%, 95%, 96%, 97%, 98%, 99%, 99.5%, or 99.9% sequence homology with the sequence set forth in SEQ ID NO: 74 and a nucleotide sequence that encodes an amino acid sequence that has at least 75%, 80%, 85%, 90%, 95%, 96%, 97%, 98%, 99%, 99.5%, or 99.9% sequence homology with the sequence set forth in SEQ ID NO: 76.

In some aspects, a phage-resistant transformed cell and the phage that the cell is resistant to are used in media (e.g., a fermentation mixture) to provide a selective advantage to the transformed cell relative to contaminating cells that are not resistant to the phage. Thus, in some embodiments of the invention, the fermentation mixture comprises the bacteriophage to which a genetic modification confers resistance.

EXEMPLARY COMPOUNDS

In certain aspects, the invention relates to a fermentation mixture (e.g., a fermentation mixture for aerobic or microaerobic fermentation), wherein: the fermentation mixture comprises a first fraction and a second fraction; the first fraction consists essentially of a fractionated grain (e.g., a fractionated grain mash); and the second fraction comprises one or more compounds. In some embodiments, the one or more compounds are selected from the group consisting of nitrogen-containing compounds, phosphorus-containing compounds, and sulfur-containing compounds; a transformed cell can metabolize the one or more compounds (i.e., the transformed cell can use the one or more compounds as a source of nitrogen, phosphorous, or sulfur); and a native cell of the same species as the transformed cell cannot metabolize the one or more compounds. In some embodiments, the nitrogen-containing compound, phosphorus-containing compound, and/or sulfur-containing compound is not naturally found in grain. In some embodiments, the fermentation mixture does not comprise an antibiotic.

1. Nitrogen-Containing Compounds

In some embodiments, the fermentation mixture comprises a fraction comprising, in an amount from about 10% by weight to about 100% by weight, one or more nitrogen-containing compounds selected from the group consisting of Formula I, Formula II, and Formula III, or a salt thereof. In certain embodiments, a native cell of the same species as the transformed cell cannot metabolize (i.e., use as a source of nitrogen) the one or more nitrogen-containing compounds. Exemplary nitrogen-containing compounds according to certain embodiments of the invention are described in PCT Patent Application Publication No. WO 2014/107660, hereby incorporated by reference.

In certain embodiments, the fermentation mixture comprises one or more nitrogen-containing compounds of formula I or a salt thereof:

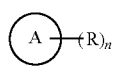

I wherein, independently for each occurrence,

is a five-, six, nine-, or ten-membered aryl or heteroaryl group;

R is —OH, —CO$_2$H, —NO$_2$, —CN, substituted or unsubstituted amino, or substituted or unsubstituted alkyl; and n is 0, 1, 2, 3, 4, or 5.

In certain embodiments, the fermentation mixture comprises one or more nitrogen-containing compounds of formula II or a salt thereof:

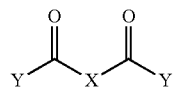

II wherein, independently for each occurrence,

X is —NH—, —N(alkyl)—, —O—, —C(R$^1$)$_2$—, —S—, or absent;

Y is —H, —NH$_2$, —N(H)(alkyl), —N(alkyl)$_2$, —CO$_2$H, —CN, or substituted or unsubstituted alkyl; and R$^1$ is —H, —OH, —CO$_2$H, —NO$_2$, —CN, substituted or unsubstituted amino, or substituted or unsubstituted alkyl.

In certain embodiments, the fermentation mixture comprises one or more nitrogen-containing compounds of formula III or a salt thereof:

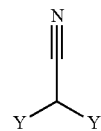

III wherein, independently for each occurrence,

Y is —H, —NH$_2$, —N(H)(alkyl), —N(alkyl)$_2$, —CO$_2$H, —CN, or substituted or unsubstituted alkyl.

In certain embodiments, the fermentation mixture comprises any one of the aforementioned nitrogen-containing compounds, wherein the one or more nitrogen-containing compounds are selected from the group consisting of:

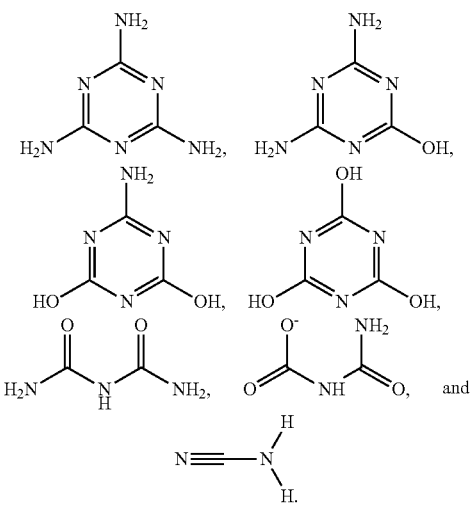

and

In certain embodiments, the fermentation mixture comprises one or more nitrogen-containing compounds, wherein the one or more nitrogen-containing compounds are selected from the group consisting of Hydrazine, 5-Aminotetrazole, Tetrazole, Melamine, Cyanamide, 2-Cyanoguanidine, Sodium azide, Carbohydrazide, 1,2,3-Triazole, 1,2,4-Triazole, 1,3-Diaminoguanidine HCl, Ammeline, 1,3,5-triazine, Aminoacetonitrile, Cyanoethylhydrazine, Azodicarbonamide, Biurea, Formamidoxime, 1,2-Dimethylhydrazine, 1,1-Dimethylhydrazine, ethylhydrazine, Ethylenediamine, Sodium dicyanamide, Guanidine carbonate, Methylamine, Ammelide, Hydroxylamine, Malononitrile, Biuret, Diethyltriamine, Hexamethylenetetramine, Triethylenetetramine, 1,3-Diaminopropane, Triethylenetetramine, 1,3-Diaminopropane, Hydroxyurea, Tetraethylenepentamine, Thiourea, Succinonitrile, Calcium cyanamide, Cyanuric acid, Aminoethylpiperazine, Piperazine, Dimethylamine, Ethylamine, dalfampridine, Tetranitromethane, Imidazolidinyl urea, Trinitromethane, malonamide, Chloramine, Allophante, Trimethylamine, Nitromethane, Acetaldoxime, Diazolidinyl urea, 1,2-Cyclohexanedione dioxime, Acetone oxime, Thioacetamide, Sodium thiocyanate, Isothiazole, Thiazole, Dimethylacetamide, Isothiazolinone, Methylene blue, Diethanolamine, Aspartame, Benzisothiazolinone, and Acesulfame potassium.

TABLE 2

Various organonitrogen compounds and the chemical formulas of each compound.

| Compound | Formula | % N |
|---|---|---|
| Hydrazine | $N_2H_4$ | 88% |
| 5-Aminotetrazole | $CH_3N_5$ | 82% |
| Tetrazole | $CH_2N_4$ | 80% |
| Melamine | $C_3H_6N_6$ | 67% |
| Cyanamide | $CH_2N_2$ | 67% |
| 2-Cyanoguanidine | $C_2H_4N_4$ | 67% |
| Sodium azide | $NaN_3$ | 65% |
| Carbohydrazide | $CH_6N_4O$ | 62% |
| 1,2,3-Triazole | $C_2H_3N_3$ | 61% |
| 1,2,4-Triazole | $C_2H_3N_3$ | 61% |
| 1,3-Diaminoguanidine HCL | $CH_7N_5 \cdot HCl$ | 56% |
| Ammeline | $C_3H_5N_5O$ | 55% |
| 1,3,5-triazine | $C_3H_3N_3$ | 52% |
| Aminoacetonitrile | $C_2H_4N_2$ | 50% |
| Cyanoethylhydrazine | $C_3H_7N_3$ | 49% |
| Azodicarbonamide | $C_2H_4O_2N_4$ | 48% |
| Biurea | $C_2H_6N_4O_2$ | 47% |
| Formamidoxime | $CH_4N_2O$ | 47% |
| 1,2-Dimethylhydrazine | $C_2H_8N_2$ | 47% |
| 1,1-Dimethylhydrazine | $C_2H_8N_2$ | 47% |
| ethylhydrazine | $C_2H_8N_2$ | 47% |
| Ethylenediamine | $C_2H_8N_2$ | 47% |
| Sodium dicyanamide | $C_2N_3Na$ | 47% |
| Guanidine carbonate | $CH_5N_3 \cdot \frac{1}{2} H_2CO_3$ | 47% |
| Methylamine | $CH_5N$ | 45% |
| Ammelide | $C_3H_4N_4O_2$ | 44% |
| Hydroxylamine | $NH_2OH$ | 42% |
| Malononitrile | $C_3H_2N_2$ | 42% |
| Biuret | $C_2H_5N_3O_2$ | 41% |
| Diethyltriamine | $C_4H_{13}N_3$ | 41% |
| Hexamethylenetetramine | $C_6H_{12}N_4$ | 40% |
| Triethylenetetramine | $C_6H_{18}N_4$ | 38% |
| 1,3-Diaminopropane | $C_3H_{10}N_2$ | 38% |
| Triethylenetetramine | $C_6H_{18}N_4$ | 38% |
| 1,3-Diaminopropane | $C_3H_{10}N_2$ | 38% |
| Hydroxyurea | $CH_4N_2O_2$ | 37% |
| Tetraethylenepentamine | $C_8H_{23}N_5$ | 37% |
| Thiourea | $CH_4N_2S$ | 37% |
| Succinonitrile | $C_4H_4N_2$ | 35% |
| Calcium cyanamide | $CaCN_2$ | 35% |
| Cyanuric acid | $C_3H_3N_3O_3$ | 33% |
| Aminoethylpiperazine | $C_6H_{15}N_3$ | 33% |
| Piperazine | $C_4H_{10}N_2$ | 33% |
| Dimethylamine | $C_2H_7N$ | 31% |
| Ethylamine | $C_2H_7N$ | 31% |
| dalfampridine | $C_5H_6N_2$ | 30% |
| Tetranitromethane | $CN_4O_8$ | 29% |
| Imidazolidinyl urea | $C_{11}H_{16}N_8O_8$ | 29% |
| Trinitromethane | $CHN_3O_6$ | 28% |
| malonamide | $C_3H_6N_2O_2$ | 27% |
| Chloramine | $NH_2Cl$ | 27% |
| Allophante | $C_2H_3N_2O_3$ | 27% |
| Trimethylamine | $C_3H_9N$ | 24% |
| Nitromethane | $CH_3NO_2$ | 23% |
| Acetaldoxime | $C_2H_5NO$ | 23% |
| Diazolidinyl urea | $C_8H_{14}N_4O_7$ | 20% |
| 1,2-Cyclohexanedione dioxime | $C_6H_{10}N_2O_2$ | 20% |
| Acetone oxime | $C_3H_7NO$ | 19% |
| Thioacetamide | $C_2H_5NS$ | 19% |
| Sodium thiocyanate | $NaSCN$ | 17% |
| Isothiazole | $C_3H_3NS$ | 16% |
| Thiazole | $C_3H_3NS$ | 16% |
| Dimethylacetamide | $C_4H_9NO$ | 16% |
| Isothiazolinone | $C_3H_3NOS$ | 14% |
| Methylene blue | $C_{16}H_{18}N_3SCl$ | 13% |
| Diethanolamine | $C_4H_{11}NO_2$ | 13% |
| Aspartame | $C_{14}H_{18}N_2O_5$ | 10% |
| Benzisothiazolinone | $C_7H_5NOS$ | 7% |
| Acesulfame potassium | $C_4H_4KNO_4S$ | 7% |

In certain embodiments, the fermentation mixture comprises one or more nitrogen-containing compounds, wherein the one or more nitrogen-containing compounds have a low molecular weight. In certain embodiments, the fermentation mixture comprises a nitrogen-containing compound, wherein the nitrogen-containing compound has a molecular weight between about 30 Da and about 800 Da. In certain embodiments, the fermentation mixture comprises a nitrogen-containing compound, wherein the nitrogen-containing compound has a molecular weight between about 40 Da and about 600 Da. In certain embodiments, the fermentation mixture comprises a nitrogen-containing compound, wherein the nitrogen-containing compound has a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, about 560 Da, about 580 Da, or about 600 Da.

In certain embodiments, the fermentation mixture comprises a nitrogen-containing compound, wherein the nitrogen-containing compound has less than 12 carbon atoms. In certain embodiments, the fermentation mixture comprises a nitrogen-containing compound, wherein the nitrogen-containing compound has less than 8 carbon atoms. In certain embodiments, the fermentation mixture comprises a nitrogen-containing compound, wherein the nitrogen-containing compound has 1, 2, 3, 4, 5, 6, or 7 carbon atoms.

In certain embodiments, the fermentation mixture comprises a nitrogen-containing compound, wherein the nitrogen-containing compound has an octanol-water partition coefficient (log P) less than about 5. In certain embodiments, the fermentation mixture comprises a nitrogen-containing compound, wherein the nitrogen-containing compound has an octanol-water partition coefficient (log P) from about −0.5 to about 5. In certain embodiments, the fermentation mixture comprises a nitrogen-containing compound, wherein the nitrogen-containing compound has an octanol-water partition coefficient (log P) of about −0.5, about 0, about 0.5, about 1, about 1.5, about 2, about 2.5, about 3, about 3.5, about 4, or about 4.5.

In certain embodiments, the fermentation mixture comprises a nitrogen-containing compound, wherein the nitrogen-containing compound is soluble in water at about 20° C. at a concentration of between about 0.01 g/L to about 1000 g/L. In certain embodiments, the fermentation mixture comprises a nitrogen-containing compound, wherein the nitrogen-containing compound is soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In some embodiments, the fermentation mixture comprises a fraction comprising one or more nitrogen-containing compounds at about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the nitrogen-containing compound is substantially non-biocidal. The nitrogen-containing compound may be substantially biodegradable.

2. Phosphorus-Containing Compounds

In certain embodiments, the invention comprises a fraction comprising from about 10% by weight to about 100% by weight, one or more phosphorus-containing compounds of any one of Formulas IV-VI, or a salt thereof. In certain embodiments, a native cell of the same species as the transformed cell cannot metabolize (i.e., use as a source of phosphorus) the one or more phosphorus-containing compounds. Exemplary phosphorous-containing compounds according to certain embodiments of the invention are described in PCT Patent Application Publication No. WO 2015/031441, hereby incorporated by reference.

In certain embodiments, the fermentation mixture comprises one or more phosphorus-containing compounds of formula IV, or a salt thereof:

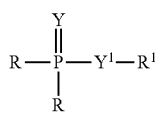

IV wherein, independently for each occurrence,

R is —H, alkyl, —OH, —OR$^2$, —SH, or —SR$^2$;

R$^1$ is —H, or alkyl;

Y is O or S;

Y$^1$ is O or S; and

R$^2$ is alkyl.

In certain embodiments, the fermentation mixture comprises one or more phosphorus-containing compounds of formula V, or a salt thereof:

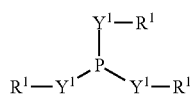

V wherein, independently for each occurrence,

R$^1$ is —H, or alkyl; and

Y$^1$ is O or S.

In certain embodiments, the fermentation mixture comprises one or more phosphorus-containing compounds of formula VI, or a salt thereof:

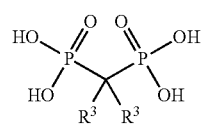

VI wherein, independently for each occurrence,

R$^3$ is —H, —OH, —OR$^4$, —SH, —SR$^4$, halo, alkyl, aryl, heteroaryl, aralkyl, or heteroaralkyl; and R$^4$ is alkyl or aryl.

In certain embodiments, the fermentation mixture comprises one or more phosphorus-containing compounds selected from the group consisting of:

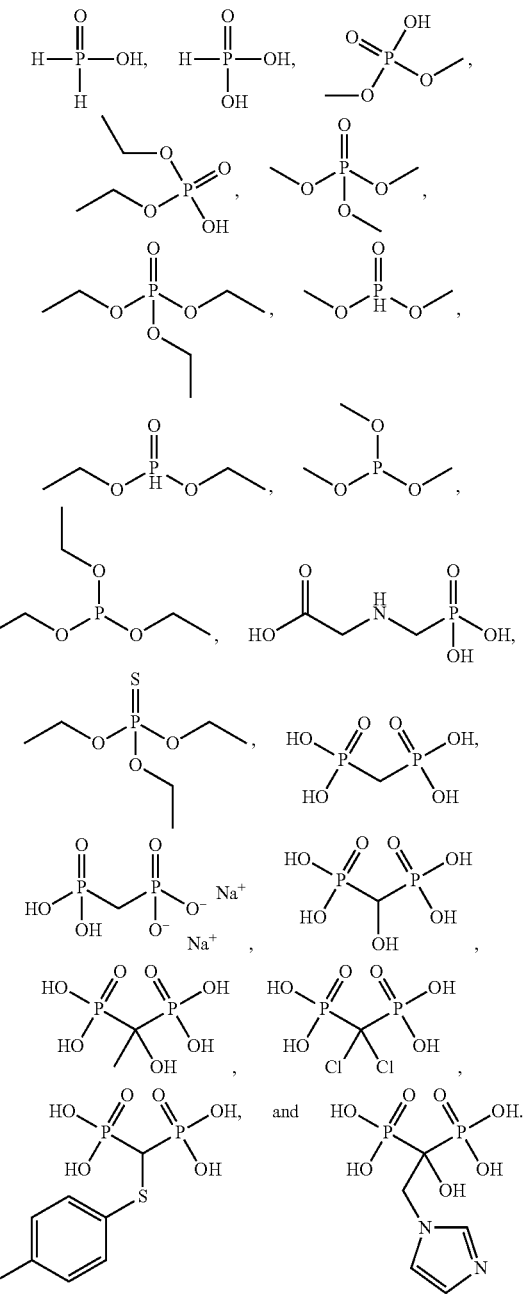

TABLE 3

Various organophosphorus compounds and the chemical formula of each compound.

| | |
|---|---|
| Hypophosphorous acid | H$_3$PO$_2$ |
| Phosphorous acid (phosphite) | H$_3$PO$_3$ |
| Diethyl phosphate | C$_4$H$_{11}$O$_4$P |
| Triethyl phosphate | C$_6$H$_{15}$O$_4$P |
| Trimethyl phosphate | (CH$_3$)$_3$PO$_4$ |
| Dimethyl phosphate (DMP) | C$_2$H$_7$O$_4$P |
| Diethyl phosphite | C$_4$H$_{11}$O$_3$P |
| Triethyl phosphite | C$_6$H$_{15}$O$_3$P |
| Trimethyl phosphite | C$_3$H$_9$O$_3$P |
| Dimethyl phosphite | C$_2$H$_7$O$_3$P |
| Glyphosate (round-up) | C$_3$H$_8$NO$_5$P |
| O,O,O-Triethyl Phosphorothioate | C$_6$H$_{15}$O$_3$PS |

TABLE 3-continued

Various organophosphorus compounds and the chemical formula of each compound.

| Etidronic acid | $C_2H_8O_7P_2$ |
| Disodium methylene diphosphonate | $CH_4Na_2O_6P_2$ |
| Medronic acid | $CH_6O_6P_2$ |
| Clodronic acid | $CH_4Cl_2O_6P_2$ |
| Tiludronic acid | $C_7H_9ClO_6P_2S$ |
| Zoledronic acid | $C_5H_{10}N_2O_7P_2$ |
| Oxidronic Acid | $CH_6O_7P_2$ |

In certain embodiments, the fermentation mixture comprises one or more phosphorus-containing compounds, wherein one or more phosphorus-containing compounds have a low molecular weight. In certain embodiments, the fermentation mixture comprises a phosphorus-containing compound, wherein the phosphorus-containing compound has a molecular weight between about 30 Da and about 800 Da. In certain embodiments, the fermentation mixture comprises a phosphorus-containing compound, wherein the phosphorus-containing compound has a molecular weight between about 40 Da and about 600 Da. In certain embodiments, the fermentation mixture comprises a phosphorus-containing compound, wherein the phosphorus-containing compound has a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, about 560 Da, about 580 Da, or about 600 Da.

In certain embodiments, the fermentation mixture comprises a phosphorus-containing compound, wherein the phosphorus-containing compound has less than 12 carbon atoms. In certain embodiments, the fermentation mixture comprises a phosphorus-containing compound, wherein the phosphorus-containing compound has less than 8 carbon atoms. In certain embodiments, the fermentation mixture comprises a phosphorus-containing compound, wherein the phosphorus-containing compound has 1, 2, 3, 4, 5, 6, or 7 carbon atoms.

In certain embodiments, the fermentation mixture comprises a phosphorus-containing compound, wherein the phosphorus-containing compound has an octanol-water partition coefficient (log P) less than about 5. In certain embodiments, the fermentation mixture comprises a phosphorus-containing compound, wherein the phosphorus-containing compound has an octanol-water partition coefficient (log P) from about −0.5 to about 5. In certain embodiments, the fermentation mixture comprises a phosphorus-containing compound, wherein the phosphorus-containing compound has an octanol-water partition coefficient (log P) of about −0.5, about 0, about 0.5, about 1, about 1.5, about 2, about 2.5, about 3, about 3.5, about 4, or about 4.5.

In certain embodiments, the fermentation mixture comprises a phosphorus-containing compound, wherein the phosphorus-containing compound is soluble in water at about 20° C. at a concentration of between about 0.01 g/L to about 1000 g/L. In certain embodiments, the fermentation mixture comprises a phosphorus-containing compound, wherein the phosphorus-containing compound is soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In some embodiments, the fermentation mixture comprises a fraction comprising one or more phosphorus-containing compounds in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the phosphorus-containing compound is substantially non-biocidal. The phosphorus-containing compound may be substantially biodegradable.

3. Sulfur-Containing Compounds

In certain embodiments, the fermentation mixture comprises one or more sulfur-containing compounds of any one of Formulas VII-XIV, or a salt thereof. In certain embodiments, a native cell of the same species as the transformed cell cannot metabolize (i.e., use as a source of sulfur) the one or more sulfur-containing compounds. Exemplary sulfur-containing compounds according to certain embodiments of the invention are described in PCT Patent Application Publication No. WO 2015/031441, hereby incorporated by reference.

In certain embodiments, the fermentation mixture comprises one or more sulfur-containing compounds of formula IV or a salt thereof:

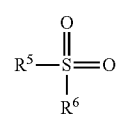

VII wherein, independently for each occurrence, $R^5$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$;

$R^6$ is —H, —OH, —$OR^7$, —SH, —$SR^7$, $R^7$, halo, alkyl, aryl, heteroaryl, aralkyl, heteroaralkyl, —$SO_2H$, —$NHR^7$, or —NH—C(=O)—$R^7$; and $R^7$ is cycloalkyl, alkyl, or aryl, or any two $R^7$, taken together, form a 5- or 6-membered ring.

In certain embodiments, the fermentation mixture comprises one or more sulfur-containing compounds of formula VIII, formula IX, or formula X, or a salt thereof:

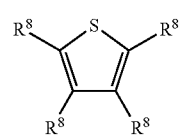

VIII

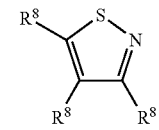

IX

-continued

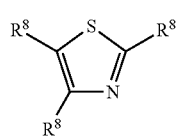

wherein, independently for each occurrence, $R^8$ is —H, —OH, —OR$^7$, —SH, —SR$^7$, R$^7$, halo, alkyl, aryl, heteroaryl, aralkyl, heteroaralkyl, —SO$_2$H, —NHR$^7$, or —NH—C(=O)—R$^7$;

$R^7$ is cycloalkyl, alkyl, or aryl, or any two R$^7$, taken together, form a 5- or 6-membered ring.

In certain embodiments, the fermentation mixture comprises one or more sulfur-containing compounds of formula XI, formula XII, or formula XIII or a salt thereof:

XI

XII

XIII wherein, independently for each occurrence, $R^9$ is —H, —OH, —OR$^7$, —SH, —SR$^7$, R$^7$, halo, alkyl, aryl, heteroaryl, aralkyl, heteroaralkyl, —SO$_2$H, —NH$_2$, —NHR$^7$, or —NH—C(=O)—R$^7$;

$R^7$ is cycloalkyl, alkyl, or aryl, or any two R$^7$, taken together, form a 5- or 6-membered ring;

$R^{10}$ is hydroxyalkyl, R$^9$, or —(CH$_2$)$_x$R$^9$; and x is 1, 2, 3, or 4.

In certain embodiments, the fermentation mixture comprises one or more sulfur-containing compounds of formula XIV or a salt thereof:

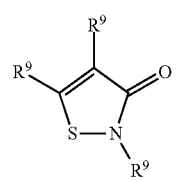

XIV wherein, independently for each occurrence, $R^9$ is —H, —OH, —OR$^7$, —SH, —SR$^7$, R$^7$, halo, alkyl, aryl, heteroaryl, aralkyl, heteroaralkyl, —SO$_2$H, —NH$_2$, —NHR$^7$, or —NH—C(=O)—R$^7$; and $R^7$ is cycloalkyl, alkyl, or aryl, or any two R$^7$, taken together, form a 5- or 6-membered ring.

In certain embodiments, the fermentation mixture comprises one or more sulfur-containing compounds selected from the group consisting of:

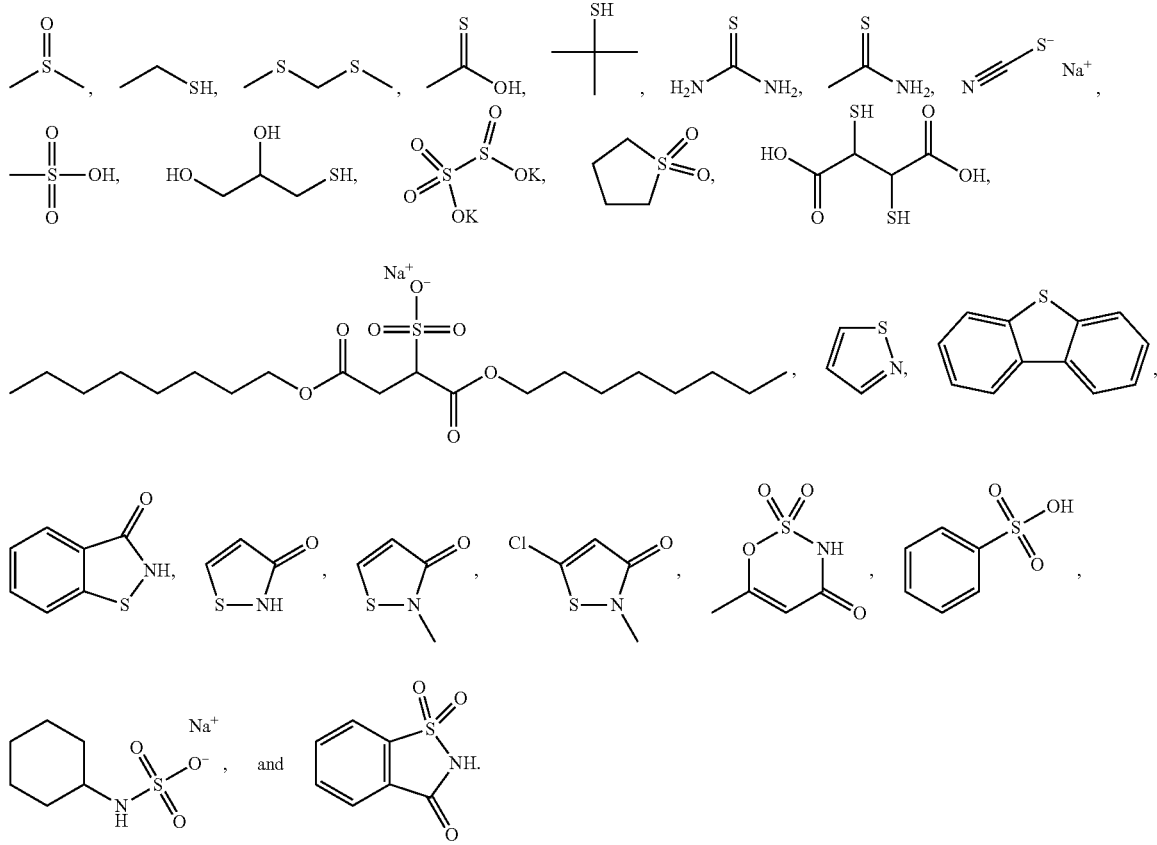

TABLE 4

Various organosulfur compounds and the chemical formula of each compound.

| Compound | Formula |
|---|---|
| Dimethylsulfoxide | $C_2H_6OS$ |
| Dibenzothiophene | $C_{12}H_8S$ |
| Ethanethiol | $C_2H_6S$ |
| Dimercaptosuccinic acid | $C_4H_6O_4S_2$ |
| Thioacetic acid | $C_2H_4OS$ |
| tert-Butylthiol | $C_4H_{10}S$ |
| Thiourea | $CH_4N_2S$ |
| Sodium thiocyanate | NaSCN |
| Thioacetamide | $C_2H_5NS$ |
| Isothiazole | $C_3H_3NS$ |
| Benzisothiazolinone | $C_7H_5NOS$ |
| Isothiazolinone | $C_3H_3NOS$ |
| Methanesulfonic acid | $CH_4O_3S$ |
| Thioglycerol | $C_3H_8O_2S$ |
| Potassium metabisulfite | $K_2O_5S_2$ |
| Acesulfame potassium | $C_4H_4KNO_4S$ |
| Benzenesulfonic acid | $C_6H_5SO_3H$ |
| Sodium cyclamate | $C_6H_{12}NNaO_3S$ |
| Saccharin | $C_7H_5NO_3S$ |
| Dioctyl sodium sulfosuccinate | $C_{20}H_{37}NaO_7S$ |
| 2,4-Dithiapentane | $C_3H_8S_2$ |
| Methylisothiazolinone | $C_4H_5NOS$ |
| Methylchloroisothiazolinone | $C_4H_4ClNOS$ |
| Sulfolane | $C_4H_8O_2S$ |

In certain embodiments, the fermentation mixture comprises one or more sulfur-containing compounds, wherein the one or more sulfur-containing compounds have a low molecular weight. In certain embodiments, the fermentation mixture comprises a sulfur-containing compound, wherein the sulfur-containing compound has a molecular weight between about 30 Da and about 800 Da. In certain embodiments, the fermentation mixture comprises a sulfur-containing compound, wherein the sulfur-containing compound has a molecular weight between about 40 Da and about 600 Da. In certain embodiments, the fermentation mixture comprises a sulfur-containing compound, wherein the sulfur-containing compound has a molecular weight of about 40 Da, about 50 Da, about 60 Da, about 70 Da, about 80 Da, about 90 Da, about 100 Da, about 110 Da, about 120 Da, about 130 Da, about 140 Da, about 150 Da, about 160 Da, about 170 Da, about 180 Da, about 190 Da, about 200 Da, about 220 Da, about 240 Da, about 260 Da, about 280 Da, about 300 Da, about 320 Da, about 340 Da, about 360 Da, about 380 Da, about 400 Da, about 420 Da, about 440 Da, about 460 Da, about 480 Da, about 500 Da, about 520 Da, about 540 Da, about 560 Da, about 580 Da, or about 600 Da.

In certain embodiments, the fermentation mixture comprises a sulfur-containing compound, wherein the sulfur-containing compound has less than 21 carbon atoms, such as less than 12 carbon atoms. In certain embodiments, the fermentation mixture comprises a sulfur-containing compound, wherein the sulfur-containing compound has less than 8 carbon atoms. In certain embodiments, the fermentation mixture comprises a sulfur-containing compound, wherein the sulfur-containing compound has 1, 2, 3, 4, 5, 6, 7, 8, 9, 10, 11, 12, 13, 14, 15, 16, 17, 18, 19, or 20 carbon atoms.

In certain embodiments, the fermentation mixture comprises a sulfur-containing compound, wherein the sulfur-containing compound has an octanol-water partition coefficient (log P) less than about 5. In certain embodiments, the fermentation mixture comprises a sulfur-containing compound, wherein the sulfur-containing compound has an octanol-water partition coefficient (log P) from about −0.5 to about 5. In certain embodiments, the fermentation mixture comprises a sulfur-containing compound, wherein the sulfur-containing compound has an octanol-water partition coefficient (log P) of about −0.5, about 0, about 0.5, about 1, about 1.5, about 2, about 2.5, about 3, about 3.5, about 4, or about 4.5.

In certain embodiments, the fermentation mixture comprises a sulfur-containing compound, wherein the sulfur-containing compound is soluble in water at about 20° C. at a concentration of between about 0.01 g/L to about 1000 g/L. In certain embodiments, the fermentation mixture comprises a sulfur-containing compound, wherein the sulfur-containing compound is soluble in water at about 20° C. at a concentration of about 0.01 g/L, about 0.05 g/L, about 0.1 g/L, about 0.5 g/L, about 1 g/L, about 5 g/L, about 10 g/L, about 15 g/L, about 20 g/L, about 25 g/L, about 30 g/L, about 35 g/L, about 40 g/L, about 45 g/L, about 50 g/L, about 55 g/L, about 60 g/L, about 65 g/L, about 70 g/L, about 75 g/L, about 80 g/L, about 85 g/L, about 90 g/L, about 95 g/L, or about 100 g/L.

In some embodiments, the fermentation mixture comprises a fraction comprising one or more sulfur-containing compounds in about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% by weight.

In certain embodiments, the sulfur-containing compound is substantially non-biocidal. The sulfur-containing compound may be substantially biodegradable.

EXEMPLARY METHODS FOR FERMENTATION

1. Use of Fractionated Grain on Improve Oxygen Transfer

In some aspects, the invention relates to compositions comprising fractionated grain and methods of using fractionated grain in aerobic or microaerobic fermentation processess. The use of fractionated grain, such as the endosperm fraction, in a fermentation mixture reduces its viscosity, which improves oxygen transfer during aerobic and microaerobic fermentation processes. The type of grain is not critical. For example, the grain may be corn, wheat, sorghum, rye, triticale, oats, rice, millets, barley, teff, wild rice, spelt, buckwheat, amaranth, quinoa, kaniwa, or fonio. The fractionated grain may be a fractionated grain mash. In some embodiments, the fractionated grain mash is a fractionated corn mash.

To process a grain, such as corn, for anaerobic fermentation, a typical dry grind facility can mill whole corn kernels to 0.5-3 mm, mix the milled grain with water, and incubate the mixture for several minutes at 70-90° C. with alpha-amylase to produce sugar dextrins (a/k/a mashing), and then proceed to fermentation with added glucoamylase to release glucose for conversion by *S. cerevisiae*. As the whole grain (e.g., corn kernel) is processed, all of the nitrogen and phosphorus of the whole grain is present during fermentation.

Alternatively, the grain can be selectively milled to create three streams—i) the endosperm fraction, which is predominantly starch, ii) the germ fraction, which is predominately protein and oil, and iii) the bran fraction, which is predominately fiber. The majority of readily fermentable carbohydrates is present in the endosperm fraction, which can be mashed per the traditional dry grind process, and carried on to fermentation. The fractionated grain may be substantially devoid of germ, substantially devoid of bran, or both. In some embodiments, the fractionated grain consists essentially of endosperm, such as corn endosperm.

Grain can be fractionated through any method, such as methods that are known in the art. Examples of grain fractionation technologies include those described in U.S. Pat. Nos. 2,108,655; 4,301,183; 8,113,447; 3,399,839; 4,986,997; 7,419,108; 7,138,257; 7,553,507; and 7,938,345; and U.S. Patent Application Publication No. 2007/0184541, each of which is hereby incorporated by reference in its entirety. Alternate fractionation methods are also known in the art, such as processes that involve initial soaking of grain and enzymatic treatment before dry grinding steps, for example, as described in Wang P, et al., Cereal Chemistry Journal, 82:734-738 (2005).

2. Combination of Fractionated Grain and Nitrogen-, Phosphorous-, and Sulfur-Containing Compounds In the fermentation industry, cell culture media is typically formulated to provide all of the nutrients necessary for the growth of a host cell line, with particular emphasis on meeting the cell line's requirements for carbon, nitrogen, phosphorus, sulfur, and other major nutrients. Some cell lines require additional components, including amino acids, trace minerals and metals, and complex growth factors. The presence of these nutrients provides a suitable growth environment for the organism of choice—and for any potential contaminating organisms. In this environment, the production organism is required to compete directly with any contaminant organisms in the cell culture.

Even with robust host organisms, the combination of opportunistic infections of the culture and the metabolic burden resulting from the demands of product manufacture is a major concern in monoculture operations. Industrial robustness is typically considered a multigenic trait specific to the host strain, and thus, robustness is difficult to predictably engineer into organisms late in the development process. The addition of selective growth inhibitors, such as bacterial antibiotics, is one method to create a robust fermentation environment for host organisms that are resistant to the growth inhibitor.

The growth and output of microorganisms may also be controlled by restricting an element, such as N, P, or S, in the cell culture, identifying or adding a known quantity of a rare or man-made chemical containing that restricted element to the cell culture, and using transformed cells that are genetically engineered so that they have the ability to degrade the rare or man-made chemical to obtain their requirements for that particular element (see PCT Patent Application Publication No. WO 2015/031441 and WO 2014/107660, hereby incorporated by reference). This strategy is particularly well designed for chemically defined media where all N, P, or S sources can be rigidly controlled. Thus, in some embodiments, the media does not comprise an antibiotic. However, many industrial-scale biotechnology applications utilize crude, non-refined carbon feedstocks, such as raw sugars (e.g., sugar cane juice, molasses), grains (e.g., corn, wheat, rice), and lignocellulosic materials (e.g., corn stover, sugarcane bagasse, grasses, woody materials, and sugar beet pulp). In addition to carbohydrates and other carbon sources, these crude materials contain varying amounts of minerals and other elements that may affect the availability of N, P, and S beyond that provided to the fermentation via nitrogen-, phosphorous-, and sulfur-containing compounds to be utilized by specifically-transformed cells.

Because it is low in phosphorus and nitrogen (e.g., low in protein, amino acids, nucleic acids, nucleotides, inorganic phosphate; see Table 5), the endosperm fraction of fractionated grain may be utilized as a feedstock supplemented with an atypical phosphorus and/or nitrogen source to provide a selective advantage for transformed cells that can metabolize added phosphorus- and/or nitrogen-containing compounds.

TABLE 5

|  | % (g/100 g) | | | | | | | ppm (mg/1000 g) | | | |
| --- | --- | --- | --- | --- | --- | --- | --- | --- | --- | --- | --- |
|  | Protein | S | P | K | Mg | Ca | Na | Fe | Mn | Cu | Zn |
| Endosperm | 8.62 | 0.1 | 0.11 | 0.21 | 0.05 | 0 | 0 | 12.4 | 2.4 | 1.8 | 9.8 |
| Germ | 18.3 | 0.2 | 1.36 | 1.7 | 0.6 | 0.02 | 0 | 95.8 | 20.4 | 8 | 89.8 |
| Bran | 9.14 | 0.09 | 0.13 | 0.37 | 0.06 | 0.04 | 0 | 25 | 9.9 | 3.9 | 17.4 |

Endosperm, which is enriched in carbohydrate and reduced in protein (nitrogen) and phosphorus, is an attractive fermentation substrate for use with transformed cells that are engineered to use non-traditional sources of nitrogen or phosphorus. Additional phosphorus can be supplied, for example, as phosphorous acid or a phosphite salt (K, Na, Mg, Ca), and utilized by a transformed cell comprising the phosphite utilization gene ptxD (phosphite:NADH oxidoreductase) for preferential growth in the fermentation environment. Bran is also depleted of nitrogen and phosphorus, and thus, bran could be a suitable substrate for use with transformed cells that are engineered to use non-traditional sources of nitrogen or phosphorus. Table 6 depicts the phosphorus distribution in corn, wheat, and rice grains.

TABLE 6

|  | Whole Grain | Germ | Endo-sperm | Hull (Bran) | Aleurone | Pericarp |
| --- | --- | --- | --- | --- | --- | --- |
| Corn | | | | | | |
| % phosphorus | 0.3 | 2.04 | 0.05 | 0.13 | 0 | 0 |
| % of total grain weight | 100 | 12 | 82 | 6 | 0 | 0 |
| Wheat | | | | | | |
| % phosphorus | 0.42 | 1.66 | 0.11 | 0.08 | 1.39 | 0 |
| % of total grain weight | 100 | 3.5 | 70.5 | 3 | 23 | 0 |
| Rice | | | | | | |
| % phosphorus | 0.31 | 1.3 | 0.11 | 0 | 0 | 1.04 |
| % of total grain weight | 100 | 2 | 77 | 0 | 0 | 21 |

In some embodiments, the fraction used of a fractionated grain comprises low or diminished (relative to the grain as a whole) quantities of nitrogen, phosphorus, and/or sulfur. In some embodiments, the nitrogen-containing compound, phosphorus-containing compound, and/or sulfur-containing compound is not naturally found in grain. In some embodiments of the invention, a fermentation comprising a fractionated grain mash does not comprise an antibiotic.

3. Fermentation Methods

In some embodiments, the invention relates to a method of fermentation, comprising incubating a transformed cell in a fermentation mixture. The fermentation may be an aerobic or microaerobic fermentation. The fermentation mixture may comprise a first fraction and a second fraction as described supra. The first fraction may comprise a fraction of a fractionated grain. The first fraction may consist essentially of a fraction of a fractionated grain. The second fraction may comprise one or more compounds selected from the group consisting of nitrogen-containing compounds, phosphorus-containing compounds, and sulfur-containing compounds, as described supra. In some embodiments, the transformed cell can metabolize the one or more compounds (i.e., use the one or more nitrogen-, phosphorous, and sulfur-containing compounds as a source of nitrogen, phosphorous, or sulfur, respectively). In some embodiments, a native cell of the same species as the transformed cell cannot metabolize the one or more compounds. The transformed cell, fermentation mixture, first fraction, second fraction, fractionated grain, fraction of fractionated grain, one or more compounds, nitrogen-containing compounds, phosphorus-containing compounds, and sulfur-containing compounds may be selected according to any of the embodiments described herein.

In some embodiments, the fermentation mixture is substantially devoid of germ, e.g., the first fraction may consist essentially of endosperm and/or bran. In some embodiments, the fraction of the fractionated grain is an endosperm fraction, e.g., the first fraction may consist essentially of an endosperm fraction.

4. Fermentation Products

Aerobic and microaerobic fermentation processes can be used to produce one or more products. In some aspects, the invention relates to methods of producing one or more products. In some embodiments, a transformed cell converts a feedstock, such as a fractionated grain, into one or more products. In certain embodiments, the invention relates to methods comprising the step of collecting one or more products. In some embodiments, the one or more products are selected from the group consisting of lipids, triacylglycerides, fatty alcohols, fatty acids, alkanes, alkenes, isoprenoids, isoprene, squalene, farnasene, alcohols, isopropanol, n-propanol, n-butanol, isobutanol, 2-butanol, butadiene, diols, 1,3 propanediol, 1,4 propanediol, succinic acid, adipic acid, nylon precursors, citric acid, malic acid, polyols, and erythritol.

EXEMPLIFICATION

Example 1

Transformed Cells that Comprise a Melamine Degradation Pathway

Cells such as *Yarrowia lipolytica, Saccharomyces cerevisiae*, and *Escherichia coli* may be engineered to convert melamine into ammonia. Melamine ($C_3N_6H_6$) is a highly nitrogenous compound that can only be degraded by a very limited number of organisms, including *Rhodococcus* sp. Strain Mel. Incorporating the pathway for melamine degradation into a cell, accompanied with a modification in a fermentation mixture to use melamine as the predominant nitrogen source, generates a more robust industrial production solution applicable to a number of applications. The advantage of this modification is significant enough to provide advantage in multiple applications including situations where the core technology is a significant genetic burden on the organism.

Genes from Table 1, or suitable homologs, are cloned into a host strain such as *Yarrowia lipolytica, Saccharomyces cerevisiae*, or *Escherichia coli*. Enzymes native to the host organism, such as allophante hydrolase or guanine deaminase are optionally overexpressed with a heterologous promoter. Functional expression is assayed by enzymatic activity and the ability to confer nitrogen-limited growth on the appropriate pathway intermediate. Ultimately, strains able to degrade melamine are selected for improved utilization of the pathway via melamine limited continuous culturing or other selective methods. Similar strategies can be devised for the nitrogen compounds listed in Table 2.

Example 2

Vector Construction Via Yeast Mediated Ligation

Figure 3:
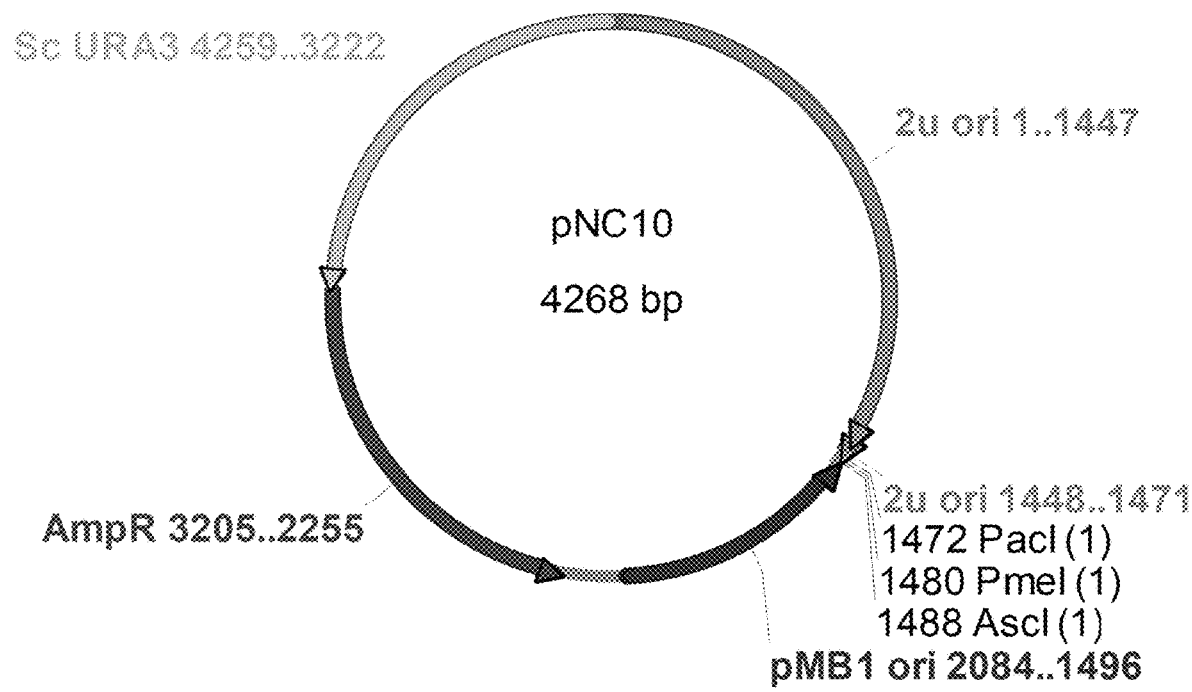
FIGS. 3-10 depict various plasmids of the invention.

Vector pNC10 (SEQ. ID NO: 55) contains an *E. coli* pMB1 origin of replication and ampicillin resistance gene, a *Saccharomyces cerevisiae* 2 μm origin of replication and URA3 gene, and a multiple cloning site containing the 8-bp recognition sequences for PacI, PmeI, and AscI. DNA of interest is inserted in the multiple cloning site via yeast mediated homologous recombination (YML) cloning (Applied & Environmental Microbiology, 72:5027-36 (2006); Plasmid, 62:88-97 (2009)). Briefly, target DNA sequences are amplified by PCR using primers with 20-40 by overhang homology to adjacent DNA segments in the final vector. pNC10 or another suitable base vector is then restriction digested, creating a linearized plasmid. PCR products and linear plasmid are transformed in *S. cerevisiae*, and the native *S. cerevisiae* gap repair mechanism assembles an intact plasmid based on homology overhangs (FIG. 3).

The complete vector is isolated from *S. cerevisiae* via a DNA extraction protocol and used to transform *E. coli* or other bacterial species for subsequent amplification. Concentrated vector can then be recovered from *E. coli* via a DNA plasmid mini-prep or other suitable standard molecular biology protocols.

Example 3

Expression of Melamine Assimilation Enzymes in *E. coli*

Genes from Table 1, or suitable homologs, are cloned into a host strain such as *Escherichia coli*. Enzymes native to the host organism, such as allophante hydrolase or guanine deaminase may be overexpressed with a heterologous promoter.

Figure 5:
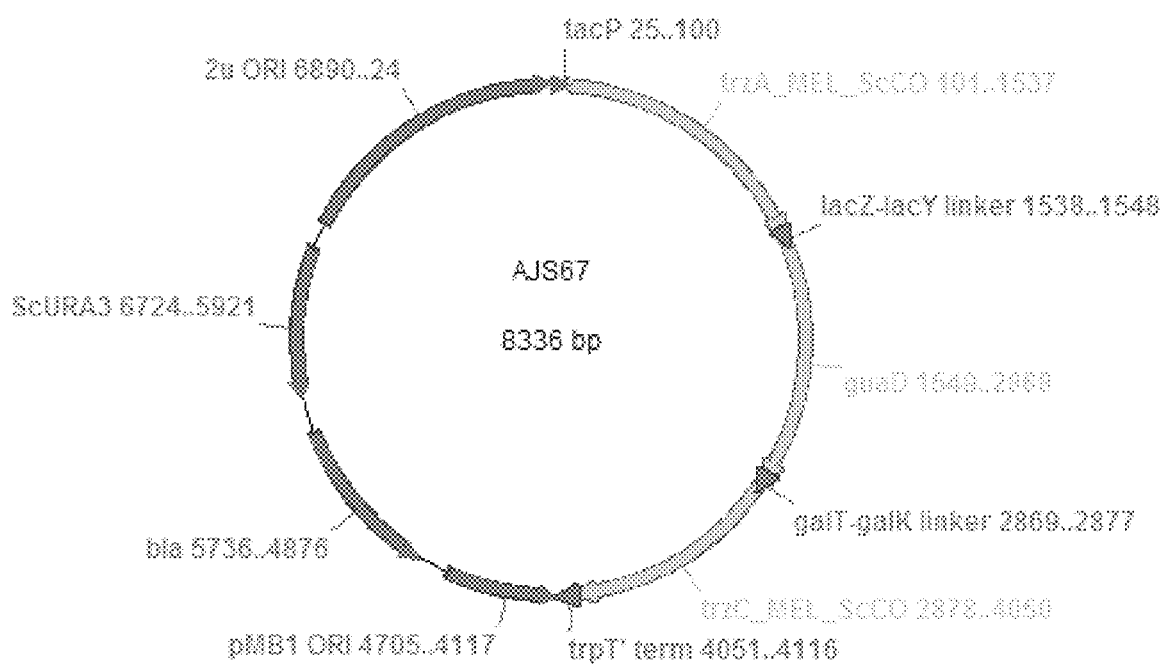
Figure 6:
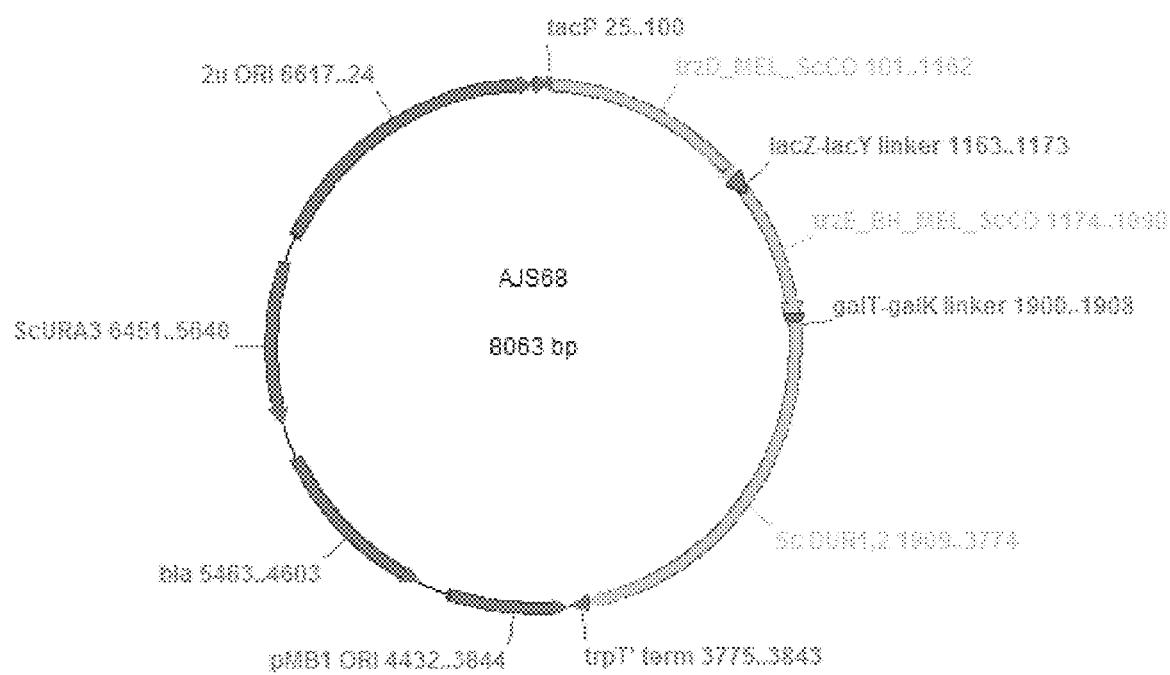
Figure 7:
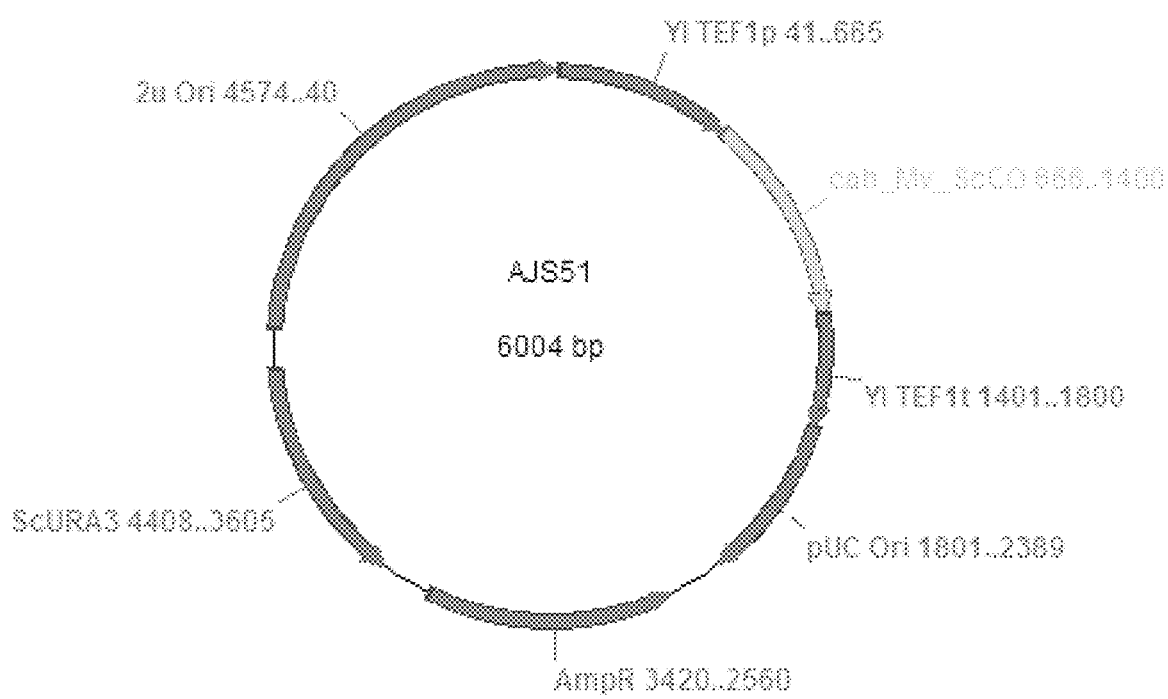

Melamine assimilation genes, or a subset of them, can be expressed in *E. coli* by the construction of a vector using the yeast mediated ligation described above. Expression vectors consist of an *E. coli* functional promoter, a gene encoding an enzyme of the melamine assimilation pathway, and an *E.* coli functional terminator. Alternatively, several genes can be expressed from a single promoter as part of a gene operon; in this case inter-gene linker sequences are placed between genes. Sequences that can act as promoters, terminators, and linkers are listed below, as well as two representative *E. coli* expression plasmids, AJS67 (FIG. 5, expressing genes for degradation of melamine to cyanuric acid with release of three $NH_3$ per melamine) and AJS68 (FIG. 6, expressing genes for degradation of cyanuric acid to $NH_3$ and $CO_2$ with release of three $NH_3$ per cyanuric acid).

```
E. coli Ptach promoter:
                                        SEQ ID NO: 103
agctggtgacaattaatcatcggctcgtataatgtgtggaattgaat
cgatataaggaggttaatca E. coli trpT' terminator:
                                        SEQ ID NO: 104
ctcaaaatatattttccctctatcttctcgttgcgcttaatttgact
aattctcattagcgaggcgcgcctttccataggctccgcccc
``` inter-gene operon linkers

```
            lacZ-lacY linker:
                                        SEQ ID NO: 105
ggaaatccatt galT-galK linker:
                                        SEQ ID NO: 106
ggaacgacc
```

Functional expression is assayed by enzymatic activity and the ability to confer nitrogen-limited growth on the appropriate pathway intermediate. Ultimately, strains able to degrade compounds in the melamine degradation pathway are selected for improved utilization of the pathway via selective methods. Similar strategies are devised for the nitrogen compounds listed in Table 2.

Example 4

Expression of Cyanamide Assimilation Enzymes in *E. coli*

Figure 8:
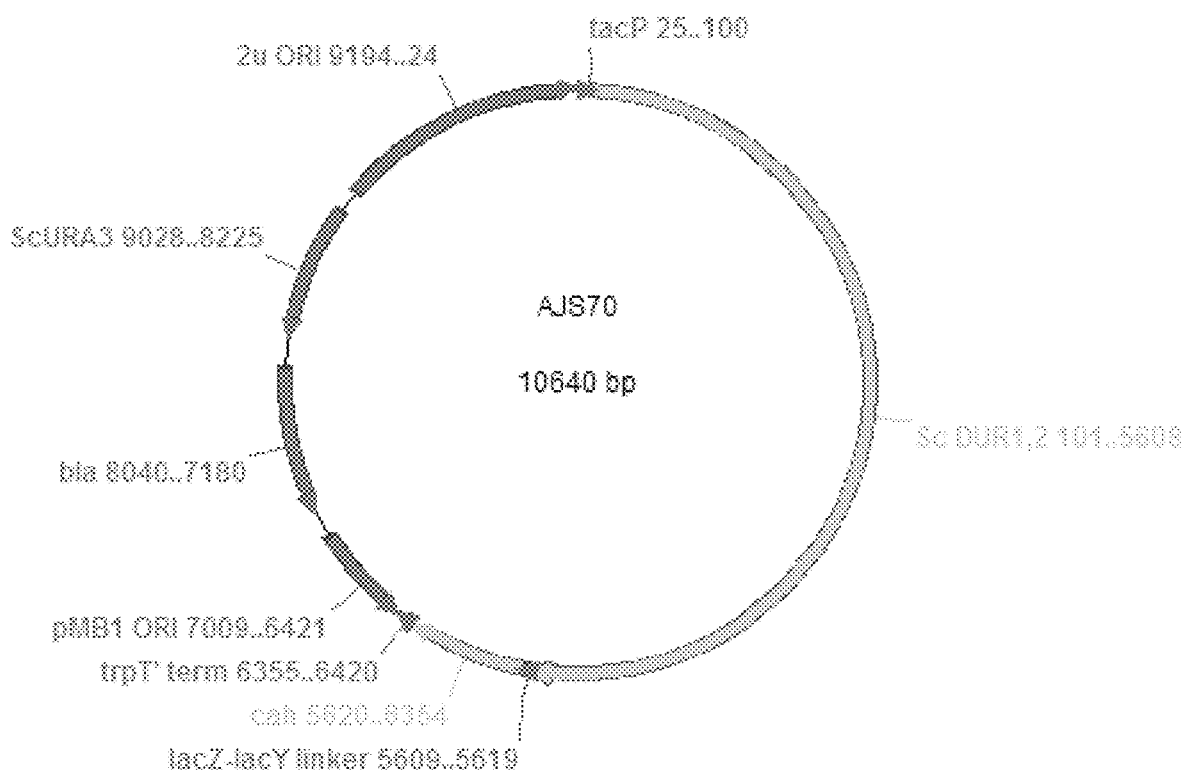

The gene expression methods described in Example 3 can also be used in Example 4. *E. coli* strains are unable to utilize urea as a nitrogen source, and thus, these additional conversion steps are also engineered. Either a urea carboxylase/ allophante hydrolase system or a urease enzyme with appropriate accessory enzymes must be expressed in addition to a cyanamide hydrolase. Urease can be found in some *E. coli* isolates (Collins & Falkow, J. Bacteriology 172:7138-44 (1990)) or heterologously expressed (Cussac et al., J. Bacteriology, 174:2466-73 (1992)). Alternatively, the DUR1,2 genes from *S. cerevisiae* may be expressed, as shown in plasmid AJS70 (FIG. 8), along with a cyanamide hydratase.

Example 5

Expression of Melamine Assimilation Enzymes in *E. coli*

Several *E. coli* strains containing partial or complete melamine utilization pathways were constructed, as shown in Tables 7 and 8. Vector and strain construction was as described in Examples 1-4. All vectors contain the ampicillin resistance gene, and 100 ug/mL ampicillin was added to all culture medium. These strains were grown in MOPS defined medium with different nitrogen sources.

*E. coli* strains and melamine utilization genes (steps correspond to FIG. 1):

NS88—triA (step 1)
NS89—trzA, guaD, trzC (steps 1, 2, 3)
NS90—trzD, trzE, DUR1,2 (steps 4, 5, 6)
NS91—none (control strain)
NS93—triA, native guaD selected for improved ammeline utilization (steps 1, 2)
NS103—triA, guaD, trzC (steps 1, 2, 3)
NS109—triA, guaD, trzC, trzD 12227, trzE, DUR1,2 (steps 1-6)
NS110—triA, guaD, trzC, atzD ADP, trzE, DUR1,2 (steps 1-6)

TABLE 7

| Plasmid | Seq ID | Description | Genotype |
| --- | --- | --- | --- |
| pNC10 | 55 | *E. coli* and *S. cerevisiae* cloning/shuttle vector | Amp, ura3 |
| pNC53 | 56 | *E. coli* promoter (pTac)-terminator (trpT') cloning vector (AJS52) | Amp, ura3 |
| pNC67 | 57 | *E. coli*, *S. cerevisiae*, and *Y. lipolytica* shuttle vector | Amp, ura3, Hyg, Nat |
| pNC85 | 58 | *E. coli* triA expression vector (AJS69) | Amp, ura3 |
| pNC86 | 59 | *E. coli* trzA, guaD, trzC expression vector (AJS67) | Amp, ura3 |
| pNC87 | 60 | *E. coli* trzD, trzE, DUR1,2 expression vector (AJS68) | Amp, ura3 |
| pNC93 | 61 | *S. cerevisiae* cah expression vector (AJS76) | Amp, ura3, Hyg |
| pNC96 | 62 | *S. cerevisiae* trzE MEL expression vector (AJS79) | Amp, ura3, Hyg |
| pNC97 | 63 | *S. cerevisiae* trzE RI expression vector (AJS80) | Amp, ura3, Hyg |
| pNC101 | 64 | *E. coli* trzC__12227, guaD, triA expression vector (AJS83) | Amp, ura3 |
| pNC120 | 65 | *E. coli* trzD__12227, trzE, DUR1,2 trzC__12227, guaD, triA expression vector (AJS88a) | Amp, ura3 |
| pNC121 | 66 | *E. coli* atzD__ADP, trzE, DUR1,2 trzC__12227, guaD, triA expression vector (AJS88b) | Amp, ura3 |

TABLE 8

| Strain | Description | Culture Collection Designation |
| --- | --- | --- |
| NS21 | *Eschericha coli* K12 | NRRL B-3707 |
| NS88 | *Eschericha coli* K12 with pNC85 | |
| NS89 | *Eschericha coli* K12 with pNC86 | |
| NS90 | *Eschericha coli* K12 with pNC87 | |
| NS91 | *Eschericha coli* K12 with pNC53 | |
| NS93 | *Eschericha coli* K12 with pNC85 selected for ammeline utilization | |
| NS103 | *Eschericha coli* K12 with pNC101 | |
| NS106 | *Eschericha coli* MG1655 | ATCC 47076 |
| NS107 | *Eschericha coli* B | ATCC 11303 |
| NS108 | *Eschericha coli* Crooks | ATCC 8739 |

TABLE 8-continued

| Strain | Description | Culture Collection Designation |
|---|---|---|
| NS109 | Eschericha coli K12 with pNC120 | |
| NS110 | Eschericha coli K12 with pNC121 | |
| NS120 | Eschericha coli MG1655 with pNC53 | |
| NS121 | Eschericha coli MG1655 with pNC121 | |
| NS122 | Eschericha coli B with pNC121 | |
| NS123 | Eschericha coli Crooks with pNC53 | |
| NS124 | Eschericha coli Crooks with pNC121 | |
| NS8 | Saccharomyces cerevisiae | NRRL Y-2223 |
| NS22 | Saccharomyces cerevisiae industrial ethanol strain | |
| NS98 | Saccharomyces cerevisiae industrial ethanol strain with pNC96 | |
| NS99 | Saccharomyces cerevisiae industrial ethanol strain with pNC97 | |
| NS100 | Saccharomyces cerevisiae industrial ethanol strain with pNC67 | |
| NS101 | Saccharomyces cerevisiae industrial ethanol strain with pNC93 | |
| NS111 | Saccharomyces cerevisiae NRRL Y-2223 with pNC93 | |
| NS112 | Saccharomyces cerevisiae NRRL Y-2223 with pNC67 | |

Figure 11:
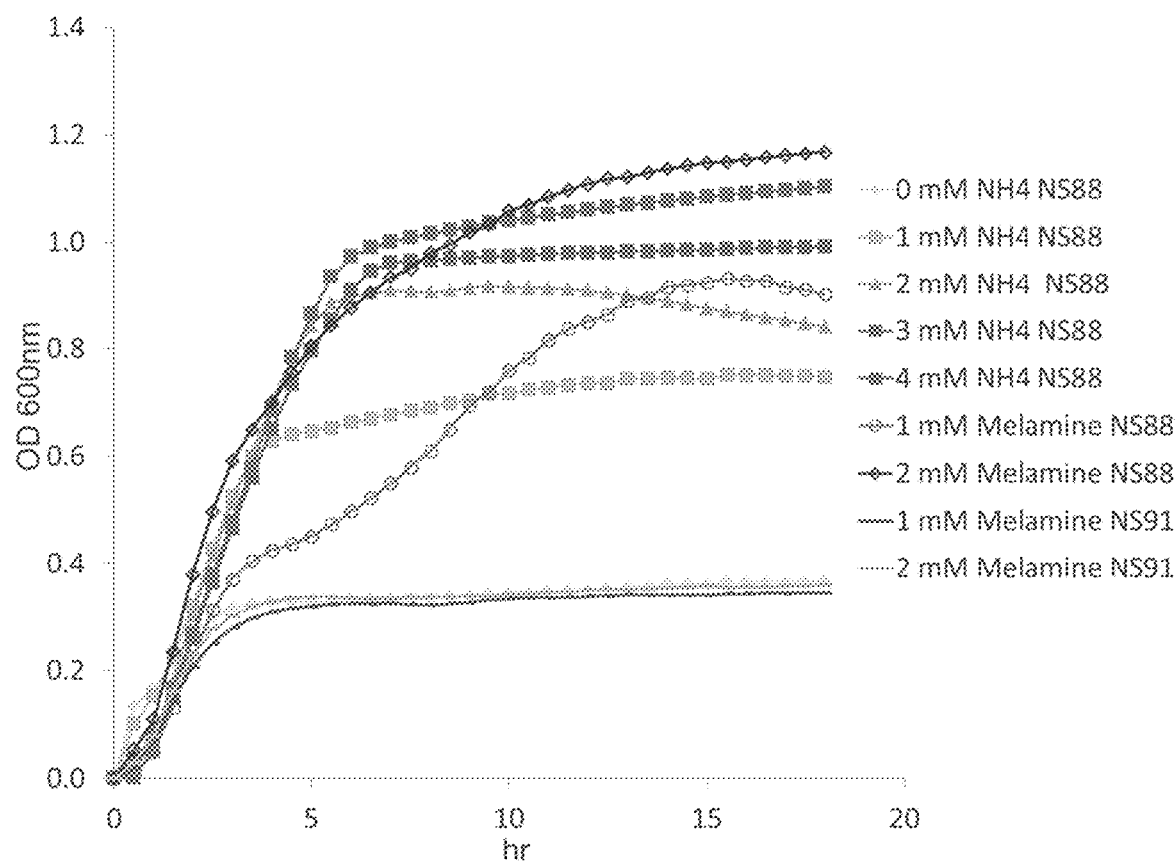
FIG. 11 depicts the growth progress of NS88 and NS91 (control) in media containing various concentrations of ammonium ion or melamine.

FIG. 11 shows the growth progress of NS88 and NS91 (control) in media containing various concentrations of ammonium chloride or melamine. NS88 grown on 1 mM melamine reaches an optical density comparable to that of the equivalent use of 2 mM ammonium chloride, suggesting that 2 mM ammonia are liberated from melamine by triA and the natively encoded guaD genes. The control strain NS91 does not grow with melamine as nitrogen source.

Figure 12:
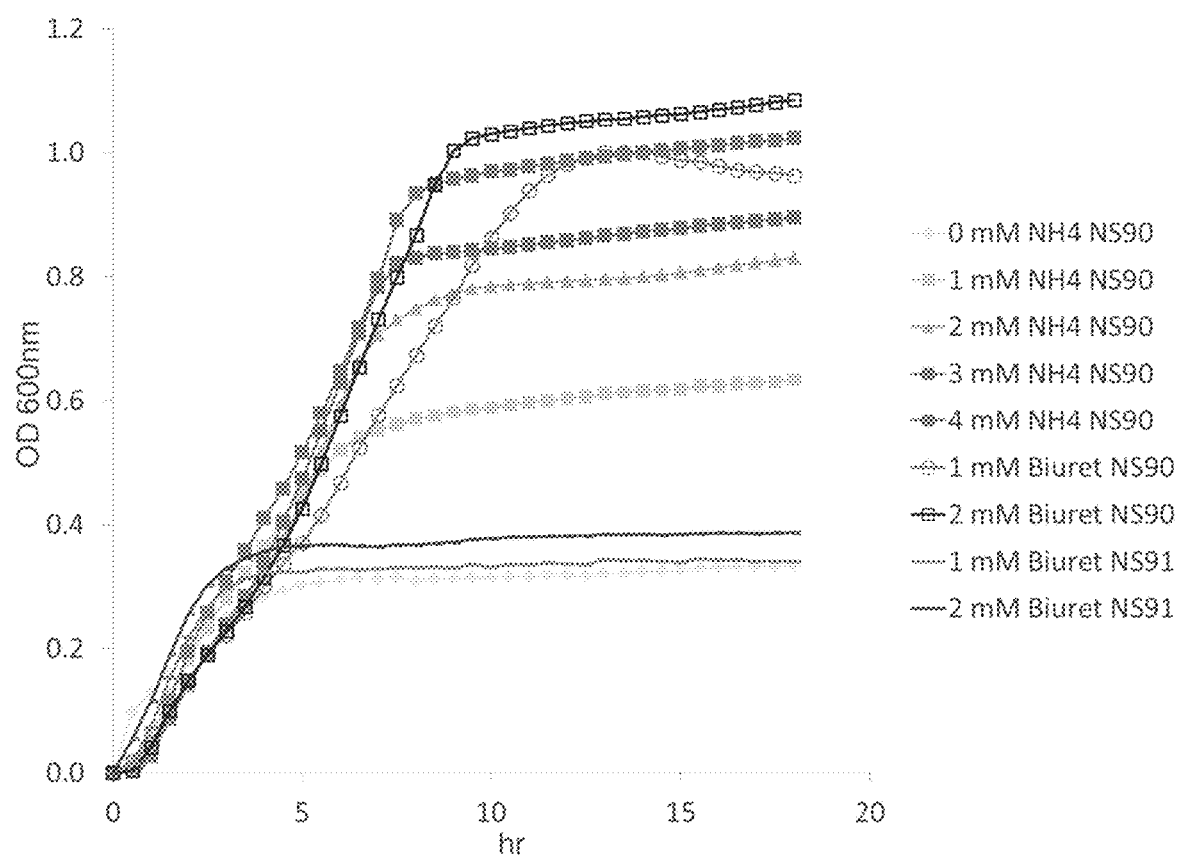
FIG. 12 depicts the growth progress of NS90 and NS91 (control) in media containing various concentrations of ammonium ion or biuret.

FIG. 12 shows the growth progress of NS90 and NS91 (control) in media containing various concentrations of ammonium chloride or biuret. NS90 grown on 1 mM biuret reaches an optical density comparable to that of the equivalent use of 3 mM ammonium chloride, suggesting that 3 mM ammonia are liberated from biuret by trzE and the DUR1,2. The control strain NS91 does not grow with biuret as nitrogen source.

Figure 14:
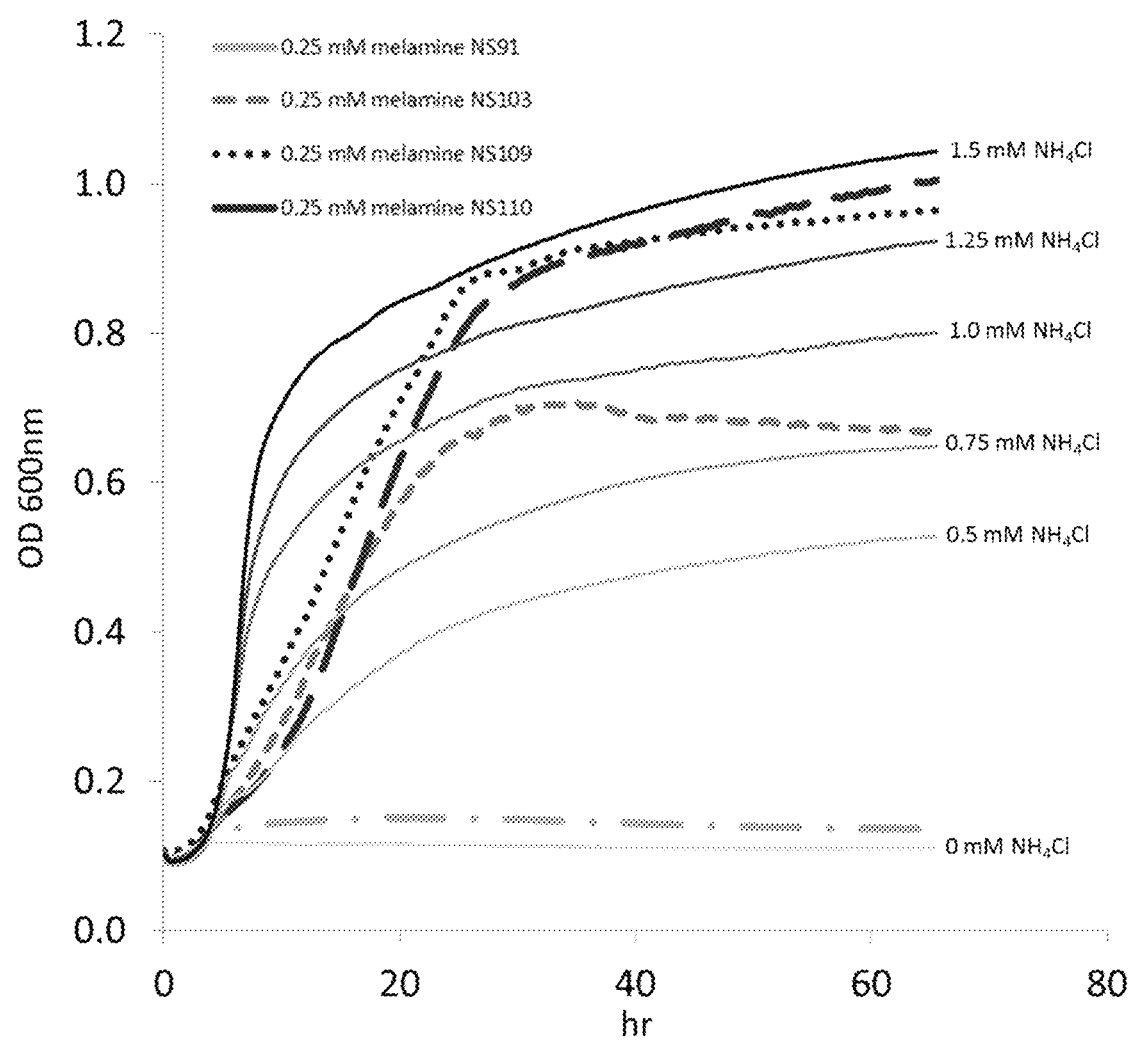
FIG. 14 depicts the growth of four organisms of the invention (NS91=control) on 0.25 mM melamine, as compared to the standard curves for a native organism on $NH_4Cl$. Because melamine has six nitrogen atoms, organisms having the ability to utilize melamine should be approximately six times more efficient (see, for example, NS110 on 0.25 mM melamine, as compared to a native organism on 1.5 mM $NH_4Cl$).

FIG. 14 shows the growth progress of NS91, NS103, NS109, and NS110 in medium containing 0.25 mM melamine as the sole nitrogen source. An average of all four strains grown on different ammonium chloride concentrations from 0 to 1.5 mM is also shown as a standard curve for growth with limiting nitrogen. NS91 grown on melamine is similar to the 0 mM ammonium chloride control. NS103 grown on 0.25 mM melamine is similar to 1-0.75 mM ammonium chloride, suggesting it is utilizating, approximately, the predicted 3 mM ammonia per 1 mM melamine. Strains NS109 and NS110 grown on 0.25 mM melamine are similar to 1.5-1.25 mM ammonium chloride, suggesting it is utilizating, approximately, the predicted 6 mM ammonia per 1 mM melamine.

Figure 15:
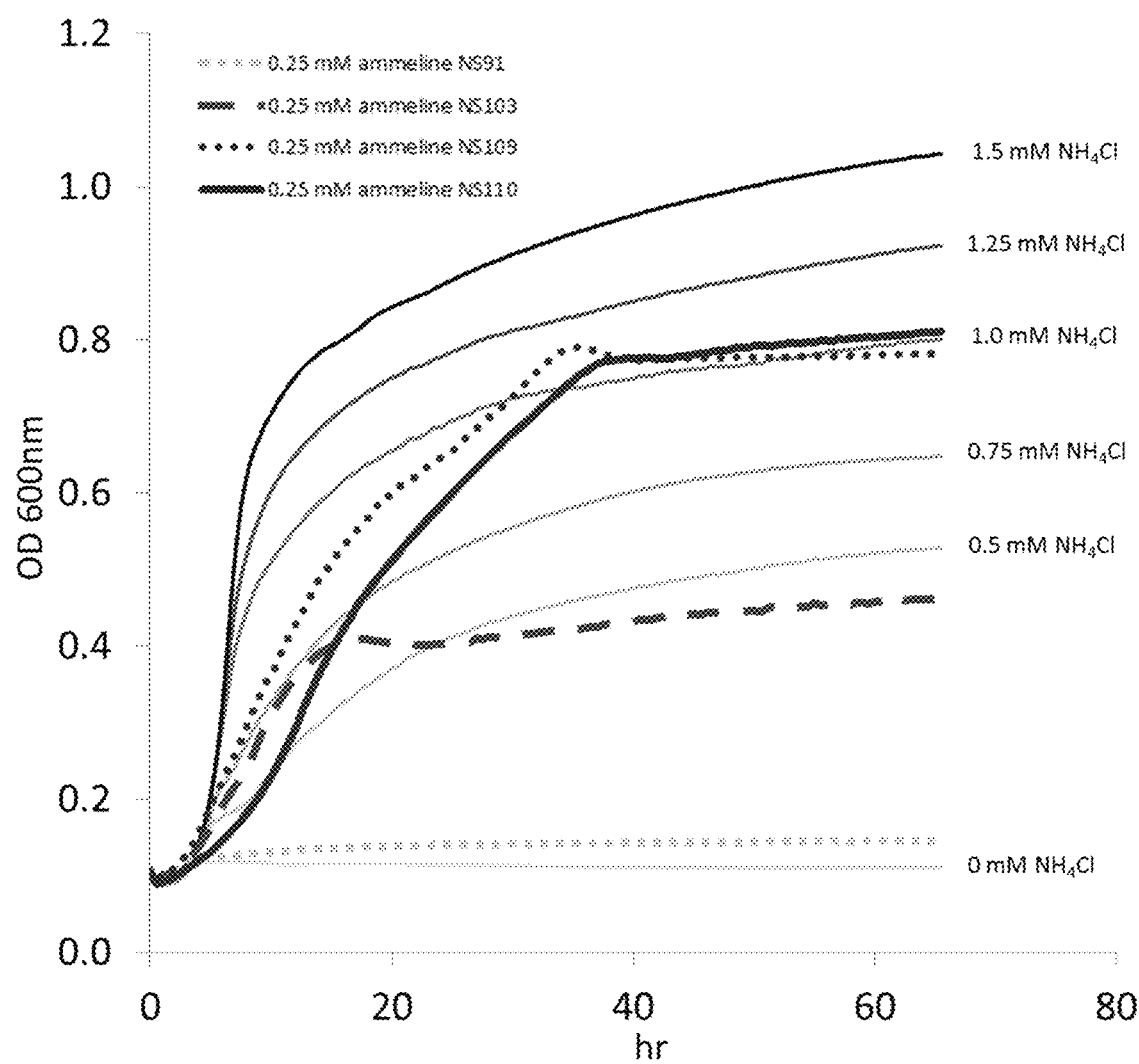
FIG. 15 depicts the growth of four organisms of the invention (NS91=control) on 0.25 mM ammeline, as compared to the standard curves for a native organism on $NH_4Cl$. Because ammeline has five nitrogen atoms, organisms having the ability to utilize melamine should be approximately five times more efficient (see, for example, NS110 on 0.25 mM ammeline, as compared to a native organism on 1.25 mM $NH_4Cl$).

FIG. 15 shows the growth progress of NS91, NS103, NS109, and NS110 in medium containing 0.25 mM ammeline as the sole nitrogen source. An average of all four strains grown on different ammonium chloride concentrations from 0 to 1.5 mM is also shown as a standard curve for growth with limiting nitrogen. NS91 grown on ammeline is similar to the 0 mM ammonium chloride control. NS103 grown on 0.25 mM ammeline is similar to 0.5 mM ammonium chloride, suggesting it is utilizating, approximately, the predicted 2 mM ammonia per 1 mM ammeline. Strains NS109 and NS110 grown on 0.25 mM ammeline are similar to 1.25-1.0 mM ammonium chloride, suggesting it is utilizating, approximately, the predicted 5 mM ammonia per 1 mM ammeline.

Figure 16:
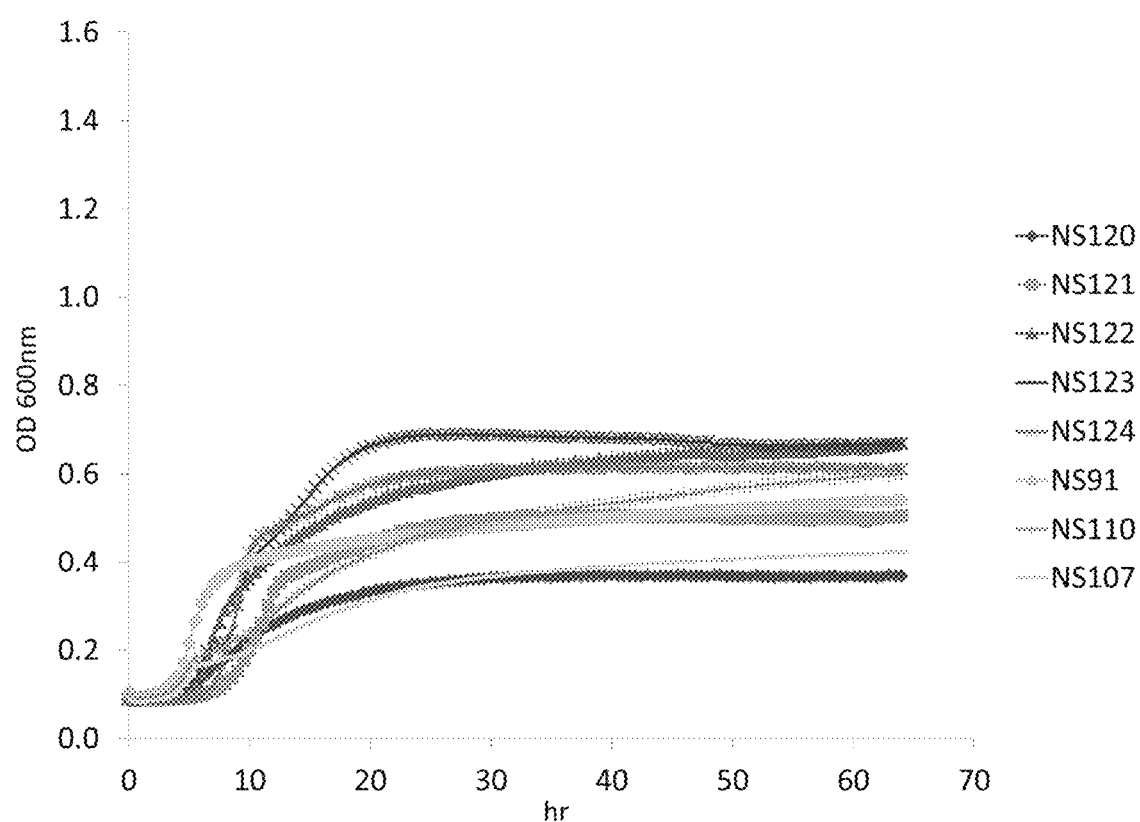
FIG. 16 depicts depicts the growth of various organisms of the invention on 0.5 mM $NH_4Cl$.
Figure 17:
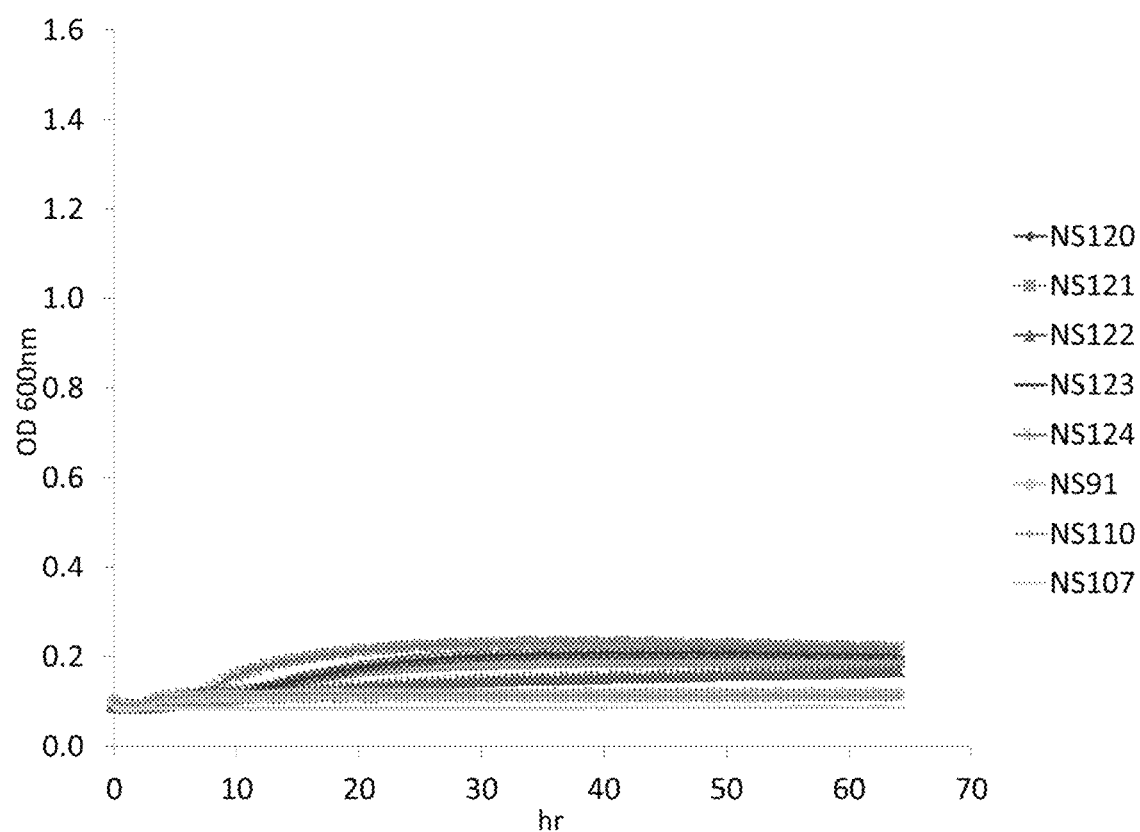
FIG. 17 depicts the growth of various organisms of the invention on a medium containing no nitrogen.
Figure 18:
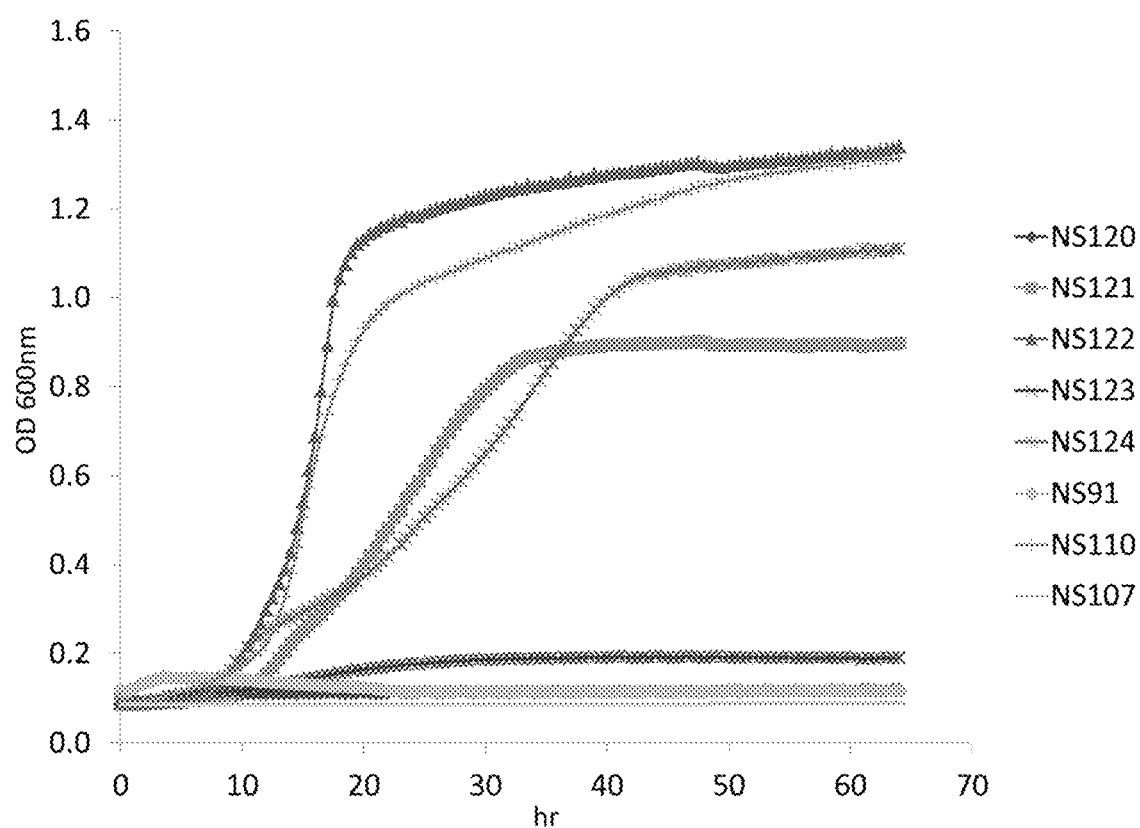
FIG. 18 depicts the growth of various organisms of the invention on a medium containing 0.5 mM melamine.
Figure 19:
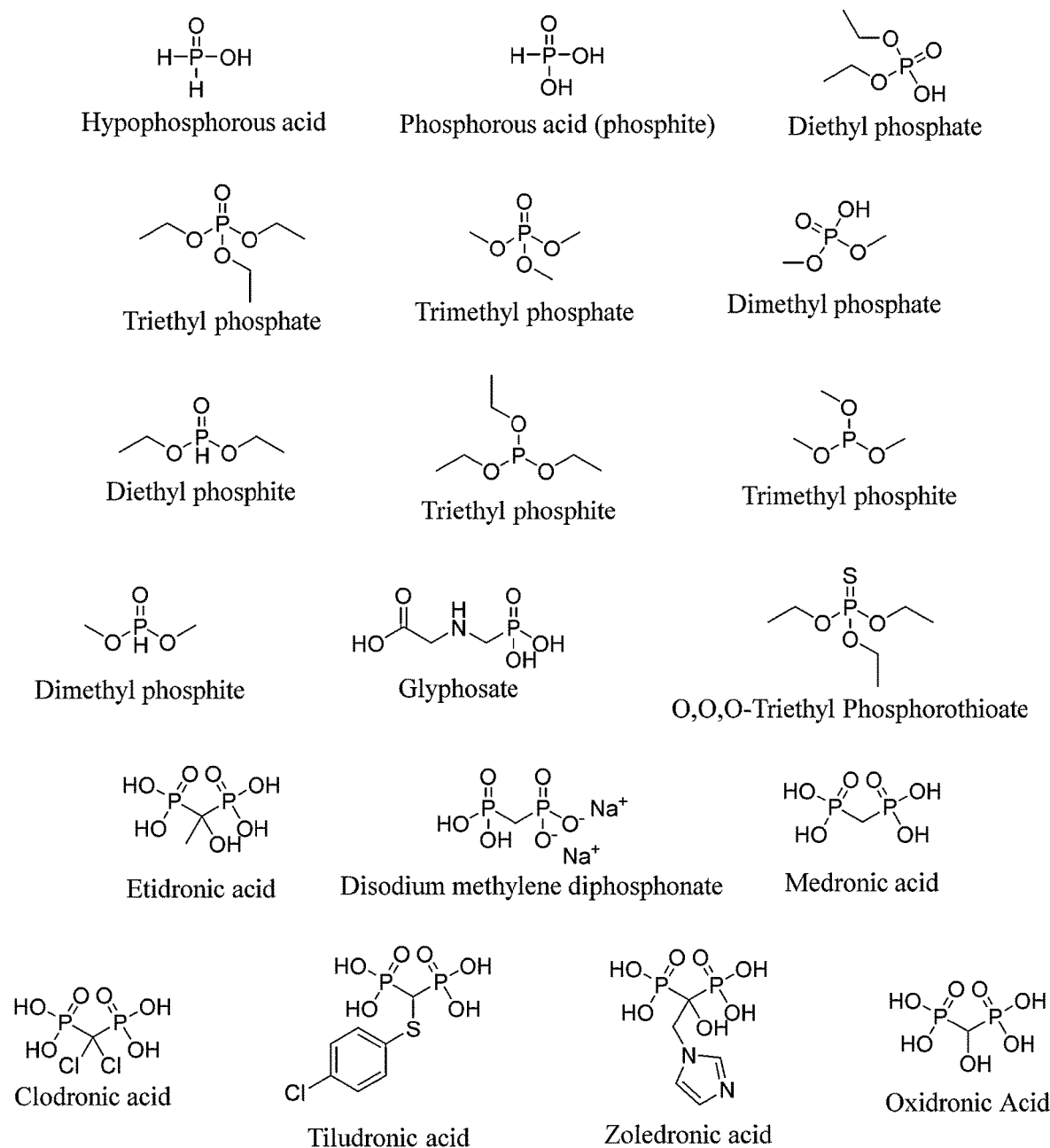
FIG. 19 depicts the names and structures of various organophosphorus compounds.
Figure 20:
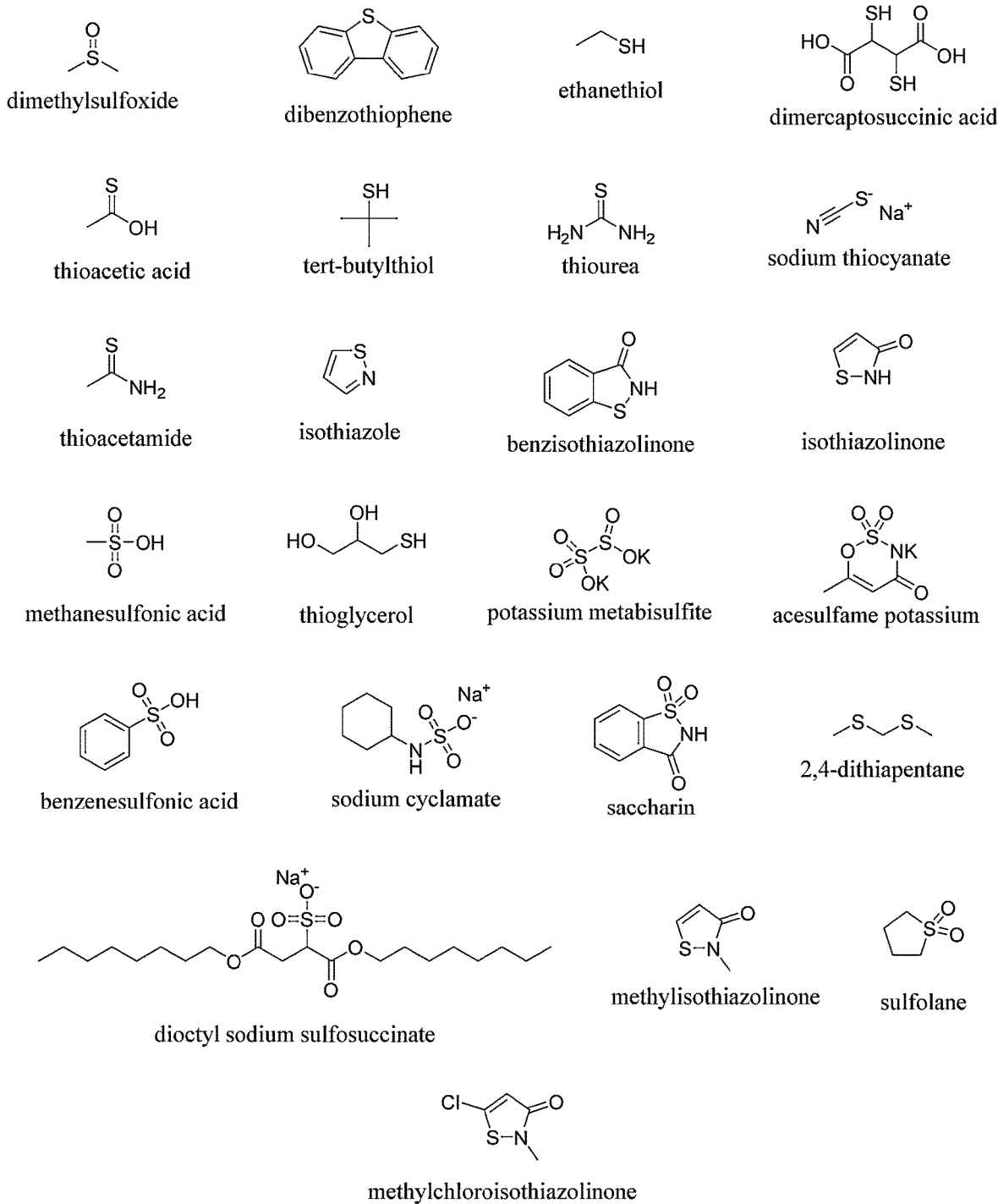
FIG. 20 depicts the names and structures of various organosulfur compounds.

FIGS. 16, 17, and 18 show E. coli strains derived from E. coli K12, E. coli MG1655, E. coli B, and E. coli Crooks (C) containing either pNC121 with the complete melamine utilization pathway, or pNC53, a control vector. See Tables 7 and 8 for strain details. All the strains containing pNC121 are able to grow on 0.5 mM melamine as sole nitrogen source (FIG. 18). This indicates that the melamine utilization pathway is broadly applicable to E. coli strains that are commonly utilized for biotechnology applications.

Strains can also be selected for improved utilization of melamine derived nitrogen sources, in one example NS88 was passaged for 11 serial transfers in MOPS defined medium with 0.5 mM ammeline as sole nitrogen source. After the final passage, single colonies were isolated, and one was designated as NS93. NS93 and NS91 were grown overnight in medium with 0.5 mM ammonium chloride as sole nitrogen source, and then inoculated in medium with 0.5 mM ammeline as sole nitrogen source. NS91 exhibited a maximum growth rate of 0.024 $hr^{-1}$ on ammeline, while NS93 exhibited a maximum growth rate of 0.087 $hr^{-1}$.

Media Utilization

Cultures were grown aerobically at 37° C. with 100 mg/L ampicillin. Pre-cultures were grown in LB media with 100 mg/L ampicillin, washed once with an equal volume of MOPS media containing no nitrogen, and inoculated at 5% v/v of the final fermentation volume. The content of the MOPS medium is outlined in Table 9.

TABLE 9

| MOPS defined medium | mM |
|---|---|
| Glucose | 11.1 |
| $K_2HPO_4$ | 1.32 |
| $K_2SO_4$ | 0.28 |
| $FeSO_4$ | 0.01 |
| $CaCl_2$ | 5E−04 |
| $MgCl_2$ | 0.52 |
| NaCl | 50 |
| MOPS | 40 |
| Tricine | 4 |
| $(NH_4)_6Mo_7O_{24}$ | 3E−06 |
| $H_3BO_3$ | 4E−04 |
| $CoCl_2$ | 3E−05 |
| $CuSO_4$ | 1E−05 |
| $MnCl_2$ | 8E−05 |
| $ZnSO_4$ | 1E−05 |
| Nitrogen source as indicated | 0.25-10 |

*Additionally 100 ug/mL ampicillin is added for plasmid maintenance.

Imaging Cultures in Various Media

Figure 13:
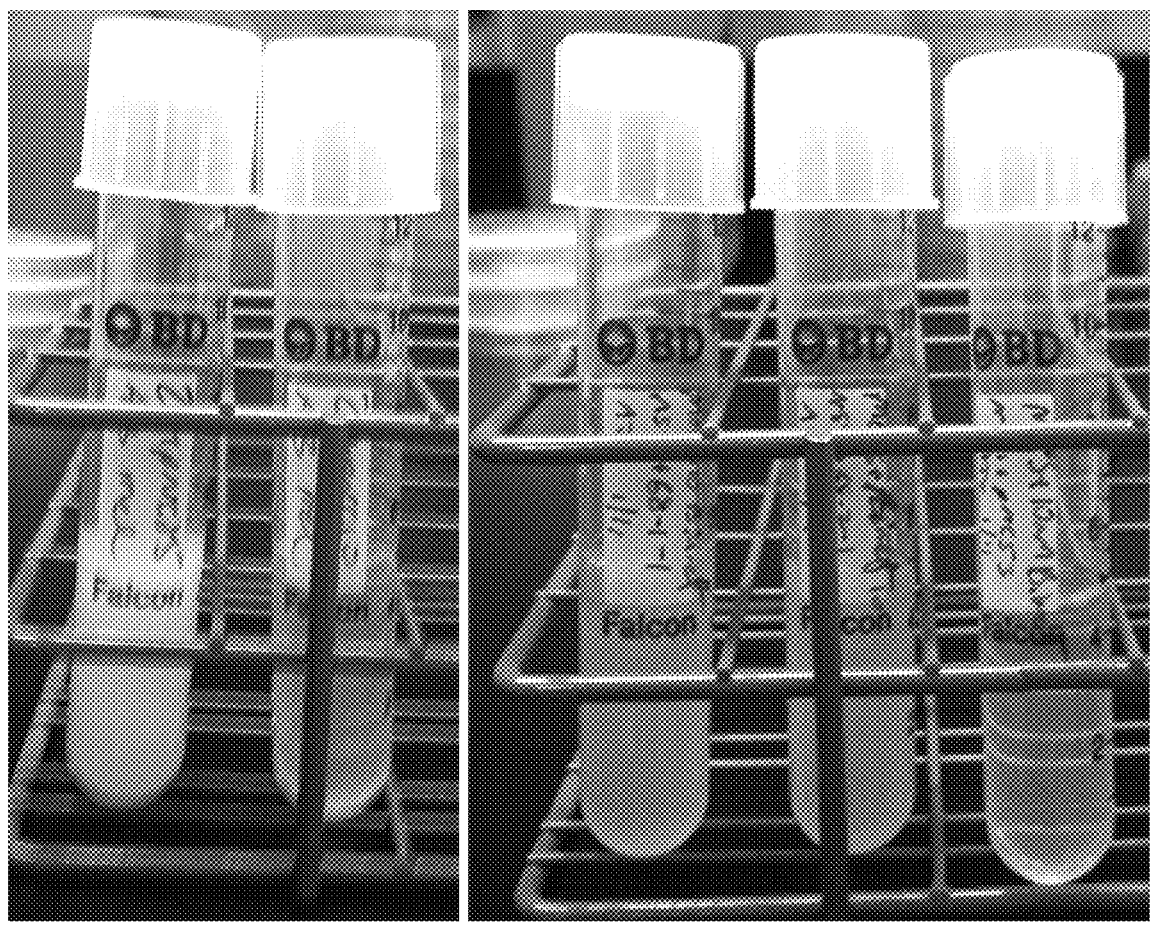
FIG. 13 depicts images, taken after 48 h, of cultures grown in MOPS media with different nitrogen sources. From left to right: NS88 with 10 mM melamine; NS91 with 10 mM melamine; NS90 with 10 mM biuret (replicate 1); NS90 with 10 mM biuret (replicate 2); and NS91 with 10 mM biuret.

Precultures were grown in LB media with 100 mg/L ampicillin, 0.1 mL of each preculture was used to directly inoculate 5 mL MOPS media containing 100 mg/L ampicillin and the indicated nitrogen source. Cells were grown at 37° C. in a drum roller at 30 rpm (FIG. 13).

Example 6

S. cerevisiae Transformation

A 5 mL culture of S. cerevisiae ura3 auxotroph strain is grown overnight in YPD at 30° C. 1.5 mL of the overnight culture is transferred into 50 mL of fresh YPD (OD~0.3) and shaken at 200 rpm, 30° C. in a flask. The culture is grown for approximately 4-5 hrs to an OD of 1.0.

Cells at centrifuged at >5,000 rpm for 1 min and resuspended in 50 mL of sterile water, then centrifuged again at >5,000 rpm for 1 min.

The supernatant is removed, 1 mL of 100 mM lithium acetate (LiAc) is added to the cell pellet, and the pellet is transferred to a 1.5 mL tube.

The cells are centrifuged for 10 sec at >12,000 rpm, the supernatant is removed, and the cells are resuspend in 400-800 μL of 100 mM LiAc (each transformation uses 50 μL of this cell suspension).

A transformation master mix is prepared: 240 μL of 50% PEG-3350, 36 μL of 1 M LiAc, 50 μL of 2 mg/mL Salmon sperm DNA (prepared by boiling for 10 min and rapidly cooling to 4° C.). A transformation reaction is prepared by adding to a 1.5 mL tube 5 μL of digested vector, 5 μL of each PCR insert (approximately 100-200 ng DNA), water to a final volume to 34 μL, 326 μL master mix, and 50 uL of cell suspension. The tubes are vortexted to completely mix their contents. The transformation reaction mixture is incubated for 30 min at 30° C., then mixed by inverting and placed in a 42° C. water bath for 30 min.

The cells are centrifuged for 10 sec at >12,000 rpm, the PEG mixture is removed, and the cells are resuspended in 1 mL of sterile water. The cells are centrifuged again, 800 μL of supernatant is removed, the cells are resuspended in the remaining supernatant, and the cells are spread onto SD-URA plates. The plates are incuabed at 30° C. for 2-4 days.

Example 7

Expression of Melamine Assimilation Enzymes in S. cerevisiae

Melamine assimilation genes, or a subset of them, can be expressed in S. cerevisiae by constructing a vector using the yeast mediated ligation described above. Expression vectors consist of an S. cerevisiae functional promoter, a gene encoding an enzyme of the melamine assimilation pathway, and an S. cerevisiae functional terminator. Assemblies of the promoter-gene-terminator motif can be incorporated into a single strain, either on a replicating plasmid or integrated into a chromosome. Possible promoters and terminators are listed below. A representative plasmid, expressing the trzA melamine hydratase under control of the Y. lipolytica TEF1 promoter and terminator is shown below.

Figure 4:
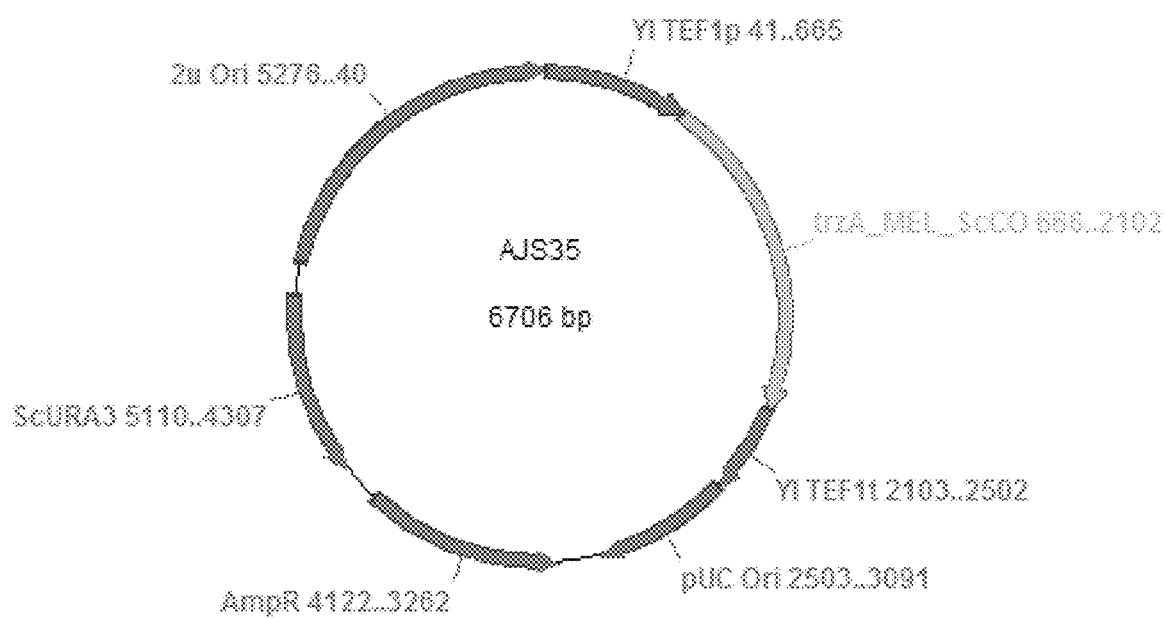

Plasmid AJS35 is an example of the melamine dehydratase trzA transcribed via the Y. lipolytica TEF1 promoter and terminator (FIG. 4).

Strains NS98 and NS99 are industrial S. cereviaie strains carrying plasmids pNC96 (hyg$^R$, and a codon optimized trzE from Rhodococcus sp. MEL and pNC97 (hyg$^R$, and a codon optimized trzE from Rhizobium leguminosarum), respectively. Strain NS100 is the same industrial S. cerevisiae stain carrying plasmid pNC67 (hyg$^R$, nat$^R$) which serves as a control strain.

Strains NS98, NS99, and NS100 were grown in defined YNB medium with 10 mM urea and 100 μg/mL hygromycin to stationary phase aerobically at 30° C. 1/1000 v/v inoculations were then made into the same defined medium with either 10 mM urea, 10 mM biuret, or no additional nitrogen and grown under the same conditions. Optical density was measured after 72 hours, as shown in Table 10.

TABLE 10

OD600 of yeast strains grown for 72 hours with different nitrogen sources

| | Optical Density 600 nm | | |
|---|---|---|---|
| | NS98 | NS99 | NS100 |
| no nitrogen | 1.43 | 1.37 | 1.09 |
| 10 mM urea | 5.09 | 5.26 | 5.22 |
| 10 mM biuret | 2.55 | 2.18 | 1.21 |

Strains NS98 and NS99 were able to grow to an optical density approximately double that of NS100 in medium containing biuret, and also approximately double that with medium with no nitrogen supply. This shows that S. cerevisiae strains expressing trzE genes are advantaged in their utilization of biuret.

Nucleotide sequences that can be used as promoters for gene transcription in S. cerevisiae are shown in SEQ ID NO: 89-95 and nucleotide sequences that can be used as transcription terminators are shown in SEQ ID NO: 96-102.

Example 8

Expression of Cyanamide Assimilation Enzyme in S. cerevisiae

The gene expression methods described in example 5 can also be used in example 7. S. cerevisiae has the native ability to convert urea to $NH_3$ and $CO_2$ via the actions of urea carboxylase and allophante hydrolase, encoded in the fusion gene DUR1,2. Therefore, functional expression of cyanamide hydrolase is sufficient to convert cyanamide to $NH_3$. A cyanamide hydratase expression vector (e.g., FIGS. 9 and 10) may comprise the Y. lipolytica TEF1 promoter and terminator and a S. cerevisiae codon-optimized cyanamide hydratase (cah) from Myrothecium verrucaria.

Example 9

Organisms Engineered to Utilize Cyanamide

Organisms

NS100—industrial S. cerevisiae strain with pNC67 (hyg$^R$, nat$^R$)

NS101—industrial S. cerevisiae strain with pNC93 (hyg$^R$, cah)

NS111—S. cerevisiae NRRL Y-2223 with pNC93 (hyg$^R$, cah)

NS112—S. cerevisiae NRRL Y-2223 with pNC67 (hyg$^R$, nat$^R$)

Figure 9:
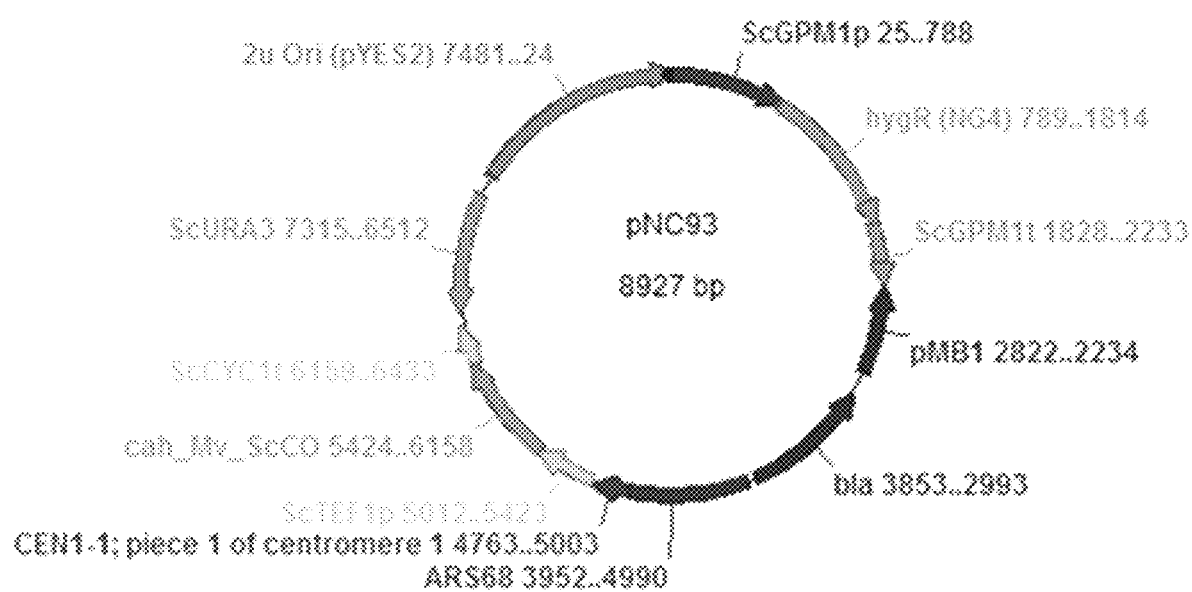
Figure 10:
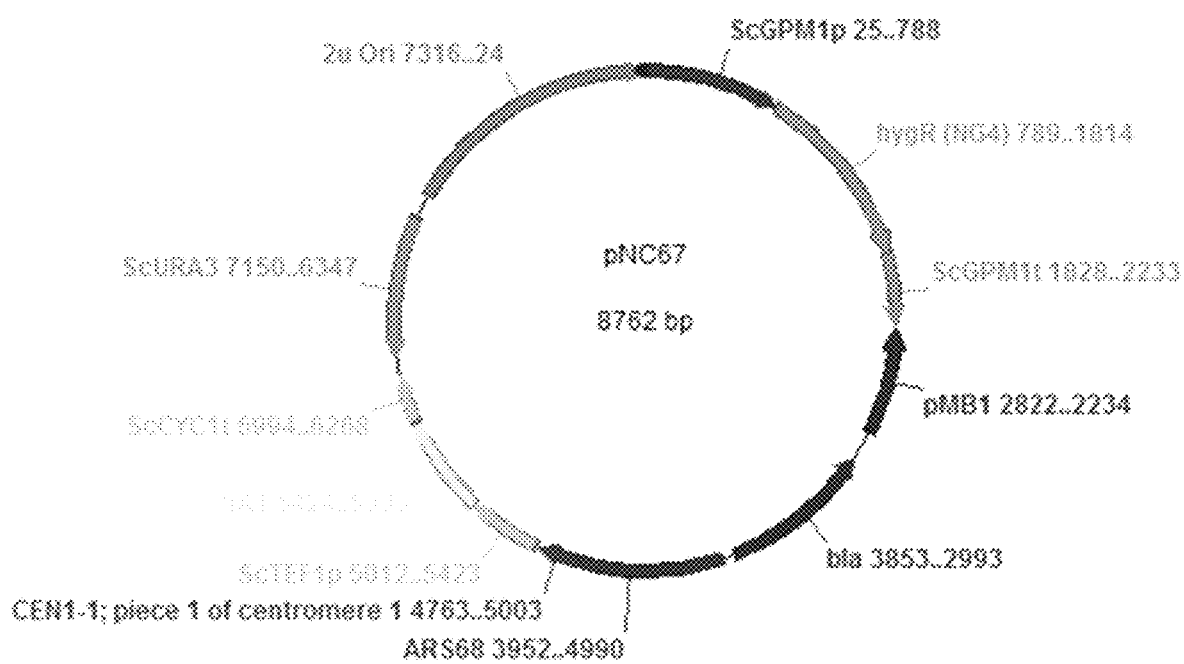

FIG. 9 depicts pNC93, and FIG. 10 depicts pNC67.

Utilization of Cyanamide in Defined Medium

Figure 21:
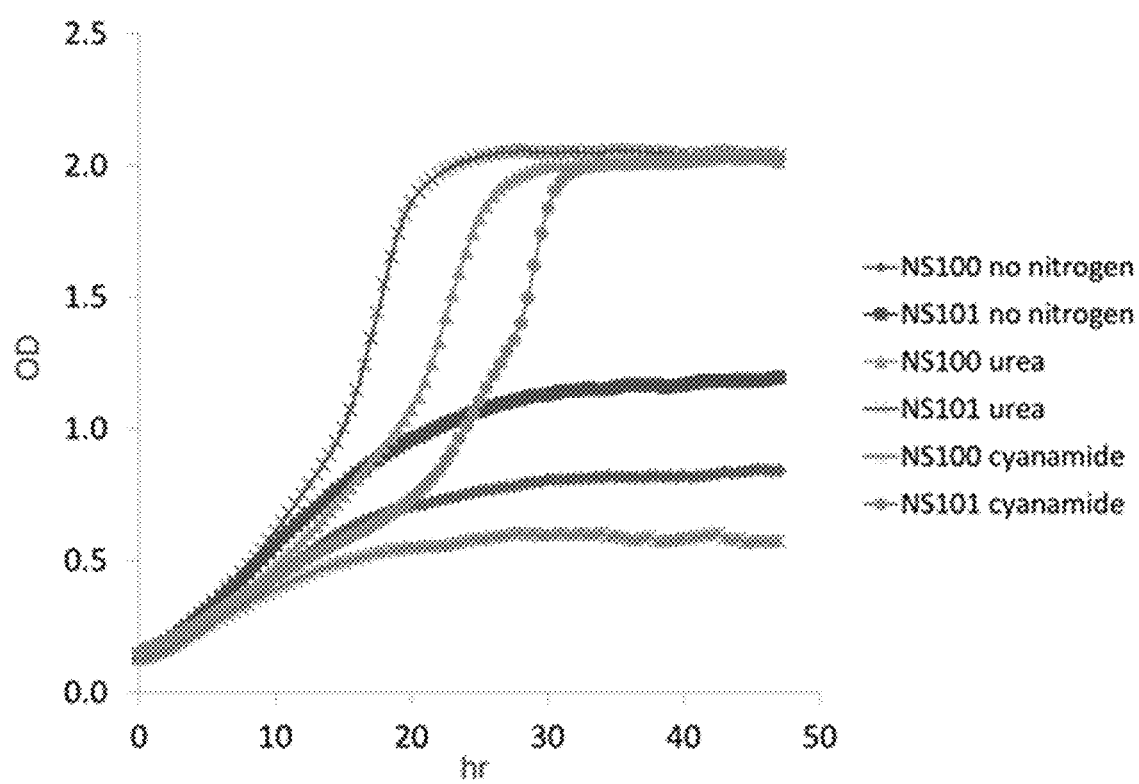
FIG. 21 depicts the growth progress of NS100 (control) and NS101 in media containing no nitrogen source, urea, or cyanamide.

The optical density of NS100 and NS101 grown in defined medium with different nitrogen sources was assessed as follows. NS100 and NS101 were grown overnight in YPD medium, washed once in an equal volume of sterile water, and inoculated at 3.33% v/v. Strain NS101 was able to grow to an optical density with cyanamide comparable to that with urea, while NS100 grew to an optical density comparable to that with no nitrogen present in the medium. Data are averages of 3 replicate wells in a 96 well plate; 150 μL per well. 30° C., YNB medium contained 20 g/L glucose, 1.7 g/L YNB base medium without amino acids or ammonium sulfate, 5 g/L sodium sulfate, 100 μg/mL hygromycin, and either 10 mM urea, 10 mM cyanamide, or no nitrogen source. Inoculation was with 5 μL of culture pregrown for 24 hours in the same medium with urea as nitrogen source (FIG. 21).

Additionally, strains NS100, NS101, NS111, and NS112 were grown in defined YNB medium with 10 mM urea and 100 μg/mL hygromycin to stationary phase aerobically at 30° C. 1/1000 v/v inoculations were then made into the same defined medium with either 10 mM urea, 10 mM cyanamide, or no additional nitrogen and grown under the same conditions. Optical density was measured after 72 hours, as shown in Table 11.

TABLE 11

| | Optical Density 600 nm | | | |
| --- | --- | --- | --- | --- |
| | NS100 | NS101 | NS111 | NS112 |
| no nitrogen | 0.18 | 0.19 | 1.31 | 0.99 |
| 10 mM urea | 3.12 | 3.60 | 3.68 | 3.05 |
| 10 mM cyanamide | 0.05 | 4.66 | 3.09 | 0.15 |

Strains NS101 and NS111, two different *S. cerevisiae* strains carrying the cah gene, were able to grow to an optical density comparable to that with urea; however, NS100 and NS112 only were able to grow to an optical density equal to or lower than in media with no nitrogen source. This shows that multiple *S. cerevisiae* strains are able to utilize cyanamide in the presence of the cah gene.

Competition in Defined Medium

Figure 25:
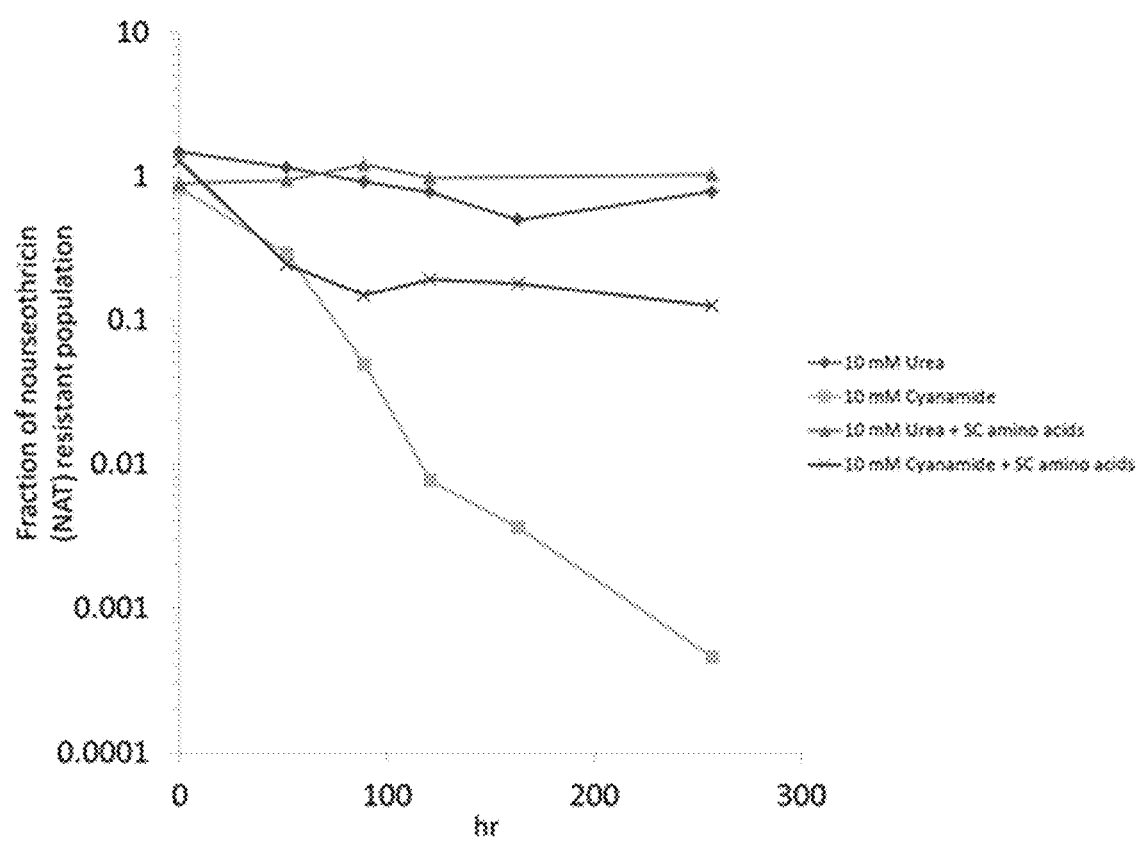
FIG. 25 depicts the growth of an organism of the invention in the presence of an antibiotic on various nitrogen-containing media.

Strains NS100 ($hyg^R$, $nat^R$) and NS101 ($hyg^R$, cah) were grown in defined medium with 100 μg/mL hygromycin with urea as nitrogen source, and then both inoculated into defined medium containing either 10 mM urea or 10 mM cyanamide as nitrogen source. Upon growth to stationary phase, 1/100 v/v serial transfers were made to fresh medium with the same composition. The culture population was monitored via counting the number of $hyg^R$, $nat^R$ colony forming units and subtracting from the number of $hyg^R$ colony forming units. (See FIG. 22 and FIG. 23 for one experiment in defined minimal medium.) A second experiment is shown in FIG. 25. The second experiment included both defined minimal (YNB) and defined complex (YNB+ SC amino acids) medium compositions. The defined YNB medium contained 20 g/L glucose, 1.7 g/L YNB base medium without amino acids or ammonium sulfate, 5 g/L sodium sulfate, and either 10 mM urea, 10 mM cyanamide, or no nitrogen source. Medium compositions are shown below.

| *S. cerevisiae* YNB media (per liter) | |
| --- | --- |
| Glucose | 20 g |
| Biotin | 2 μg |
| Calcium pantothenate | 400 μg |
| Folic acid | 2 μg |
| Inositol | 2000 μg |
| Niacin | 400 μg |
| p-Aminobenzoic acid | 200 μg |
| Pyridoxine hydrochloride | 400 μg |
| Riboflavin | 200 μg |
| Thiamine hydrochloride | 400 μg |
| Boric acid | 500 μg |
| Copper sulfate | 40 μg |
| Potassium iodide | 100 μg |

| *S. cerevisiae* YNB media (per liter) — continued | |
| --- | --- |
| Ferric chloride | 200 μg |
| Manganese sulfate | 400 μg |
| Sodium molybdate | 200 μg |
| Zinc sulfate | 400 μg |
| Potassium phosphate monobasic | 1 g |
| Magnesium sulfate | 500 mg |
| Sodium chloride | 100 mg |
| Calcium chloride | 100 mg |

Additionally a nitrogen source at 10 mM concentration is added, as well as the antibiotics hygromycin (300 ug/mL) or nourseothricin (100 ug/mL), as appropriate for plasmid maintenance.

| SC amino acid composition (total 2 g/L) | |
| --- | --- |
| SC amino acids | mg/L |
| Adenine | 21 |
| L-Alanine | 85.6 |
| L-Arginine | 85.6 |
| L-Asparagine | 85.6 |
| L-Aspartic Acid | 85.6 |
| L-Cysteine | 85.6 |
| Glutamine | 85.6 |
| L-Glutamic Acid | 85.6 |
| Glycine | 85.6 |
| L-Histidine | 85.6 |
| Myo-Inositol | 85.6 |
| L-Isoleucine | 85.6 |
| L-Leucine | 173.4 |
| L-Lysine | 85.6 |
| L-Methionine | 85.6 |
| Para-AminoBenzoic Acid (PABA) | 8.6 |
| L-Phenylalenine | 85.6 |
| L-Proline | 85.6 |
| L-Serine | 85.6 |
| L-Threonine | 85.6 |
| L-Tryptophan | 85.6 |
| L-Tyrosine | 85.6 |
| Uracil | 85.6 |
| L-Valine | 85.6 |

Figure 22:
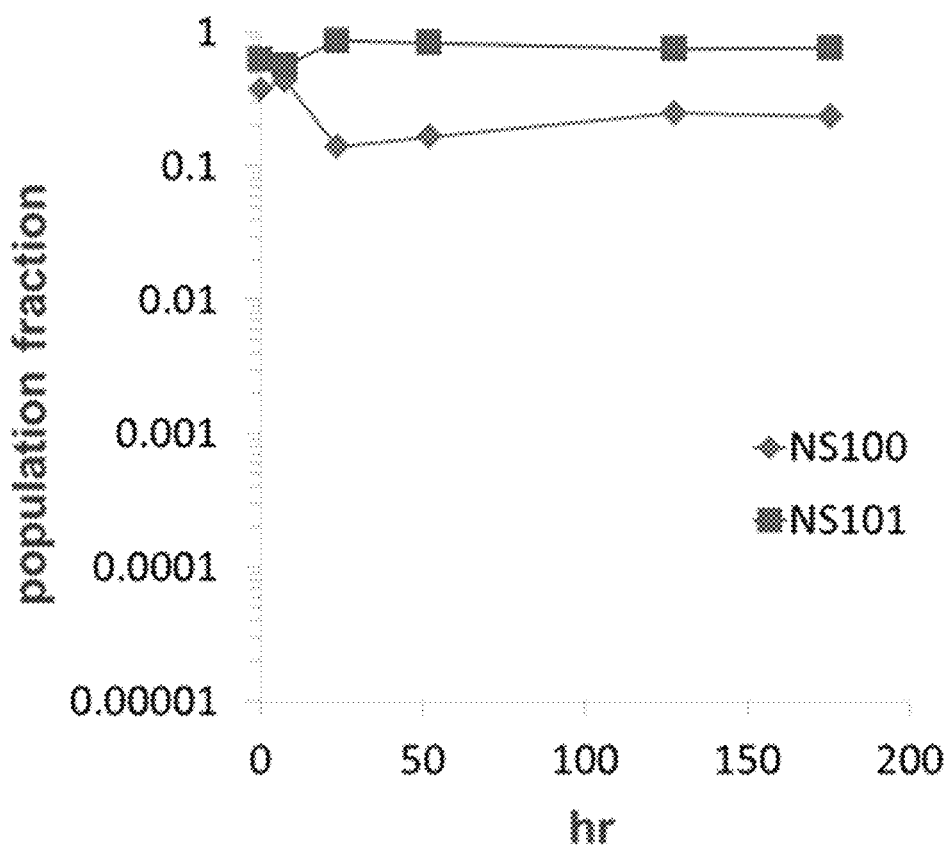
FIG. 22 depicts the population fraction of NS100 (control) and NS101 in a urea-containing medium.
Figure 23:
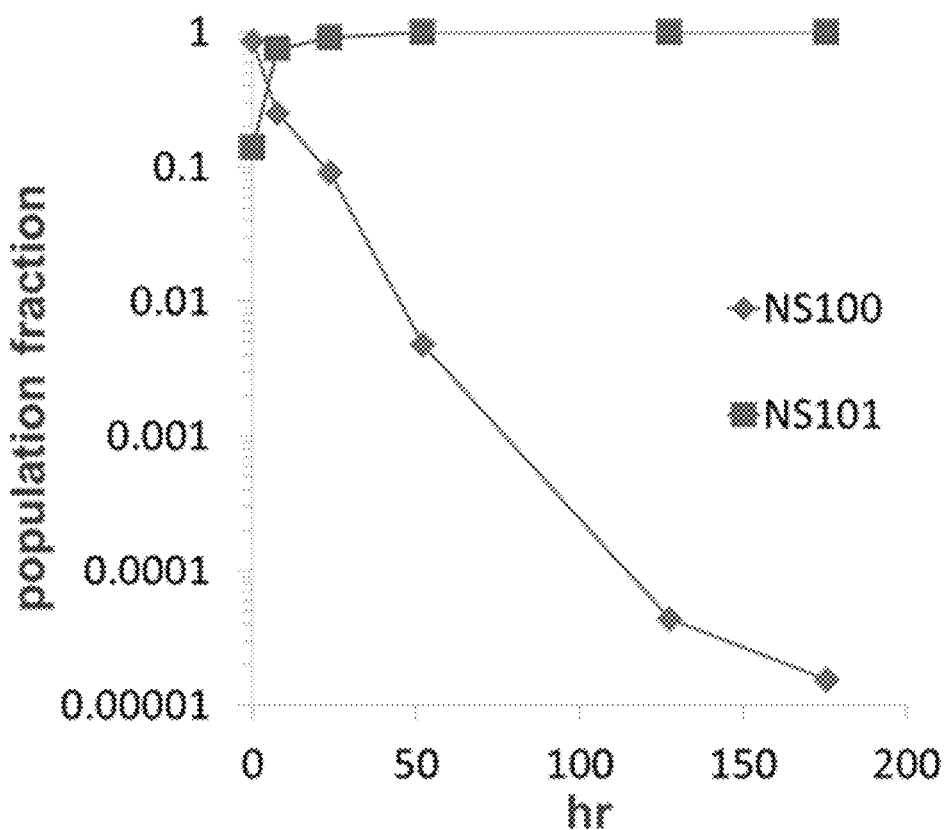
FIG. 23 depicts the population fraction of NS100 (control) and NS101 in a cyanamide-containing medium.

Growth occurred aerobically at 30° C. Colony forming units were counted by serial dilutions in YPD media with either 300 μg/mL hygromycin or 100 μg/mL nourseothricin, and are the average of 3 dilution counts (FIG. 22 and FIG. 23).

Utilization of Cyanamide in Rich Medium

Figure 24:
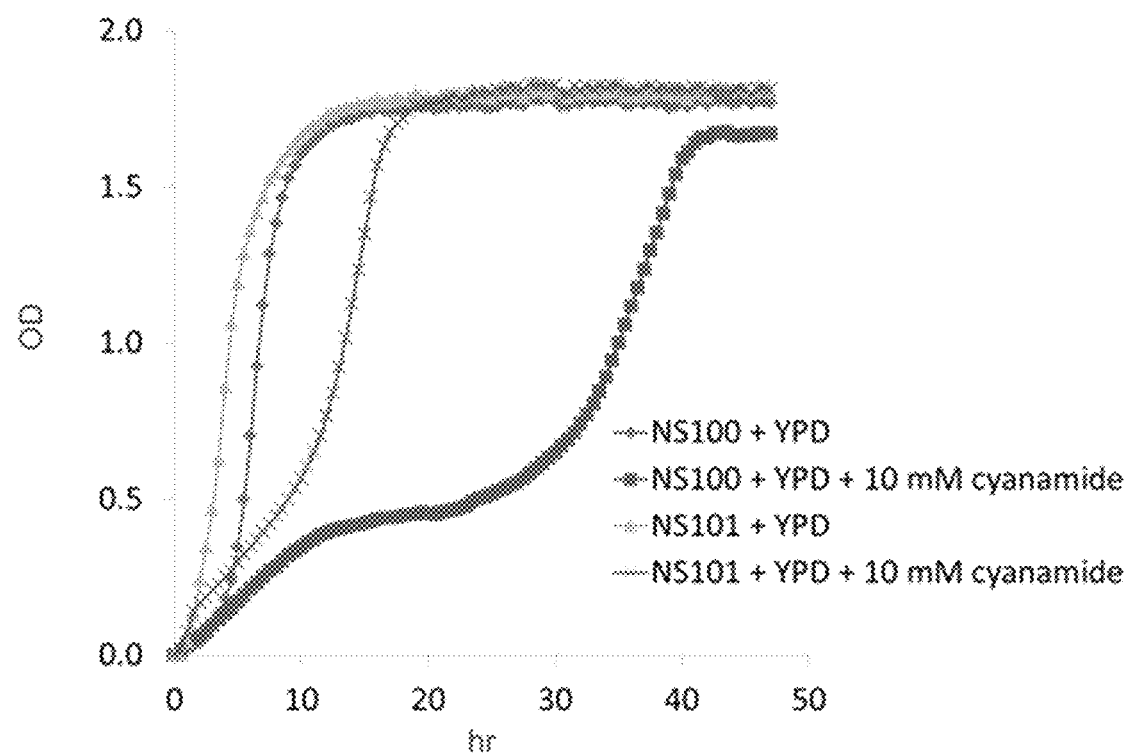
FIG. 24 depicts the growth progress of NS100 (control) and NS101 in media containing no nitrogen source, or media containing cyanamide.

The optical density of NS100 and NS101 grown in rich YPD medium with 100 μg/mL hygromycin and with and without 10 mM cyanamide was assessed as follows. NS100 and NS101 were grown overnight in YNB medium, and inoculated at 3.33% v/v. NS101 displayed a shorter lag phase than NS100 in the presence of 10 mM cyanamide. Thus, cyanamide, in addition to functioning as a sole source of nitrogen, may also act as a deterrent for microbial growth. Data are averages of 3 replicate wells in a 96 well plate; 150 μL per well. 30° C., YPD medium or YPD medium with 10 mM cyanamide. Inoculation was with 5 μL of culture pregrown for 24 hours in the YNB medium with urea as nitrogen source (FIG. 24).

Example 10

Production of Lipids in a Fermentation Mixture Comprising a Fraction of Fractionated Grain The oleaginous yeast, *Yarrowia lipolytica* was introduced into three fermentation conditions. The growth media and glucose equivalents were identical across the three fermentations. In one fermentation, the carbon source was soluble corn syrup (as would be produced from a wet mill process). In the second reactor, the carbon source was fractionated corn mash (provided by NCERC from Cereal Process Technologies pilot scale fractionation system). And in the third reactor, the carbon source was whole corn mash (provided by NCERC).

Figure 26:
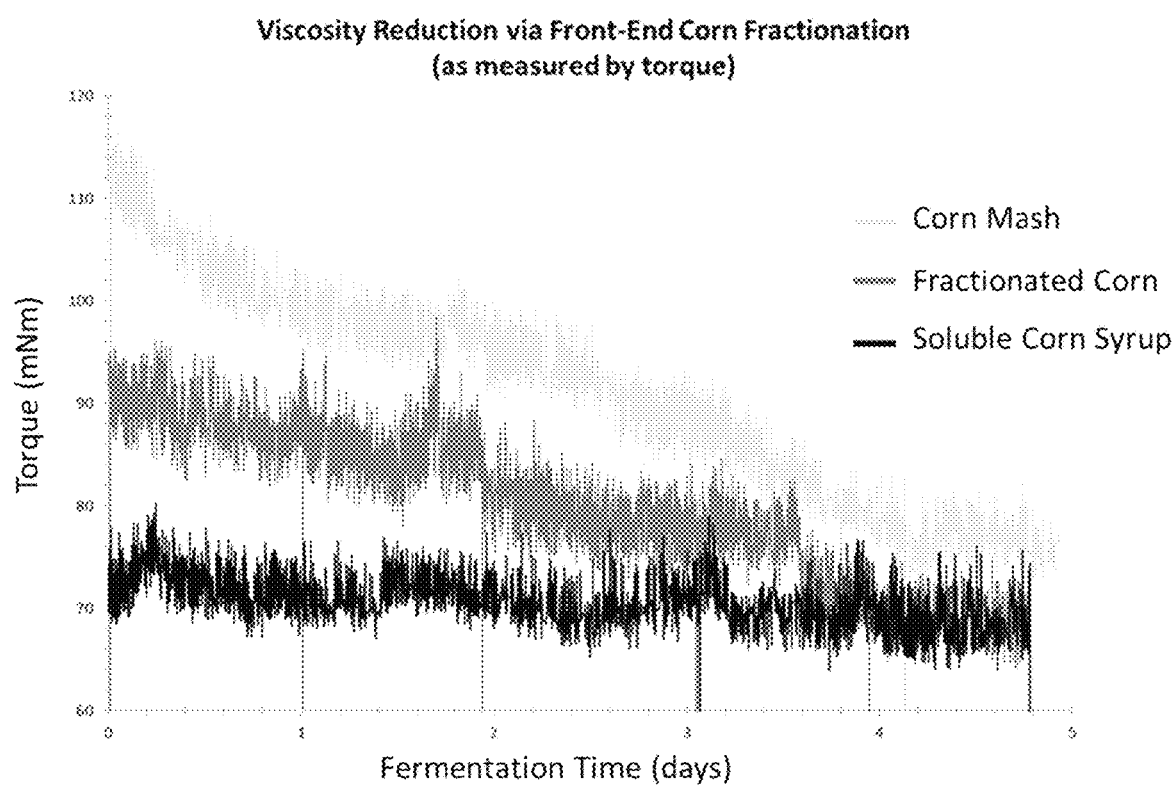
FIG. 26 is a graph that shows the torque required to mix a fermentation mixture in a 1 liter bioreactor at 1000 rpm using three different feedstocks.
Figure 27:
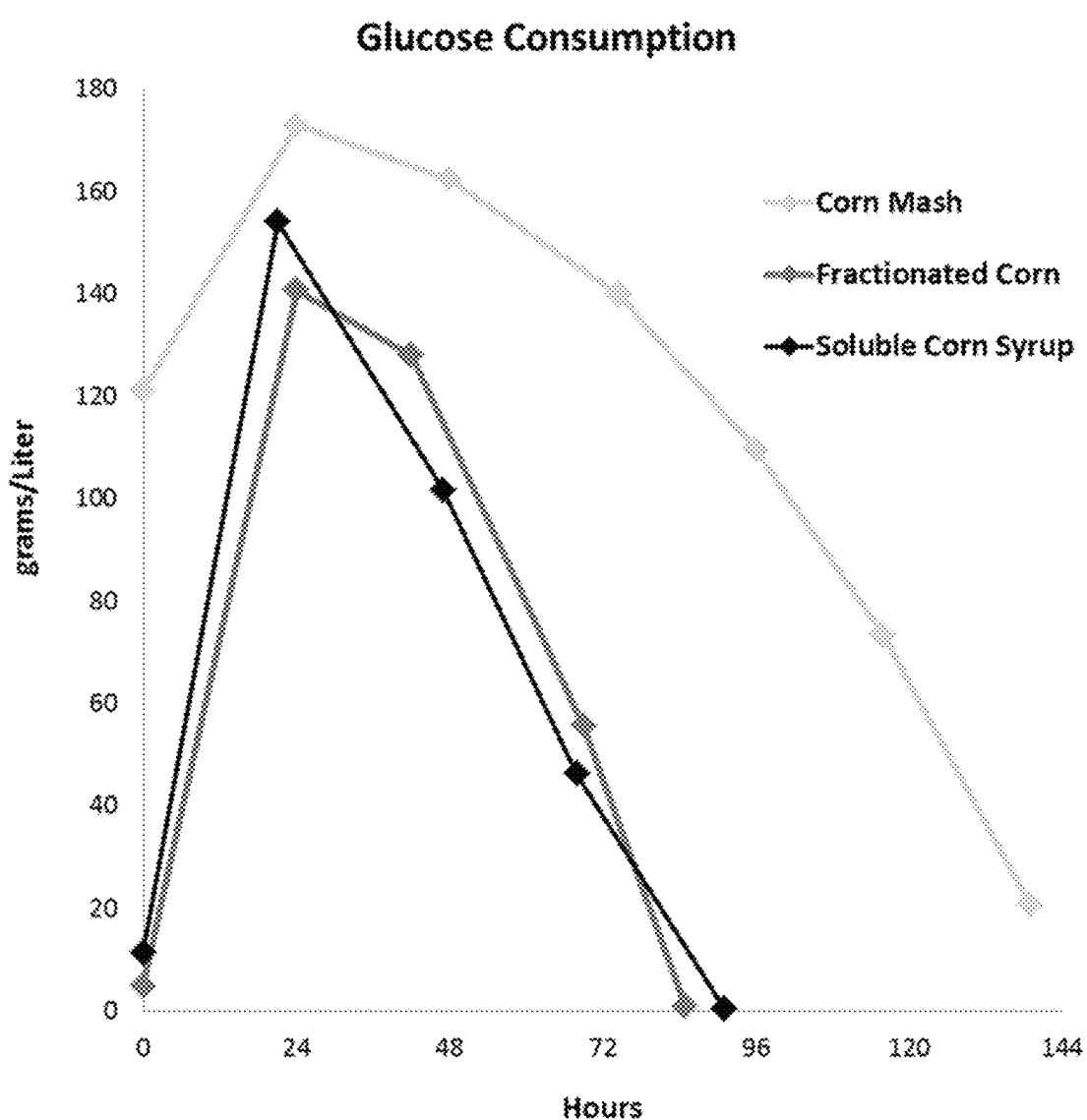
FIG. 27 is a graph that shows the glucose consumption for 1 liter fermentation mixtures using three different feedstocks.

FIG. 26 shows the torque required to mix each condition in a 1 L bioreactor at 1000 rpm. At the start of fermentation, the torque required to mix whole corn mash is about 50% greater than the torque required to mix the soluble corn syrup. When non-carbohydrate portions of the corn kernel are removed via front-end fractionation, the torque is still greater than that required to mix the corn syrup, but it is only about 25% greater, rather than 50% greater. As demonstrated in FIG. 27, this viscosity reduction is sufficient to allow for improved oxygen transfer such that the cells are no longer limited for oxygen in the fractionated corn mash and are able to consume glucose at a rate equivalent to that observed in the soluble corn syrup.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising
   a) a fermentation mixture comprising
      i) a first fraction consisting essentially of a fraction of a fractionated grain, and
      ii) a second fraction comprising one or more nitrogen-containing compounds; and
   b) a transformed cell comprising an exogenous nucleic acid molecule that encodes an enzyme for metabolizing the one or more nitrogen-containing compounds as a source of nitrogen; wherein the one or more nitrogen-containing compounds cannot be metabolized by a native, untransformed cell of the same species, and wherein the enzyme is a melamine deaminase (EC 3.5.4.45), a guanine deaminase (EC 3.5.4.3), a N-isopropylammelide isopropylamino (Ammelide) hydrolyase (EC 3.5.99.4), a cyanuric acid hydrolyase (EC 3.5.2.15), a biuret amidohydrolase (EC 3.5.1.84), an allophanate hydrolyase (EC 3.5.1.54), a cyanamide hydratase (EC 4.2.1.69), a urease (EC 3.5.1.5), or a urea carboxylase (EC 6.3.4.6).

2. The composition of claim 1, wherein the one or more nitrogen-containing compounds are not naturally found in the grain.

3. The composition of claim 1, wherein the fraction of the fractionated grain is an endosperm fraction.

4. The composition of claim 1, wherein the grain is corn, wheat, sorghum, rye, triticale, oats, rice, millets, barley, teff, wild rice, spelt, buckwheat, amaranth, quinoa, kaniwa, or fonio.

5. The composition of claim 1, wherein:
   the second fraction comprises, in an amount from about 10% by weight to about 100% by weight, one or more nitrogen-containing compounds of any one of formulas I-III, or a salt thereof; and
   the compound of formula I is

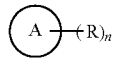

I wherein, independently for each occurrence,

is a five-, six, nine-, or ten-membered aryl or heteroaryl group; R is —OH, —CO$_2$H, —NO$_2$, —CN, substituted or unsubstituted amino, or substituted or unsubstituted alkyl; and
   n is 0, 1, 2, 3, 4, or 5;
the compound of formula II is

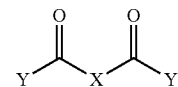

II wherein, independently for each occurrence,
   X is —NH—, —N(alkyl)—, —O—, —C(R$^1$)$_2$—, —S—, or absent;
   Y is —H, —NH$_2$, —N(H)(alkyl), —N(alkyl)$_2$, —CO$_2$H, —CN, or substituted or unsubstituted alkyl; and
   R$^1$ is —H, —OH, —CO$_2$H, —NO$_2$, —CN, substituted or unsubstituted amino, or substituted or unsubstituted alkyl; and
the compound of formula III is

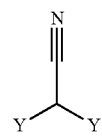

III wherein, independently for each occurrence,
   Y is —H, —NH$_2$, —N(H)(alkyl), —N(alkyl)$_2$, —CO$_2$H, —CN, or substituted or unsubstituted alkyl.

6. The composition of claim 5, wherein the one or more nitrogen-containing compounds are selected from the group consisting of Hydrazine, 5-Aminotetrazole, Tetrazole, Melamine, Cyanamide, 2-Cyanoguanidine, Sodium azide, Carbohydrazide, 1,2,3-Triazole, 1,2,4-Triazole, 1,3-Diaminoguanidine HCl, Ammeline, 1,3,5-triazine, Aminoacetonitrile, Cyanoethylhydrazine, Azodicarbonamide, Biurea, Formamidoxime, 1,2-Dimethylhydrazine, 1,1-Dimethylhydrazine, ethylhydrazine, Ethylenediamine, Sodium dicyanamide, Guanidine carbonate, Methylamine, Ammelide, Hydroxylamine, Malononitrile, Biuret, Diethylenetriamine, Hexamethylenetetramine, Triethylenetetramine, 1,3-Diaminopropane, Triethylenetetramine, 1,3-Diaminopropane, Hydroxyurea, Tetraethylenepentamine, Thiourea, Succinonitrile, Calcium cyanamide, Cyanuric acid, Aminoethylpiperazine, Piperazine, Dimethylamine, Ethylamine, dalfampridine, Tetranitromethane, Imidazolidinyl urea, Trinitromethane, malonamide, Chloramine, Allophanate, Trimethylamine, Nitromethane, Acetaldoxime, Diazolidinyl urea, 1,2-Cyclohexanedione dioxime, Acetone oxime, Thioacetamide, Sodium thiocyanate, Isothiazole, Thiazole, Dimethylacetamide, Isothiazolinone, Methylene blue, Diethanolamine, Aspartame, Benzisothiazolinone, urea, and Acesulfame potassium.

7. The composition of claim 1, wherein the enzyme is an allophanate hydrolase.

8. The composition of claim 1, wherein the transformed cell is selected from the group consisting of algae, bacteria, molds, fungi, plants, and yeasts.

9. The composition of claim 8, wherein:
the transformed cell is a bacterium;
the transformed cell comprises a second genetic modification; and
said second genetic modification confers resistance to a bacteriophage.

10. The composition of claim 9, wherein the second genetic modification confers resistance to a bacteriophage selected from the group consisting of Wphi, Mu, T1, T2, T3, T4, T5, T6, T7, P1, P2, P4, P22, fd, phi6, phi29, phi31, phiC31, phi35, phi36, phi48, phi50, phi80, phiX174, SP01, M13, MS2, PM2, SSV-1, L5, PRD1, Qbeta, lambda, UC-1, HK97, and HK022.

11. The composition of claim 1, wherein the transformed cell comprises one or more exogenous nucleic acid molecules that encode a melamine deaminase (EC 3.5.4.45), a guanine deaminase (EC 3.5.4.3), a N-isopropylammelide isopropylamino (Ammedlide) hydrolyase (EC 3.5.99.4), a cyanuric acid hydrolyase (EC 3.5.2.15), a biuret amidohydrolase (EC 3.5.1.84), and an allophanate hydrolyase (EC 3.5.1.54).

12. The composition of claim 1, wherein the transformed cell comprises one or more exogenous nucleic acid molecule that encode a cyanamide hydratase (EC 4.2.1.69), a urea carboxylase (EC 6.3.4.6), and an allophanate hydrolyase (EC 3.5.1.54).

13. The composition of claim 1, wherein the fermentation mixture does not comprise a source of nitrogen other than the one or more nitrogen-containing compounds.

14. The composition of claim 8, wherein the yeast is an oleaginous yeast.

15. The composition of claim 8, wherein the yeast is a *Saccharomyces cerevisiae* or *Yarrowia lipolytica*.

16. A method for fermentation, comprising incubating the composition of claim 1, thereby producing a fermentation product and
wherein the transformed cell of the said composition is selected from the group consisting of algae, bacteria, molds, fungi, plants, and yeasts.

17. The method of claim 16, wherein the yeast is an oleaginous yeast.

18. The method of claim 16, wherein the yeast is a *Saccharomyces cerevisiae* or *Yarrowia lipolytica*.

19. The method of claim 16, wherein the grain is corn, wheat, sorghum, rye, triticale, oats, rice, millets. barley, teff, wild rice, spelt, buckwheat, amaranth, quinoa, kaniwa, or fonio.

20. The method of claim 16, wherein the one or more nitrogen-containing compounds are selected from the group consisting of Hydrazine, 5-Aminotetrazole, Tetrazole, Melamine, Cyanamide, 2-Cyanoguanidine, Sodium azide, Carbohydrazide, 1,2,3-Triazole, 1,2,4-Triazole, 1,3-Diaminoguanidine HCl, Ammeline, 1,3,5-triazine, Aminoacetonitrile, Cyanoethylhydrazine, Azodicarbonamide, Biurea, Formamidoxime, 1,2-Dimethylhydrazine, 1,1-Dimethylhydrazine, ethylhydrazine, Ethylenediamine, Sodium dicyanamide, Guanidine carbonate, Methylamine, Ammelide, Hydroxylamine, Malononitrile, Biuret, Diethylenetriamine, Hexamethylenetetramine, Triethylenetetramine, 1,3-Diaminopropane, Triethylenetetramine, 1,3-Diaminopropane, Hydroxyurea, Tetraethylenepentamine, Thiourea, Succinonitrile, Calcium cyanamide, Cyanuric acid, Aminoethylpiperazine, Piperazine, Dimethylamine, Ethylamine, dalfampridine, Tetranitromethane, Imidazolidinyl urea, Trinitromethane, malonamide, Chloramine, Allophanate, Trimethylamine, Nitromethane, Acetaldoxime, Diazolidinyl urea, 1,2-Cyclohexanedione dioxime, Acetone oxime, Thioacetamide, Sodium thiocyanate, Isothiazole, Thiazole, Dimethylacetamide, Isothiazolinone, Methylene blue, Diethanolamine, Aspartame, Benzisothiazolinone, urea, and Acesulfame potassium.

\* \* \* \* \*